(12) United States Patent
Gross et al.

(10) Patent No.: US 12,138,165 B2
(45) Date of Patent: *Nov. 12, 2024

(54) ANNULOPLASTY IMPLANTS

(71) Applicant: Edwards Lifesciences Innovation (Israel) Ltd., Caesarea (IL)

(72) Inventors: Amir Gross, Tel Aviv-Jaffa (IL); Tal Sheps, Givat Shmuel (IL); Tal Hammer, Ramat Gan (IL); Tal Reich, Moledat (IL); Ehud Aviv, Costa Mesa, CA (US)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 450 days.

This patent is subject to a terminal disclaimer.

(21) Appl. No.: 17/473,786

(22) Filed: Sep. 13, 2021

(65) Prior Publication Data

US 2021/0401576 A1 Dec. 30, 2021

Related U.S. Application Data

(63) Continuation of application No. 16/601,289, filed on Oct. 14, 2019, now Pat. No. 11,116,634, which is a (Continued)

(51) Int. Cl.
*A61F 2/24* (2006.01)
*A61B 17/068* (2006.01)
(Continued)

(52) U.S. Cl.
CPC .......... *A61F 2/2445* (2013.01); *A61B 17/068* (2013.01); *A61B 17/072* (2013.01); (Continued)

(58) Field of Classification Search
None
See application file for complete search history.

(56) References Cited

U.S. PATENT DOCUMENTS

| 3,604,488 A | 9/1971 | Wishart et al. |
| 3,656,185 A | 4/1972 | Carpentier |

(Continued)

FOREIGN PATENT DOCUMENTS

| CA | 2728078 A1 * | 1/2010 | ........... A61F 2/2442 |
| CN | 113331995 A | 9/2021 | |

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Leslie A Lopez
(74) *Attorney, Agent, or Firm* — Thomas C. Richardson

(57) ABSTRACT

A method for treating a native heart valve of a patient includes anchoring a plurality of anchors of an implant into tissue around an annulus of the valve. At the annulus, a force-distribution element is incorporated into the implant such that the force-distribution element extends along a longitudinal portion of the elongate contracting member. The method can also include circumferentially tightening the annulus by pulling the plurality of anchors closer together, such as by actuating a contracting mechanism of a contracting system, such that (i) the contracting mechanism, coupled to an elongate contracting member of the implant, applies a longitudinal tensioning force to the elongate contracting member, and (ii) the force-distributing element distributes the longitudinal tensioning force over at least two of the anchors. Other embodiments are also described.

26 Claims, 45 Drawing Sheets

Related U.S. Application Data continuation of application No. 15/474,543, filed on Mar. 30, 2017, now Pat. No. 10,470,882, which is a continuation of application No. 14/128,756, filed as application No. PCT/IL2012/000250 on Jun. 21, 2012, now Pat. No. 9,662,209, which is a continuation-in-part of application No. 13/167,492, filed on Jun. 23, 2011, now Pat. No. 8,926,697, and a continuation-in-part of application No. 13/167,476, filed on Jun. 23, 2011, now Pat. No. 8,940,044, and a continuation-in-part of application No. 13/167,444, filed on Jun. 23, 2011, now Pat. No. 9,011,530.

(51) Int. Cl.
*A61B 17/072* (2006.01)
*A61B 17/00* (2006.01)
*A61B 17/04* (2006.01)
*A61B 17/064* (2006.01)

(52) U.S. Cl.
CPC .. *A61F 2/2466* (2013.01); *A61B 2017/00243* (2013.01); *A61B 2017/003* (2013.01); *A61B 2017/0441* (2013.01); *A61B 2017/0464* (2013.01); *A61B 2017/0649* (2013.01); *A61F 2/2448* (2013.01); *A61F 2220/0016* (2013.01); *A61F 2250/0004* (2013.01); *A61F 2250/0007* (2013.01); *A61F 2250/001* (2013.01)

(56) References Cited

U.S. PATENT DOCUMENTS

| | | | |
|---|---|---|---|
| 3,840,018 | A | 10/1974 | Heifetz |
| 3,874,388 | A | 4/1975 | King et al. |
| 3,881,366 | A | 5/1975 | Bradley et al. |
| 3,898,701 | A | 8/1975 | La Russa |
| 4,042,979 | A * | 8/1977 | Angell ............ A61F 2/2448 |
| | | | 623/2.37 |
| 4,118,805 | A | 10/1978 | Reimels |
| 4,214,349 | A | 7/1980 | Munch |
| 4,261,342 | A | 4/1981 | Aranguren Duo |
| 4,290,151 | A | 9/1981 | Massana |
| 4,340,091 | A | 7/1982 | Skelton et al. |
| 4,434,828 | A | 3/1984 | Trincia |
| 4,473,928 | A | 10/1984 | Johnson |
| 4,506,669 | A | 3/1985 | Blake, III |
| 4,590,937 | A | 5/1986 | Deniega |
| 4,602,911 | A * | 7/1986 | Ahmadi ............ A61F 2/2445 |
| | | | 623/2.37 |
| 4,625,727 | A | 12/1986 | Leiboff |
| 4,693,248 | A | 9/1987 | Failla |
| 4,712,549 | A | 12/1987 | Peters et al. |
| 4,778,468 | A | 10/1988 | Hunt et al. |
| 4,803,983 | A | 2/1989 | Siegel |
| 4,917,698 | A | 4/1990 | Carpentier et al. |
| 4,935,027 | A | 6/1990 | Yoon |
| 4,961,738 | A | 10/1990 | Mackin |
| 5,042,707 | A | 8/1991 | Taheri |
| 5,061,277 | A | 10/1991 | Carpentier et al. |
| 5,064,431 | A | 11/1991 | Gilbertson et al. |
| 5,104,407 | A | 4/1992 | Lam et al. |
| 5,108,420 | A | 4/1992 | Marks |
| 5,125,895 | A | 6/1992 | Buchbinder et al. |
| 5,171,252 | A | 12/1992 | Friedland |
| 5,195,962 | A | 3/1993 | Martin et al. |
| 5,201,880 | A | 4/1993 | Wright et al. |
| 5,258,008 | A | 11/1993 | Wilk |
| 5,292,326 | A | 3/1994 | Green et al. |
| 5,300,034 | A | 4/1994 | Behnke et al. |
| 5,306,296 | A | 4/1994 | Wright et al. |
| 5,325,845 | A | 7/1994 | Adair |
| 5,327,905 | A | 7/1994 | Avitall |
| 5,346,498 | A | 9/1994 | Greelis et al. |
| 5,363,861 | A | 11/1994 | Edwards et al. |
| 5,370,685 | A | 12/1994 | Stevens |
| 5,383,852 | A | 1/1995 | Stevens-Wright |
| 5,389,077 | A | 2/1995 | Melinyshyn et al. |
| 5,411,552 | A | 5/1995 | Andersen et al. |
| 5,449,368 | A | 9/1995 | Kuzmak |
| 5,450,860 | A | 9/1995 | O'Connor |
| 5,456,674 | A | 10/1995 | Bos et al. |
| 5,464,404 | A | 11/1995 | Abela et al. |
| 5,474,057 | A | 12/1995 | Makower et al. |
| 5,474,518 | A | 12/1995 | Farrer Velazquez |
| 5,477,856 | A | 12/1995 | Lundquist |
| 5,478,353 | A | 12/1995 | Yoon |
| 5,487,746 | A | 1/1996 | Yu et al. |
| 5,501,683 | A | 3/1996 | Trott |
| 5,565,004 | A | 10/1996 | Christoudias |
| 5,593,424 | A * | 1/1997 | Northrup, III ..... A61B 17/0401 |
| | | | 606/1 |
| 5,601,572 | A | 2/1997 | Middleman et al. |
| 5,607,462 | A | 3/1997 | Imran |
| 5,609,598 | A | 3/1997 | Laufer et al. |
| 5,611,794 | A | 3/1997 | Sauer et al. |
| 5,626,607 | A | 5/1997 | Malecki et al. |
| 5,626,609 | A | 5/1997 | Zvenyatsky et al. |
| 5,643,317 | A | 7/1997 | Pavonik et al. |
| 5,669,919 | A | 9/1997 | Sanders et al. |
| 5,674,279 | A | 10/1997 | Wright et al. |
| 5,676,653 | A | 10/1997 | Taylor et al. |
| 5,683,402 | A | 11/1997 | Cosgrove et al. |
| 5,695,504 | A | 12/1997 | Gifford, III et al. |
| 5,702,397 | A | 12/1997 | Goble et al. |
| 5,702,398 | A | 12/1997 | Tarabishy |
| 5,709,695 | A | 1/1998 | Northrup, III |
| 5,716,370 | A | 2/1998 | Williamson, IV et al. |
| 5,716,397 | A | 2/1998 | Myers |
| 5,716,417 | A | 2/1998 | Girard et al. |
| 5,727,569 | A | 3/1998 | Benetti et al. |
| 5,728,116 | A | 3/1998 | Rosenman |
| 5,730,150 | A | 3/1998 | Peppel et al. |
| 5,741,297 | A | 4/1998 | Simon |
| 5,749,371 | A | 5/1998 | Zadini et al. |
| 5,752,963 | A | 5/1998 | Allard et al. |
| 5,782,746 | A | 7/1998 | Wright |
| 5,782,844 | A | 7/1998 | Yoon et al. |
| 5,782,862 | A | 7/1998 | Bonutti |
| 5,797,960 | A | 8/1998 | Stevens et al. |
| 5,810,882 | A | 9/1998 | Bolduc et al. |
| 5,824,066 | A | 10/1998 | Gross |
| 5,830,221 | A | 11/1998 | Stein et al. |
| 5,836,311 | A | 11/1998 | Borst et al. |
| 5,843,076 | A | 12/1998 | Webster, Jr. et al. |
| 5,843,120 | A | 12/1998 | Israel et al. |
| 5,855,590 | A | 1/1999 | Malecki et al. |
| 5,855,614 | A | 1/1999 | Stevens et al. |
| 5,876,373 | A | 3/1999 | Giba et al. |
| 5,885,271 | A | 3/1999 | Hamilton et al. |
| 5,888,247 | A | 3/1999 | Benetti |
| 5,891,017 | A | 4/1999 | Swindle et al. |
| 5,891,112 | A | 4/1999 | Samson |
| 5,894,843 | A | 4/1999 | Benetti et al. |
| 5,921,979 | A | 7/1999 | Kovac et al. |
| 5,935,098 | A | 8/1999 | Blaisdell et al. |
| 5,944,738 | A | 8/1999 | Amplatz et al. |
| 5,957,835 | A | 9/1999 | Anderson et al. |
| 5,957,953 | A | 9/1999 | DiPoto et al. |
| 5,961,440 | A | 10/1999 | Schweich, Jr. et al. |
| 5,961,539 | A | 10/1999 | Northrup, III et al. |
| 5,972,020 | A | 10/1999 | Carpentier et al. |
| 5,980,534 | A | 11/1999 | Gimpelson |
| 5,984,959 | A | 11/1999 | Robertson et al. |
| 5,993,459 | A | 11/1999 | Larsen et al. |
| 6,004,329 | A | 12/1999 | Myers et al. |
| 6,010,531 | A | 1/2000 | Donlon et al. |
| 6,017,358 | A | 1/2000 | Yoon et al. |
| 6,042,554 | A | 3/2000 | Rosenman et al. |
| 6,045,497 | A | 4/2000 | Schweich, Jr. et al. |
| 6,050,936 | A | 4/2000 | Schweich, Jr. et al. |
| 6,059,715 | A | 5/2000 | Schweich, Jr. et al. |
| 6,074,341 | A | 6/2000 | Anderson et al. |
| 6,074,401 | A | 6/2000 | Gardiner et al. |

(56) References Cited

U.S. PATENT DOCUMENTS

| | | |
|---|---|---|
| 6,074,417 A | 6/2000 | Peredo |
| 6,086,582 A | 7/2000 | Altman et al. |
| 6,086,600 A | 7/2000 | Kortenbach |
| 6,102,945 A | 8/2000 | Campbell |
| 6,106,550 A | 8/2000 | Magovern et al. |
| 6,110,200 A | 8/2000 | Hinnenkamp |
| 6,120,496 A | 9/2000 | Whayne et al. |
| 6,132,370 A | 10/2000 | Furnish et al. |
| 6,132,390 A | 10/2000 | Cookston et al. |
| 6,143,024 A | 11/2000 | Campbell et al. |
| 6,159,240 A | 12/2000 | Sparer et al. |
| 6,162,239 A | 12/2000 | Manhes |
| 6,165,119 A | 12/2000 | Schweich, Jr. et al. |
| 6,165,183 A | 12/2000 | Kuehn et al. |
| 6,174,332 B1 | 1/2001 | Loch et al. |
| 6,182,664 B1 | 2/2001 | Cosgrove |
| 6,183,411 B1 | 2/2001 | Mortier et al. |
| 6,187,040 B1 | 2/2001 | Wright |
| 6,193,732 B1 | 2/2001 | Frantzen et al. |
| 6,193,734 B1 | 2/2001 | Bolduc et al. |
| 6,200,315 B1 | 3/2001 | Gaiser et al. |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,241,743 B1 | 6/2001 | Levin et al. |
| 6,251,092 B1 | 6/2001 | Qin et al. |
| 6,269,819 B1 | 8/2001 | Oz et al. |
| 6,269,829 B1 | 8/2001 | Chen et al. |
| 6,296,656 B1 | 10/2001 | Bolduc et al. |
| 6,312,447 B1 | 11/2001 | Grimes |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,468,285 B1 | 10/2002 | Hsu et al. |
| 6,470,892 B1 | 10/2002 | Forsell |
| 6,503,274 B1 | 1/2003 | Howanec, Jr. et al. |
| 6,508,806 B1 | 1/2003 | Hoste |
| 6,508,825 B1 | 1/2003 | Selmon et al. |
| 6,524,338 B1 | 2/2003 | Gundry |
| 6,527,780 B1 | 3/2003 | Wallace et al. |
| 6,530,933 B1 | 3/2003 | Yeung et al. |
| 6,530,952 B2 | 3/2003 | Vesely |
| 6,533,772 B1 | 3/2003 | Sherts et al. |
| 6,537,290 B2 | 3/2003 | Adams et al. |
| 6,537,314 B2 | 3/2003 | Langberg et al. |
| 6,544,215 B1 | 4/2003 | Bencini et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,767 B1 | 4/2004 | Kimblad |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,837,867 B2 | 1/2005 | Kortelling |
| 6,855,126 B2 | 2/2005 | Flinchbaugh |
| 6,855,137 B2 | 2/2005 | Bon |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,913,614 B2 | 7/2005 | Marino et al. |
| 6,918,917 B1 | 7/2005 | Nguyen et al. |
| 6,926,730 B1 | 8/2005 | Nguyen et al. |
| 6,939,337 B2 | 9/2005 | Parker et al. |
| 6,945,956 B2 | 9/2005 | Waldhauser et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,048,754 B2 | 5/2006 | Martin et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |

(56) References Cited

U.S. PATENT DOCUMENTS

| | | |
|---|---|---|
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoullan et al. |
| 7,364,588 B2 | 4/2008 | Mathis et al. |
| 7,371,210 B2 | 5/2008 | Brock et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,464,712 B2 | 12/2008 | Oz et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,509,959 B2 | 3/2009 | Oz et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,731,706 B2 | 6/2010 | Potter |
| 7,736,388 B2 | 6/2010 | Goldfarb et al. |
| 7,744,609 B2 | 6/2010 | Allen et al. |
| 7,748,389 B2 | 7/2010 | Salahieh et al. |
| 7,753,924 B2 | 7/2010 | Starksen et al. |
| 7,753,932 B2 | 7/2010 | Gingrich et al. |
| 7,758,596 B2 | 7/2010 | Oz et al. |
| 7,758,632 B2 | 7/2010 | Hojeibane et al. |
| 7,780,723 B2 | 8/2010 | Taylor |
| 7,780,726 B2 | 8/2010 | Seguin |
| 7,803,185 B2 | 9/2010 | Gabbay |
| 7,824,443 B2 | 11/2010 | Salahieh et al. |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,123 B2 | 7/2011 | Seguin |
| 7,981,152 B1 | 7/2011 | Webler et al. |
| 7,988,724 B2 | 8/2011 | Salahieh et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,052,750 B2 | 11/2011 | Tuval et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,096,985 B2 | 1/2012 | Legaspi et al. |
| 8,100,964 B2 | 1/2012 | Spence |
| 8,104,149 B1 | 1/2012 | McGarity |
| 8,123,801 B2 | 2/2012 | Milo |
| 8,133,239 B2 | 3/2012 | Oz et al. |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,172,856 B2 | 5/2012 | Eigler et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,437 B2 | 6/2012 | Bonhoeffer et al. |
| 8,206,439 B2 | 6/2012 | Gomez Duran |
| 8,216,301 B2 | 7/2012 | Bonhoeffer et al. |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keldar et al. |
| 8,292,884 B2 | 10/2012 | Levine et al. |
| 8,303,608 B2 | 11/2012 | Goldfarb et al. |
| 8,303,653 B2 | 11/2012 | Bonhoeffer et al. |
| 8,313,525 B2 | 11/2012 | Tuval et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,414,643 B2 | 4/2013 | Tuval et al. |
| 8,419,825 B2 | 4/2013 | Burgler et al. |
| 8,425,404 B2 | 4/2013 | Wilson et al. |
| 8,430,926 B2 | 4/2013 | Kirson |
| 8,449,573 B2 | 5/2013 | Chu |
| 8,449,599 B2 | 5/2013 | Chau et al. |
| 8,449,606 B2 | 5/2013 | Eliasen et al. |
| 8,454,686 B2 | 6/2013 | Alkhatib |
| 8,460,368 B2 | 6/2013 | Taylor et al. |
| 8,460,370 B2 | 6/2013 | Zakay |
| 8,460,371 B2 | 6/2013 | Hlavka et al. |
| 8,470,028 B2 | 6/2013 | Thornton et al. |

(56) References Cited

U.S. PATENT DOCUMENTS

| | | |
|---|---|---|
| 8,475,491 B2 | 7/2013 | Milo |
| 8,475,525 B2 | 7/2013 | Maisano et al. |
| 8,480,730 B2 | 7/2013 | Maurer et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,540,767 B2 | 9/2013 | Zhang |
| 8,545,553 B2 | 10/2013 | Zipory et al. |
| 8,551,161 B2 | 10/2013 | Dolan |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,668,733 B2 | 3/2014 | Haug et al. |
| 8,679,174 B2 | 3/2014 | Ottma et al. |
| 8,685,086 B2 | 4/2014 | Navia et al. |
| 8,721,665 B2 | 5/2014 | Oz et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,918 B2 | 6/2014 | Seguin |
| 8,740,920 B2 | 6/2014 | Goldfarb et al. |
| 8,747,463 B2 | 6/2014 | Fogarty et al. |
| 8,771,347 B2 | 7/2014 | DeBoer et al. |
| 8,778,017 B2 | 7/2014 | Eliasen et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,834,564 B2 | 9/2014 | Tuval et al. |
| 8,840,663 B2 | 9/2014 | Salahieh et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,876,894 B2 | 11/2014 | Tuval et al. |
| 8,876,895 B2 | 11/2014 | Tuval et al. |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,177 B2 | 2/2015 | Dell et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,034,032 B2 | 5/2015 | McLean et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,198,757 B2 | 12/2015 | Schroeder et al. |
| 9,220,507 B1 | 12/2015 | Patel et al. |
| 9,226,825 B2 | 1/2016 | Starksen et al. |
| 9,259,317 B2 | 2/2016 | Wilson et al. |
| 9,265,608 B2 | 2/2016 | Miller et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,326,857 B2 | 5/2016 | Cartledge et al. |
| 9,387,071 B2 | 7/2016 | Tuval et al. |
| 9,414,921 B2 | 8/2016 | Miller et al. |
| 9,427,316 B2 | 8/2016 | Schweich, Jr. et al. |
| 9,427,327 B2 | 8/2016 | Parrish |
| 9,439,763 B2 | 9/2016 | Geist et al. |
| 9,474,606 B2 | 10/2016 | Zipory et al. |
| 9,510,837 B2 | 12/2016 | Seguin |
| 9,510,946 B2 | 12/2016 | Chau et al. |
| 9,526,613 B2 | 12/2016 | Gross et al. |
| 9,561,104 B2 | 2/2017 | Miller et al. |
| 9,572,660 B2 | 2/2017 | Braido et al. |
| 9,579,090 B1 | 2/2017 | Simms et al. |
| 9,642,704 B2 | 5/2017 | Tuval et al. |
| 9,693,865 B2 | 7/2017 | Gilmore et al. |
| 9,700,445 B2 | 7/2017 | Martin et al. |
| 9,724,084 B2 | 8/2017 | Groothuis et al. |
| 9,730,793 B2 | 8/2017 | Reich et al. |
| 9,775,963 B2 | 10/2017 | Miller |
| 9,788,941 B2 | 10/2017 | Hacohen |
| 9,801,720 B2 | 10/2017 | Gilmore et al. |
| D809,139 S | 1/2018 | Marsot et al. |
| 9,889,002 B2 | 2/2018 | Bonhoeffer et al. |
| 9,907,547 B2 | 3/2018 | Gilmore et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,099,050 B2 | 10/2018 | Chen et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,368,852 B2 | 8/2019 | Gerhardt et al. |
| 10,376,673 B2 | 8/2019 | Van Hoven et al. |
| 10,575,841 B1 | 3/2020 | Paulos |
| 2001/0005787 A1 | 6/2001 | Oz et al. |
| 2001/0021874 A1 | 9/2001 | Carpentier et al. |
| 2002/0013571 A1 | 1/2002 | Goldfarb et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0095139 A1 | 7/2002 | Keogh et al. |
| 2002/0103532 A1 | 8/2002 | Langberg et al. |
| 2002/0107531 A1 | 8/2002 | Schreck et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0173811 A1 | 11/2002 | Tu et al. |

(56) References Cited

U.S. PATENT DOCUMENTS

| | | |
|---|---|---|
| 2002/0177904 A1 | 11/2002 | Huxel et al. |
| 2002/0183787 A1 | 12/2002 | Wahr et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0018358 A1 | 1/2003 | Saadat |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0093148 A1 | 5/2003 | Bolling et al. |
| 2003/0100943 A1 | 5/2003 | Bolduc |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144573 A1 | 7/2003 | Heilman et al. |
| 2003/0144657 A1 | 7/2003 | Bowe et al. |
| 2003/0171760 A1 | 9/2003 | Gambale |
| 2003/0187467 A1 | 10/2003 | Schreck |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0208208 A1 | 11/2003 | Chu |
| 2003/0208231 A1 | 11/2003 | Williamson et al. |
| 2003/0229350 A1 | 12/2003 | Kay |
| 2003/0229395 A1 | 12/2003 | Cox |
| 2004/0002735 A1 | 1/2004 | Lizardi et al. |
| 2004/0003819 A1 | 1/2004 | St. Goar et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0030382 A1 | 2/2004 | St. Goar et al. |
| 2004/0034365 A1 | 2/2004 | Lentz et al. |
| 2004/0039442 A1 | 2/2004 | St. Goar et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122448 A1 | 6/2004 | Levine |
| 2004/0122514 A1 | 6/2004 | Fogarty et al. |
| 2004/0127981 A1 | 7/2004 | Rahdert et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0147943 A1 | 7/2004 | Kobayashi |
| 2004/0148019 A1 | 7/2004 | Vidlund et al. |
| 2004/0148020 A1 | 7/2004 | Vidlund et al. |
| 2004/0148021 A1* | 7/2004 | Cartledge ............ A61B 17/068 623/2.37 |
| 2004/0176788 A1 | 9/2004 | Opolski |
| 2004/0181135 A1 | 9/2004 | Drysen |
| 2004/0181206 A1 | 9/2004 | Chiu et al. |
| 2004/0181238 A1 | 9/2004 | Zarbatany et al. |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0210307 A1 | 10/2004 | Khairkhahan |
| 2004/0220593 A1 | 11/2004 | Greenhalgh |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049618 A1 | 3/2005 | Masuda et al. |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070926 A1 | 3/2005 | Ortiz |
| 2005/0070999 A1 | 3/2005 | Spence |
| 2005/0075654 A1 | 4/2005 | Kelleher |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137690 A1 | 6/2005 | Salahieh et al. |
| 2005/0137695 A1 | 6/2005 | Salahieh et al. |
| 2005/0143767 A1 | 6/2005 | Kimura et al. |
| 2005/0159728 A1 | 7/2005 | Armour et al. |
| 2005/0159810 A1 | 7/2005 | Filsoufi |
| 2005/0165429 A1 | 7/2005 | Douglas et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0187613 A1 | 8/2005 | Bolduc et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0245821 A1 | 11/2005 | Govari et al. |
| 2005/0251183 A1 | 11/2005 | Buckman et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2005/0288786 A1 | 12/2005 | Chanduszko |
| 2006/0004442 A1 | 1/2006 | Spenser et al. |
| 2006/0004443 A1 | 1/2006 | Liddicoat et al. |
| 2006/0020275 A1 | 1/2006 | Goldfarb et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0089671 A1 | 4/2006 | Goldfarb et al. |
| 2006/0095009 A1 | 5/2006 | Lampropoulos et al. |
| 2006/0100649 A1 | 5/2006 | Hart |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0122647 A1 | 6/2006 | Callaghan et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0173251 A1 | 8/2006 | Govari et al. |
| 2006/0178700 A1 | 8/2006 | Quinn |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0224169 A1 | 10/2006 | Weisenburgh et al. |
| 2006/0241622 A1 | 10/2006 | Zergiebel |

(56) References Cited

U.S. PATENT DOCUMENTS

| | | |
|---|---|---|
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0016287 A1 | 1/2007 | Cartledge et al. |
| 2007/0016288 A1 | 1/2007 | Gurskis et al. |
| 2007/0021779 A1 | 1/2007 | Garvin et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032807 A1 | 2/2007 | Ortiz et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0060922 A1 | 3/2007 | Dreyfuss |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0093857 A1 | 4/2007 | Rogers et al. |
| 2007/0093890 A1 | 4/2007 | Eliasen et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0156197 A1 | 7/2007 | Root et al. |
| 2007/0162111 A1 | 7/2007 | Fukamachi et al. |
| 2007/0173931 A1 | 7/2007 | Tremulis et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0265491 A1 | 11/2007 | Krag et al. |
| 2007/0265700 A1 | 11/2007 | Eliasen et al. |
| 2007/0270679 A1 | 11/2007 | Nguyen et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282414 A1 | 12/2007 | Soltis et al. |
| 2007/0282429 A1 | 12/2007 | Hauser et al. |
| 2007/0293943 A1 | 12/2007 | Quinn |
| 2007/0295172 A1 | 12/2007 | Swartz |
| 2007/0299387 A1 | 12/2007 | Williams et al. |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039743 A1 | 2/2008 | Fox et al. |
| 2008/0039935 A1 | 2/2008 | Buch et al. |
| 2008/0039953 A1 | 2/2008 | Davis et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065149 A1 | 3/2008 | Thielen et al. |
| 2008/0065204 A1 | 3/2008 | Macoviak et al. |
| 2008/0071366 A1 | 3/2008 | Tuval et al. |
| 2008/0077144 A1 | 3/2008 | Crofford |
| 2008/0082132 A1 | 4/2008 | Annest et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140089 A1 | 6/2008 | Kogiso et al. |
| 2008/0140116 A1 | 6/2008 | Bonutti |
| 2008/0147093 A1 | 6/2008 | Roskopf et al. |
| 2008/0147112 A1 | 6/2008 | Sheets et al. |
| 2008/0149685 A1 | 6/2008 | Smith et al. |
| 2008/0167713 A1 | 7/2008 | Bolling |
| 2008/0167714 A1 | 7/2008 | St. Goar et al. |
| 2008/0177300 A1 | 7/2008 | Mas et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0208332 A1 | 8/2008 | Lamphere et al. |
| 2008/0221672 A1 | 9/2008 | Lamphere et al. |
| 2008/0228030 A1 | 9/2008 | Godin |
| 2008/0228223 A1 | 9/2008 | Alkhatib |
| 2008/0234729 A1 | 9/2008 | Page et al. |
| 2008/0255427 A1 | 10/2008 | Satake et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294247 A1 | 11/2008 | Yang et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keldar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0187216 A1 | 7/2009 | Schmieding et al. |
| 2009/0222083 A1 | 9/2009 | Nguyen et al. |
| 2009/0234280 A1 | 9/2009 | Tah et al. |

(56) References Cited

U.S. PATENT DOCUMENTS

| | | |
|---|---|---|
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0275902 A1 | 11/2009 | Heeps et al. |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0022823 A1 | 1/2010 | Goldfarb et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0057192 A1 | 3/2010 | Celermajer |
| 2010/0063542 A1 | 3/2010 | van der Burg et al. |
| 2010/0063550 A1 | 3/2010 | Felix et al. |
| 2010/0069834 A1 | 3/2010 | Schultz |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0094317 A1 | 4/2010 | Goldfarb et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121434 A1 | 5/2010 | Paul et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168827 A1 | 7/2010 | Schultz |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0280604 A1 | 11/2010 | Zipory et al. |
| 2010/0280605 A1 | 11/2010 | Hammer et al. |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324595 A1 | 12/2010 | Linder et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106247 A1 | 5/2011 | Miller et al. |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0245855 A1 | 10/2011 | Matsuoka et al. |
| 2011/0257433 A1 | 10/2011 | Walker |
| 2011/0257633 A1 | 10/2011 | Cartledge et al. |
| 2011/0257723 A1 | 10/2011 | McNamara |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0295281 A1 | 12/2011 | Mizumoto et al. |
| 2011/0301498 A1 | 12/2011 | Maenhout et al. |
| 2012/0022557 A1 | 1/2012 | Cabiri et al. |
| 2012/0022633 A1 | 1/2012 | Olson et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0101571 A1 | 4/2012 | Thambar et al. |
| 2012/0109155 A1 | 5/2012 | Robinson et al. |
| 2012/0109160 A1 | 5/2012 | Martinez et al. |
| 2012/0116419 A1 | 5/2012 | Sigmon, Jr. |
| 2012/0123531 A1* | 5/2012 | Tsukashima ........ A61F 2/2448 623/2.37 |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0209318 A1 | 8/2012 | Qadeer |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0277853 A1 | 11/2012 | Rothstein |
| 2012/0283757 A1 | 11/2012 | Miller et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0035759 A1 | 2/2013 | Gross et al. |
| 2013/0041314 A1 | 2/2013 | Dillon |
| 2013/0046373 A1 | 2/2013 | Cartledge et al. |
| 2013/0053884 A1 | 2/2013 | Roorda |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0110254 A1 | 5/2013 | Osborne |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190798 A1 | 7/2013 | Kapadia |
| 2013/0190861 A1 | 7/2013 | Chau et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0304197 A1 | 11/2013 | Buchbinder et al. |
| 2013/0325110 A1 | 12/2013 | Khalil et al. |
| 2013/0331930 A1 | 12/2013 | Rowe et al. |
| 2014/0031928 A1 | 1/2014 | Murphy et al. |
| 2014/0046433 A1 | 2/2014 | Kovalsky |

(56) References Cited

U.S. PATENT DOCUMENTS

| | | |
|---|---|---|
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0067048 A1 | 3/2014 | Chau et al. |
| 2014/0067052 A1 | 3/2014 | Chau et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135685 A1 | 5/2014 | Kabe et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194975 A1 | 7/2014 | Quill et al. |
| 2014/0194976 A1 | 7/2014 | Starksen et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0243968 A1 | 8/2014 | Padala |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0343668 A1 | 11/2014 | Zipory et al. |
| 2014/0350660 A1 | 11/2014 | Cocks et al. |
| 2014/0371843 A1 | 12/2014 | Wilson et al. |
| 2014/0379006 A1 | 12/2014 | Sutherland et al. |
| 2015/0018940 A1 | 1/2015 | Quill et al. |
| 2015/0039084 A1 | 2/2015 | Levi et al. |
| 2015/0051697 A1 | 2/2015 | Spence et al. |
| 2015/0057704 A1 | 2/2015 | Takahashi |
| 2015/0081014 A1 | 3/2015 | Gross et al. |
| 2015/0094800 A1 | 4/2015 | Chawla |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0148896 A1 | 5/2015 | Karapetian et al. |
| 2015/0157268 A1 | 6/2015 | Winshtein et al. |
| 2015/0182336 A1 | 7/2015 | Zipory et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0313592 A1 | 11/2015 | Coillard-Lavirotte et al. |
| 2015/0351904 A1 | 12/2015 | Cooper et al. |
| 2015/0351906 A1 | 12/2015 | Hammer et al. |
| 2015/0351910 A1 | 12/2015 | Gilmore et al. |
| 2015/0366666 A1 | 12/2015 | Khairkhahan et al. |
| 2016/0008129 A1 | 1/2016 | Siegel |
| 2016/0008131 A1 | 1/2016 | Christianson et al. |
| 2016/0008132 A1 | 1/2016 | Cabiri et al. |
| 2016/0022970 A1 | 1/2016 | Forcucci et al. |
| 2016/0029920 A1 | 2/2016 | Kronstrom et al. |
| 2016/0051796 A1 | 2/2016 | Kanemasa et al. |
| 2016/0058557 A1 | 3/2016 | Reich et al. |
| 2016/0074164 A1 | 3/2016 | Naor |
| 2016/0074165 A1 | 3/2016 | Spence et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0155987 A1 | 6/2016 | Yoo et al. |
| 2016/0158008 A1 | 6/2016 | Miller et al. |
| 2016/0174979 A1 | 6/2016 | Wei |
| 2016/0174981 A1 | 6/2016 | Fago et al. |
| 2016/0242762 A1 | 8/2016 | Gilmore et al. |
| 2016/0242906 A1 | 8/2016 | Morriss et al. |
| 2016/0256149 A1 | 9/2016 | Sampson et al. |
| 2016/0262755 A1 | 9/2016 | Zipory et al. |
| 2016/0287387 A1 | 10/2016 | Wei |
| 2016/0302811 A1 | 10/2016 | Rodriguez-Navarro et al. |
| 2016/0302917 A1 | 10/2016 | Schewel |
| 2016/0317290 A1 | 11/2016 | Chau et al. |
| 2016/0317302 A1 | 11/2016 | Madjarov et al. |
| 2016/0331523 A1 | 11/2016 | Chau et al. |
| 2016/0346084 A1 | 12/2016 | Taylor et al. |
| 2016/0354082 A1 | 12/2016 | Oz et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042670 A1 | 2/2017 | Shaolian et al. |
| 2017/0042678 A1 | 2/2017 | Ganesan et al. |
| 2017/0049455 A1 | 2/2017 | Seguin |
| 2017/0100119 A1 | 4/2017 | Baird et al. |
| 2017/0100236 A1 | 4/2017 | Robertson et al. |
| 2017/0224489 A1 | 8/2017 | Starksen et al. |
| 2017/0224955 A1 | 8/2017 | Douglas et al. |
| 2017/0239048 A1 | 8/2017 | Goldfarb et al. |
| 2017/0245993 A1 | 8/2017 | Gross et al. |
| 2017/0252154 A1 | 9/2017 | Tubishevitz et al. |
| 2017/0266413 A1 | 9/2017 | Khuu et al. |
| 2017/0281330 A1 | 10/2017 | Liljegren et al. |
| 2017/0325959 A1 | 11/2017 | Sheps et al. |
| 2017/0348102 A1 | 12/2017 | Cousins et al. |
| 2018/0008311 A1 | 1/2018 | Shiroff et al. |
| 2018/0008409 A1 | 1/2018 | Kutzik et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0049875 A1 | 2/2018 | Iflah et al. |
| 2018/0078271 A1 | 3/2018 | Thrasher, III |
| 2018/0078361 A1 | 3/2018 | Naor et al. |
| 2018/0092661 A1 | 4/2018 | Prabhu |
| 2018/0126124 A1 | 5/2018 | Winston et al. |
| 2018/0133008 A1 | 5/2018 | Kizuka et al. |
| 2018/0140420 A1 | 5/2018 | Hayoz et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0185154 A1 | 7/2018 | Cao |

(56) References Cited

U.S. PATENT DOCUMENTS

| | | |
|---|---|---|
| 2018/0221147 A1 | 8/2018 | Ganesan et al. |
| 2018/0228608 A1 | 8/2018 | Sheps et al. |
| 2018/0235657 A1 | 8/2018 | Abunassar |
| 2018/0243086 A1 | 8/2018 | Barbarino et al. |
| 2018/0256334 A1 | 9/2018 | Sheps et al. |
| 2018/0258665 A1 | 9/2018 | Reddy et al. |
| 2018/0263767 A1 | 9/2018 | Chau et al. |
| 2018/0289480 A1 | 10/2018 | D'ambra et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0318080 A1 | 11/2018 | Quill et al. |
| 2018/0318083 A1 | 11/2018 | Bolling et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0038411 A1 | 2/2019 | Alon |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0117113 A1 | 4/2019 | Curran |
| 2019/0117400 A1 | 4/2019 | Medema et al. |
| 2019/0125325 A1 | 5/2019 | Sheps et al. |
| 2019/0142589 A1 | 5/2019 | Basude |
| 2019/0151093 A1 | 5/2019 | Keidar et al. |
| 2019/0159782 A1 | 5/2019 | Kamaraj et al. |
| 2019/0159898 A1 | 5/2019 | Kutzik et al. |
| 2019/0167197 A1 | 6/2019 | Abunassar et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183644 A1 | 6/2019 | Hacohen |
| 2019/0183648 A1 | 6/2019 | Trapp et al. |
| 2019/0192296 A1 | 6/2019 | Schwartz et al. |
| 2019/0209323 A1 | 7/2019 | Metchik et al. |
| 2019/0240023 A1 | 8/2019 | Spence et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0290260 A1 | 9/2019 | Caffes et al. |
| 2019/0290431 A1 | 9/2019 | Genovese et al. |
| 2019/0314155 A1 | 10/2019 | Franklin et al. |
| 2019/0321049 A1 | 10/2019 | Herman et al. |
| 2019/0321166 A1 | 10/2019 | Freschauf et al. |
| 2019/0343633 A1 | 11/2019 | Garvin et al. |
| 2020/0015971 A1 | 1/2020 | Brauon et al. |
| 2020/0113683 A1 | 4/2020 | Dale et al. |
| 2020/0138569 A1 | 5/2020 | Basude et al. |
| 2020/0205979 A1 | 7/2020 | O'Carroll et al. |
| 2020/0237512 A1 | 7/2020 | McCann et al. |
| 2020/0289267 A1 | 9/2020 | Peleg et al. |
| 2020/0337840 A1 | 10/2020 | Reich |
| 2020/0337842 A1 | 10/2020 | Metchik et al. |
| 2020/0352717 A1 | 11/2020 | Kheradvar et al. |
| 2020/0360054 A1 | 11/2020 | Walsh et al. |
| 2020/0360132 A1 | 11/2020 | Spence |
| 2020/0368016 A1 | 11/2020 | Pesce et al. |
| 2021/0015475 A1 | 1/2021 | Lau |
| 2021/0022850 A1 | 1/2021 | Basude et al. |
| 2021/0052387 A1 | 2/2021 | Greenan et al. |
| 2021/0059680 A1 | 3/2021 | Lin et al. |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2021/0169650 A1 | 6/2021 | Dai et al. |
| 2021/0186698 A1 | 6/2021 | Abunassar et al. |
| 2021/0251757 A1 | 8/2021 | Siegel et al. |
| 2021/0259835 A1 | 8/2021 | Tyler, II et al. |
| 2021/0267781 A1 | 9/2021 | Metchik et al. |
| 2021/0307900 A1 | 10/2021 | Hacohen |
| 2021/0330456 A1 | 10/2021 | Hacohen et al. |
| 2021/0338418 A1 | 11/2021 | Feld |
| 2021/0361416 A1 | 11/2021 | Stearns |
| 2021/0361422 A1 | 11/2021 | Gross et al. |
| 2021/0361428 A1 | 11/2021 | Dixon |
| 2021/0378818 A1 | 12/2021 | Manash et al. |
| 2021/0401434 A1 | 12/2021 | Tien et al. |
| 2022/0039943 A1 | 2/2022 | Phan |
| 2022/0039954 A1 | 2/2022 | Nia et al. |
| 2022/0071620 A1 | 3/2022 | Brauon et al. |
| 2022/0071767 A1 | 3/2022 | Dixon et al. |
| 2022/0096232 A1 | 3/2022 | Skaro et al. |
| 2022/0133327 A1 | 5/2022 | Zhang et al. |
| 2022/0142779 A1 | 5/2022 | Sharon |
| 2022/0142780 A1 | 5/2022 | Zhang et al. |
| 2022/0142781 A1 | 5/2022 | Zhang et al. |
| 2022/0176076 A1 | 6/2022 | Keidar |
| 2022/0226108 A1 | 7/2022 | Freschauf et al. |
| 2022/0233312 A1 | 7/2022 | Delgado et al. |
| 2022/0233316 A1 | 7/2022 | Sheps et al. |
| 2022/0257196 A1 | 8/2022 | Massmann |
| 2022/0273436 A1 | 9/2022 | Aviv et al. |
| 2022/0287841 A1 | 9/2022 | Freschauf et al. |
| 2022/0296248 A1 | 9/2022 | Abunassar et al. |
| 2022/0313433 A1 | 10/2022 | Ma et al. |
| 2022/0313438 A1 | 10/2022 | Chappel-Ram |
| 2022/0323221 A1 | 10/2022 | Sharon et al. |
| 2023/0014540 A1 | 1/2023 | Metchik et al. |
| 2023/0016867 A1 | 1/2023 | Tennenbaum |
| 2023/0149170 A1 | 5/2023 | Giese et al. |
| 2023/0218291 A1 | 7/2023 | Zarbatany et al. |
| 2023/0270549 A1 | 8/2023 | Guidotti et al. |

FOREIGN PATENT DOCUMENTS

| | | | |
|---|---|---|---|
| EP | 1034753 A1 | 9/2000 | |
| EP | 3531975 A1 | 9/2019 | |
| WO | 9205093 A1 | 4/1992 | |
| WO | 9846149 A1 | 10/1998 | |
| WO | 02085250 A3 | 2/2003 | |
| WO | 03047467 A1 | 6/2003 | |
| WO | 2007098512 A1 | 9/2007 | |
| WO | 2008088716 A1 | 7/2008 | |
| WO | 2010000454 A1 | 1/2010 | |
| WO | WO-2010004546 A1 * | 1/2010 | ........... A61F 2/2442 |
| WO | 2010085649 A1 | 7/2010 | |
| WO | 2011051942 A1 | 5/2011 | |
| WO | 2012176195 A3 | 3/2013 | |
| WO | 2014064964 A1 | 5/2014 | |
| WO | 2019145941 A1 | 8/2019 | |
| WO | 2019145947 A1 | 8/2019 | |
| WO | 2019182645 A1 | 9/2019 | |

(56) References Cited

FOREIGN PATENT DOCUMENTS

| | | |
|---|---|---|
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |
| WO | 2022064401 A2 | 3/2022 |
| WO | 2022090907 A1 | 5/2022 |
| WO | 2022101817 A2 | 5/2022 |
| WO | 2022153131 A1 | 7/2022 |
| WO | 2022157592 A1 | 7/2022 |
| WO | 2022172108 A1 | 8/2022 |
| WO | 2022172149 A1 | 8/2022 |
| WO | 2022200972 A1 | 9/2022 |
| WO | 2022224071 A1 | 10/2022 |
| WO | 2022229815 A1 | 11/2022 |
| WO | 2022250983 A1 | 12/2022 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al."Novel Suture Device for Beating-Heart Mitral Leaflet Approximation", Ann Thorac Surg. 2002, 74:1488-1493.

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

AMPLATZER® Cribriform Occluder. A patient guide to Percutaneous, Transcatheter, Atrial Septal Defect Closuer, AGA Medical Corporation, Apr. 2008.

AMPLATZER® Septal Occluder. A patient guide to the Non-Surgical Closuer of the Atrial Septal Defect Using the AMPLATZER Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success—midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. Ring+String, Successful Repair technique for Ischemic mitral regurgitation with severe leaflet Tethering, The Department of Thoracic Cardiovascular surgery, Hamburg, Germany, Nov. 2008.

Maisano, "The double-orifice technique as a standardized approach to treat mitral," European Journal of Cardio-thoracic Surgery 17 (2000) 201-205.

Odell JA et al., "Early Results 04yf a Simplified Method of Mitral Valve Annuloplasty," Circulation 92:150-154 (1995).

O'Reilly S et al., "Heart valve surgery pushes the envelope," Medtech Insight 8(3): 73, 99-108 (2006).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

\* cited by examiner

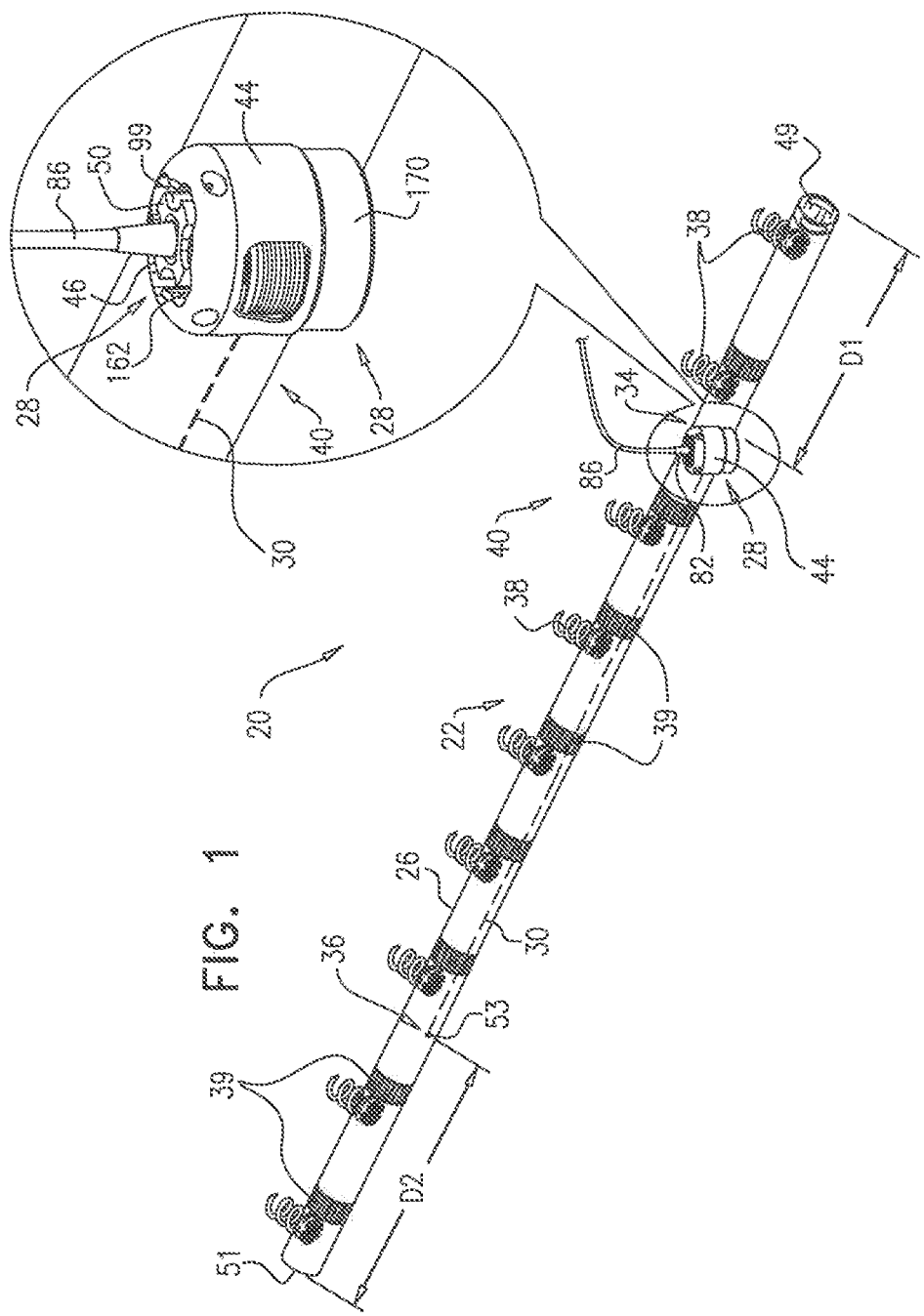

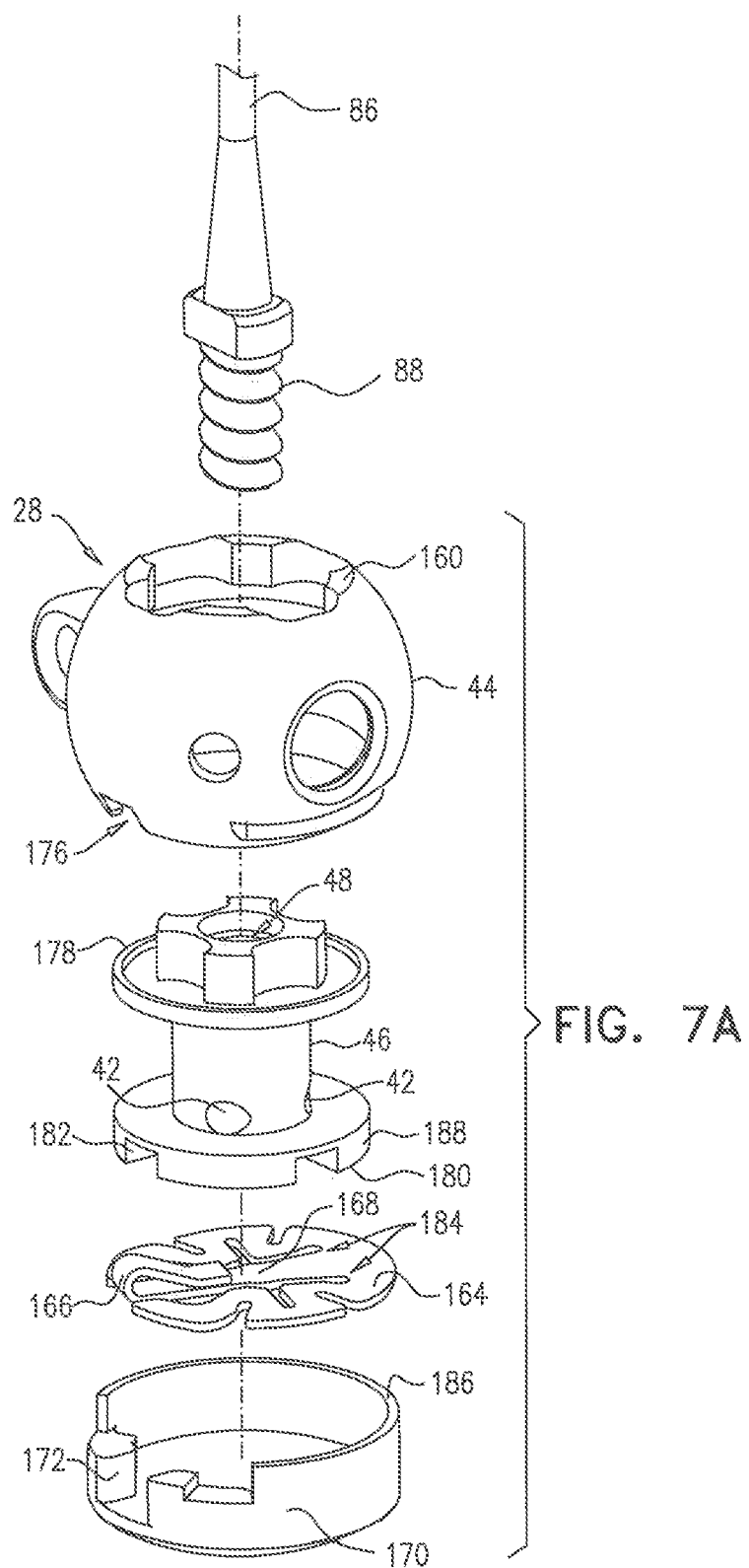

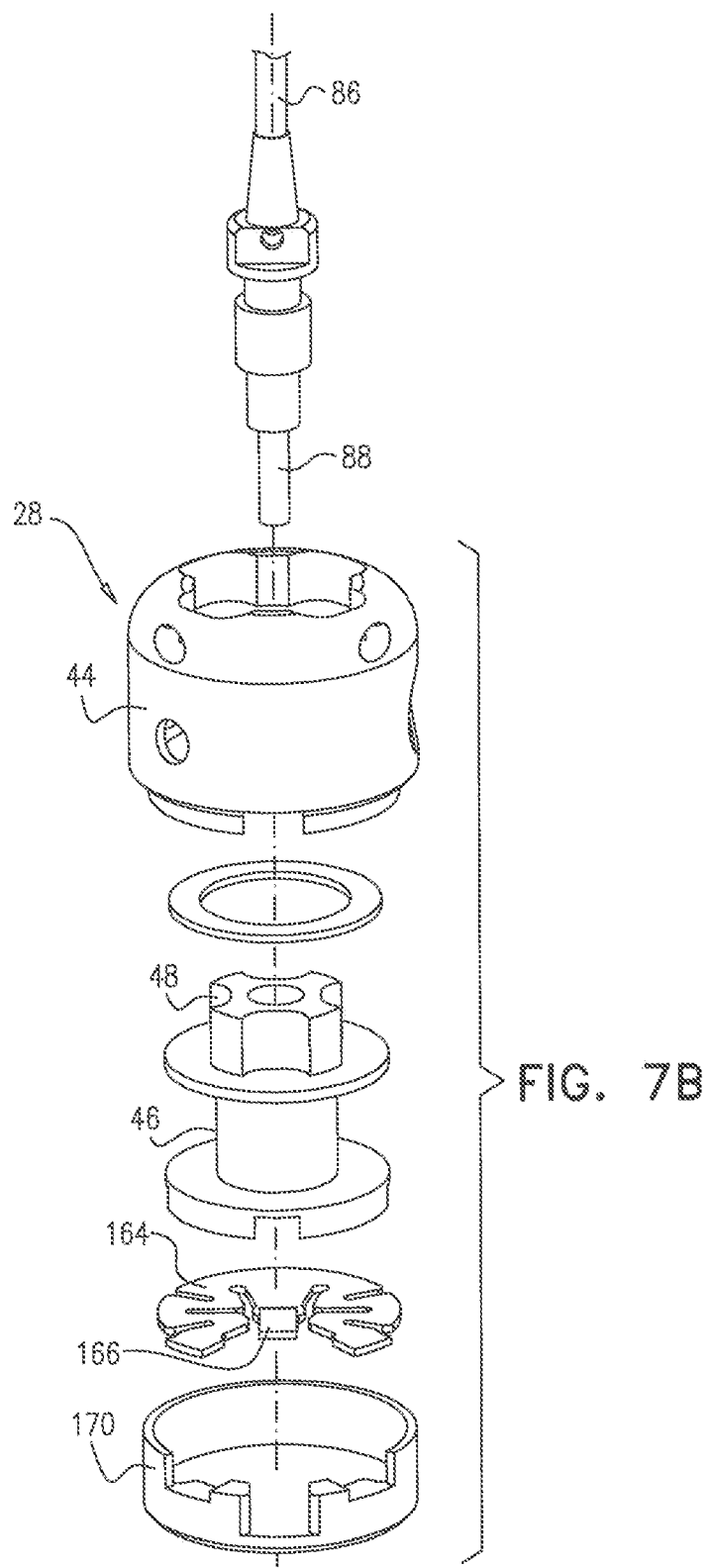

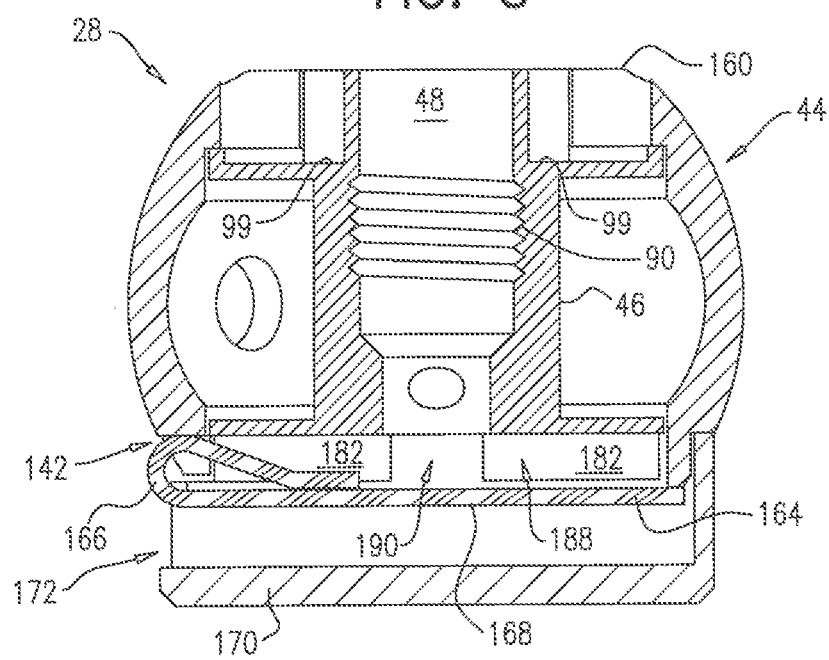

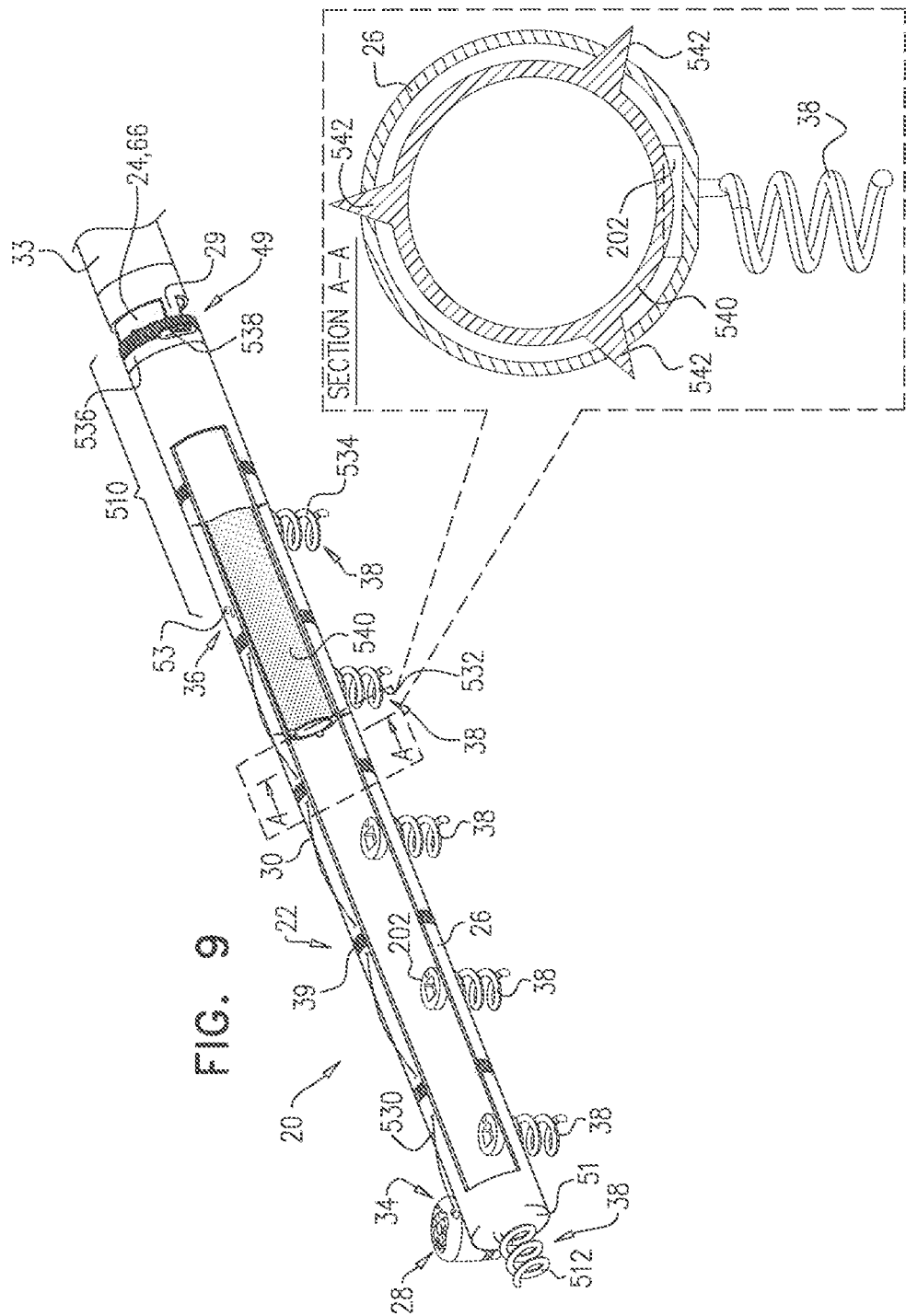

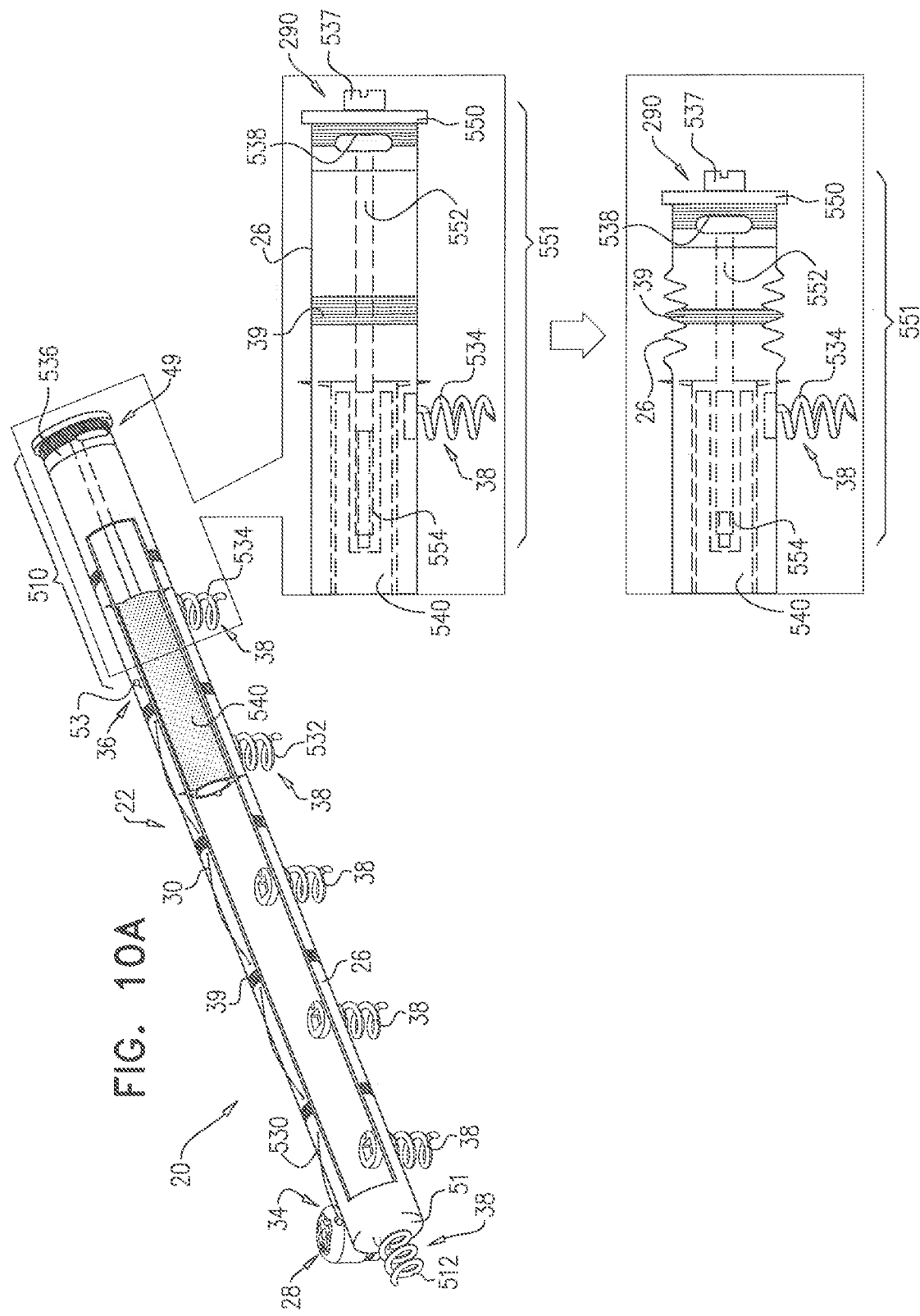

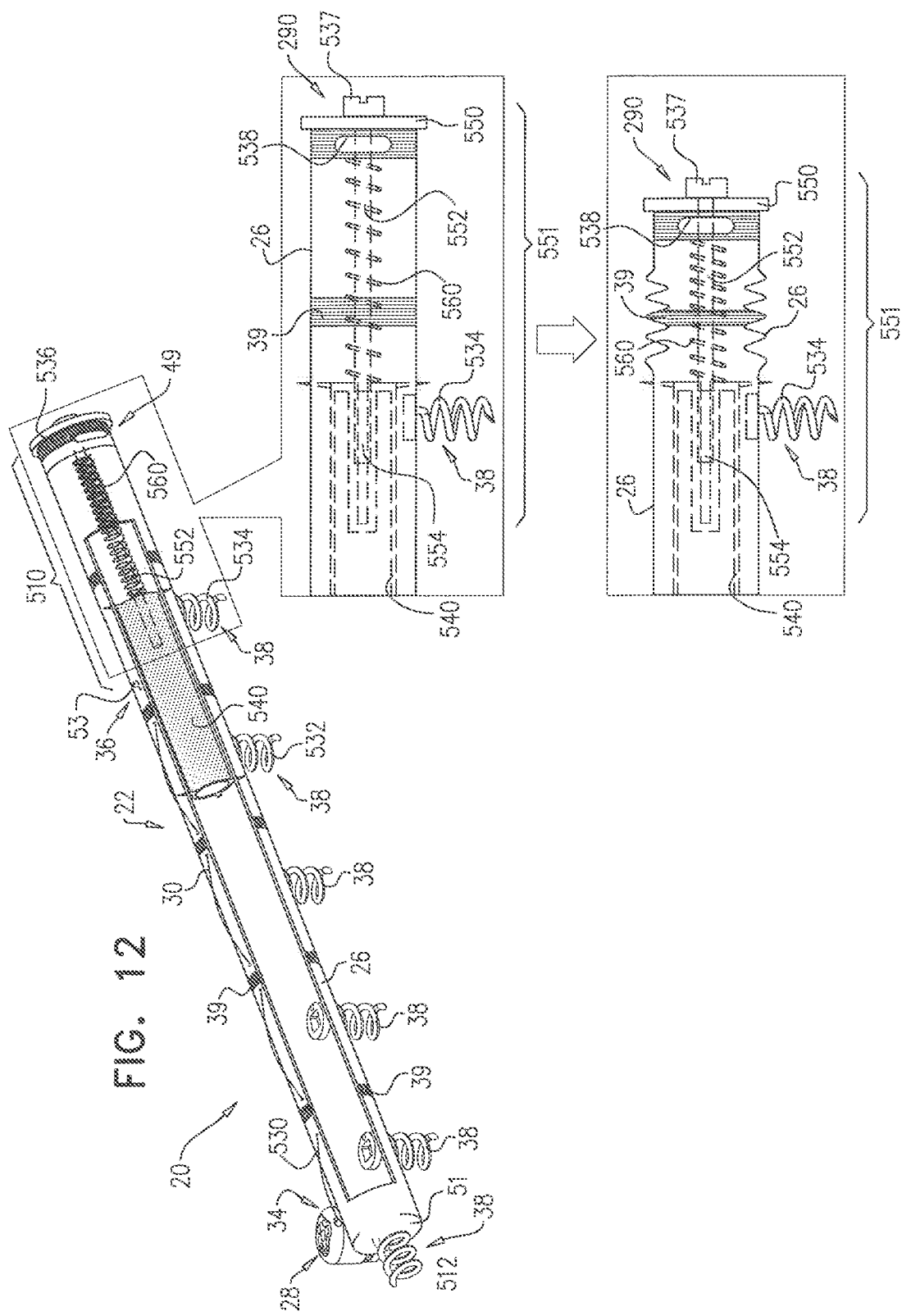

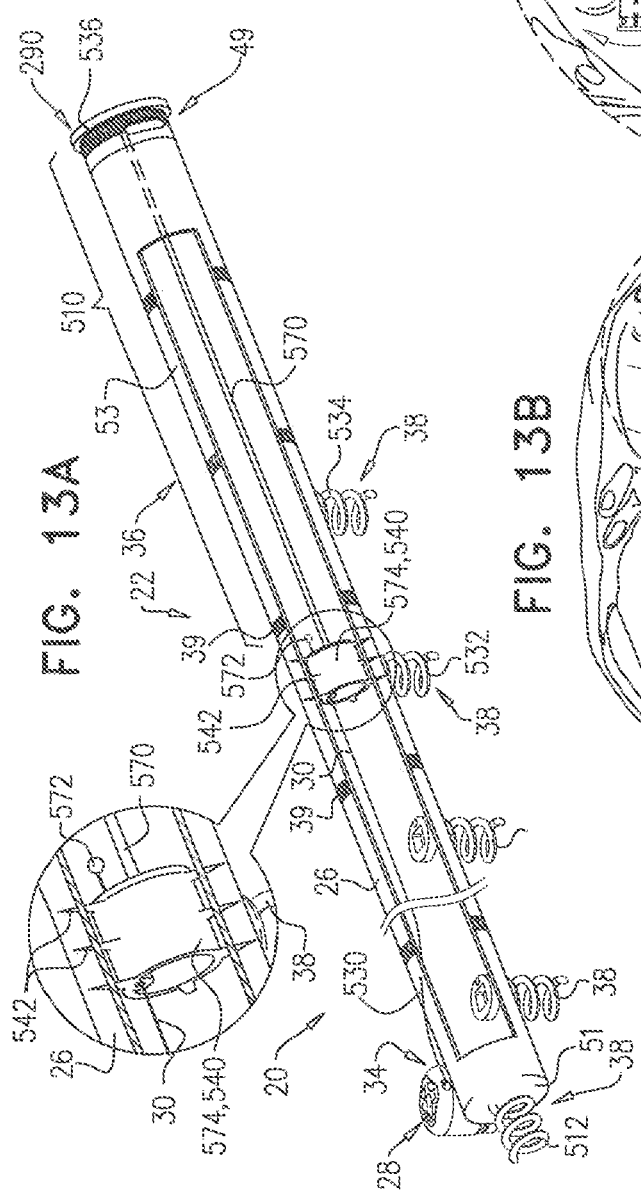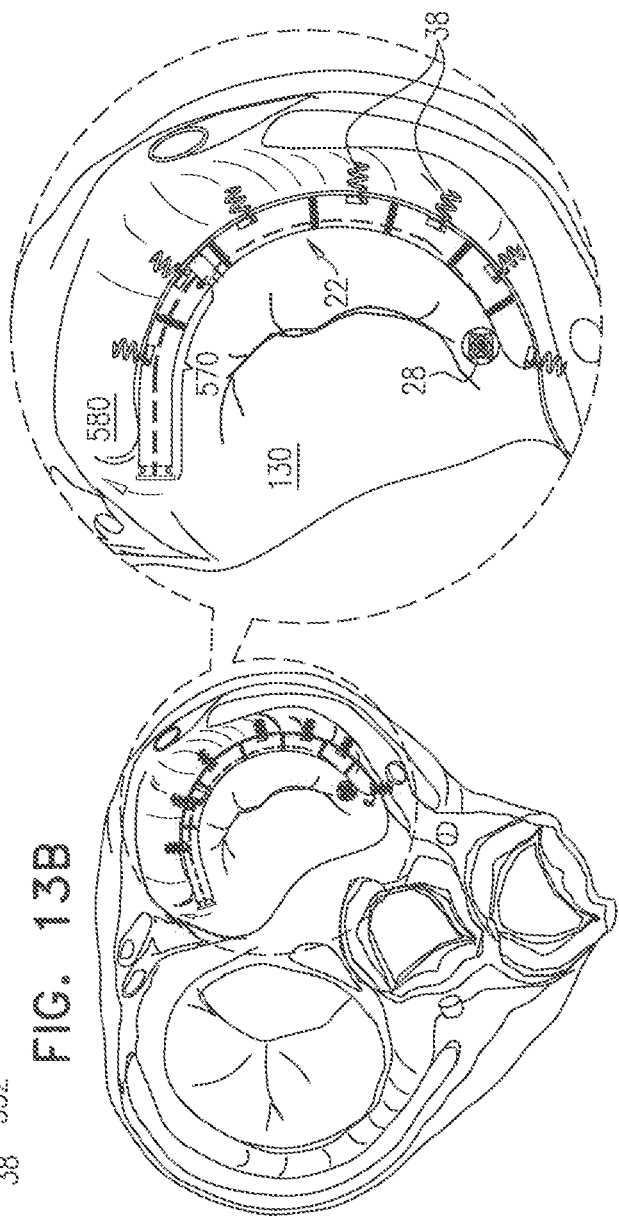
FIG. 13A
FIG. 13B

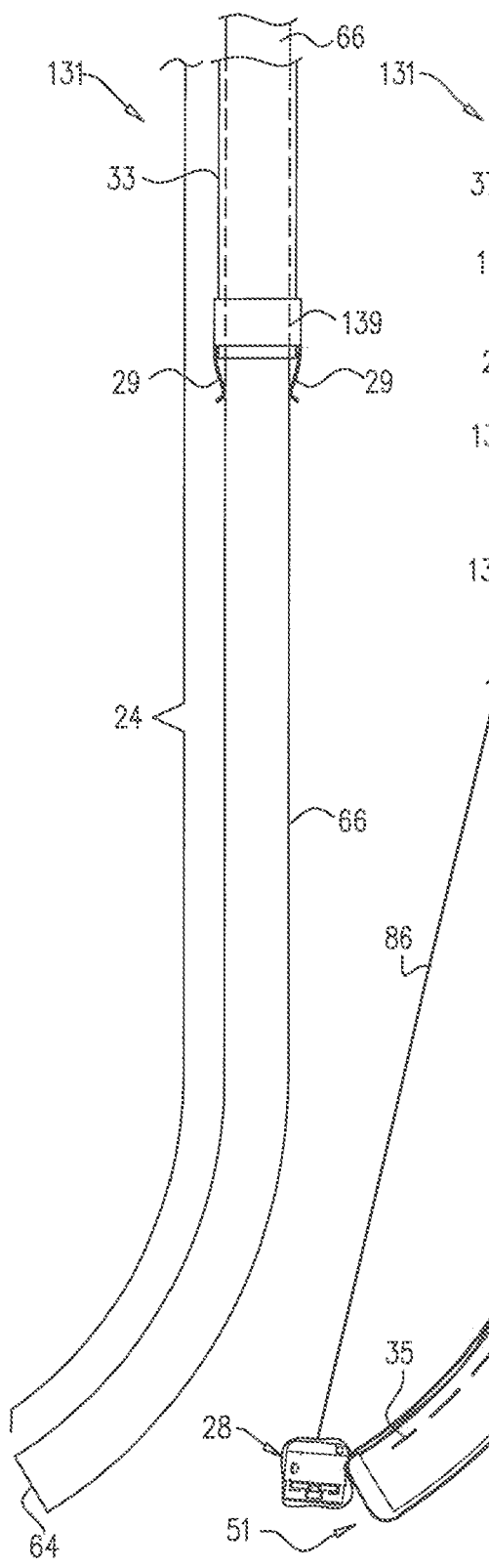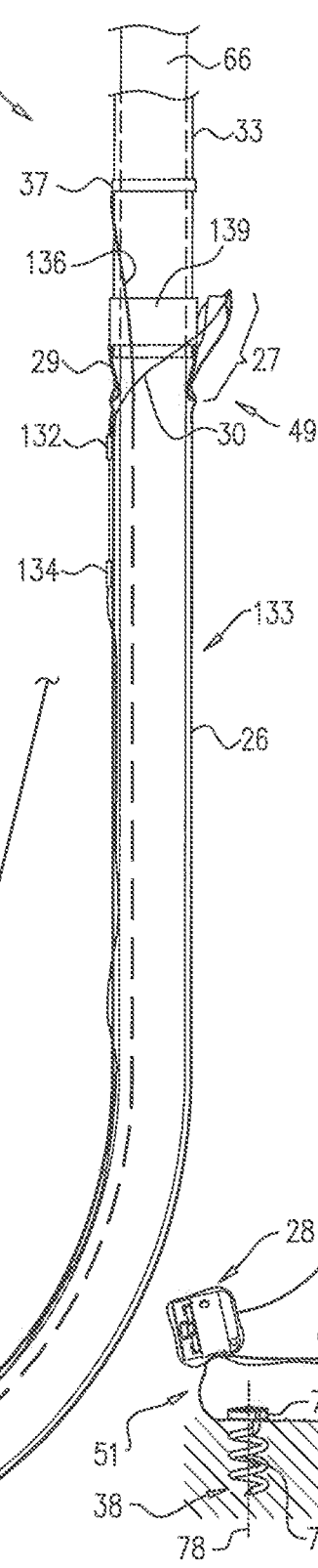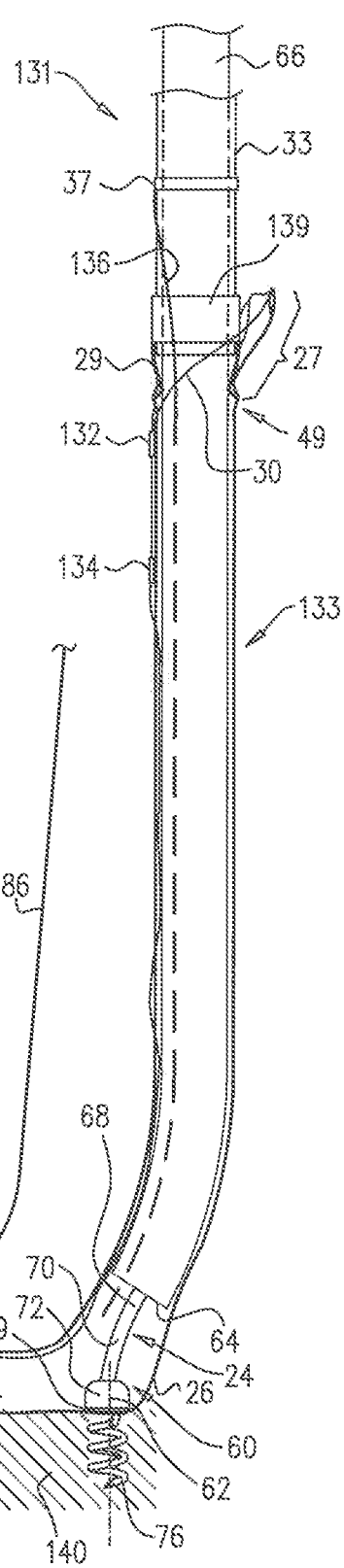

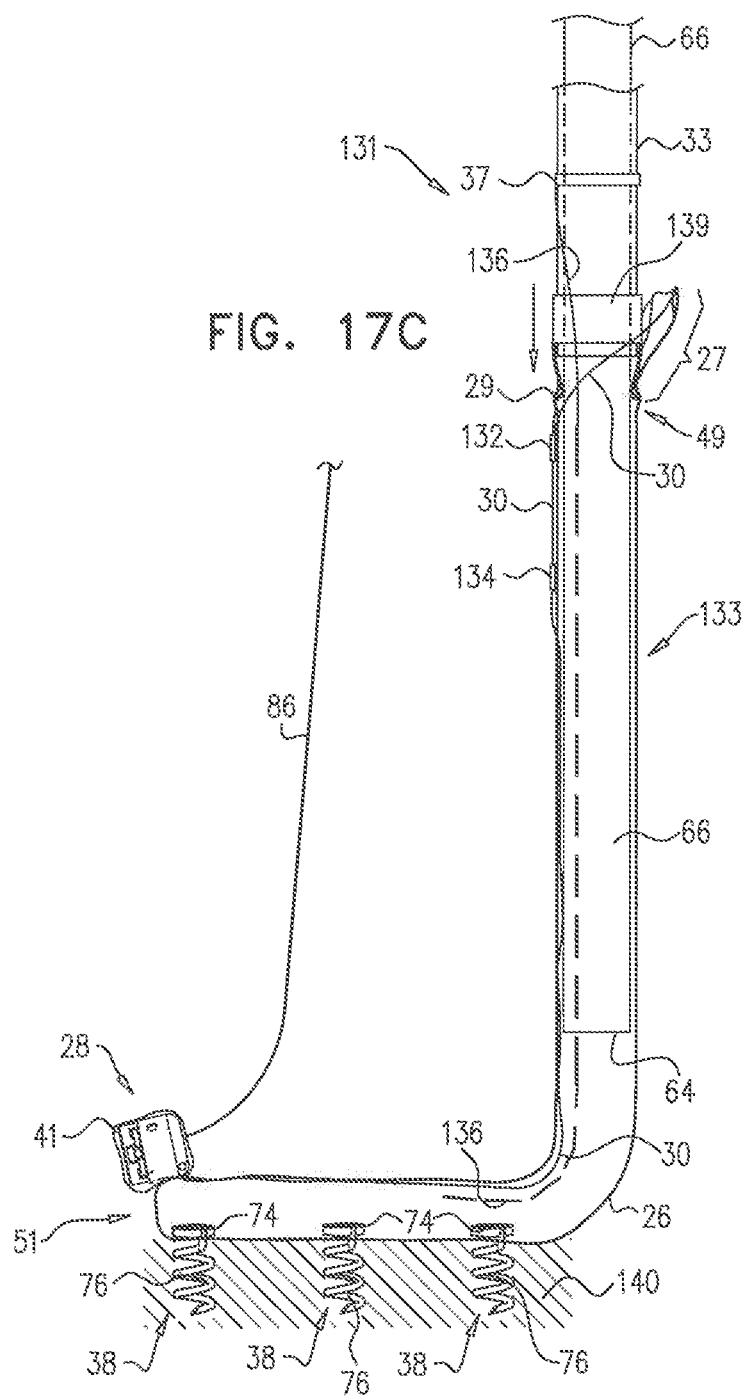

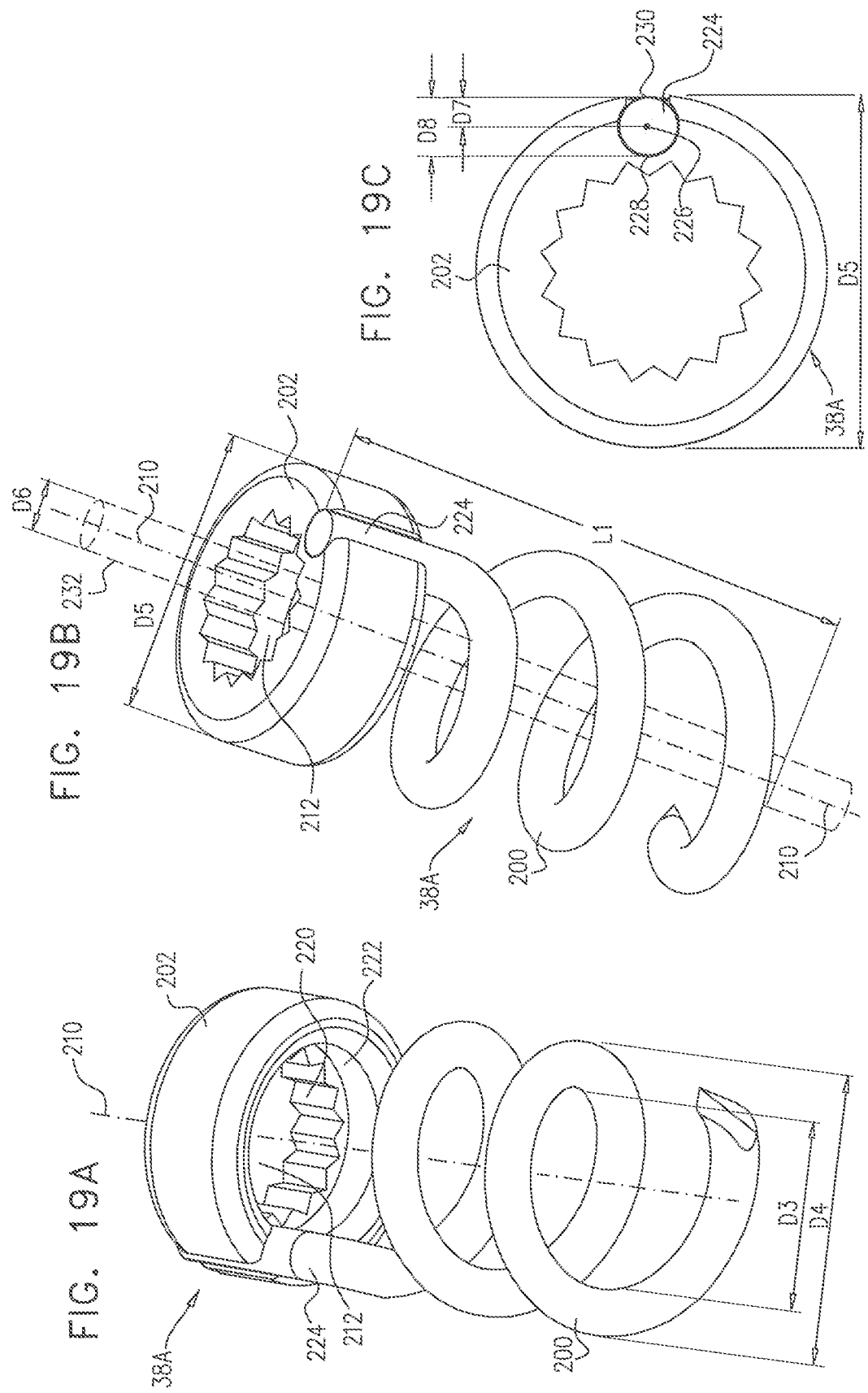

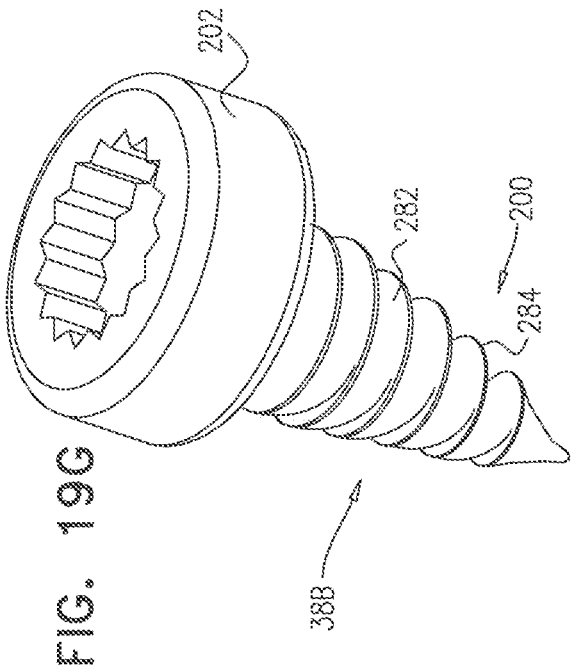
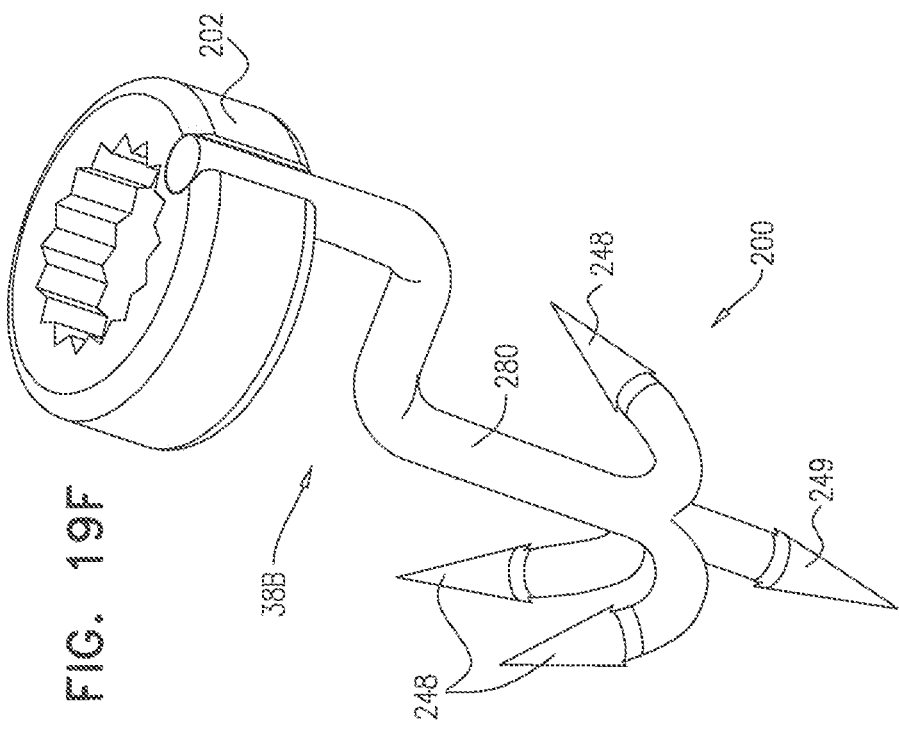

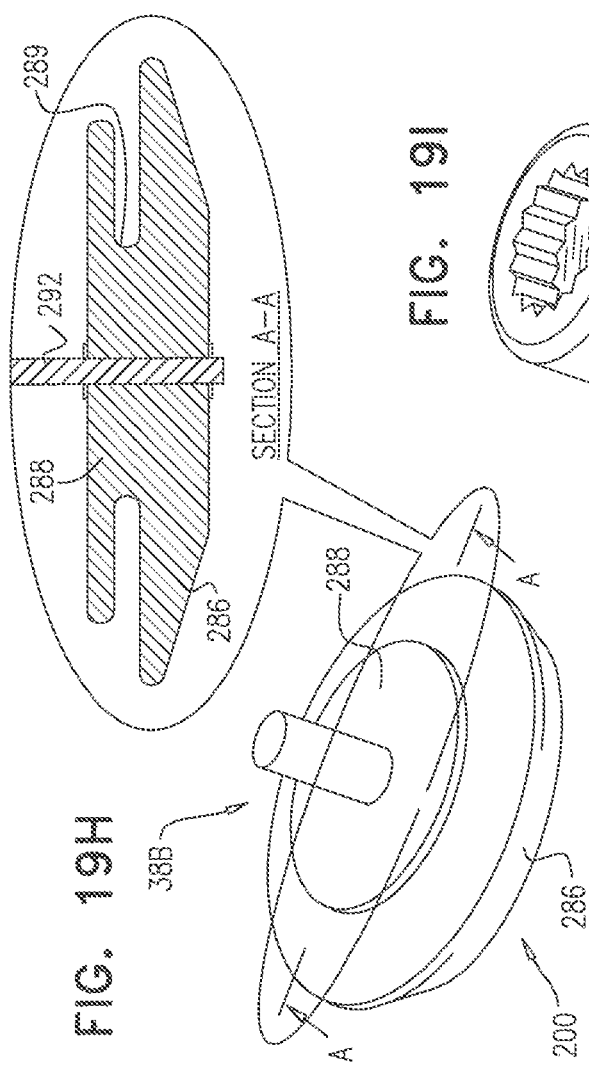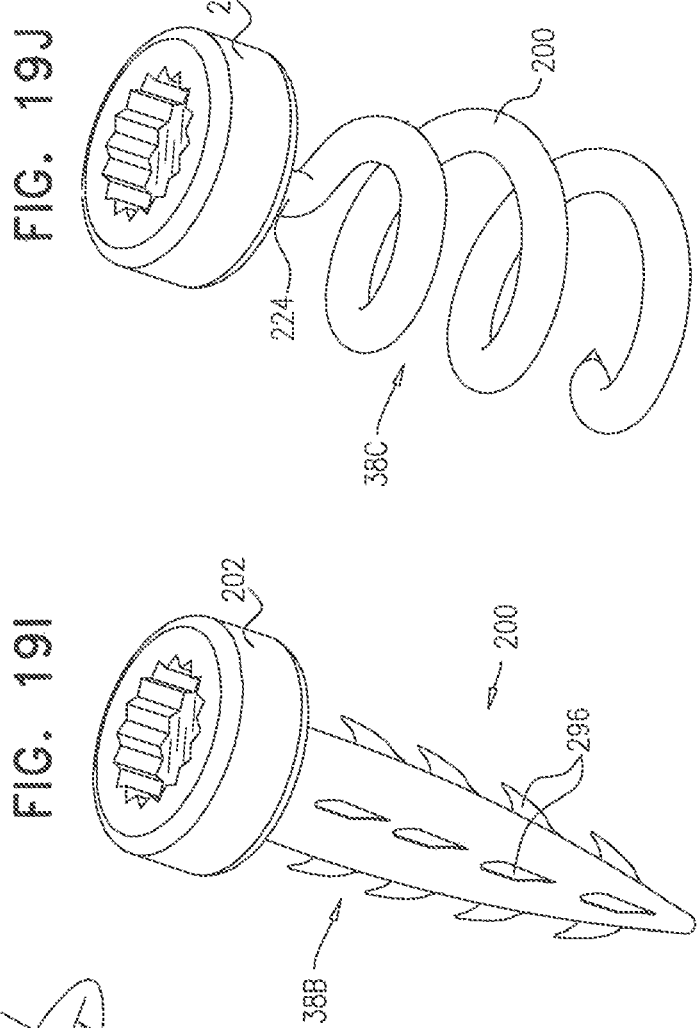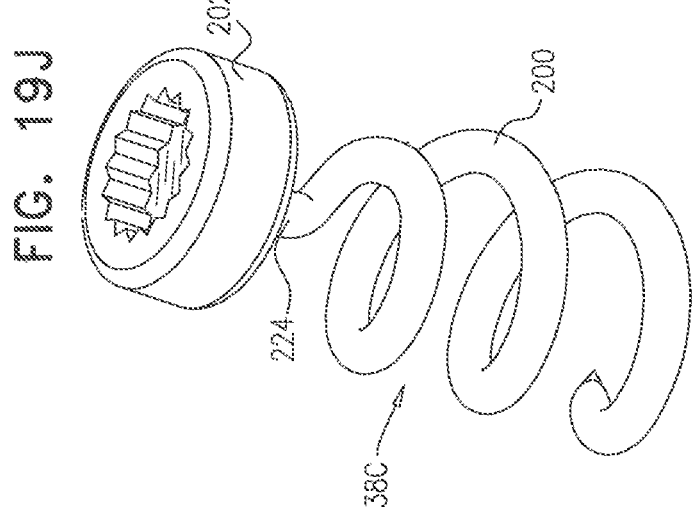

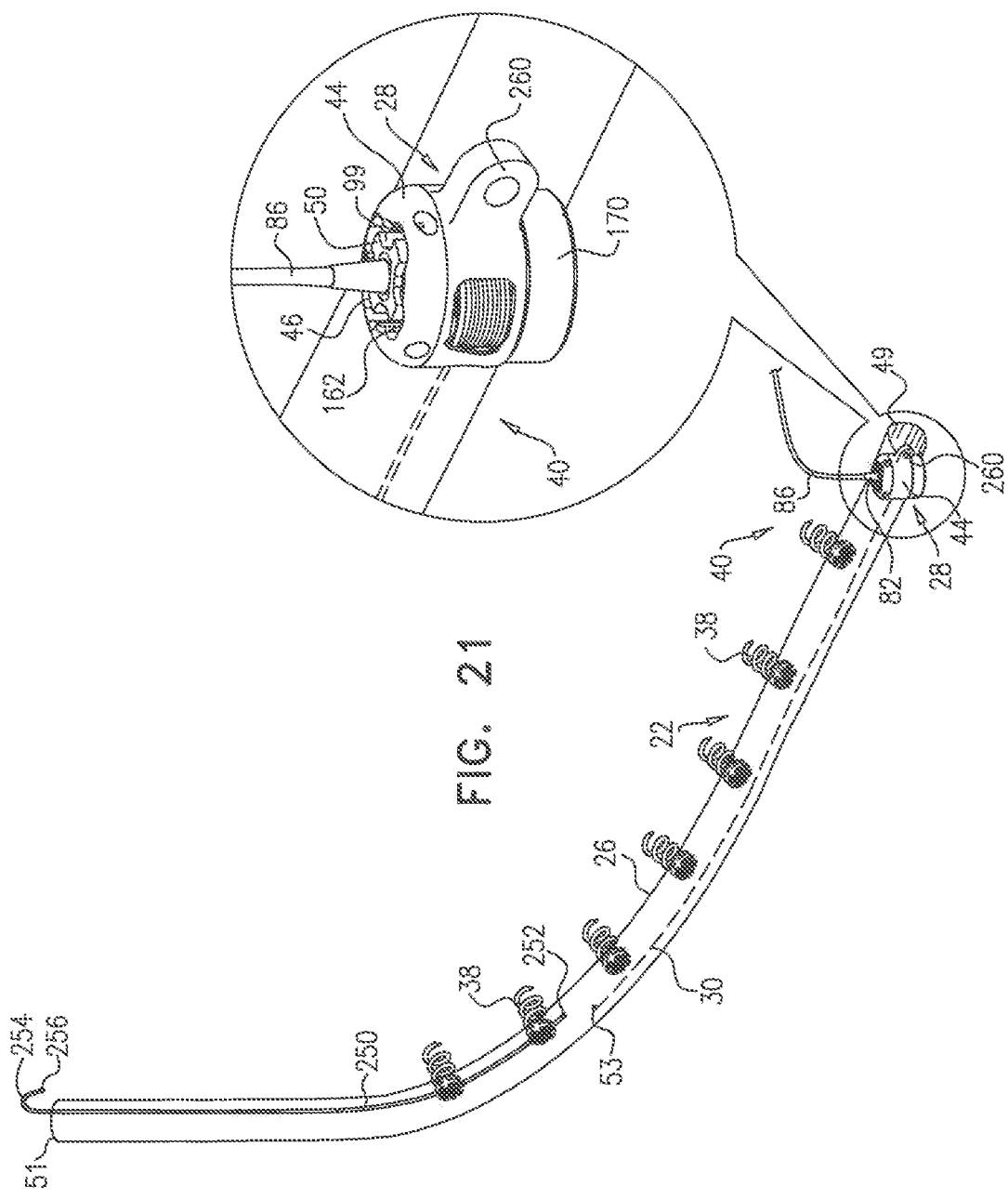

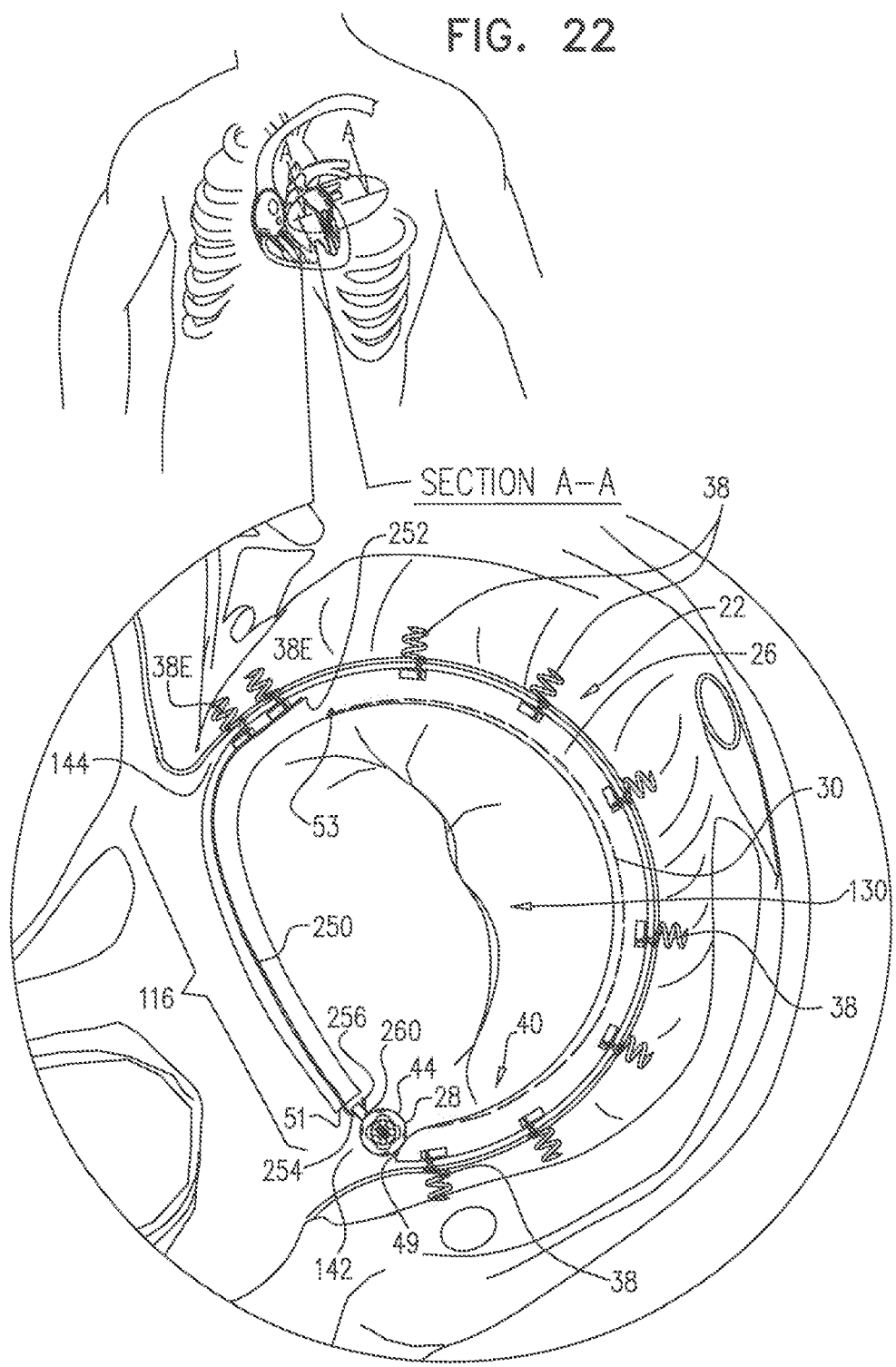

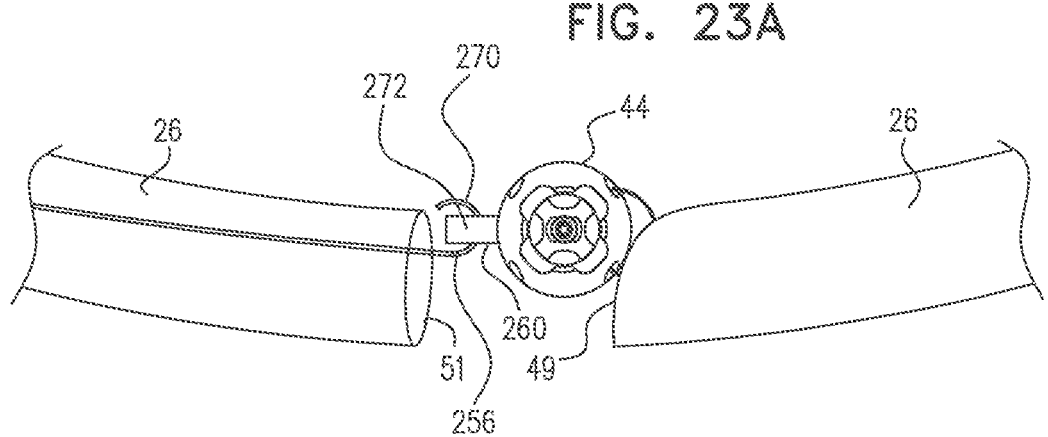
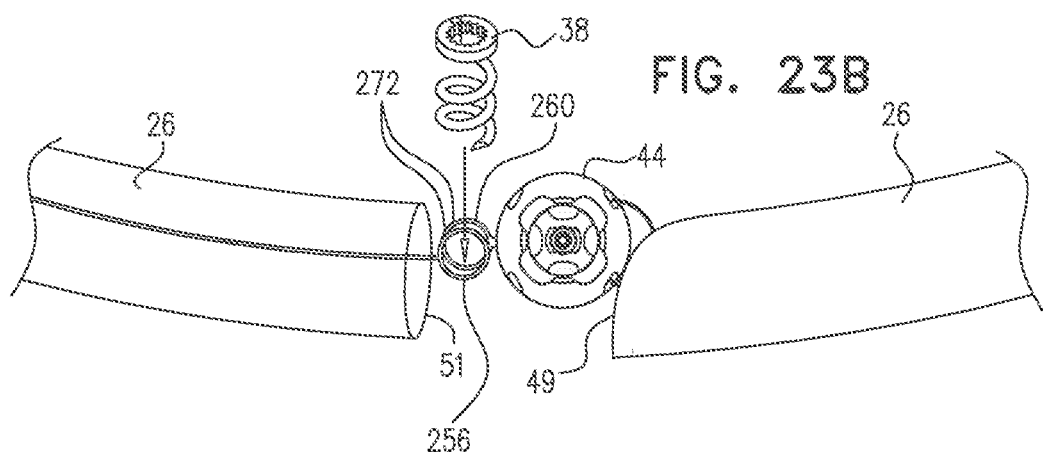

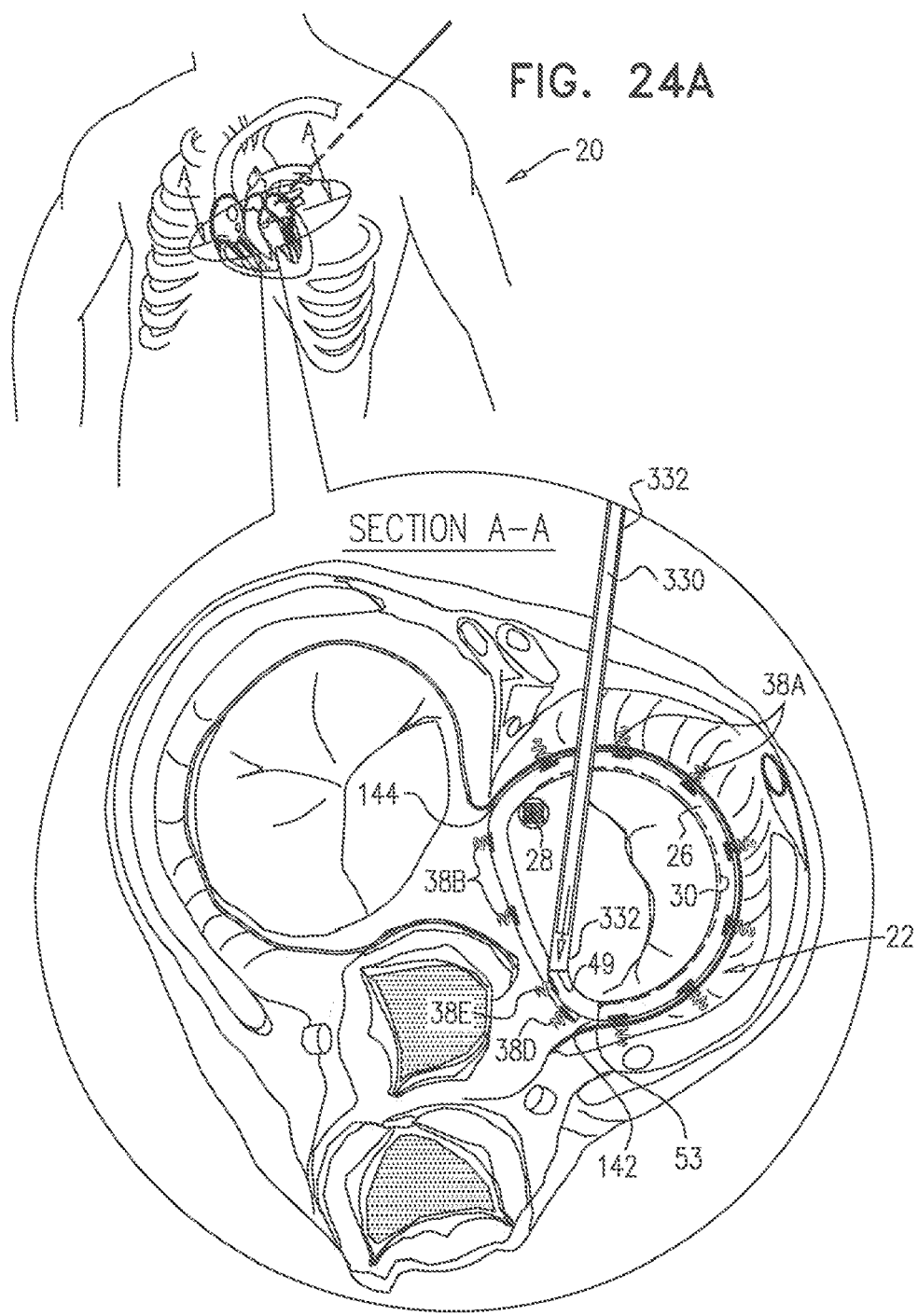

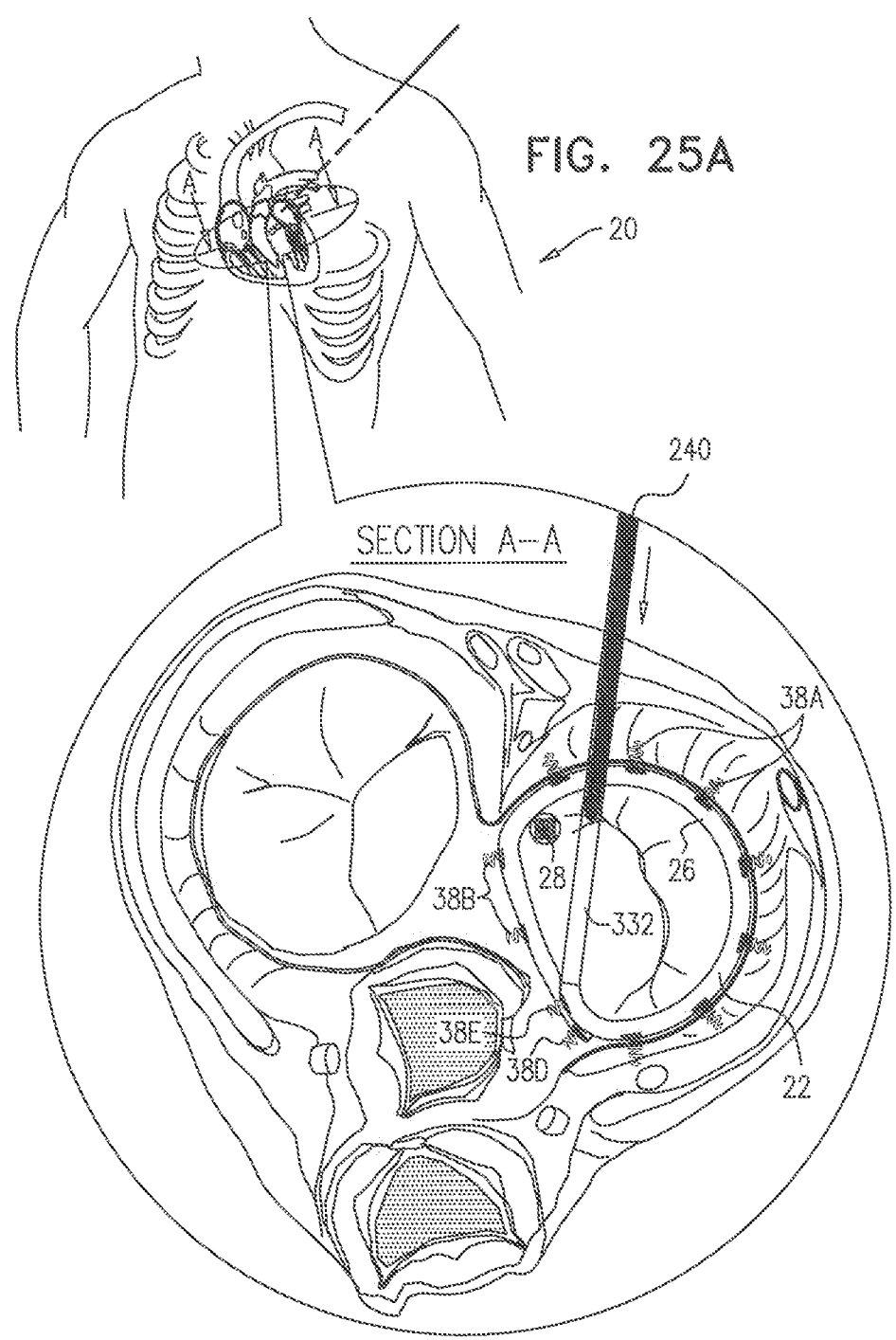

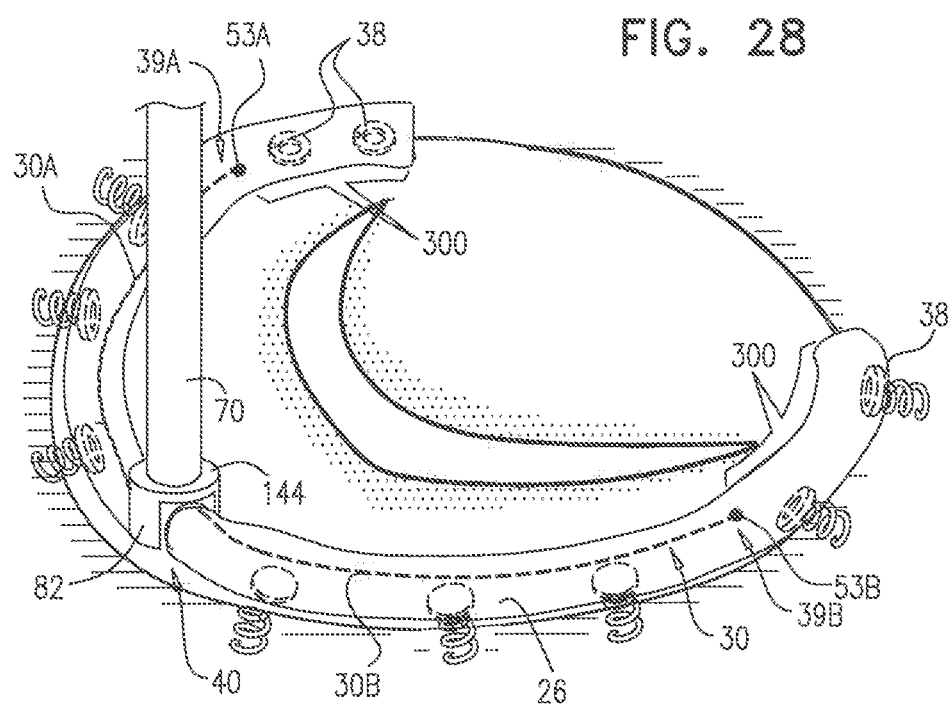

ANNULOPLASTY IMPLANTS

CROSS-REFERENCE TO RELATED APPLICATIONS

The present patent application is a continuation of U.S. patent application Ser. No. 16/601,289, filed Oct. 14, 2019, which published as US 2020/0038186, which is a continuation of U.S. patent application Ser. No. 15/474,543, filed Mar. 30, 2017, now U.S. Pat. No. 10,470,882, which is a continuation of U.S. patent application Ser. No. 14/128,756, filed Feb. 6, 2014, now U.S. Pat. No. 9,662,209, which is the US national phase application of PCT/IL2012/000250, filed Jun. 21, 2012, which claims priority from and is a continuation-in-part of:

(a) U.S. patent application Ser. No. 13/167,444 to Reich et al., entitled, "Partially-adjustable annuloplasty structure," filed Jun. 23, 2011, now U.S. Pat. No. 9,011,530;

(b) U.S. patent application Ser. No. 13/167,476 to Hammer et al., entitled, "Closure element for use with annuloplasty structure," filed Jun. 23, 2011, now U.S. Pat. No. 8,940,044; and (c) U.S. patent application Ser. No. 13/167,492 to Gross, et al., entitled, "Closed band for percutaneous annuloplasty," filed Jun. 23, 2011, now U.S. Pat. No. 8,926,697.

All of these applications are incorporated herein by reference.

FIELD OF THE INVENTION

Some embodiments of the present invention relate in general to valve repair, and more specifically to repair of an atrioventricular valve of a patient.

BACKGROUND

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

SUMMARY

In some applications of the present invention, apparatus is provided that comprises an implant structure comprising a flexible sleeve having a first and second sleeve end, a lumen, and at least one opening at a first end of the implant structure (i.e., one of the first and second sleeve ends). The implant structure additionally comprises a closure element (e.g., a closure mechanism) configured to close the at least one opening at the first end of the implant structure. The implant structure comprises a contracting assembly configured to longitudinally contract and expand the implant structure at least in part. For some applications, the closure mechanism comprises at least one end flap, and the contracting mechanism is configured to actuate the end flap so as to cover the at least one opening. For other applications, the closure mechanism comprises self-closing strips which are biased to close around the portion of the implant structure that defines the at least one opening. For some applications, the closure mechanism is configured to compress (e.g., by gathering together) excess portions of the sleeve which do not need to be anchored to tissue of a patient.

Typically, the implant structure comprises at least part of an annuloplasty structure (e.g., a partial annuloplasty ring) for repairing a dilated valve annulus of a native atrioventricular valve, such as a mitral or tricuspid valve, of a patient. Typically, the one or more flexible, longitudinal contracting members (e.g., a wire, string, or suture) are coupled to the sleeve by being threaded one or more times through the sleeve.

In some applications of the present invention, the contracting assembly includes one or more longitudinal contracting members coupled to the contracting mechanism. Typically, the implantable structure is placed completely around the annulus, such that none of the one or more longitudinal contracting members is positioned along an anterior portion of the annulus between fibrous trigones of the valve. The implantable structure is fastened to the annulus. The contracting assembly is then actuated to contract a longitudinal portion of the sleeve not positioned along the anterior portion of the annulus. Tightening of the implantable structure therefore tightens at least a portion of the posterior portion of the annulus, while preserving the length of the anterior portion of the annulus. (The anterior portion of the annulus should generally not be contracted because its tissue is part of the skeleton of the heart.) However, the portion of the sleeve deployed along the anterior portion of the annulus prevents dilation of the anterior annulus, because the sleeve is anchored at both ends of the anterior annulus, and the sleeve typically comprises a longitudinally non-extensible material. This deployment configuration may help prevent long-term resizing of annulus, especially the anterior annulus, which sometimes occurs after implantation of partial annuloplasty rings, such as C-bands.

The contracting assembly is configured to longitudinally contract the sleeve, and comprises a contracting mechanism and a longitudinal contracting member having first and second member ends. Typically, the contracting mechanism is disposed longitudinally at a first site of the sleeve, and the second member end is coupled to the sleeve (e.g., by being directly coupled or by being coupled to an element coupled to the sleeve) longitudinally at a second site longitudinally between the first site and the second sleeve end, exclusive. The contracting member also has a first member end portion, which extends from the first member end toward the second member end along only a longitudinal portion of the contracting member, and is coupled to the contracting mechanism. A first portion of the sleeve longitudinally extends from the first sleeve end toward the first site, and a second portion of the sleeve longitudinally extends from the second sleeve end toward the second site. The implantable structure is configured such that the contracting assembly applies a longitudinal contracting force only between the first and the second sites.

In some applications of the present invention, one or more of the tissue anchors are coupled to the sleeve at respective third sites longitudinally between the second site and the second sleeve end, exclusive. Typically, the implantable structure is configured such that the contracting assembly applies a longitudinal contracting force only between the first and the second sites. The longitudinal contracting force contracts at least a portion of the sleeve only between the first and the second sites. Providing the one or more anchors beyond the ends of the contracting member generally distributes force applied by contraction of the contracting assembly over the tissue interfaces of these anchors. In contrast, in some configurations of the implantable structure in which anchors are not provided beyond the ends of the contracting member, the force applied by the contracting assembly is applied predominantly to the single anchor nearest the first end of the contracting member, and the single anchor nearest the second end of the contracting member.

For some applications, at least two of the tissue anchors are coupled to the sleeve at respective third sites longitudinally between the second member end and the second sleeve end, exclusive. For some applications, the second site is at least 5 mm from the second sleeve end, measured when the sleeve is in a straight, relaxed, non-contracted state, such as at least 9 mm, e.g., at least 18 mm. For some applications, the second site is at a longitudinal distance from the second sleeve end, which distance is no greater than 30% of a total length of the sleeve, the distance and length measured when the sleeve is in the straight, relaxed, non-contracted state. For some applications, at least three of the tissue anchors are coupled to the sleeve alongside the contracting member, longitudinally between the first and second sites, exclusive. Typically, the sleeve is substantially longitudinally non-extensible.

For some applications, the sleeve has first and second sleeve ends, and first and second portions that longitudinally extend from the first and the second sleeve ends, respectively. The sleeve is arranged in a closed loop, such that the first and second portions of the sleeve together define a longitudinally overlapping portion of the sleeve positioned at least partially along the anterior portion of the annulus, and none of the one or more longitudinal contracting members is positioned along the overlapping portion of the sleeve. For some applications, at least one of the tissue anchors penetrates both the first and second portions of the sleeve at the overlapping portion. Such a mutual anchor helps ensure that the first and second portions remain tightly coupled together and to the tissue, so that the sleeve retains its closed loop shape. Alternatively, for some applications, the sleeve is shaped so as to define an integrally closed loop having no sleeve ends. For such applications in which the sleeve is shaped so as to define a closed loop and/or has the overlapping portion, the implantable structure is configured such that the contracting assembly applies a longitudinal contracting force only between the first and the second sites, and not along the overlapping portion. The longitudinal contracting force longitudinally contracts at least a portion of the sleeve only between the first and the second sites, and not along the overlapping portion. Typically, the contracting member extends along neither the first nor the second portion of the sleeve.

The implantable structure, when in this closed-loop configuration, is deployed around the entire annulus of the native valve, including an anterior portion of the annulus (on the aortic side of the valve) between the fibrous trigones. Typically, the contracting member does not extend along the portion of the sleeve deployed along the anterior portion of the annulus, and thus does not extend along the first portion, the second portion, or the overlapping portion of the sleeve. The portion of the sleeve deployed along the anterior portion of the annulus (between the trigones) is thus non-contractible. As mentioned above, tightening of the implantable structure therefore tightens the posterior portion of the annulus, while preserving the length of the anterior portion of the annulus. For some applications, this deployment configuration may also help achieve a closed loop that serves as a base ring to which a prosthetic valve is coupled.

In some applications of the present invention, the implantable structure further comprises an elongated linking member, which is positioned along an anterior portion of the annulus, so as to join the ends of the implantable structure in a complete loop. Over time after implantation, the linking member becomes fixed to the anterior portion of the annulus, thereby helping prevent long-term dilation of the anterior annulus. Typically, at least a portion of the linking member is disposed within and covered by the sleeve, into and/or over which fibrous tissue grows over time, helping anchor the linking member to tissue of the anterior annulus. Typically, in this configuration of the implantable structure, none of the anchors is coupled to the anterior portion of the annulus.

A first end of the linking member is typically fixed between 2 and 6 cm from a first end of the sleeve. A second end of the linking member is positioned within 1.5 cm of the same end of the sleeve, either protruding from the end of the sleeve, or recessed within the sleeve. The second end of the linking member comprises (e.g., is shaped so as to define) a first coupling element. The implantable structure further comprises a second coupling element, which is configured to be coupleable to the first coupling element. The second coupling element is coupled to the implantable structure within 1.5 cm of the second end of the sleeve. The second coupling element may be coupled to the housing, directly to the sleeve, or otherwise coupled to the implantable structure. Typically, the linking member is substantially longitudinally non-extensible, i.e., its length is fixed.

For some applications, the linking member is configured as a spring, which is typically curved, so as to be elastic in a radial direction, i.e., to be compressible like a bow or deflected beam. In these applications, the linking member is oriented such that it is pressed by elasticity against the anterior portion of the mitral annulus, i.e., the outer wall of the aorta, thereby holding the sleeve covering the linking member against the aortic wall. For some applications, at least two of the tissue anchors are coupled to the sleeve at respective, different longitudinal sites alongside the linking member, within 6 cm of the first end of the linking member. These tissue anchors may help set the proper direction of curvature of the linking member, for applications in which the linking member is curved.

As described hereinabove, the contracting member is coupled at the first member end portion thereof to the contracting mechanism. For applications in which the closure mechanism comprises the end flap, a second member end portion of the contracting member is coupled to the end flap. When the contracting mechanism is actuated in a first actuation direction, the contracting mechanism pulls on the contracting member which, in turn, pulls on the end flap, thereby covering the opening at least in part. One or more contraction-restricting elements are coupled to the implant structure and/or to the contracting member. The one or more contraction-restricting elements are configured to restrict contraction of at least a first portion of the implant structure beyond a predetermined amount while the contraction of the remaining portion(s) of the implant structure is ongoing.

For some applications, the contracting mechanism comprises a rotatable structure, and a housing in which the rotatable structure is positioned. The contracting mechanism and the longitudinal contracting member are arranged such that rotation of the rotatable structure contracts the implant structure and/or adjusts a perimeter of the implant structure. Typically, an anchor deployment manipulator is advanced into a lumen of the sleeve, and, from within the lumen, deploys the anchors through a wall of the sleeve and into cardiac tissue, thereby anchoring the sleeve around a portion of a valve annulus. The anchor deployment manipulator is typically deflectable.

In some applications of the present invention, the anchor deployment manipulator comprises a steerable tube in which is positioned an anchor driver having an elongated, flexible shaft. Rotation of the anchor driver screws the anchors into the cardiac tissue. The anchors may, for example, be helical in shape. For some applications, one or more stiffening elements, e.g., wires or sutures, are threaded through one or more portions of the sleeve in order to maintain relative positioning of the anchor driver relative to the implant structure during deflection of the anchor driver within the sleeve.

A rotation tool is provided for rotating the rotatable structure. The tool is configured to be guided along (e.g., over, alongside, or through) the longitudinal guide member, to engage the rotatable structure, and to rotate the rotatable structure in response to a rotational force applied to the tool.

For some applications, the implantable structure comprises an adjustable annuloplasty ring structure for repairing a dilated valve annulus of an atrioventricular valve, such as a mitral valve. The annuloplasty ring structure may be used for treating functional mitral regurgitation (FMR) or degenerative mitral valve disease. For other applications, a prosthetic heart valve is further provided, which is configured to be coupled to the sleeve.

For some applications in which the implantable structure is implanted around the annulus of a valve, the implantable structure may be advanced toward the annulus of a valve in any suitable procedure, e.g., a transluminal or transcatheter procedure, a percutaneous procedure, a minimally invasive procedure, or an open heart procedure.

For some applications, the annuloplasty ring is typically configured to be placed only partially around the valve annulus (e.g., to assume a C-shape), and, once anchored in place, to be contracted so as to circumferentially tighten the valve annulus. To this end, the annuloplasty ring comprises the flexible contracting member. For some applications of the present invention, the implant structure comprises one or more contraction-restricting elements configured to restrict contraction of at least a portion of the implant structure. Thus, the implant structure is partially-contractible.

Typically, a first anchor is deployed at or in a vicinity of a first trigone of the valve, and a second anchor is deployed at or in a vicinity of a second trigone. For valves which are particularly distended, the implant structure is anchored to the first trigone at a first free end thereof and is anchored to the second trigone at a second free end thereof. For applications in which the implant structure is implanted along an annulus of a mitral valve, the body portion of the implant structure extends from the first trigone and toward and along a portion of the annulus that is adjacent to the posterolateral leaflet. For such an application, the contraction-restricted portion is disposed along the annulus and therefore, a portion of the implant structure is contracted (i.e., a contraction-facilitated portion), thereby contracting a portion of the annulus that is between the first and second trigones and adjacent to the posterolateral leaflet and, thereby, reducing a perimeter of the valve annulus and drawing the leaflets together.

For other applications, the second free end is not anchored to the trigone, but is instead anchored to a portion of the atrial wall (e.g., a portion of the interatrial septum or a portion of a free wall) of the heart of the patient while the first free end or a first portion of the implant structure adjacent the first free end is anchored to the first trigone. For some applications, the entire contraction-restricted portion is attached to the portion of the atrial wall and the contraction-facilitated portion is disposed between the first and second trigones and runs along the portion of the annulus that is adjacent to the posterolateral leaflet. For such applications in which the implant structure is implanted at the mitral valve, the entire portion of the annulus that is between the first and second trigones and adjacent the posterolateral leaflet is contracted, thereby reducing a perimeter of the valve annulus and drawing the leaflets together.

For some applications, the contracting mechanism comprises a spool to which a first end of the contracting member is coupled. Rotation of the spool winds a portion of the contracting member around the spool, thereby contracting the implant structure. For some applications, the contracting mechanism comprises a housing that houses the spool, and the rotation tool is configured to engage and rotate the spool with respect to the housing. For some applications, the rotation tool comprises a tube, which is configured to be passed over the longitudinal member coupled to the contracting mechanism, and to engage the housing, such that the housing is held rotationally stationary when the tube is held rotationally stationary.

For some application in which the implant structure comprises an annuloplasty ring structure, all of the tools and elements of the annuloplasty system that are introduced into left atrium are contained within the sleeve of the annuloplasty ring structure, which reduces the risk that any elements of the system will accidentally be released to the blood circulation, or damage surrounding tissue. In addition, the lumen of the sleeve provides guidance if it should be necessary to return to a previously deployed anchor, such as to tighten, loosen, remove, or relocate the anchor. For some applications, the anchors comprise helical screws, which facilitate such adjusting or removing.

There is therefore provided, in accordance with some applications of the present invention, apparatus including an implantable structure, including:
  a flexible sleeve, having first and second sleeve ends;
  a contracting assembly, which is configured to longitudinally contract the sleeve, and which includes:
    a contracting mechanism, which is disposed at a first site of the sleeve; and
    a longitudinal contracting member, having (a) a first member end, (b) a second member end, which is coupled to the sleeve longitudinally at a second site, which is longitudinally between the first site and the second sleeve end, exclusive, and (c) a first member end portion, which (i) extends from the first member end toward the second member end along only a longitudinal portion of the contracting member, and (ii) is coupled to the contracting mechanism; and
  a force-distributing element configured to be coupled to the sleeve in a vicinity of the second sleeve end, the force-distributing element is configured to distribute a contraction force by the contracting member between the second member end and the second sleeve end.

In some applications of the present invention, the apparatus includes a first anchor couplable to the sleeve at a third site longitudinally between the second member end and the second sleeve end; and a second anchor couplable to the sleeve in a vicinity of the second site, the force-distributing element is configured to distribute a contraction force between the first and second anchors.

In some applications of the present invention, the force-distributing element includes an element that is longitudinally non-compressible.

In some applications of the present invention, the force-distributing element includes a coiled element having a plurality of longitudinally-non-compressible coils.

In some applications of the present invention, the force-distributing element is advanceable within the sleeve through an opening at the second sleeve end, and the force-distributing element is shaped so as to define one or more protrusions to engage and couple the force-distributing element to the sleeve.

In some applications of the present invention, the apparatus includes a plurality of tissue anchors, one or more of which are coupled to the sleeve at respective third sites longitudinally between the second site and the second sleeve end, exclusive.

In some applications of the present invention, the apparatus includes a plurality of tissue anchors, one or more of which are coupled to the sleeve at respective third sites longitudinally between the second member end and the second sleeve end, exclusive.

In some applications of the present invention, the apparatus includes: second-sleeve-end coupling element couplable to the second sleeve end; and an approximating element coupled at a first end portion thereof to the second-sleeve-end coupling element, and at a second end portion of the approximating element to the force-distributing element, the approximating element being configured to change a spatial orientation of at least a portion of a portion of the sleeve that is between the force-distributing element and the second sleeve end.

In some applications of the present invention, the approximating includes a screw shaft, the approximating element is shaped so as to define screw thread for receiving the screw shaft, and the approximating element is configured to shorten the at least the portion of the sleeve between the force-distributing element and the second sleeve end.

In some applications of the present invention, the force-distributing element is shaped so as to define the screw thread.

In some applications of the present invention, the approximating element includes a spring, and the approximating element is configured to shorten the at least the portion of the sleeve between the force-distributing element and the second sleeve end.

In some applications of the present invention, the spring has a tendency to compress in order to compress the portion of the sleeve between the force-distributing element and the second sleeve end.

In some applications of the present invention, the approximating element includes an elongate deflectable structural element coupled to the sleeve at the at least the portion, the elongate deflectable structural element having a shape-memory element so as to facilitate deflecting of the at least the portion.

In some applications of the present invention, the flexible sleeve is configured to provide an opening at at least the second sleeve end, and the second-sleeve-end coupling element includes a closure element configured to close the opening.

In some applications of the present invention, the closure element includes a plug.

There is additionally provided, in accordance with some applications of the present invention apparatus including an implantable structure, which includes:

a flexible sleeve, having first and second sleeve ends;

a second-sleeve-end coupling element couplable to the second sleeve end;

a structural, reference-force component coupled to the sleeve at a portion of the sleeve that is between the first and second sleeve ends; and an approximating element coupled at a first end portion thereof to the second-sleeve-end coupling element, and at a second end portion of the approximating element to the structural, reference-force component, the approximating element being configured to change a spatial orientation of at least a portion of a portion of the sleeve that is between the structural, reference-force component and the second sleeve end.

In some applications of the present invention, the structural, reference-force component includes a force-distributing element configured to distribute a contraction force by the contracting member between the second member end and the second sleeve end.

There is further additionally provided, in accordance with some applications of the present invention, apparatus including an implantable structure, including:

a flexible sleeve, having first and second sleeve ends;

a contracting assembly, which is configured to longitudinally contract the sleeve, and which includes:
  a contracting mechanism, which is disposed at a first site of the sleeve; and
  a longitudinal contracting member, having (a) a first member end, (b) a second member end, which is longitudinally between the first site and the second sleeve end, exclusive, and (c) a first member end portion, which (i) extends from the first member end toward the second member end along only a longitudinal portion of the contracting member, and (ii) is coupled to the contracting mechanism;

a contracting-member-receiving element coupled to the sleeve between the first site and the second sleeve end, exclusive, the contracting member being slidable with respect to the contracting-member-receiving element; and a stopper coupled to the second member end, the stopper being advanceable toward the contracting-member-receiving element during contraction of the sleeve by the contracting mechanism.

In some applications of the present invention, the contracting member slides within a portion of the contracting-member-receiving element.

In some applications of the present invention, the contracting-member-receiving element includes a coupler to engage the stopper to the contracting-member-receiving element.

In some applications of the present invention:
the sleeve defines a contracting-assembly-contraction-facilitated portion between the first sleeve end and the contracting-member-receiving element, the contracting-assembly-contraction-facilitated portion being contractible and expandable by the contracting assembly; and
the sleeve defines a contracting-assembly-non-contraction-facilitated portion between the contracting-member-receiving element and the second sleeve end.

In some applications of the present invention, the apparatus includes an elongate deflectable structural element coupled to the sleeve at the contracting-assembly-non-contraction-facilitated portion, the elongate deflectable structural element having a shape-memory element so as to facilitate deflecting of the contracting-assembly-non-contraction-facilitated portion.

There is also provided, in accordance with some applications of the present invention, apparatus including an implantable structure, which includes:

a flexible sleeve, having first and second sleeve ends, the sleeve defining:
an anchor-coupling region between the first sleeve end and a vicinity of the sleeve between the first and second sleeve ends, exclusive of the second sleeve end, and
a deflectable region between the second sleeve end, and a vicinity of the sleeve between the first and second sleeve ends, exclusive of the first sleeve end; and
an elongate deflectable structural element coupled to the sleeve at the deflectable region, the elongate deflectable structural element having a shape-memory element so as to facilitate deflecting of the deflectable region of the sleeve.

There is further provided, in accordance with some applications of the present invention, apparatus including an implantable structure, including:

a flexible sleeve, having first and second sleeve ends;
a contracting assembly, which is configured to longitudinally contract the sleeve, and which includes:
a contracting mechanism, which is disposed at a first site of the sleeve; and
a longitudinal contracting member, having (a) a first member end, (b) a second member end, which is coupled to the sleeve longitudinally at a second site, which is longitudinally between the first site and the second sleeve end, exclusive, and (c) a first member end portion, which (i) extends from the first member end toward the second member end along only a longitudinal portion of the contracting member, and (ii) is coupled to the contracting mechanism; and
a sleeve-shortening element configured to shorten the at least a portion of a portion of the sleeve between the second site and the second sleeve end.

In some applications of the present invention, contracting mechanism includes a spool around which at least the first member end portion is wound.

In some applications of the present invention, the sleeve-shortening element includes a screw shaft, the sleeve-shortening element is shaped so as to define screw thread for receiving the screw shaft. In some applications of the present invention, the sleeve-shortening element includes a spring. In some applications of the present invention, the spring has a tendency to compress in order to compress the portion of the sleeve between the second site and the second sleeve end.

There is also provided, in accordance with an application of the present invention, apparatus including an implantable structure, which includes:

a flexible sleeve, having first and second sleeve ends; and
a contracting assembly, which is configured to longitudinally contract the sleeve, and which includes:
a contracting mechanism, which is disposed at a first site of the sleeve; and
a longitudinal contracting member, having (a) a first member end, (b) a second member end, which is coupled to the sleeve longitudinally at a second site longitudinally between the first site and the second sleeve end, exclusive, and (c) a first member end portion, which (i) extends from the first member end toward the second member end along only a longitudinal portion of the contracting member, and (ii) is coupled to the contracting mechanism, a first portion of the sleeve longitudinally extends from the first sleeve end toward the first site, and a second portion of the sleeve longitudinally extends from the second sleeve end toward the second site, the sleeve is arranged in a closed loop, such that the first and second portions of the sleeve together define a longitudinally overlapping portion of the sleeve, and the implantable structure is configured such that the contracting assembly applies a longitudinal contracting force only between the first and the second sites, and not along the overlapping portion.

For some applications, the implantable structure further includes a plurality of tissue anchors, at least one of which penetrates both the first and second portions of the sleeve at the overlapping portion. For some applications, the at least one of the tissue anchors includes a coupling head and a tissue coupling element, the tissue coupling element penetrates both the first and second portions of the sleeve at the overlapping portion, and the coupling head is positioned within one of the first and second portions of the sleeve at the overlapping portion. For some applications, the plurality of tissue anchors includes: (a) a plurality of first tissue anchors of a first configuration, coupled to the sleeve at intervals along a first longitudinally-contiguous portion of the loop; and (b) a plurality of second tissue anchors of a second configuration different from the first configuration, coupled to the sleeve at intervals along a second longitudinally-contiguous portion of the loop different from the first longitudinally-contiguous portion, which second longitudinally contiguous portion includes the longitudinally overlapping portion. The first and second tissue anchors are optionally configured as described below.

For some applications, the overlapping portion has a length of between 5 and 60 mm.

For some applications, the contracting member does not extend along the first portion of the sleeve, and does not extend along the second portion of the sleeve.

For some applications, the first site is a first longitudinal distance from the first sleeve end; the second site is at a second longitudinal distance from the second sleeve end, which first and second longitudinal distances are measured when the sleeve is in a straight, relaxed, non-contracted state; and at least one of the first and second longitudinal distances, taken separately, is at least 18 mm.

For any of the applications described above, the contracting mechanism may include a housing and a rotatable structure positioned within the housing, which housing is disposed at the first site of the sleeve, and the rotatable structure and the longitudinal contracting member may be arranged such that rotation of the rotatable structure longitudinally contracts the sleeve.

For any of the applications described above, at least three of the tissue anchors may be coupled to the sleeve alongside the contracting member, longitudinally between the first and second sites, exclusive.

For any of the applications described above, the sleeve may be substantially longitudinally non-extensible.

There is further provided, in accordance with an application of the present invention, apparatus including an implantable structure, which includes:

a flexible sleeve, having first and second sleeve ends;
a contracting assembly, which is configured to longitudinally contract the sleeve, and which includes:
a contracting mechanism, which is disposed at a first site of the sleeve; and
a longitudinal contracting member, having (a) a first member end, (b) a second member end, which is coupled to the sleeve longitudinally at a second site, which is longitudinally between the first site and the second sleeve end, exclusive, and (c) a first member end portion, which (i) extends from the first member end toward the second member end along only a longitudinal portion of the contracting member, and (ii) is coupled to the contracting mechanism; and a plurality of tissue anchors, one or more of which are coupled to the sleeve at respective third sites longitudinally between the second site and the second sleeve end, exclusive.

For some applications, at least two of the tissue anchors are coupled to the sleeve at respective third sites longitudinally between the second member end and the second sleeve end, exclusive.

For some applications, the second site is at least 5 mm from the second sleeve end, such as at least 9 mm, e.g., at least 18 mm, measured when the sleeve is in a straight, relaxed, non-contracted state.

For some applications, the second site is at a longitudinal distance from the second sleeve end, which distance is no greater than 30% of a total length of the sleeve, the distance and length measured when the sleeve is in the straight, relaxed, non-contracted state.

For some applications, a first portion of the sleeve longitudinally extends from the first sleeve end toward the first site, a second portion of the sleeve longitudinally extends from the second sleeve end toward the second site, and the sleeve is arranged in a closed loop, such that the first and second portions of the sleeve together define a longitudinally overlapping portion of the sleeve. For some applications, at least one of the tissue anchors penetrates both the first and second portions of the sleeve at the overlapping portion. For some applications, the at least one of the tissue anchors includes a coupling head and a tissue coupling element, the tissue coupling element penetrates both the first and second portions of the sleeve at the overlapping portion, and the coupling head is positioned within one of the first and second portions of the sleeve at the overlapping portion.

For some applications, the overlapping portion has a length of between 5 and 60 mm. For some applications, the contracting member does not extend along the first portion of the sleeve, and does not extend along the second portion of the sleeve.

For any of the applications described above, the contracting mechanism may include a housing and a rotatable structure positioned within the housing, which housing is disposed at the first site of the sleeve, and the rotatable structure and the longitudinal contracting member may be arranged such that rotation of the rotatable structure longitudinally contracts the sleeve.

For any of the applications described above, at least three of the tissue anchors may be coupled to the sleeve alongside the contracting member, longitudinally between the first and second sites, exclusive.

For any of the applications described above, the implantable structure may be configured such that the contracting assembly applies a longitudinal contracting force only between the first and the second sites.

For any of the applications described above, the sleeve may be substantially longitudinally non-extensible.

There is still further provided, in accordance with an application of the present invention, apparatus including an implantable structure, which includes:

a flexible sleeve, having first and second sleeve ends; and a contracting assembly, which includes:

a contracting mechanism, which is disposed at a first site of the sleeve; and a longitudinal contracting member, having (a) a first member end, (b) a second member end, which is coupled to the sleeve longitudinally at a second site, which is longitudinally between the first site and the second sleeve end, exclusive, and (c) a first member end portion, which (i) extends from the first member end toward the second member end along only a longitudinal portion of the contracting member, and (ii) is coupled to the contracting mechanism, the contracting mechanism is configured to apply a longitudinal contracting force only between the first and the second sites; and a plurality of tissue anchors, one or more of which are coupled to the sleeve at respective third sites selected from the group of sites consisting of: one or more sites longitudinally between the first site and the first sleeve end, exclusive, and one or more sites longitudinally between the second site and the second sleeve end, exclusive.

For some applications, at least one of the third sites is longitudinally between the first site and the first sleeve end, exclusive. For some applications, at least two of the third sites are longitudinally between the first site and the first sleeve end, exclusive.

For some applications, at least one of the third sites is longitudinally between the second site and the second sleeve end, exclusive. For some applications, at least two of the third sites are longitudinally between the second site and the second sleeve end, exclusive.

For some applications, at least one of the third sites is longitudinally between the first site and the first sleeve end, exclusive, and at least one of the third sites is longitudinally between the second site and the second sleeve end, exclusive.

For some applications, the first site is a first longitudinal distance from the first sleeve end; the second site is at a second longitudinal distance from the second sleeve end, which first and second longitudinal distances are measured when the sleeve is in a straight, relaxed, non-contracted state; and at least one of the first and second longitudinal distances, taken separately, is at least 5 mm. For some applications, the first distance is at least 5 mm. Alternatively or additionally, for some applications, the second distance is at least 5 mm. For some applications, at least one of the first and second longitudinal distances, taken separately, is at least 9 mm, such as at least 18 mm.

For some applications, a first portion of the sleeve longitudinally extends from the first sleeve end toward the first site, a second portion of the sleeve longitudinally extends from the second sleeve end toward the second site, and the sleeve is arranged in a closed loop, such that the first and second portions of the sleeve together define a longitudinally overlapping portion of the sleeve. For some applications, at least one of the tissue anchors penetrates both the first and second portions of the sleeve at the overlapping portion. For some applications, the at least one of the tissue anchors includes a coupling head and a tissue coupling element, the tissue coupling element penetrates both the first and second portions of the sleeve at the overlapping portion, and the coupling head is positioned within one of the first and second portions of the sleeve at the overlapping portion.

For some applications, the overlapping portion has a length of between 5 and 60 mm. For some applications, the contracting member does not extend along the first portion of the sleeve, and does not extend along the second portion of the sleeve.

For any of the applications described above, the contracting mechanism may include a housing and a rotatable structure positioned within the housing, which housing is disposed at the first site of the sleeve, and the rotatable structure and the longitudinal contracting member may be arranged such that rotation of the rotatable structure applies the longitudinal contracting force only between the first and the second sites.

For any of the applications described above, at least three of the tissue anchors may be coupled to the sleeve alongside the contracting member, longitudinally between the first and second sites, exclusive.

For any of the applications described above, the sleeve may be substantially longitudinally non-extensible.

There is additionally provided, in accordance with an application of the present invention, apparatus including an implantable structure, which includes:
  a flexible sleeve, having first and second sleeve ends; and
  a contracting assembly, which is configured to longitudinal contract the sleeve, and which includes:
    a contracting mechanism;
    a first longitudinal contracting member, which has first and second member ends, and a first member end portion, which extends from the first member end toward the second member end along only a longitudinal portion of the first contracting member; and
    a second longitudinal contracting member, which has first and second member ends, and a first member end portion, which extends from the first member end toward the second member end along only a longitudinal portion of the second contracting member; and
  wherein (a) the first member end of the first contracting member and the first member end of the second contracting member are coupled to the contracting mechanism, (b) the second member end of the first longitudinal contracting member is coupled to the sleeve at a first site that is a first longitudinal distance from the first sleeve end, and (c) the second member end of the second longitudinal contracting member is coupled to the sleeve at a second site that is a second longitudinal distance from the second sleeve end, wherein the contracting mechanism is disposed at a third site of the sleeve that is longitudinally between the first and second sites, exclusive, and wherein the first and second longitudinal distances are measured when the sleeve is in a straight, relaxed, non-contracted state, and at least one of the first and second longitudinal distances, taken separately, is at least 5 mm.

For some applications, the implantable structure further includes a plurality of tissue anchors, one or more of which are coupled to the sleeve at respective fourth sites selected from the group of sites consisting of: one or more sites longitudinally between the first site and the first sleeve end, exclusive, and one or more sites longitudinally between the second site and the second sleeve end, exclusive. For some applications, at least three of the tissue anchors are coupled to the sleeve alongside the contracting member, longitudinally between the first and second sites, exclusive.

For some applications, each of the first and second longitudinal distances is at least 5 mm. Alternatively, for some applications, one of the first and second longitudinal distances is at least 5 mm, and the other of the first and second longitudinal distances is less than 5 mm, such as equal to 0 mm.

For any of the applications described above, the contracting mechanism may include a housing and a rotatable structure positioned within the housing, which housing is disposed at the third site of the sleeve, and the rotatable structure and the longitudinal contracting member may be arranged such that rotation of the rotatable structure longitudinally contracts the sleeve.

For any of the applications described above, each of the first and second longitudinal contracting members includes at least one wire.

There is yet additionally provided, in accordance with an application of the present invention, apparatus including an implantable structure, which includes:
  a flexible sleeve, arranged as a loop;
  a plurality of first tissue anchors of a first configuration, coupled to the sleeve at intervals along a first longitudinally-contiguous portion of the loop; and
  a plurality of second tissue anchors of a second configuration different from the first configuration, coupled to the sleeve at intervals along a second longitudinally-contiguous portion of the loop different from the first longitudinally-contiguous portion.

For some applications, the first and second configurations are different from each other in size. For some applications, the first tissue anchors include first coupling heads and first tissue coupling elements, respectively, the second tissue anchors include second coupling heads and second tissue coupling elements, respectively, and lengths of the first tissue coupling elements are greater than lengths of the second tissue coupling elements. For some applications, the implantable structure includes more first tissue anchors than second tissue anchors, such as at least twice as many first tissue anchors as second tissue anchors.

For some applications, the first and second tissue coupling elements are shaped so as to define a shape selected from the group consisting of: a helix, a spiral, and a screw shaft, and the lengths of the first and second coupling elements are measured along a longitudinal axis of the shape. For some applications, each of the second tissue coupling elements is shaped so as to define no more than two turns.

For some applications, the first tissue anchors include first coupling heads and first tissue coupling elements, respectively, the second tissue anchors include second coupling heads and second tissue coupling elements, respectively; the first and second tissue coupling elements are shaped so as to define a shape selected from the group consisting of: a helix, a spiral, and a screw shaft; and each of the second tissue coupling elements has fewer turns than does each of the first tissue coupling elements.

For some applications, each of the second tissue coupling elements is selected from the group consisting of: a harpoon anchor, an anchor including spiked arms, a mesh shaped so as to define two discs, an anchor including a barbed shaft. For some applications, each of the second tissue coupling elements includes a suture.

For any of the applications described above, the flexible sleeve may be shaped so as to define an integrally closed loop having no sleeve ends.

For any of the applications described above, the flexible sleeve may be shaped so as to define first and second sleeve ends, which are coupled to each other to form the loop. For some applications, the first and second sleeve ends are coupled to each other at an overlapping portion.

There is also provided, in accordance with an application of the present invention, apparatus including an implantable structure, which includes:
  a flexible sleeve, having first and second sleeve ends;
  a contracting assembly, which is configured to longitudinally contract the sleeve;
  an elongated linking member, having a first and second linking member ends, which second linking member end includes a first coupling element, wherein the linking member is coupled to the sleeve such that (a) at least a portion of the linking member is disposed within the sleeve, and (b) the first linking member end is longitudinally between the second linking member end and the first sleeve end, exclusive; and a second coupling element, which is configured to be coupleable to the first coupling element, and which is coupled to the implantable structure within 1.5 cm of the first sleeve end, measured when the sleeve is fully longitudinally extended.

For some applications, the implantable structure further includes a plurality of tissue anchors, at least two of which are coupled to the sleeve at respective, different longitudinal sites alongside the linking member.

For some applications, the contracting assembly includes a contracting mechanism and a longitudinal contracting member, and the contracting mechanism is coupled to the sleeve within 1.5 cm of the first sleeve end. For some applications, the second coupling element is coupled to the contracting mechanism.

For some applications, the linking member is configured as a spring. For some applications, the linking member is curved.

For some applications, the linking member has a length of between 2 and 6 cm.

For some applications, the linking member includes metal, such as Nitinol.

For some applications, the linking member is substantially longitudinally non-extensible.

For some applications, at least 30% of a length of the linking member is disposed within the sleeve.

For some applications, the flexible sleeve is a first flexible sleeve, and the implantable structure further includes a second flexible sleeve, and at least 20% of a length of the linking member is disposed within the second flexible sleeve.

For some applications, at least one of the first and second coupling elements includes a hook. For some applications, at least one of the first and second coupling elements includes a loop.

For any of the applications described above, the longitudinal contracting member may include at least one wire.

For any of the applications described above, the implantable structure may further include one or more contraction-restricting elements coupled to at least a contraction-restricted portion of the implant structure, each of which contraction-restricting elements includes a coiled element, a portion of which is non-compressible.

There is further provided, in accordance with an application of the present invention, apparatus including an implantable structure, which includes:

a flexible sleeve, which includes a plurality of radiopaque markers, positioned along the sleeve at respective longitudinal sites; and a plurality of tissue anchors, which are configured to be coupled to the sleeve.

For some applications, the radiopaque markers include a radiopaque ink.

For some applications, at least three of the radiopaque markers are longitudinally spaced at a constant interval. For some applications, at least three of the anchors are coupled to the sleeve, longitudinally spaced at the constant interval.

For some applications, the radiopaque markers have respective edges selected from the group consisting of: respective proximal edges, and respective distal edges; the radiopaque markers include first, second, and third radiopaque markers, which first and second markers are adjacent, and which second and third markers are adjacent; and a first longitudinal distance between the selected edge of the first marker and the selected edge of the second marker equals a second longitudinal distance between the selected edge of the second marker and the selected edge of the first marker. For some applications, the anchors include first, second, and third anchors, which first and second anchors are adjacently coupled to the sleeve with the first longitudinal distance therebetween, and which second and third anchors are adjacently coupled to the sleeve with the second longitudinal distance therebetween.

For any of the applications described above, the implantable structure may include an annuloplasty ring, which is configured to be implanted along an annulus of an atrioventricular valve of a subject, and to contract the annulus as the sleeve is longitudinally contracted.

For any of the applications described above, the apparatus may further include a prosthetic heart valve, which is configured to be coupled to the sleeve.

There is still further provided, in accordance with an application of the present invention, a method including:

providing an implantable structure, which includes (a) a flexible sleeve and (b) a contracting assembly, which is configured to longitudinally contract the sleeve, and which includes (i) a contracting mechanism and (ii) one or more longitudinal contracting members coupled to the contracting mechanism;

placing (typically in a percutaneous procedure) the implantable structure completely around an annulus of an atrioventricular valve of a subject, such that none of the one or more longitudinal contracting members is positioned along an anterior portion of the annulus between fibrous trigones of the valve;

fastening the implantable structure to the annulus; and actuating the contracting assembly to contract a longitudinal portion of the sleeve not positioned along the anterior portion of the annulus.

For some applications, providing the implantable structure includes providing the implantable structure in which the sleeve is shaped so as to define an integrally closed loop having no sleeve ends.

For some applications, providing the implantable structure includes providing the implantable structure in which the sleeve has first and second sleeve ends, and first and second portions that longitudinally extend from the first and the second sleeve ends, respectively; placing the implantable structure includes arranging the sleeve in a closed loop, such that the first and second portions of the sleeve together define a longitudinally overlapping portion of the sleeve positioned at least partially along the anterior portion of the annulus; and none of the one or more longitudinal contracting members is positioned along the overlapping portion of the sleeve. For some applications, fastening the implantable structure to the annulus includes fastening the sleeve to the annulus using a plurality of tissue anchors, at least one of which penetrates both the first and second portions of the sleeve at the overlapping portion.

For some applications, the at least one of the tissue anchors includes a coupling head and a tissue coupling element, and fastening includes fastening the sleeve to the annulus such that the tissue coupling element penetrates both the first and second portions of the sleeve at the overlapping portion, and the coupling head is positioned within one of the first and second portions of the sleeve at the overlapping portion.

For some applications, the plurality of tissue anchors includes a plurality of first tissue anchors of a first configuration, and a plurality of second tissue anchors of a second configuration different from the first configuration, and fastening includes: (a) coupling the first tissue anchors to the sleeve at intervals along a first longitudinally-contiguous portion of the loop positioned along a portion of the annulus other than the anterior portion of the annulus, and (b) coupling the second tissue anchors to the sleeve at intervals along a second longitudinally-contiguous portion of the loop positioned along the anterior portion of the annulus. The first and second tissue anchors are optionally configured as described below. The For some applications, the contracting member does not extend along the first portion of the sleeve, and does not extend along the second portion of the sleeve.

For some applications, placing includes placing the implantable structure such that the one or more longitudinal contracting members are positioned along a non-anterior portion of the annulus, which non-anterior portion does not reach either of the fibrous trigones.

For some applications, the contracting mechanism includes a housing and a rotatable structure positioned within the housing, which housing is disposed at the first site of the sleeve, and actuating the contracting assembly includes rotating the rotatable structure to longitudinally contract the sleeve.

There is additionally provided, in accordance with an application of the present invention, a method including:

providing an implantable structure, which includes (a) a flexible sleeve, having first and second sleeve ends, and (b) a contracting assembly, which is configured to longitudinally contract the sleeve, and which includes (i) a contracting mechanism, which is disposed longitudinally at a first site of the sleeve, and (ii) a longitudinal contracting member, having (x) a first member end, (y) a second member end, which is coupled to the sleeve longitudinally at a second site, which is longitudinally between the first site and the second sleeve end, exclusive, and (z) a first member end portion, which (1) extends from the first member end toward the second member end along only a longitudinal portion of the contracting member, and (2) is coupled to the contracting mechanism;

placing (typically in a percutaneous procedure) the implantable structure at least partially around an annulus of an atrioventricular valve of a subject;

using a plurality of tissue anchors, fastening the implantable structure to the annulus, including coupling one or more of the tissue anchors to the sleeve and tissue of the annulus at respective third sites longitudinally between the second site and the second sleeve end, exclusive; and actuating the contracting assembly to contract a longitudinal portion of the sleeve.

For some applications, coupling the one or more tissue anchors includes coupling at least two of the tissue anchors to the sleeve and the tissue at respective third sites longitudinally between the second member end and the second sleeve end, exclusive.

For some applications, providing the implantable structure includes providing the implantable structure in which the second site is at least 5 mm from the second sleeve end, measured when the sleeve is in a straight, relaxed, non-contracted state.

For some applications, providing the implantable structure includes providing the implantable structure in which the second site is at a longitudinal distance from the second sleeve end, which distance is no greater than 30% of a total length of the sleeve, the distance and length measured when the sleeve is in the straight, relaxed, non-contracted state.

For some applications, a first portion of the sleeve longitudinally extends from the first sleeve end toward the first site, a second portion of the sleeve longitudinally extends from the second sleeve end toward the second site, and placing the implantable structure includes arranging the sleeve in a closed loop, such that the first and second portions of the sleeve together define a longitudinally overlapping portion of the sleeve. For some applications, placing the implantable structure includes placing the implantable structure such that the overlapping portion is positioned along an anterior portion of the annulus between fibrous trigones of the valve. For some applications, fastening includes coupling at least one of the tissue anchors to the tissue such that the anchor penetrates both the first and second portions of the sleeve at the overlapping portion. For some applications, the at least one of the tissue anchors includes a coupling head and a tissue coupling element, and fastening includes fastening the sleeve to the annulus such that the tissue coupling element penetrates both the first and second portions of the sleeve at the overlapping portion, and the coupling head is positioned within one of the first and second portions of the sleeve at the overlapping portion.

For some applications, providing the implantable structure includes providing the implantable structure in which the overlapping portion has a length of between 5 and 60 mm. For some applications, providing the implantable structure includes providing the implantable structure in which the contracting member does not extend along the first portion of the sleeve, and does not extend along the second portion of the sleeve.

For some applications, the contracting mechanism includes a housing and a rotatable structure positioned within the housing, which housing is disposed at the first site of the sleeve, and actuating the contracting assembly includes rotating the rotatable structure to longitudinally contract the sleeve.

For some applications, coupling includes coupling at least three of the tissue anchors to the sleeve alongside the contracting member, longitudinally between the first and second sites, exclusive.

For some applications, actuating includes actuating the contracting assembly to apply a longitudinal contracting force only between the first and the second sites.

There is yet additionally provided, in accordance with an application of the present invention, a method including:

providing an implantable structure, which includes (a) a flexible sleeve, having first and second sleeve ends, and (b) a contracting assembly, which includes (i) a contracting mechanism, which is disposed longitudinally at a first site of the sleeve, and (ii) a longitudinal contracting member, having (x) a first member end, (y) a second member end, which is coupled to the sleeve longitudinally at a second site, which is longitudinally between the first site and the second sleeve end, exclusive, and (z) a first member end portion, which (1) extends from the first member end toward the second member end along only a longitudinal portion of the contracting member, and (2) is coupled to the contracting mechanism, wherein the contracting mechanism is configured to apply a longitudinal contracting force only between the first and the second sites; and placing (typically in a percutaneous procedure) the implantable structure at least partially around an annulus of an atrioventricular valve of a subject;

using a plurality of tissue anchors, fastening the implantable structure to the annulus, including coupling one or more of the tissue anchors to the sleeve and tissue of the annulus at respective third sites selected from the group of sites consisting of: one or more sites longitudinally between the first site and the first sleeve end, exclusive, and one or more sites longitudinally between the second site and the second sleeve end, exclusive; and actuating the contracting assembly to contract a longitudinal portion of the sleeve.

For some applications, at least one of the third sites is longitudinally between the first site and the first sleeve end, exclusive. For some applications, at least two of the third sites are longitudinally between the first site and the first sleeve end, exclusive.

For some applications, at least one of the third sites is longitudinally between the second site and the second sleeve end, exclusive. For some applications, at least two of the third sites are longitudinally between the second site and the second sleeve end, exclusive.

For some applications, at least one of the third sites is longitudinally between the first site and the first sleeve end, exclusive, and at least one of the third sites is longitudinally between the second site and the second sleeve end, exclusive.

For some applications, providing the implantable structure includes providing the implantable structure in which the first site is a first longitudinal distance from the first sleeve end, the second site is at a second longitudinal distance from the second sleeve end, which first and second longitudinal distances are measured when the sleeve is in a straight, relaxed, non-contracted state, and at least one of the first and second longitudinal distances, taken separately, is at least 5 mm. For some applications, the first distance is at least 5 mm. Alternatively or additionally, for some applications, the second distance is at least 5 mm.

For some applications, a first portion of the sleeve longitudinally extends from the first sleeve end toward the first site, a second portion of the sleeve longitudinally extends from the second sleeve end toward the second site, and placing the implantable structure includes arranging the sleeve in a closed loop, such that the first and second portions of the sleeve together define a longitudinally overlapping portion of the sleeve. For some applications, placing the implantable structure includes placing the implantable structure such that the overlapping portion is positioned along an anterior portion of the annulus between fibrous trigones of the valve.

For some applications, fastening includes coupling at least one of the tissue anchors to the tissue such that the anchor penetrates both the first and second portions of the sleeve at the overlapping portion. For some applications, the at least one of the tissue anchors includes a coupling head and a tissue coupling element, and fastening includes fastening the sleeve to the annulus such that the tissue coupling element penetrates both the first and second portions of the sleeve at the overlapping portion, and the coupling head is positioned within one of the first and second portions of the sleeve at the overlapping portion.

For some applications, providing the implantable structure includes providing the implantable structure in which the overlapping portion has a length of between 5 and 60 mm. For some applications, providing the implantable structure includes providing the implantable structure in which the contracting member does not extend along the first portion of the sleeve, and does not extend along the second portion of the sleeve.

For some applications, the contracting mechanism includes a housing and a rotatable structure positioned within the housing, which housing is disposed at the first site of the sleeve, and actuating the contracting assembly includes rotating the rotatable structure to longitudinally contract the sleeve.

For some applications, coupling includes coupling at least three of the tissue anchors to the sleeve alongside the contracting member, longitudinally between the first and second sites, exclusive.

There is also provided, in accordance with an application of the present invention, a method including:

providing an implantable structure, which includes (a) a flexible sleeve, having first and second sleeve ends, and (b) a contracting assembly, which is configured to longitudinal contract the sleeve, and which includes (i) a contracting mechanism, (ii) a first longitudinal contracting member, which has first and second member ends, and a first member end portion, which extends from the first member end toward the second member end along only a longitudinal portion of the first contracting member, and (iii) a second longitudinal contracting member, which has first and second member ends, and a first member end portion, which extends from the first member end toward the second member end along only a longitudinal portion of the second contracting member, wherein (a) the first member end of the first contracting member and the first member end of the second contracting member are coupled to the contracting mechanism, (b) the second member end of the first longitudinal contracting member is coupled to the sleeve at a first site that is a first longitudinal distance from the first sleeve end, (c) the second member end of the second longitudinal contracting member is coupled to the sleeve at a second site that is a second longitudinal distance from the second sleeve end, (d) the contracting mechanism is disposed at a third site of the sleeve that is longitudinally between the first and second sites, exclusive, and (e) the first and second longitudinal distances are measured when the sleeve is in a straight, relaxed, non-contracted state, and at least one of the first and second longitudinal distances, taken separately, is at least 5 mm;

placing (typically in a percutaneous procedure) the implantable structure at least partially around an annulus of an atrioventricular valve of a subject;

fastening the implantable structure to the annulus; and actuating the contracting assembly to contract two longitudinal portions of the sleeve.

For some applications, fastening includes fastening the implantable structure to the annulus using a plurality of tissue anchors, including coupling one or more of the tissue anchors to the sleeve and tissue of the annulus at respective fourth sites selected from the group of sites consisting of: one or more sites longitudinally between the first site and the first sleeve end, exclusive, and one or more sites longitudinally between the second site and the second sleeve end, exclusive. For some applications, fastening includes coupling at least three of the tissue anchors to the sleeve alongside the contracting member, longitudinally between the first and second sites, exclusive.

For some applications, each of the first and second longitudinal distances is at least 5 mm.

For some applications, one of the first and second longitudinal distances is at least 5 mm, and the other of the first and second longitudinal distances is less than 5 mm, such as equal to 0 mm.

For any of the applications described above, the contracting mechanism may include a housing and a rotatable structure positioned within the housing, which housing is disposed at the third site of the sleeve, and actuating the contracting assembly may include rotating the rotatable structure to longitudinally contract the sleeve.

There is further provided, in accordance with an application of the present invention, a method including:

placing (typically in a percutaneous procedure) a flexible sleeve as a loop completely around an annulus of an atrioventricular valve of a subject, such that (a) a first longitudinally-contiguous portion of the loop is positioned along a portion of the annulus other than an anterior portion of the annulus between fibrous trigones of the valve, and (b) a second longitudinally-contiguous portion of the loop is positioned along the anterior portion of the annulus;

coupling a plurality of first tissue anchors of a first configuration to the sleeve and tissue of the annulus at intervals along the first longitudinally-contiguous portion of the loop; and coupling a plurality of second tissue anchors of a second configuration different from the first configuration to the sleeve and the tissue at intervals along the second longitudinally-contiguous portion of the loop.

For some applications, the first and second configurations are different from each other in size. For some applications, the first tissue anchors included first coupling heads and first tissue coupling elements, respectively, the second tissue anchors include second coupling heads and second tissue coupling elements, respectively, and lengths of the first tissue coupling elements are greater than lengths of the second tissue coupling elements. For some applications, coupling the first and the second tissue anchors includes coupling more first tissue anchors than second tissue anchors. For some applications, coupling the first and the second tissue anchors includes coupling at least twice as many first tissue anchors as second tissue anchors.

For some applications, the first and second tissue coupling elements are shaped so as to define a shape selected from the group consisting of: a helix, a spiral, and a screw shaft, and the lengths of the first and second coupling elements are measured along a longitudinal axis of the shape. For some applications, each of the second tissue coupling elements is shaped so as to define no more than two turns.

For some applications, the first tissue anchors include first coupling heads and first tissue coupling elements, respectively; the second tissue anchors include second coupling heads and second tissue coupling elements, respectively; the first and second tissue coupling elements are shaped so as to define a shape selected from the group consisting of: a helix, a spiral, and a screw shaft; and each of the second tissue coupling elements has fewer turns than does each of the first tissue coupling elements.

For some applications, each of the second tissue coupling elements is selected from the group consisting of: a harpoon anchor, an anchor including spiked arms, a mesh shaped so as to define two discs, an anchor including a barbed shaft.

For some applications, each of the second tissue coupling elements includes a suture.

For some applications, the flexible sleeve is shaped so as to define an integrally closed loop having no sleeve ends.

For some applications, the flexible sleeve is shaped so as to define first and second sleeve ends, and placing includes placing the flexible sleeve includes coupling the first and the second sleeve ends to each other to form the loop. For some applications, coupling the first and the second sleeve ends includes coupling the first and the second sleeve ends to each other at an overlapping portion.

There is still further provided, in accordance with an application of the present invention, a method including:

providing an implantable structure, which includes (a) a flexible sleeve, having first and second sleeve ends, (b) a contracting assembly, which is configured to longitudinally contract the sleeve, (c) an elongated linking member, having a first and second linking member ends, which second linking member end includes a first coupling element, the linking member is coupled to the sleeve such that (i) at least a portion of the linking member is disposed within the sleeve, and (ii) the first linking member end is longitudinally between the second linking member end and the first sleeve end, exclusive, and (d) a second coupling element, which is coupled to the implantable structure within 1.5 cm of the first sleeve end, measured when the sleeve is fully longitudinally extended;

placing (typically in a percutaneous procedure) the flexible sleeve around a portion of an annulus of an atrioventricular valve of a subject, which portion includes a posterior portion of the annulus;

placing the linking member along an anterior portion of the annulus between fibrous trigones of the valve;

fastening the flexible sleeve to the portion of the annulus;

coupling the first and the second coupling elements together;

actuating the contracting assembly to contract a longitudinal portion of the sleeve.

For some applications, fastening includes fastening the sleeve to the annulus using a plurality of tissue anchors, including coupling at least two of the anchors to the sleeve and tissue of the annulus at respective, different longitudinal sites alongside the linking member.

For some applications, the contracting assembly includes a contracting mechanism and a longitudinal contracting member, and the contracting mechanism is coupled to the sleeve within 1.5 cm of the first sleeve end. For some applications, the second coupling element is coupled to the contracting mechanism.

For some applications, the linking member is configured as a spring. For some applications, the linking member is curved.

For some applications, the linking member has a length of between 2 and 6 cm.

For some applications, the linking member includes metal, such as Nitinol.

For some applications, the linking member is substantially longitudinally non-extensible.

For some applications, at least 30% of a length of the linking member is disposed within the sleeve.

For some applications, the flexible sleeve is a first flexible sleeve, and the implantable structure further includes a second flexible sleeve, and at least 20% of a length of the linking member is disposed within the second flexible sleeve.

For some applications, at least one of the first and second coupling elements includes a hook. For some applications, at least one of the first and second coupling elements includes a loop.

There is additionally provided, in accordance with an application of the present invention, a method including:

placing (typically in a percutaneous procedure), at least partially around an annulus of an atrioventricular valve of a subject, a flexible sleeve, which includes a plurality of radiopaque markers, positioned along the sleeve at respective longitudinal sites;

generating a radiographic image of the sleeve; and using the radiographic image, coupling a plurality of tissue anchors to the sleeve and tissue of the annulus.

For some applications, coupling includes using the radiographic image to enable setting a desired distance between the anchors along the sleeve.

For some applications, the radiopaque markers include a radiopaque ink.

For some applications, at least three of the radiopaque markers are longitudinally spaced at a constant interval. For some applications, at least three of the anchors are coupled to the sleeve, longitudinally spaced at the constant interval.

For some applications, the radiopaque markers have respective edges selected from the group consisting of: respective proximal edges, and respective distal edges; the radiopaque markers include first, second, and third radiopaque markers, which first and second markers are adjacent, and which second and third markers are adjacent; and a first longitudinal distance between the selected edge of the first marker and the selected edge of the second marker equals a second longitudinal distance between the selected edge of the second marker and the selected edge of the first marker. For some applications, the anchors include first, second, and third anchors, and coupling includes adjacently coupling the first and the second anchors to the sleeve with the first longitudinal distance therebetween, and adjacently coupling the second and the third anchors to the sleeve with the second longitudinal distance therebetween.

There is also provided, in accordance with some applications of the present invention, apparatus, including:
  an implant structure configured to treat a native atrioventricular valve of a patient, the implant structure including:
    a sleeve having a lumen and at least one end, the at least one end being shaped so as to define an opening; and
    a closure element disposed in a vicinity of the at least one end, the closure element being configured to facilitate closure of the opening; and
  a contracting mechanism coupled to the implant structure and configured to contract at least a contraction-facilitated portion of the implant structure.

For some applications, the implant structure has a length of between 50 mm and 150 mm.

For some applications, the implant structure has a diameter of between 1 mm and 10 mm.

For some applications, the apparatus is configured to be implanted along an annulus of a mitral valve of the patient in a manner in which the implant structure is formed into at least a portion of an annuloplasty ring.

For some applications, the closure element includes a closure mechanism that includes one or more strips coupled to the sleeve in the vicinity of the at least one end of the sleeve, and the one or more strips have a tendency to be in a closed state in which the one or more strips close around at least a portion of the opening.

For some applications, the apparatus further includes a delivery tool advanceable within the lumen of the sleeve through the opening, and the tool is configured to expand the one or more strips while advanceable within the lumen of the sleeve and to facilitate positioning of the one or more strips in the closed state when removed from within the lumen of the sleeve.

For some applications, the apparatus further includes a contracting member coupled to the sleeve that facilitates contraction of the contraction-facilitated portion of the implant structure, the contracting member having a first portion thereof that is coupled to the contracting element.

For some applications, the contracting member is threaded through the sleeve one or more times to facilitate generally-even contraction of the implant structure.

For some applications, the apparatus further includes one or more contraction-restricting elements coupled to at least a contraction-restricted portion of the implant structure, the one or more contraction-restricting elements being configured to restrict contraction of at least the contraction-restricted portion of the implant structure beyond a predetermined amount.

For some applications, the one or more contraction-restricting elements is coupled to an outer surface of the implant structure.

For some applications, each one of the one or more contraction-restricting elements includes a segment having at least a portion thereof that is non-compressible along a longitudinal axis of the segment.

For some applications, at least one of contraction-restricting elements is disposed adjacently to one or more contraction-facilitated elements that are compressible along the longitudinal axis of the segment and facilitate contraction of respective portions of the implant structure in vicinities of the one or more contraction-facilitating elements.

For some applications, each one of the contraction restriction-elements is configured to restrict contraction of the contraction-restricted portion of the implant structure while facilitating radial movement of the contraction-restricted portion of the implant structure.

For some applications, at least one of the contraction-restricting elements includes a coiled element, and at least a portion of the coiled element is non-compressible.

For some applications, the coiled element includes a shape-memory material and is configured to be generally straightened from a coiled state during delivery of the implant structure to an implantation site of a body of the patient.

For some applications, the coiled element includes an elongate coiled element disposed within the lumen of the sleeve.

For some applications, the coiled element includes an elongate coiled element that is coupled to a portion of an outer surface of the sleeve and is disposed alongside the portion of the outer surface of the sleeve.

For some applications, the implant is configured for implantation along a native annulus of the native atrioventricular valve of the patient in a manner in which the contraction-restricted portion of the implant structure is disposed along a portion of the annulus at a posterior leaflet of the valve, and the contraction-restricting element is coupled to the contraction-restricted portion.

For some applications, the contraction restriction-element is configured to restrict contraction of the contraction-restricted portion while facilitating radial movement of the contraction-restricted portion.

For some applications:
  the closure element includes at least one end flap that is disposed at the at least one end of the sleeve, and
  the first portion of the contracting member is coupled to the end flap in a manner in which, in response to at least initial actuation of the contracting mechanism, the contracting member draws the end flap at least partially over the opening at the at least one end of the sleeve.

For some applications, the one or more contraction-restricting elements each have a length of between 3 and 120 mm.

For some applications:
  the one or more contraction-restricting elements are coupled to the contracting member in a vicinity of the first portion thereof, the one or more contraction-restricting elements are disposed along the implant structure at a distance of between 3 and 45 mm from the at least one end of the sleeve, the contraction-restricted portion of the implant structure is between 3 and 45 mm from the at least one end of the sleeve, and the one or more contraction-restricting elements are configured to restrict contraction of the contraction-restricted portion of the implant structure during contraction of a remaining portion of the implant structure by the contracting member.

For some applications, the contracting mechanism is disposed at a first portion of the implant structure, and the contracting member extends along the implant structure from the first portion thereof to the at least one end of the sleeve.

For some applications, the one or more contraction-restricting elements are disposed in a vicinity of the at least one end of the sleeve, and the contracting member is looped through a portion of the flap and extends back toward the one or more contraction-restricting elements.

For some applications, the contracting mechanism includes a rotatable structure, and the actuation includes rotation of the rotatable structure in a first rotational direction in order to actuate the contracting member to draw the flap over the opening.

For some applications, in response to rotation of the rotatable structure in a second rotational direction that is opposite the first rotational direction, the contracting member draws the end flap at least partially away from the opening at the at least one end of the sleeve.

For some applications:
the at least one end of the sleeve defines a first free end of the implant structure,
the implant structure is shaped so as to define a second free end,
the apparatus is configured to be implanted along an annulus of an atrioventricular valve of the patient, and
in response to actuation of the contracting mechanism, the first and second free ends of the implant structure are drawn toward one another.

For some applications, the apparatus is configured to be implanted along an annulus of a mitral valve of the patient,
the first end of the implant structure is configured to be coupled to a first location along the annulus in a vicinity of a first trigone adjacent to the mitral valve, and
the second end of the implant structure is configured to be coupled to a second location along the annulus in a vicinity of a second trigone adjacent to the mitral valve.

For some applications, the contracting mechanism includes a rotatable structure, and the actuation includes rotation of the rotatable structure in a first rotational direction to contract the implant structure.

For some applications, in response to rotation of the rotatable structure in a second rotational direction that is opposite the first rotational direction, the contracting member expands the implant structure.

For some applications, in response to rotation of the rotatable structure in a first rotational direction, successive portions of the contracting member advance in a first advancement direction with respect to the rotatable structure and contact the rotatable structure.

For some applications, the rotatable structure includes a spool, and, in response to the rotation of the spool in the first rotational direction, the contracting member is configured to be wound around the spool.

For some applications, in response to continued advancement of the contracting member in the first advancement direction by continued rotation of the rotatable structure in the first rotational direction, the at least one end of the sleeve is pulled toward the contracting mechanism.

For some applications:
the implant structure is configured to be implanted along an annulus of a mitral valve of the patient,
the contracting member is configured to contract the implant structure in response to the rotation of the rotatable structure in the first rotational direction, and
the implant structure is configured to contract the annulus in response to the contraction of the implant structure.

For some applications, the successive portions of the contracting member are configured to be advanced in a second advancement direction with respect to the rotatable structure and thereby to facilitate expansion of the implant structure in response to rotation of the rotatable structure in a second rotational direction, the second rotational direction being opposite the first rotational direction, and the second advancement direction being opposite the first advancement direction.

For some applications:
the rotatable structure has a first end shaped to define a first opening, and a second end shaped to define a second opening, the rotatable structure being shaped to define a channel extending from the first opening to the second opening, the channel being configured for passage therethrough of an elongate tool, and
the second end of the rotatable structure has a lower surface thereof shaped to define one or more recesses.

For some applications, the apparatus further includes a mechanical element having a planar surface coupled to the lower surface of the rotatable structure, the mechanical element being shaped to provide:
a protrusion protruding out of a plane of the planar surface of the mechanical element, the protrusion being disposed within one of the recesses during a resting state of the mechanical element, in a manner that restricts rotation of the rotatable structure, and
a depressible portion coupled to the protrusion, the depressible portion being disposed in communication with the second opening of the lower surface, and configured to dislodge the protrusion from within the recess in response to a force applied thereto by the elongate tool.

For some applications, the apparatus further includes: one or more tissue anchors; and
a deployment manipulator tube, which is configured to be removably positioned at least partially within the lumen of the sleeve, such that the deployment manipulator tube extends out of the at least one end of the sleeve; and
an anchor driver which is reversibly coupleable to the one or more tissue anchors and which is configured to be at least partially positioned within the deployment manipulator tube, and, while so positioned, to deploy the one or more tissue anchors through a wall of the sleeve.

For some applications, the anchor driver is deflectable within the sleeve of the implant structure, and the apparatus further includes one or more stiffening elements, the one or more stiffening elements being threaded through one or more portions of the sleeve in order to maintain relative positioning of the manipulator tube relative to the implant structure during deflection of the anchor driver within the sleeve.

For some applications, the manipulator tube is deflectable within the sleeve of the implant structure, and the one or more stiffening elements are configured to maintain relative positioning of the implant structure relative to the manipulator tube during deflection of the manipulator tube.

For some applications, the apparatus further includes a pusher tube, which is configured to pass over a portion of the deployment manipulator tube, such that a distal end of the pusher tube is in contact with the at least one end of the sleeve.

For some applications, the distal end of the pusher tube is removably coupled to the at least one end of the sleeve.

For some applications, the pusher tube includes one or more coupling elements, which are configured to removably couple the distal end of the pusher tube to the at least one end of the sleeve.

For some applications, the apparatus is configured such that:
when the deployment manipulator tube is positioned within the lumen of the sleeve, the deployment manipulator tube causes the coupling elements to engage the sleeve, thereby removably coupling the distal end of the pusher tube to the at least one end of the sleeve, and
when the deployment manipulator tube is withdrawn from the sleeve, the coupling elements disengage from the sleeve, thereby decoupling the distal end of the pusher tube from the at least one end of the sleeve.

For some applications, the coupling elements are configured to have a natural tendency to flex inwards toward a central longitudinal axis of the sleeve that passes through the at least one end of the sleeve, and the deployment manipulator tube, when positioned within the lumen of the sleeve, pushes the coupling elements outwards away from the longitudinal axis, thereby causing the coupling elements to engage the sleeve.

There is further provided, in accordance with some applications of the present invention, apparatus, including:
an implant structure configured to treat a native atrioventricular valve of a patient, the implant structure including:
a sleeve having a lumen and at least one end, the at least one end being shaped so as to define an opening; and
a closure element disposed in a vicinity of the at least one end, the closure element being configured to facilitate closure of the opening; and
an anchor delivery tool advanceable through the opening and within the lumen of the sleeve when the closure element does not facilitate closure of the opening.

There is additionally provided in accordance with some applications of the present invention, apparatus, including:
an implant structure configured to treat a native atrioventricular valve of a patient, the implant structure having a length of between 50 mm and 150 mm and a diameter of between 1 mm and 10 mm, the implant structure including:
a sleeve having a lumen and at least one end, the at least one end being shaped so as to define an opening; and
a closure element disposed in a vicinity of the at least one end, the closure element being configured to facilitate closure of the opening.

There is further provided, in accordance with some applications of the present invention, a method, including:
positioning an implant structure along an annulus of an atrioventricular valve of a patient, the implant structure including a sleeve having a lumen and at least one end, the at least one end being shaped so as to define an opening;
fastening at least a portion of the implant structure to the annulus; and
closing the opening of the at least one end of the sleeve by actuating a closure element of the implant structure to close.

For some applications, positioning the implant structure along the annulus of the atrioventricular valve includes transcatheterally positioning the implant structure along the annulus of the atrioventricular valve.

For some applications, the method further includes driving one or more tissue anchors through a wall of the sleeve from within the lumen of the sleeve.

For some applications, positioning the implant structure along the annulus of the atrioventricular valve includes positioning the implant structure along the annulus in a manner in which the implant structure is formed into a least a portion of an annuloplasty ring.

For some applications, the closure element includes a closure mechanism that includes one or more strips coupled to the sleeve in a vicinity of the at least one end of the implant structure, the one or more strips have a tendency to be in a closed state in which the one or more strips close around at least a portion of the opening, and the method further includes:
expanding the one or more strips from the closed state by introducing a tool within the lumen of the sleeve, and
facilitating positioning of the one or more strips in the closed state by extracting the tool from within the lumen of the sleeve.

For some applications, fastening includes:
anchoring a first location of the implant structure to a first trigone of the valve; and
anchoring a second location of the implant structure to a second trigone of the valve.

For some applications, anchoring the first location includes anchoring a first free end of the implant structure to the first trigone, and anchoring the second location includes anchoring a second free end of the implant structure to the second trigone.

For some applications, the method further includes contracting at least a first portion of the implant structure by actuating a contracting mechanism coupled to the implant structure.

For some applications, the method further includes restricting the contracting of at least a second portion of the implant structure that is less than the entire implant structure, during ongoing contracting of the first portion of the implant structure.

For some applications, restricting the contracting of the second portion of the implant structure includes restricting contraction of a contraction-restricted portion of the implant structure that has a length of between 3 mm and 120 mm.

For some applications, restricting the contracting includes coupling to the second portion of the implant structure a segment having at least a portion thereof that is non-compressible along a longitudinal axis of the segment.

For some applications, coupling the segment to the second portion of the implant structure includes coupling the segment to an outer surface of the implant structure in a vicinity of the second portion of the implant structure.

For some applications, coupling the segment to the outer surface of the implant structure includes restricting contraction of the portion of the implant structure while facilitating radial movement of the portion of the implant structure.

For some applications, positioning the implant structure along the annulus of the atrioventricular valve includes positioning the implant structure in a manner in which the second portion of the implant structure is disposed along a portion of the annulus at a posterior leaflet of the valve, and restricting contraction of the second portion of the implant structure includes restricting contraction of the portion of the annulus at the posterior leaflet of the valve.

For some applications, restricting the contracting of the second portion of the implant structure includes advancing into at least a portion of the lumen of the sleeve, a segment having at least a portion thereof that is non-compressible along a longitudinal axis of the segment.

For some applications, advancing the segment into the portion of the lumen of the sleeve includes advancing a segment that is disposed adjacently to one or more portions that are compressible along the longitudinal axis of the segment.

For some applications, advancing the segment into the portion of the lumen of the sleeve includes advancing a coiled segment into the portion of the sleeve.

For some applications, the method further includes, prior to advancing the coiled segment within the sleeve, advancing the coiled segment toward the sleeve in a generally straightened configuration, and advancing the coiled segment into the portion of the sleeve includes allowing the segment to form a coil within the sleeve.

For some applications, advancing the segment into the portion of the lumen of the sleeve includes restricting contraction of the second portion of the implant structure while facilitating radial movement of the second portion of the implant structure.

For some applications, positioning the implant structure along the annulus of the atrioventricular valve includes positioning the implant structure in a manner in which the second portion of the implant structure is disposed along a portion of the annulus at a posterior leaflet of the valve, and restricting contraction of the second portion of the implant structure includes restricting contraction of the portion of the annulus at the posterior leaflet of the valve.

For some applications, restricting the contracting of the second portion of the implant structure includes restricting contraction of a contraction-restricted portion of the implant structure that is between 3 and 45 mm from the at least one end of the sleeve, while facilitating contraction of a contraction-facilitated portion of the implant structure.

For some applications:
the at least one end of the sleeve defines a first free end of the implant structure,
the implant structure defines a second free end, and
the method further includes:
fastening the implant structure to a first trigone of the valve by fastening the implant structure to the valve in a vicinity of the first free end; and
fastening the implant structure to a second trigone of the valve by fastening the implant structure to the valve in a vicinity of the second free end.

For some applications:
fastening the implant structure to the first trigone includes fastening the first free end of the of the implant structure to the first trigone,
fastening the implant structure to the second trigone includes fastening the second free end of the of the implant structure to the second trigone,
fastening the at least the portion of implant structure to the annulus includes fastening the entire implant structure along the annulus between the first and second trigones, and
contracting the first portion of the implant structure includes contracting the contraction-facilitated portion of the implant structure that is between the second end and the contraction-restricted portion of the implant structure.

For some applications:
fastening the implant structure to the first trigone includes:
fastening the first free end of the of the implant structure to a portion of an atrial wall of a heart of the patient, and
fastening a portion of the implant structure that is adjacent to the first free end to the first trigone, and
anchoring the implant structure to the second trigone includes anchoring the second free end of the of the implant structure to the second trigone.

For some applications:
fastening the first free end of the of the implant structure to the portion of the atrial wall includes fastening the contraction-restricted portion of the implant structure to the portion of the atrial wall,
fastening the portion of the implant structure to the annulus includes fastening the contraction-facilitated portion of the implant to a posterior portion of the annulus between the first and second trigones, and
contracting the implant structure includes contracting the contraction-facilitated portion of the implant structure that is between the first and second trigones.

For some applications:
the atrioventricular valve includes a mitral valve;
the at least one end of the sleeve defines a first end of the implant structure,
the implant structure is shaped so as to define a second end, and positioning the implant structure along the annulus includes:
positioning the first end of the implant structure at a first trigone of the mitral valve; and
positioning the second end of the implant structure at a second trigone of the mitral valve.

For some applications, contracting the first portion of the implant structure includes drawing the first and second ends of the implant structure toward one another.

For some applications, actuating the contracting mechanism includes rotating a rotatable structure of the contracting mechanism, and contracting the implant includes rotating the rotatable structure in a first rotational direction.

For some applications, the method further includes locking the contracting mechanism during a period that is subsequent to the rotating of the rotating structure.

For some applications, the closure element includes a flap at a vicinity of the opening of the sleeve, and the method further includes at least partially drawing the flap over the opening during a first period, by rotating the rotating mechanism in the first rotational direction.

For some applications, the method further includes, during a second period, drawing the end flap at least partially away from the opening at the at least one end of the sleeve by rotating the rotatable structure in a second rotational direction that is opposite the first rotational direction.

For some applications, responsively to rotating the rotatable structure, advancing in a first advancement direction with respect to the rotatable structure successive portions of a contracting member that is coupled to the implant structure, the contracting member is and is configured to contract the implant structure.

For some applications, the rotatable structure includes a spool, and advancing the successive portions of the contracting member in the first advancement direction includes winding the successive portions of the contracting member around the spool.

For some applications, contracting the first portion of the implant structure includes rotating further the rotatable member and advancing further successive portions of the contracting member in the first advancement direction, and the contracting includes drawing the at least one end of the sleeve toward the contracting mechanism.

For some applications, contracting the implant structure includes contracting the annulus of the atrioventricular valve.

For some applications, the method further includes expanding the implant structure by advancing the successive portions of the contracting member in a second advancement direction that is opposite the first advancement direction by rotating the rotatable structure in a second rotational direction that is opposite the first rotational direction.

For some applications, fastening the at least the portion of the implant structure to the annulus includes:

removably positioning a deployment manipulator tube through the opening and at least partially within the lumen of the sleeve of the implant structure, such that the deployment manipulator tube extends out of the at least one end of the sleeve; and driving one or more tissue anchors through a wall of the sleeve from within the lumen of the sleeve.

For some applications:

driving the one or more anchors includes advancing through the deployment manipulator tube an anchor driver that is reversibly couplable to the one or more anchors, exposing a distal end of the anchor driver from within a distal end of the deployment manipulator tube; and deflecting through the sleeve the distal end of the anchor driver.

For some applications, the method further includes maintaining relative positioning of the implant structure relative to the manipulator tube during the deflecting by applying a force to one or more stiffening elements that are threaded through the sleeve of the implant structure.

For some applications, the method further includes placing a pusher tube over the deployment manipulator tube such that a distal end of the pusher tube is in contact with the at least one end of the sleeve.

For some applications, the at least one end of the sleeve includes a proximal end of the sleeve, and the method further includes withdrawing the sleeve from the deployment manipulator tube in a distal direction, and, while withdrawing, pushing the pusher tube against the proximal end of the sleeve.

For some applications, the method further includes, following the withdrawing, removably coupling the distal end of the pusher tube to the proximal end of the sleeve.

For some applications, removably coupling includes using one or more one or more coupling elements of the pusher tube to removably couple the distal end of the pusher tube to the proximal end of the sleeve.

For some applications, removably coupling includes positioning the deployment manipulator tube within the lumen of the sleeve such that the deployment manipulator tube causes the coupling elements to engage the sleeve, and the method further includes decoupling the distal end of the pusher tube from the proximal end of the sleeve by withdrawing the deployment manipulator tube from the sleeve such that the coupling elements disengage from the sleeve.

For some applications, positioning the implant structure along the annulus, and closing the opening of the at least one end of the sleeve include positioning the implant structure along the annulus, and closing the opening of the at least one end of the sleeve during a single procedure.

For some applications, positioning the implant structure along the annulus, and closing the opening of the at least one end of the sleeve include positioning the implant structure along the annulus, and closing the opening of the at least one end of the sleeve via a single catheter.

There is further provided, in accordance with some applications of the present invention, apparatus, including:

an annuloplasty structure configured for implantation along an annulus of an atrioventricular valve of a heart of a subject, the structure including:

a coiled element including:

at least one first portion thereof which is flexible and longitudinally compressible; and at least one second portion thereof in series with the first portion, the second portion being flexible and less longitudinally compressible than the first portion.

For some applications, the coiled element is shaped such that a pitch of the coiled element at the second portion is smaller than a pitch of the coiled element at the first portion.

For some applications, a radius of curvature at a center of the first portion is smaller than a radius of curvature at a center of the second portion, when no external force is applied to the annuloplasty structure.

For some applications, the annuloplasty structure includes an annuloplasty ring.

For some applications, the annuloplasty structure includes a partial annuloplasty ring.

For some applications, the apparatus further includes a contraction-restricting element configured to be coupled to the second portion of the coiled element, and the second portion is configured to be flexible and less longitudinally compressible than the first portion at least in part by virtue of the contraction-restricting element being coupled thereto.

For some applications, the contraction-restricting element includes an element selected from the group consisting of: a suture, a staple, a ratchet mechanism, and a bracket.

For some applications, a total length of the first portion includes less than 50% of a resting length of the coiled element.

For some applications, a total length of the first portion includes less than 30% of a resting length of the coiled element.

For some applications, the valve includes a native mitral valve of the subject, and the structure is configured for implantation along the native mitral valve in a manner in which at least the second portion of the implant structure is disposed along a portion of the annulus at a posterior leaflet of the valve.

For some applications, the second portion is configured to restrict contraction of the second portion while facilitating radial movement of the second portion of the implant structure.

For some applications, the atrioventricular valve includes a mitral valve, the coiled element includes a plurality of second portions, and the annuloplasty structure is configured for implantation along the annulus in a manner in which:

a first one of the second portions is configured to be coupled to the annulus in a vicinity of a left trigone adjacent to the mitral valve, and a second one of the second portions is configured to be coupled to the annulus in a vicinity of a right trigone adjacent to the mitral valve.

For some applications, the combined length of the first and second of the second portions is 10-50 mm.

For some applications, the annuloplasty structure is configured for implantation along the annulus in a manner in which a third one of the second portions is disposed along a portion of the annulus at a posterior leaflet of the valve.

For some applications, a length of the third one of the second portions is 3-120 mm.

For some applications, a length of the third one of the second portions includes more than 20% of a resting length of the coiled element.

For some applications, the annuloplasty structure includes:
a sleeve, the sleeve having first and second end portions, respectively, and a body portion that is between the first and second end portions; and
a contracting member that extends along the body portion between the first and second end portions of the sleeve, the contracting member having first and second end portions, the first end portion of the contracting member being coupled to the sleeve in a vicinity of the first end portion thereof, and the second end portion of the contracting member being coupled to the sleeve in a vicinity of the second end portion thereof,
the coiled element being configured to be coupled to the sleeve.

For some applications, the annuloplasty structure has a length of between 50 mm and 150 mm.

For some applications, the annuloplasty structure has a diameter of between 1 mm and 10 mm.

For some applications, the annuloplasty structure is configured to be implanted along an annulus of a mitral valve of the subject in a manner in which the annuloplasty structure is formed into at least a portion of an annuloplasty ring.

For some applications, the annuloplasty structure includes a partial annuloplasty ring having first and second free ends, the first end of the sleeve defining the first free end of the partial annuloplasty ring, and the second end of the sleeve defining the second free end of the partial annuloplasty ring.

For some applications, the coiled element includes a shape-memory material configured to be generally straightened from a coiled state during delivery of the annuloplasty structure to an implantation site of a body of the subject.

For some applications, the sleeve defines a lumen, and the coiled element includes an elongate coiled element disposed within the lumen of the sleeve.

For some applications, the coiled element includes an elongate coiled element that is configured to be coupled to a portion of an outer surface of the sleeve and rest alongside the portion of the outer surface of the sleeve.

There is additionally provided, in accordance with some applications of the present invention, apparatus, including:
an implant structure that is contractible at least in part, the implant structure including a sleeve, the sleeve having first and second end portions, respectively, and a body portion that is between the first and second end portions;
a contracting member that extends along the body portion between the first and second end portions of the sleeve, the contracting member having first and second end portions, the first end portion of the contracting member being coupled to the sleeve in a vicinity of the first end portion thereof, and the second end portion of the contracting member being coupled to the sleeve in a vicinity of the second end portion thereof; and
at least one contraction-restricting element that is coupled to the sleeve and configured to restrict contraction of a contraction-restricted portion of the implant structure during contraction of a remaining portion of the implant structure by the contracting member,
the one or more contraction-restricting elements being coupled to the first end portion of the contracting member and disposed along the implant structure at a distance of between 3 and 45 mm from the first end of the sleeve,
the contraction-restricting element being configured to restrict contraction of the contraction-restricted portion of the implant structure during contraction of a remaining portion of the implant structure by the contracting member.

For some applications, the implant is configured for implantation along a native annulus of a native atrioventricular valve of a patient in a manner in which at least the contraction-restricted portion of the implant structure is disposed along a portion of the annulus in a vicinity of a trigone of the valve, and the contraction-restriction element is coupled to the contraction-restricted portion.

For some applications, the apparatus further includes a contracting mechanism coupled to the implant structure and configured to contract at least a contraction-facilitated portion of the implant structure.

For some applications, the contracting mechanism is disposed at a first portion of the implant structure, and the contracting member extends along the implant structure toward the second end of the sleeve.

There is additionally provided, in accordance with some applications of the present invention, a method, including:
positioning an annuloplasty structure along an annulus of an atrioventricular valve of a subject, the implant structure including a sleeve;
fastening the annuloplasty structure to the annulus;
while the annuloplasty structure is in a fastened state with respect to the annulus, coupling at least one contraction-restricting element to at least one contraction-restricted portion of the annuloplasty structure; and
subsequently, contracting at least one contraction-facilitated portion of the annuloplasty structure, the contraction-restricting element restricting contraction of the contraction-restricted portion during the contracting.

For some applications, coupling the contraction-restricting element to the contraction-restricted portion of the annuloplasty structure includes coupling the contraction-restricting element to a portion of the annuloplasty structure disposed along a portion of the annulus at a posterior leaflet of the valve.

For some applications, coupling the contraction-restricting element to the contraction-restricted portion of the annuloplasty structure includes coupling the contraction-restricting element to an outer surface of the annuloplasty structure.

For some applications, coupling the contraction-restricting element to the contraction-restricted portion of the annuloplasty structure includes restricting contraction of the contraction-restricted portion of the annuloplasty structure while facilitating radial movement of the contraction-restricted portion of the annuloplasty structure.

For some applications, positioning the annuloplasty structure along the annulus of the atrioventricular valve includes positioning the annuloplasty structure in a manner in which the contraction-restricted portion of the annuloplasty structure is disposed along a portion of the annulus at a posterior leaflet of the valve, and coupling the contraction-restricting element to the contraction-restricted portion of the annuloplasty structure includes restricting contraction of the contraction-restricted portion of the annulus at the posterior leaflet of the valve.

For some applications, coupling the contraction-restricting element to the contraction-restricted portion of the annuloplasty structure includes advancing into at least a portion of a lumen of the sleeve of the annuloplasty structure, a segment having at least a portion thereof that is non-compressible along a longitudinal axis of the segment.

For some applications, advancing the segment into the portion of the lumen of the sleeve includes advancing a segment that is disposed adjacently to one or more portions that are compressible along the longitudinal axis of the segment.

For some applications, advancing the segment into the portion of the lumen of the sleeve includes restricting contraction of the contraction-restricted of the annuloplasty structure while facilitating radial movement of the contraction-restricted portion of the annuloplasty structure.

For some applications, advancing the segment into the portion of the lumen of the sleeve includes advancing a coiled segment into the portion of the sleeve.

For some applications, the method further includes, prior to advancing the coiled segment within the sleeve, advancing the coiled segment toward the sleeve in a generally straightened configuration, and advancing the coiled segment into the portion of the sleeve includes allowing the segment to form a coil within the sleeve.

For some applications, fastening the annuloplasty structure to the annulus includes:
removably positioning a deployment manipulator tube through the opening and at least partially within the lumen of the sleeve of the annuloplasty structure, such that the deployment manipulator tube extends out of the at least one end of the sleeve; and
driving one or more tissue anchors through a wall of the sleeve from within the lumen of the sleeve.

For some applications:
driving the one or more anchors includes advancing through the deployment manipulator tube an anchor driver that is reversibly couplable to the one or more anchors,
exposing a distal end of the anchor driver from within a distal end of the deployment manipulator tube; and
deflecting through the sleeve the distal end of the anchor driver.

For some applications, the method further includes maintaining relative positioning of the annuloplasty structure relative to the manipulator tube during the deflecting by applying a force to one or more stiffening elements that are threaded through the sleeve of the annuloplasty structure.

For some applications, coupling the contraction-restricting element to the contraction-restricted portion includes coupling the contraction-restricting element to a portion of the annuloplasty structure that is between 3 and 45 mm from at least one end of the sleeve, while facilitating contraction of the contraction-facilitated portion of the annuloplasty structure.

For some applications:
the at least one end of the sleeve defines a first free end of the annuloplasty structure,
the annuloplasty structure defines a second free end, and
fastening the annuloplasty structure to the annulus includes:
fastening the first free end of the of the annuloplasty structure to the portion of the atrial wall by fastening the contraction-restricted portion of the annuloplasty structure to the portion of the atrial wall,
fastening the contraction-facilitated portion of the annuloplasty to a posterior portion of the annulus between the first and second trigones, and
contracting the first portion of the annuloplasty structure includes contracting the contraction-facilitated portion of the annuloplasty structure that is between the first and second trigones.

For some applications:
the at least one end of the sleeve defines a first free end of the annuloplasty structure,
the annuloplasty structure defines a second free end, and
fastening the annuloplasty structure to the annulus includes:
fastening the annuloplasty structure to a first trigone of the valve by fastening the annuloplasty structure to the valve in a vicinity of the first free end; and
fastening the annuloplasty structure to a second trigone of the valve by fastening the annuloplasty structure to the valve in a vicinity of the second free end.

For some applications:
fastening the annuloplasty structure to the first trigone includes fastening the first free end of the of the annuloplasty structure to the first trigone,
fastening the annuloplasty structure to the second trigone includes fastening the second free end of the of the annuloplasty structure to the second trigone,
fastening the annuloplasty structure to the annulus includes fastening the entire annuloplasty structure along the annulus between the first and second trigones, and
contracting the contraction-facilitated portion of the annuloplasty structure includes contracting a portion of the annuloplasty structure that is between the second end and the contraction-restricted portion of the annuloplasty structure.

For some applications:
fastening the annuloplasty structure to the first trigone includes:
fastening the first free end of the of the annuloplasty structure to a portion of an atrial wall of a heart of the subject, and
fastening a portion of the annuloplasty structure that is adjacent to the first free end to the first trigone, and
fastening the annuloplasty structure to the second trigone includes fastening the second free end of the of the annuloplasty structure to the second trigone.

For some applications:
the atrioventricular valve includes a mitral valve;
the annuloplasty structure is shaped so as to define a first end and a second end, and
positioning the annuloplasty structure along the annulus includes:
positioning the first end of the annuloplasty structure at a first trigone of the mitral valve; and
positioning the second end of the annuloplasty structure at a second trigone of the mitral valve.

For some applications, contracting the first portion of the annuloplasty structure includes drawing the first and second ends of the annuloplasty structure toward one another.

For some applications, fastening includes:
anchoring a first location of annuloplasty structure to a first trigone of the valve; and
anchoring a second location of the annuloplasty structure to a second trigone of the valve.

For some applications, anchoring the first location includes anchoring a first free end of the annuloplasty structure to the first trigone, and anchoring the second location includes anchoring a second free end of the annuloplasty structure to the second trigone.

The present invention will be more fully understood from the following detailed description of embodiments thereof taken together with the drawings, in which:

BRIEF DESCRIPTION OF THE DRAWINGS

FIG. 1 is a schematic illustration of a system for repairing a dilated atrioventricular valve, such as a mitral valve, in accordance with an application of the present invention;

FIGS. 2A-I are schematic illustrations of a procedure for implanting the implantable structure of FIG. 1 to repair a mitral valve, in accordance with an application of the present invention;

FIGS. 7A-B show individual components of a contracting mechanism, in accordance with some applications of the present invention;

FIG. 8 is another cross-sectional illustration of the contracting mechanism of FIG. 6, in accordance with some applications of the present invention;

FIG. 9 is a schematic illustration of the implant structure of FIG. 1 comprising a force-distributing element in a vicinity of a proximal end of the structure, in accordance with some applications of the present invention;

FIGS. 10A-B, 11-12 and 13A-B are schematic illustrations of the implant structure of FIG. 1 comprising an approximating element in a vicinity of a proximal end of the structure, in accordance with some applications of the present invention;

FIG. 16 is a schematic illustration of an anchor deployment manipulator that facilitates deployment of one or more anchors through the sleeve of the implant structure of FIG. 15, in accordance with some applications of the present invention;

FIGS. 17A-C are schematic illustrations of the anchor deployment manipulator of FIG. 16 advancing and deploying anchors from within the sleeve of the implant structure of FIG. 15, in accordance with some applications of the present invention;

FIGS. 19A-J are schematic illustrations of different configurations of tissue anchors, in accordance with respective applications of the present invention;

FIG. 22 is a schematic illustration of the implantable structure of FIG. 21 after implantation around the annulus of a mitral valve, in accordance with an application of the present invention;

FIGS. 23A-B are schematic illustrations of coupling elements, in accordance with respective applications of the present invention;

FIGS. 24A-E are schematic illustrations of configurations of the system of FIG. 1 comprising a coiled element, in accordance with respective applications of the present invention;

FIGS. 25A-E are schematic illustrations of additional configurations of the system of FIG. 1 comprising a coiled element, in accordance with respective applications of the present invention;

FIG. 28 is a schematic illustration of still another configuration of the implantable structure of FIG. 1, in accordance with an application of the present invention.

DETAILED DESCRIPTION OF EMBODIMENTS

Figure 2A:
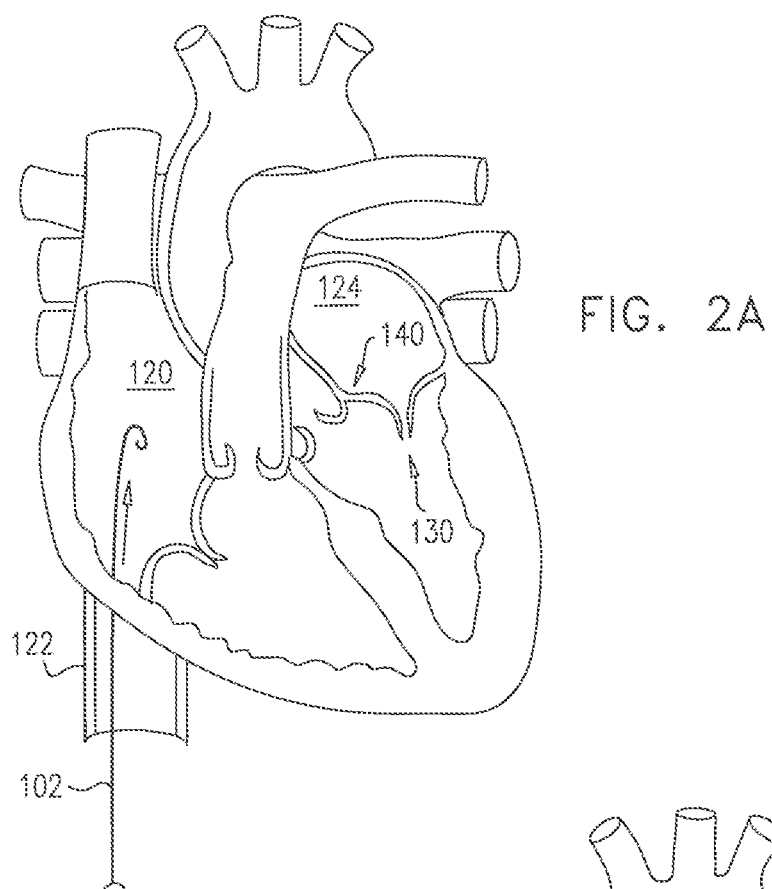

FIG. 1 is a schematic illustration of a system 20 for repairing a dilated atrioventricular valve, such as a mitral valve or a tricuspid valve, in accordance with an application of the present invention. System 20 comprises an adjustable implantable structure 22, shown in FIG. 1 in a straight, relaxed, non-contracted state, and an anchor deployment manipulator 24 (shown in FIGS. 2G-H). For some applications, implantable structure 22 is configured to be deployed as an annuloplasty ring, while for other applications, implantable structure 22 is configured to be deployed as a base ring to which a prosthetic valve is coupled, such as described hereinbelow with reference to FIG. 29A-B or 30. Implantable structure 22 comprises a flexible sleeve 26. Anchor deployment manipulator 24 is advanced into sleeve 26, as shown in FIGS. 2G-H, and, from within the sleeve, deploys tissue anchors through a wall of the sleeve into cardiac tissue, thereby anchoring the ring around at least a portion of the valve annulus. For some applications, anchor deployment manipulator is implemented using techniques described in US Patent Application Publication 2010/0280604, which is incorporated herein by reference, with reference to FIGS. 2, 3, 4, 5A, 5B, 6A, 6B, 7, 8, 13, and/or 20A-E thereof.

For some applications, implantable structure 22 comprises a partial annuloplasty ring. In these applications, sleeve 26 is configured to be placed only partially around the valve annulus (i.e., to assume a C-shape), and, once anchored in place, to be contracted so as to circumferentially tighten the valve annulus. For other applications, sleeve 26 is configured to be implanted entirely around the valve annulus in a closed loop, such as described hereinbelow with reference to FIG. 5. 20, 22, or 29A-B.

Implantable structure 22 further comprises a contracting assembly 40, which facilitates contracting of the implantable structure. Contracting assembly 40 comprises a contracting mechanism 28, and a longitudinal contracting member 30, which is coupled to contracting mechanism 28, extends along a portion of the sleeve, and is typically flexible. For example, contracting member 30 may comprise at least one wire. Contracting assembly 40 is described in more detail hereinbelow. In addition, the implantable structure typically comprises a plurality of tissue anchors 38, typically between about 5 and about 20 anchors, such as about 10 or about 16 anchors. In FIG. 1, anchors 38 are shown coupled to implantable structure 22, deployed through the wall of sleeve 26. For some applications, anchors 38 are configured as described hereinbelow with reference to FIGS. 19A-C, 19D, 19E, 19F, 19G, 19H, 19I, and/or 19J, while for other applications, anchors 38 comprise tissue anchors known in the art.

Flexible sleeve 26 may comprise a braided, knitted, or woven mesh or a tubular structure comprising ePTFE. For some applications, the braid comprises metal and fabric fibers. The metal fibers, which may comprise Nitinol for example, may help define the shape of the sleeve, e.g., hold the sleeve open to provide space for passage and manipulation of deployment manipulator 24 within the sleeve. The fabric fibers may promote tissue growth into the braid. Typically, sleeve 26 is substantially longitudinally non-extensible, i.e., a length thereof is substantially constant, i.e., cannot be longitudinally stretched, under normal usage conditions. Alternatively, the sleeve is somewhat elastic, which gives the sleeve a tendency to longitudinally contract, thereby helping tighten the sleeve. For example, the sleeve may be bellows- or accordion-shaped.

For some applications, the sleeve is configured to have a tendency to assume a straight shape when in its relaxed, non-contracted state. This straightness may help the surgeon locate the next site for each subsequent anchor during the implantation procedure. For example, because the sleeve assumes a generally straight shape, the sleeve may help provide an indication of distance between adjacent anchoring sites. For some applications, the sleeve is configured to have a controllably variable stiffness. For example, a somewhat stiff wire may be placed in the sleeve to provide the stiffness, and subsequently be removed at the conclusion of the implantation procedure when the stiffness is no longer useful.

For some applications, sleeve 26 comprises a plurality of radiopaque markers 39, which are positioned along the sleeve at respective longitudinal sites. The markers may provide an indication in a radiographic image (such as a fluoroscopy image) of how much of the sleeve has been deployed at any given point during an implantation procedure, in order to enable setting a desired distance between anchors 38 along the sleeve. For some applications, the markers comprise a radiopaque ink.

Typically, at least a portion (e.g., at least three, such as all) of the longitudinal sites are longitudinally spaced at a constant interval. Typically, the longitudinal distance between the distal edges of adjacent markers, and/or the distance between the proximal edges of adjacent markers, is set equal to the desired distance between adjacent anchors. For example, the markers may comprise first, second, and third markers, which first and second markers are adjacent, and which second and third markers are adjacent, and the distance between the proximal and/or distal edges of the first and second markers equal the corresponding distance between the proximal and/or distal edges of the second and third markers. For example, the distance may be between 3 and 15 mm, such as 6 mm, and the longitudinal length of each marker may be between 0.1 and 14 mm, such as 2 mm. (If, for example, the distance were 6 mm and the length were 2 mm, the longitudinal gaps between adjacent markers would have lengths of 4 mm.)

(In this context, in the specification and in the claims, "proximal" means closer to the orifice through which system 20 is originally placed into the body of the patient, and "distal" means further from this orifice.)

Longitudinal contracting member 30 comprises a wire, a ribbon, a rope, or a band, which typically comprises a flexible and/or superelastic material, e.g., nitinol, polyester, HDPE, stainless steel, or cobalt chrome. For some applications, the wire comprises a radiopaque material. For some applications, longitudinal contracting member 30 comprises a braided polyester suture (e.g., TICRON™). For some applications, longitudinal contracting member 30 is coated with polytetrafluoroethylene (PTFE). For some applications, contracting member 30 comprises a plurality of wires that are intertwined to form a rope structure. For some applications, implantable structure 22 comprises a plurality of contracting members 30, which may extend along generally the same longitudinal portion of sleeve 26, or along respective, different portions of sleeve 26 (e.g., as described hereinbelow with reference to FIG. 28).

For some applications, contracting member 30 is positioned at least partially within a lumen of the sleeve 26, such as entirely within the lumen (as shown in FIGS. 1, 2H-I, 4, 5, 21, and 22, for example). For some applications in which the contracting member is positioned partially within the lumen, the contracting member is sewn into the wall of the sleeve, such that the contracting member is alternatingly inside and outside of the sleeve along the length of the sleeve (configuration not shown). Optionally, sleeve 26 defines an internal channel within which member 30 is positioned (configuration not shown). Alternatively, the contracting member is disposed outside the lumen of the sleeve, such as alongside an outer wall of the sleeve. For example, sleeve 26 may define an external channel within which contracting member 30 is positioned, or the sleeve may comprise or be shaped so as to define external coupling elements, such as loops or rings (configuration not shown). For some applications, contracting member 30 is positioned approximately opposite the anchors.

For some applications of the present invention, contracting mechanism 28 comprises a rotatable structure, such as a spool 46. The rotatable structure is arranged such that rotation thereof applies a longitudinal contracting force, thereby contracting at least a longitudinal portion of implantable structure 22. Typically, in these applications, contracting mechanism 28 further comprises a housing 44 in which the rotatable structure, e.g., the spool, is positioned. Contracting member 30 has first and second member ends, and a first member end portion, which extends from the first member end toward the second member end along only a longitudinal portion of the contracting member. For some applications, the first member end portion, e.g., the first member end of contracting member 30, is coupled to contracting mechanism 28, such as the rotatable structure, e.g., the spool (alternatively, although the first member end portion is coupled to the contracting mechanism, the first member end protrudes beyond the contracting mechanism). For example, spool 46 may be shaped to provide a hole 42 or other coupling mechanism for coupling the first end of contracting member 30 to the spool, and thereby to contracting mechanism 28. Contracting assembly 40 is arranged such that rotation of the spool winds a portion of the contracting member around the spool. Alternatively, contracting member 30 may comprise at least one wire (e.g., exactly one wire) that passes through a coupling mechanism of spool 46, in order to couple the wire to the spool. The ends of the wire are brought together, and together serve as a second end 53 of contracting member 30. In this configuration, approximately the longitudinal center of the wire serves as the first end of the contracting member.

Alternatively, contracting mechanism 28 may comprise a ratchet contracting mechanism, which typically comprises a ratchet-coupling housing. Contracting member 30 is shaped so as to define engaging structures, such as grooves or teeth. Techniques may be used that are described in International Application PCT/IL2009/000593, filed Jun. 15, 2009, which published as PCT Publication WO 10/004546, and in U.S. application Ser. No. 12/996,954, which published as US Patent Application Publication 2011/0166649, in the national stage thereof, all of which applications and publications are incorporated herein by reference.

Further alternatively, contracting mechanism 28 may comprise a housing or other structure (e.g., a ring or an eyelet) which is shaped so as to define an opening therethrough. Contracting member 30 is drawn through the opening (such that the first member end protrudes beyond the opening), and, once a desired length has been achieved, is locked, such as using a locking bead, or by crimping or knotting.

Contracting member 30 extends along less than the entire length of sleeve 26. Contracting mechanism 28 (e.g., housing 44 thereof) is disposed at a first site 34 of sleeve 26 that is a first longitudinal distance D1 from a first end of the sleeve, either a proximal end 49 of sleeve 26, as shown in FIG. 1, or a distal end 51 of sleeve 26, as shown in FIGS. 2G-I. (Longitudinal distance D1 is measured between the first end of the sleeve and the portion of contracting mechanism 28 that is closest to the first end.) For some applications, second end 53 of contracting member 30 is coupled to the sleeve at a second site 36 that is a second longitudinal distance D2 from a second end of the sleeve, which second end is longitudinally opposite the first end of the sleeve. For applications in which contracting mechanism 28 comprises a rotatable structure, rotation of the rotatable structure, such as spool 46, longitudinally contracts at least a portion of the sleeve, such as by winding a portion of the contracting member around the spool, thereby pulling the far end of the implantable structure toward the spool and shortening and tightening the implantable structure. Such rotation of the rotatable structure, or other actuation of contracting assembly 40, typically applies a longitudinal contracting force only between first and second sites 34 and 36, which longitudinally contracts at least a portion, e.g. all, of the sleeve only between first and second sites 34 and 36. (For example, the longitudinal force may longitudinally contract less than the entire sleeve between first and second sites 34 and 36 in applications in which system 20 comprises coiled element 240, which provides a contraction-restricting portion of the sleeve, as described hereinbelow with reference to FIGS. 24A-E and/or 25A-E.) Therefore, the portions of the sleeve beyond first and second sites 34 and 36 (towards the ends of the sleeve) are not contracted by contracting assembly 40.

Typically, contracting member 30 extends along (i.e., a distance along the sleeve between first and second sites 34 and 36 equals) no more than 80% of the length of the sleeve, e.g., no more than 60% or no more than 50% of the length. Typically, contracting member 30 extends along no more than 80% of a circumference of the loop when the sleeve is placed around the annulus (i.e., the total length of the loop less the length of any overlapping portion). Typically, contracting member 30 extends along (i.e., a distance along the sleeve between first and second sites 34 and 36 equals) at least 20% of the length of the sleeve, e.g., at least than 40% or at least than 50% of the length. Typically, contracting member 30 extends along at least 20% of the circumference of the loop when the sleeve is placed around the annulus, e.g., at least 30% or at least 50%.

For some applications, first longitudinal distance D1, measured when sleeve 26 is in a straight, relaxed, non-contracted state, is at least 3 mm, e.g., at least 5 mm, such as at least 9 mm, e.g., at least 14 mm; no greater than 20 mm, such as no greater than 15 mm; and/or between 5 and 20 mm, such as between 9 and 15 mm. Alternatively or additionally, for some applications, second longitudinal distance D2, measured when sleeve 26 is in a straight, relaxed, non-contracted state, is at least 3 mm, e.g., at least 5 mm, such as at least 9 mm, e.g., at least 14 mm; no greater than 20 mm, such as no greater than 15 mm; and/or between 5 and 20 mm, such as between 9 and 15 mm. Further alternatively or additionally, first longitudinal distance D1, measured when sleeve 26 is in a straight, relaxed, non-contracted state, is no greater than 20%, such as no greater than 10% of a total length of the sleeve, measured when sleeve 26 is in a straight, relaxed, non-contracted state. Further alternatively or additionally, second longitudinal distance D2, measured when sleeve 26 is in a straight, relaxed, non-contracted state, is no greater than 30%, such as no greater than 20%, e.g., no greater than 10% of the total length of the sleeve measured, when sleeve 26 is in a straight, relaxed, non-contracted state. For some applications, the total length of the sleeve, measured when the sleeve is in a straight, relaxed, non-contracted state is at least 5 cm, no more than 25 cm, and/or between 5 and 25 cm. For some applications in which the sleeve is implanted in a closed loop, the total length of the sleeve is selected to be between 1.3 and 1.4 times a circumference of the annulus, in order to provide overlapping portion 114, described hereinbelow with reference to FIGS. 4 and 5.

For some applications, at least one of tissue anchors 38 (e.g., exactly one, at least two, exactly two, at least three, exactly three, or at least four, or no more than four) is coupled to sleeve 26 longitudinally between contracting mechanism 28 (e.g., housing 44 thereof) and the first sleeve end (i.e., the end of the sleeve to which contracting mechanism 28 is closest), exclusive, and at least 3, such as at least 6, of tissue anchors 38 are coupled to the sleeve alongside contracting member 30, longitudinally between first site 34 and second site 36 (second member end 53), exclusive. (As used in the present application, including in the claims, "exclusive," when used with respect to a range of locations, means excluding the endpoints of the range.)

Alternatively or additionally, for some applications, at least one of tissue anchors 38 (e.g., exactly one, at least two, exactly two, at least three, exactly three, or at least four, or no more than four) is coupled to sleeve 26 longitudinally between second site 36 (second member end 53) and the second sleeve end (i.e., the end of the sleeve to which second member end 53 is closest), exclusive, and at least 3, such as at least 6, of tissue anchors 38 are coupled to the sleeve alongside contracting member 30, longitudinally between first site 34 and second site 36 (second member end 53), exclusive.

In the exemplary configuration shown in FIG. 1, exactly two tissue anchors 38 are coupled to the sleeve longitudinally between the contracting mechanism (e.g., the housing) (first site 34) and the first sleeve end, exclusive, exactly two tissue anchors are coupled to the sleeve longitudinally between first site 34 and second site 36 (second member end 53), exclusive, and exactly six tissue anchors 38 are coupled to the sleeve alongside the contracting member, longitudinally between first site 34 and second site 36 (second member end 53), exclusive.

Providing the one or more anchors beyond first and second sites 34 and 36 (i.e., beyond the contracting portion of contracting member 30) generally distributes force applied by contraction of contracting assembly 40 over these anchors. In contrast, in some configurations of implantable structure 22 in which anchors are not provided beyond first and second sites 34 and 36, the force applied by the contracting assembly is applied predominantly to the single anchor nearest the first end of the contracting member, and the single anchor nearest to second end of the contracting member.

For some applications, anchors 38 are positioned along sleeve 26 with a longitudinal distance of between 4.5 and 9 mm, such as 6 mm, between each pair of longitudinally-adjacent anchors.

It is noted that the anchors may be positioned as described above by a surgeon during an implantation procedure, such as described hereinbelow with reference to FIGS. 2A-I, or the anchors may be prepositioned in the sleeve.

Reference is now made to FIGS. 2A-I, which are schematic illustrations of a procedure for implanting implantable structure 22 to repair a mitral valve 130, in accordance with an application of the present invention. The procedure is typically performed with the aid of imaging, such as fluoroscopy, transesophageal echo, and/or echocardiography.

The procedure typically begins by advancing a semi-rigid guidewire 102 into a right atrium 120 of the patient, as shown in FIG. 2A.

Figure 2B:
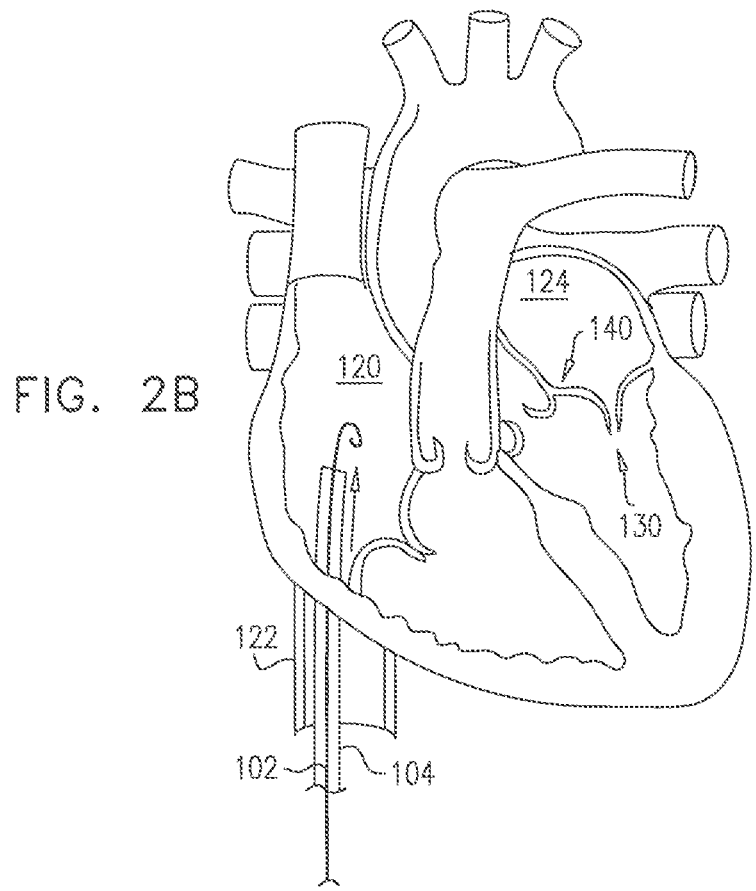
Figure 2C:
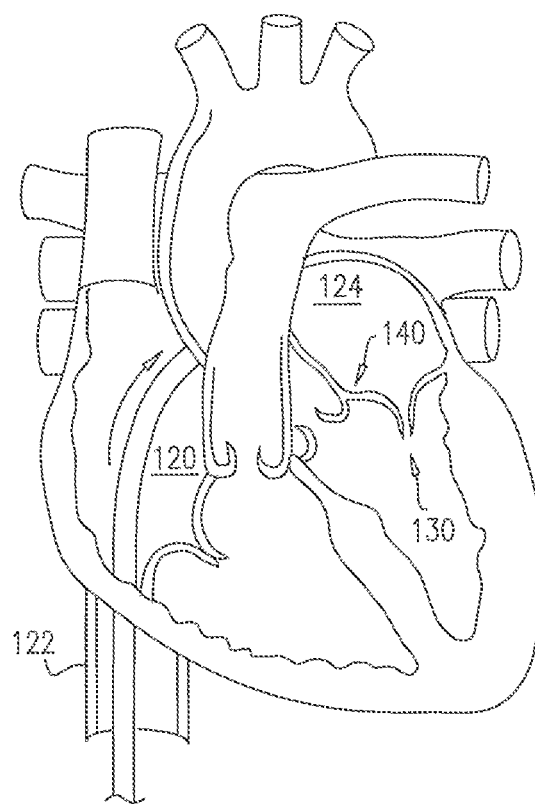

As show in FIG. 2B, guidewire 102 provides a guide for the subsequent advancement of a sheath 104 therealong and into the right atrium. Once sheath 104 has entered the right atrium, guidewire 102 is retracted from the patient's body. Sheath 104 typically comprises a 14-20 F sheath, although the size may be selected as appropriate for a given patient. Sheath 104 is advanced through vasculature into the right atrium using a suitable point of origin typically determined for a given patient. For example:

sheath 104 may be introduced into the femoral vein of the patient, through an inferior vena cava 122, into right atrium 120, and into a left atrium 124 transseptally, typically through the fossa ovalis;

sheath 104 may be introduced into the basilic vein, through the subclavian vein to the superior vena cava, into right atrium 120, and into left atrium 124 transseptally, typically through the fossa ovalis;

sheath 104 may be introduced into the external jugular vein, through the subclavian vein to the superior vena cava, into right atrium 120, and into left atrium 124 transseptally, typically through the fossa ovalis; or sheath 104 may be introduced into left atrium 124 transatrially, e.g., via the interatrial groove, or via the upper surface of the left atrium.

For some applications, sheath 104 is advanced through an inferior vena cava 122 of the patient (as shown) and into right atrium 120 using a suitable point of origin typically determined for a given patient.

Sheath 104 is advanced distally until the sheath reaches the interatrial septum.

Figure 2D:
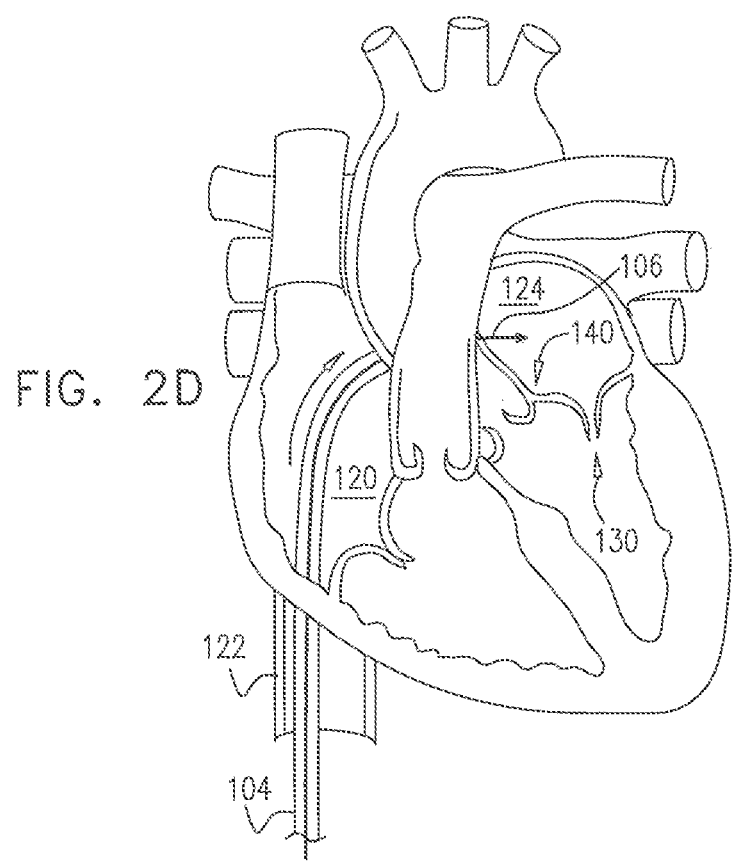

As shown in FIG. 2D, a resilient needle 106 and a dilator (not shown) are advanced through sheath 104 and into the heart. In order to advance sheath 104 transseptally into left atrium 124, the dilator is advanced to the septum, and needle 106 is pushed from within the dilator and is allowed to puncture the septum to create an opening that facilitates passage of the dilator and subsequently sheath 104 therethrough and into left atrium 124. The dilator is passed through the hole in the septum created by the needle. Typically, the dilator is shaped to define a hollow shaft for passage along needle 106, and the hollow shaft is shaped to define a tapered distal end. This tapered distal end is first advanced through the hole created by needle 106. The hole is enlarged when the gradually increasing diameter of the distal end of the dilator is pushed through the hole in the septum.

Figure 2E:
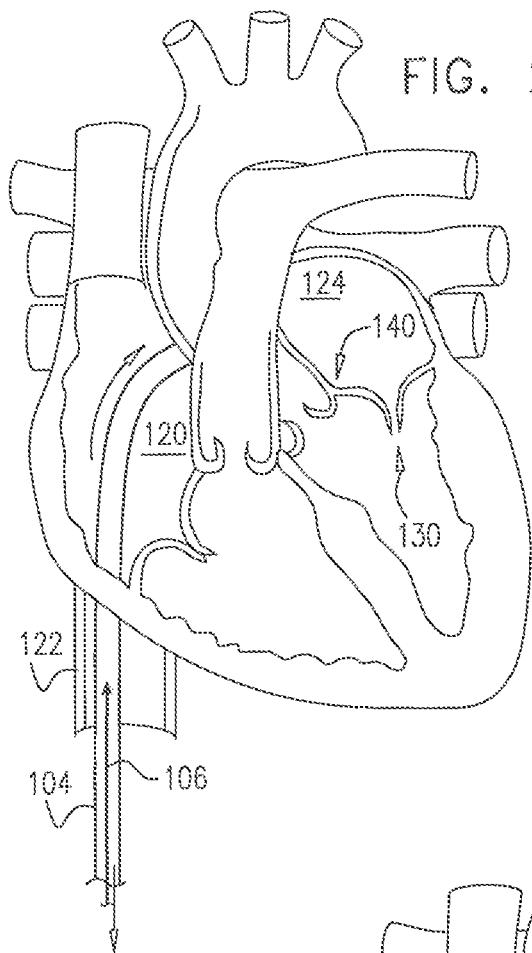

The advancement of sheath 104 through the septum and into the left atrium is followed by the extraction of the dilator and needle 106 from within sheath 104, as shown in FIG. 2E.

Figure 2F:
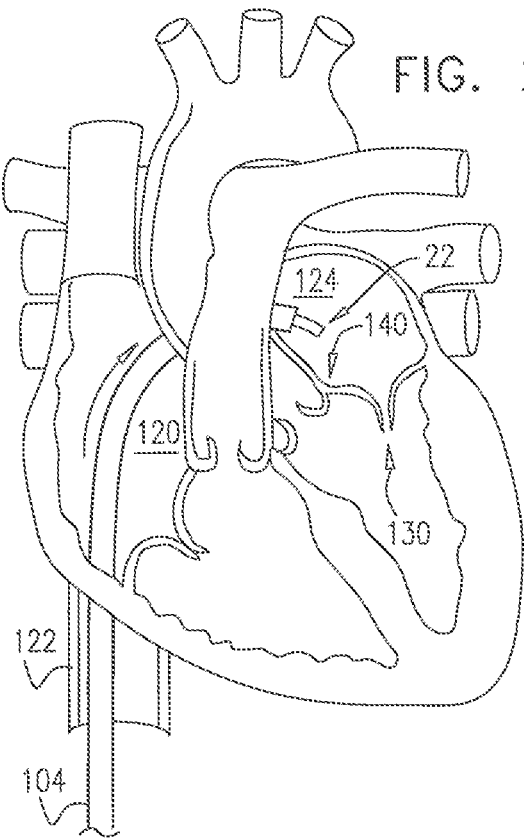
Figure 2G:
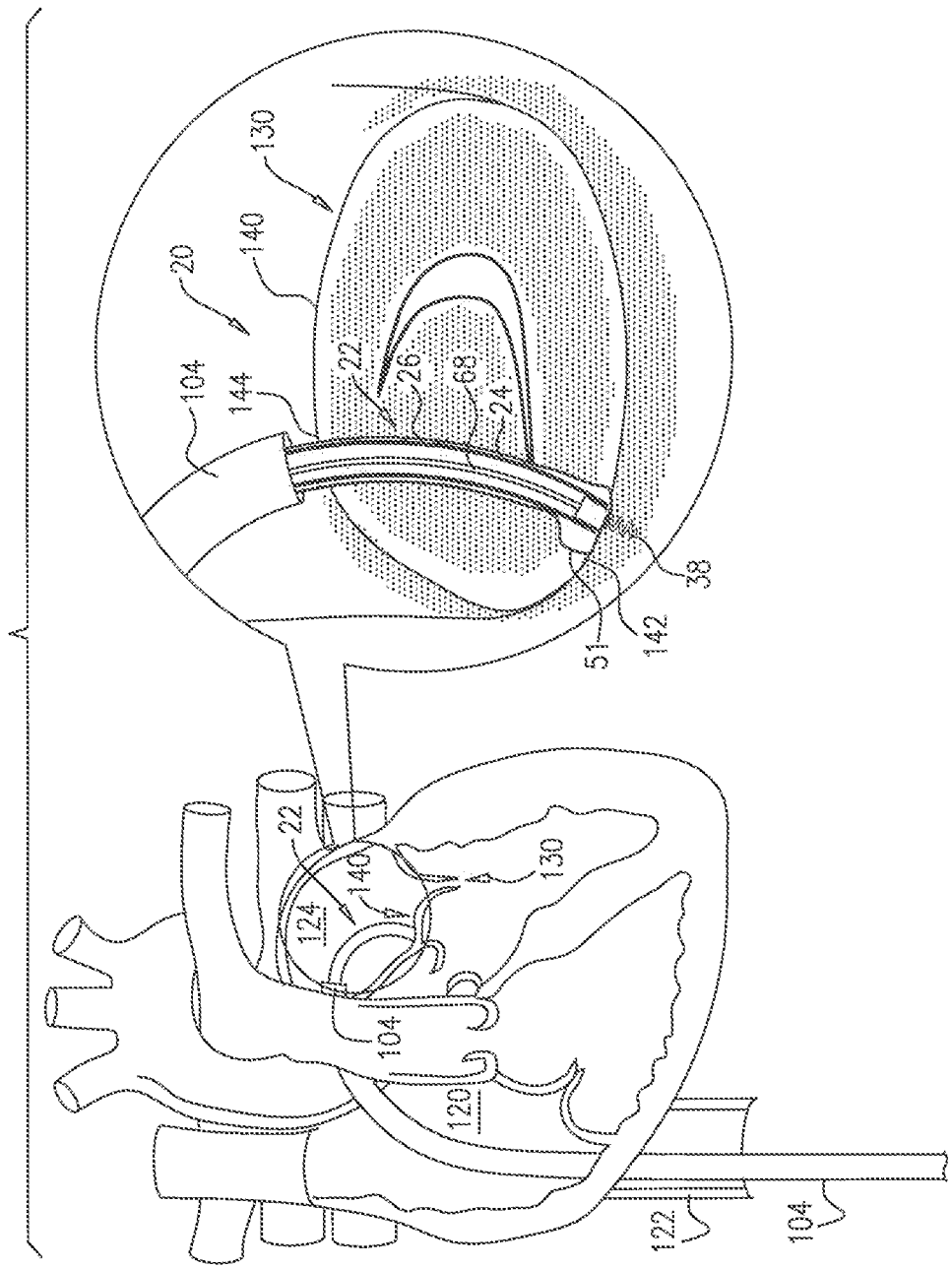
Figure 2H:
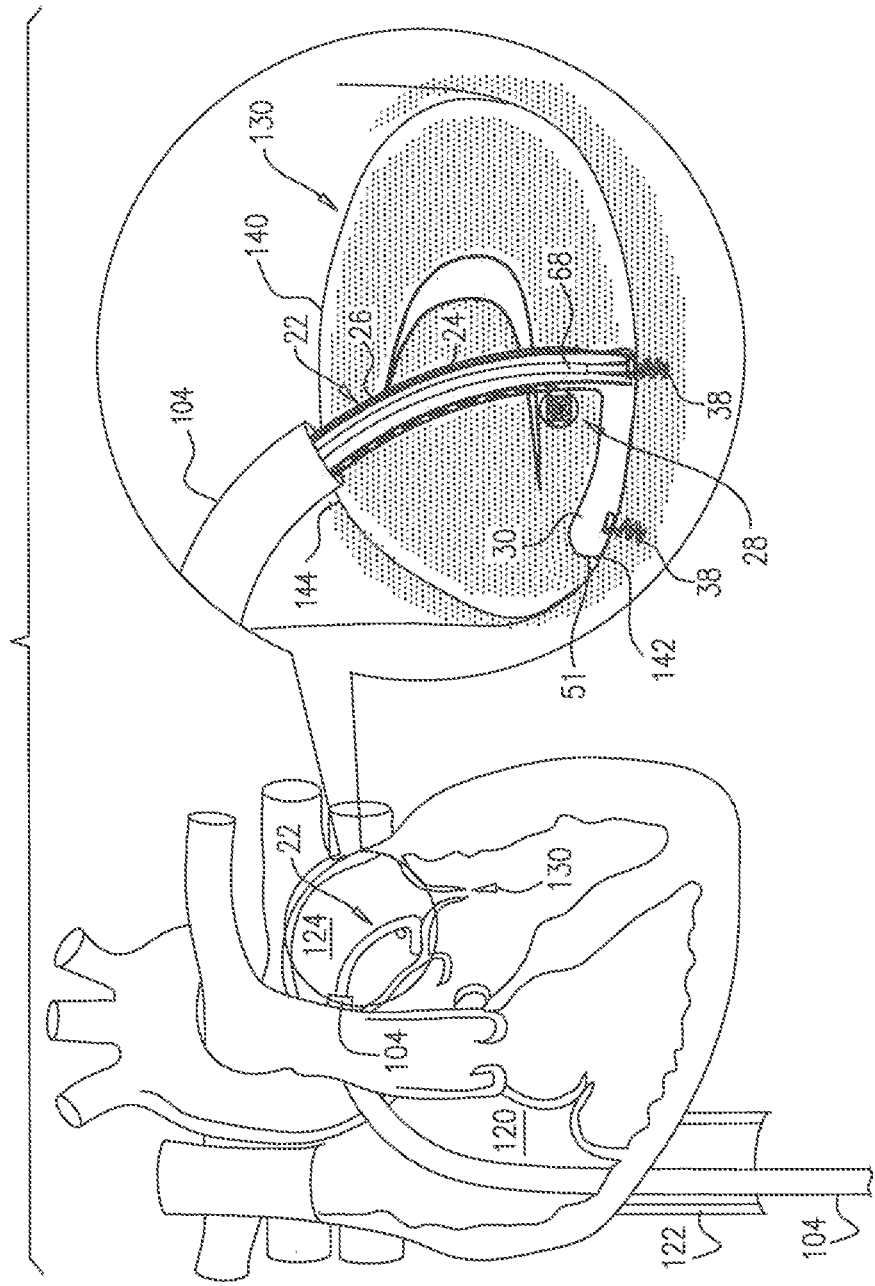

As shown in FIG. 2F, implantable structure 22 (with anchor deployment manipulator 24 therein) is advanced through sheath 104 into left atrium 124.

As shown in FIG. 2G, distal end 51 of sleeve 26 is positioned in a vicinity of a left fibrous trigone 142 of an annulus 140 of mitral valve 130. (It is noted that for clarity of illustration, distal end 51 of sleeve 26 is shown schematically in the cross-sectional view of the heart, although left trigone 142 is in reality not located in the shown cross-sectional plane, but rather out of the page closer to the viewer.) Alternatively, the distal end is positioned in a vicinity of a right fibrous trigone 144 of the mitral valve (configuration not shown). Further alternatively, the distal end of the sleeve is not positioned in the vicinity of either of the trigones, but is instead positioned elsewhere in a vicinity of the mitral valve, such as in a vicinity of the anterior or posterior commissure. Still further alternatively, for some applications, the distal end is positioned along an anterior portion of the annulus, such as described hereinbelow with reference to FIG. 5. For some applications, outer tube 66 of anchor deployment manipulator 24 is steerable, as is known in the catheter art, while for other applications, a separate steerable tube is provided, such as described in the above-mentioned '604 publication, with reference to FIG. 15 and FIG. 16 thereof. In either case, the steering functionality typically allows the area near the distal end of the deployment manipulator to be positioned with six degrees of freedom. Once positioned at the desired site near the selected trigone, deployment manipulator 24 deploys a first anchor 38 through the wall of sleeve 26 into cardiac tissue near the trigone.

As shown in FIG. 2H, deployment manipulator 24 is repositioned along annulus 140 to another site selected for deployment of a second anchor 38. Typically, the first anchor is deployed most distally in the sleeve (generally at or within a few millimeters of the distal end of the sleeve), and each subsequent anchor is deployed more proximally, such that the sleeve is gradually pulled off (i.e., withdrawn from) the deployment manipulator in a distal direction during the anchoring procedure. The already-deployed first anchor 38 holds the anchored end of sleeve 26 in place, so that the sleeve is drawn from the site of the first anchor towards the site of the second anchor. Typically, as the sleeve is pulled off (i.e., withdrawn from) the deployment manipulator, the deployment manipulator is moved generally laterally along the cardiac tissue, as shown in FIG. 2H. Deployment manipulator 24 deploys the second anchor through the wall of the sleeve into cardiac tissue at the second site. Depending on the tension applied between the first and second anchor sites, the portion of sleeve 26 therebetween may remain tubular in shape, or may become flattened, which may help reduce any interference of the implantable structure with blood flow.

For some applications, in order to provide the second and subsequent anchors, anchor driver 68 is withdrawn from the subject's body via sheath 104 (typically while leaving outer tube 66 of the deployment manipulator in place in the sleeve), provided with an additional anchor, and then reintroduced into the subject's body and into the outer tube. Alternatively, the entire deployment manipulator, including the anchor driver, is removed from the body and subsequently reintroduced upon being provided with another anchor. Further alternatively, deployment manipulator 24 is configured to simultaneously hold a plurality of anchors, and to deploy them one at a time at the selected sites. Yet further alternatively, the entire deployment manipulator, including the anchor driver, is removed from the body and subsequently reintroduced upon being provided with another anchor. Further alternatively, deployment manipulator 24 is configured to simultaneously hold a plurality of anchors, and to deploy them one at a time at the selected sites.

As shown in FIG. 2I, deployment manipulator 24 is repositioned along the annulus to additional sites, at which respective anchors are deployed, until the last anchor is deployed in a vicinity of right fibrous trigone 144 (or left fibrous trigone 142 if the anchoring began at the right trigone), thereby fastening sleeve 26 and implantable structure 22 to the annulus. Alternatively, the last anchor is not deployed in the vicinity of a trigone, but is instead deployed elsewhere in a vicinity of the mitral valve, such as in a vicinity of the anterior or posterior commissure.

For applications in which contracting mechanism 28 comprises spool 46, a rotation tool is typically used to rotate spool 46 of contracting mechanism 28, in order to tighten implantable structure 22. For some applications, the rotation tool is used that is described and shown in the above-mentioned '604 publication, with reference to FIGS. 6A-B, 7, and 8 thereof, and with reference to FIG. 6 hereinbelow. As described therein, contracting mechanism 28 comprises longitudinal member 86 that is attached to the contracting mechanism and passes out of the body of the subject, typically via sheath 104. In order to readily bring the rotation tool to a driving interface of contracting mechanism 28, the rotation tool is guided over longitudinal member 86. For some applications, spool 46 is configured as described in the '604 publication with reference to FIGS. 1-4, 6A-B, 7, and/or 8 thereof.

Spool 46 typically comprises a locking mechanism that prevents rotation of the spool after contracting member 30 has been tightened. For example, locking techniques may be used that are described and shown in US Application Publication 2010/0161047, which is incorporated herein by reference, with reference to FIG. 4 thereof, and/or with reference to FIGS. 6B, 7, and 8 of the above-mentioned '604 publication. Alternatively, for some applications, contracting mechanism 28 is configured to tighten contracting member 30, crimp the contracting member to hold the contracting member taut, and subsequently cut the excess length of the contracting member.

For some applications, a rotation handle is used to tighten the implantable structure, such as described and shown in the above-mentioned '604 publication, with reference to FIGS. 9A-C and 10A-D thereof. As mentioned above, deploying the one or more anchors beyond the contracting portion of contracting member 30 generally distributes force applied by contraction of contracting assembly 40 over these anchors. Alternatively or additionally, for some applications, a force-distributing element (e.g., such as element 540 shown hereinbelow with reference to FIGS. 9, 10A-B, 11-12, and 13A-B) is coupled to sleeve 26 in order to distribute the force applied by contraction of contraction assembly over these anchors.

For some applications, sleeve 26 is filled with a material (e.g., polyester, polytetrafluoroethylene (PTFE), polyethylene terephthalate (PET), or expanded polytetrafluoroethylene (ePTFE)) after being implanted. The material is packed within at least a portion, e.g., 50%, 75%, or 100%, of the lumen of sleeve 26. The filler material functions to prevent (1) formation within the lumen of sleeve 26 of clots or (2) introduction of foreign material into the lumen which could obstruct the sliding movement of contracting member 30. Typically, sleeve 26 comprises DACRON™.

For some applications, proximal end 49 of sleeve 26 is closed upon completion of the implantation procedure. For some applications, in order to close sleeve 26, a closure element 290 is coupled to proximal end 49 of sleeve 26, as described hereinbelow with reference to FIGS. 10A-B, 11-12, 13A-B, 14A-B, 15-16, 17A-F, and 18. Alternatively, the proximal end of the sleeve may have a natural tendency to close when not held open by deployment manipulator 24.

For some applications, following initial contraction of implantable structure 22 during the implantation procedure, the structure may be further contracted or relaxed at a later time after the initial implantation, such as between several weeks and several months after the initial implantation. Using real-time monitoring, tactile feedback and optionally in combination with fluoroscopic imaging, a rotation tool or anchor driver of a deployment manipulator may be reintroduced into the heart and used to contract or relax implantable structure 22.

Figure 3:
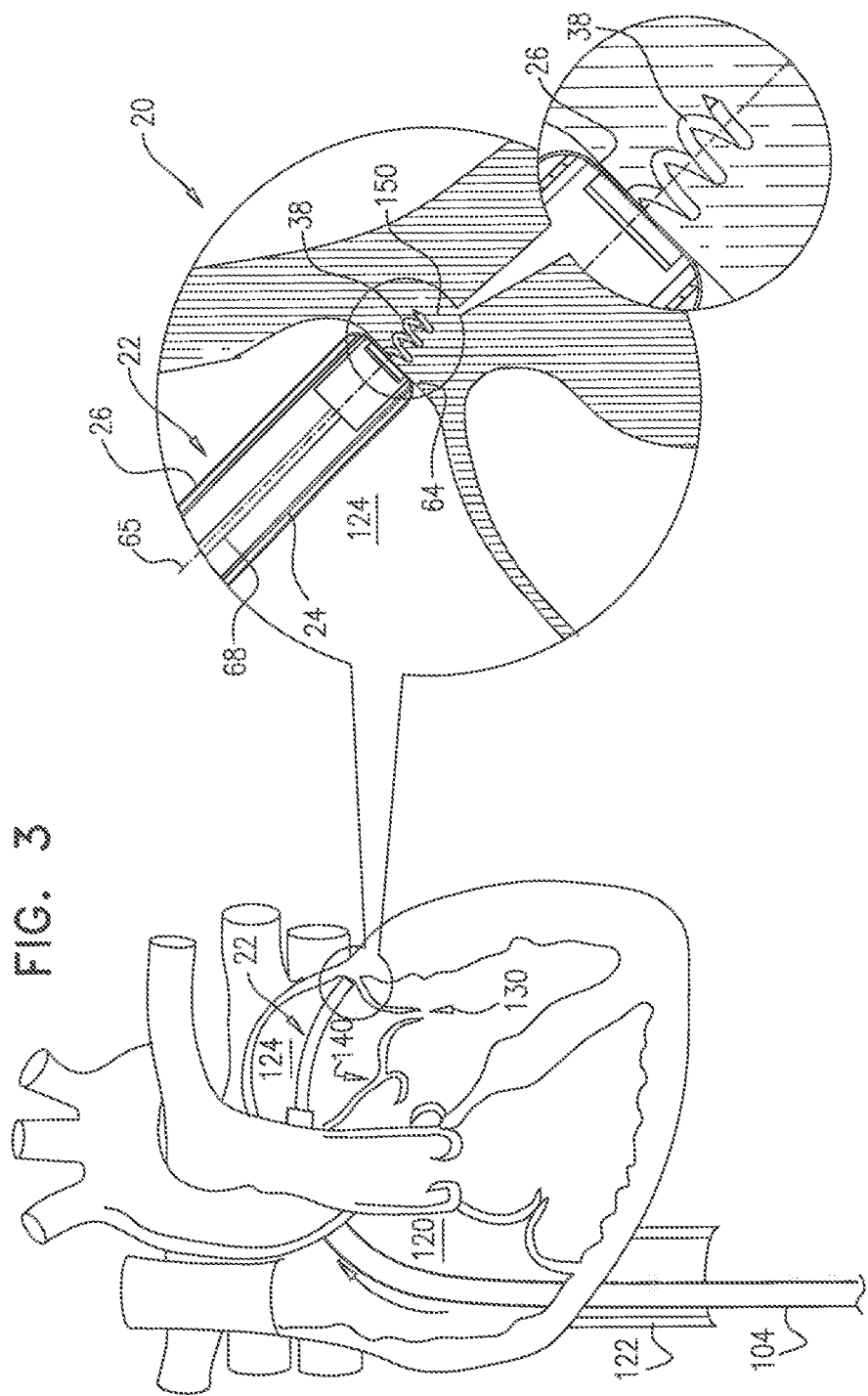
FIG. 3 is a schematic illustration of the deployment of a tissue anchor into cardiac tissue, in accordance with some applications of the present invention.

Reference is made to FIG. 3, which is a schematic illustration of the deployment of one of anchors 38 into cardiac tissue, in accordance with an application of the present invention. For these applications, one or more (such as all) of anchors 38 are deployed from left atrium 124, through tissue of the atrial wall, and into tissue of an upper region of a ventricular wall 150 near the atrium. Because the tissue of the upper region of ventricular wall is thicker than that of the atrial wall, deploying the anchors into the upper region of the ventricular wall generally provides more secure anchoring. In addition, because the anchors are not deployed laterally through the atrial wall, the risk of perforating the atrial wall is reduced.

Figure 4:
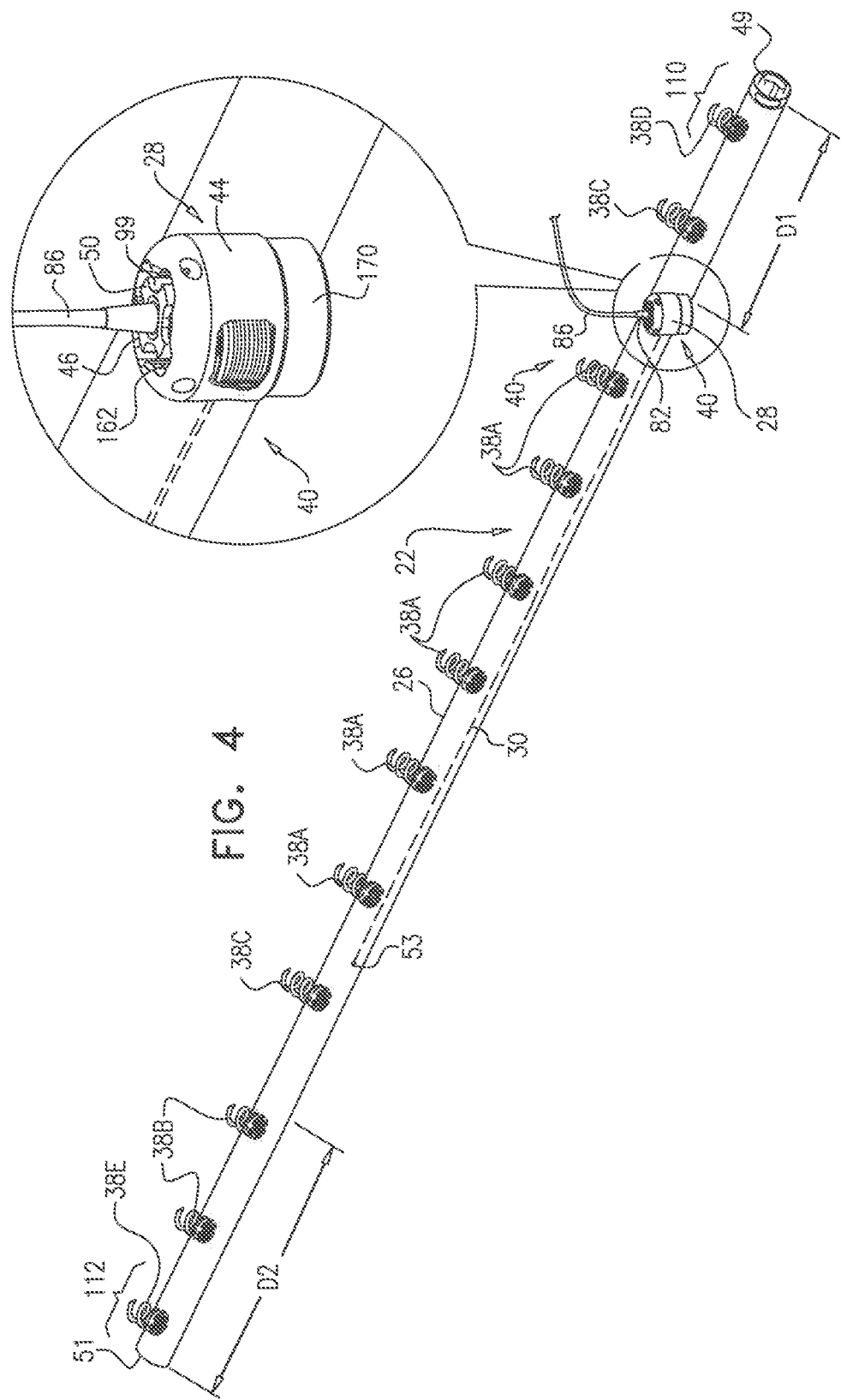
FIG. 4 is a schematic illustration of another configuration of the implantable structure of FIG. 1, prior to implantation, in accordance with an application of the present invention.
Figure 5:
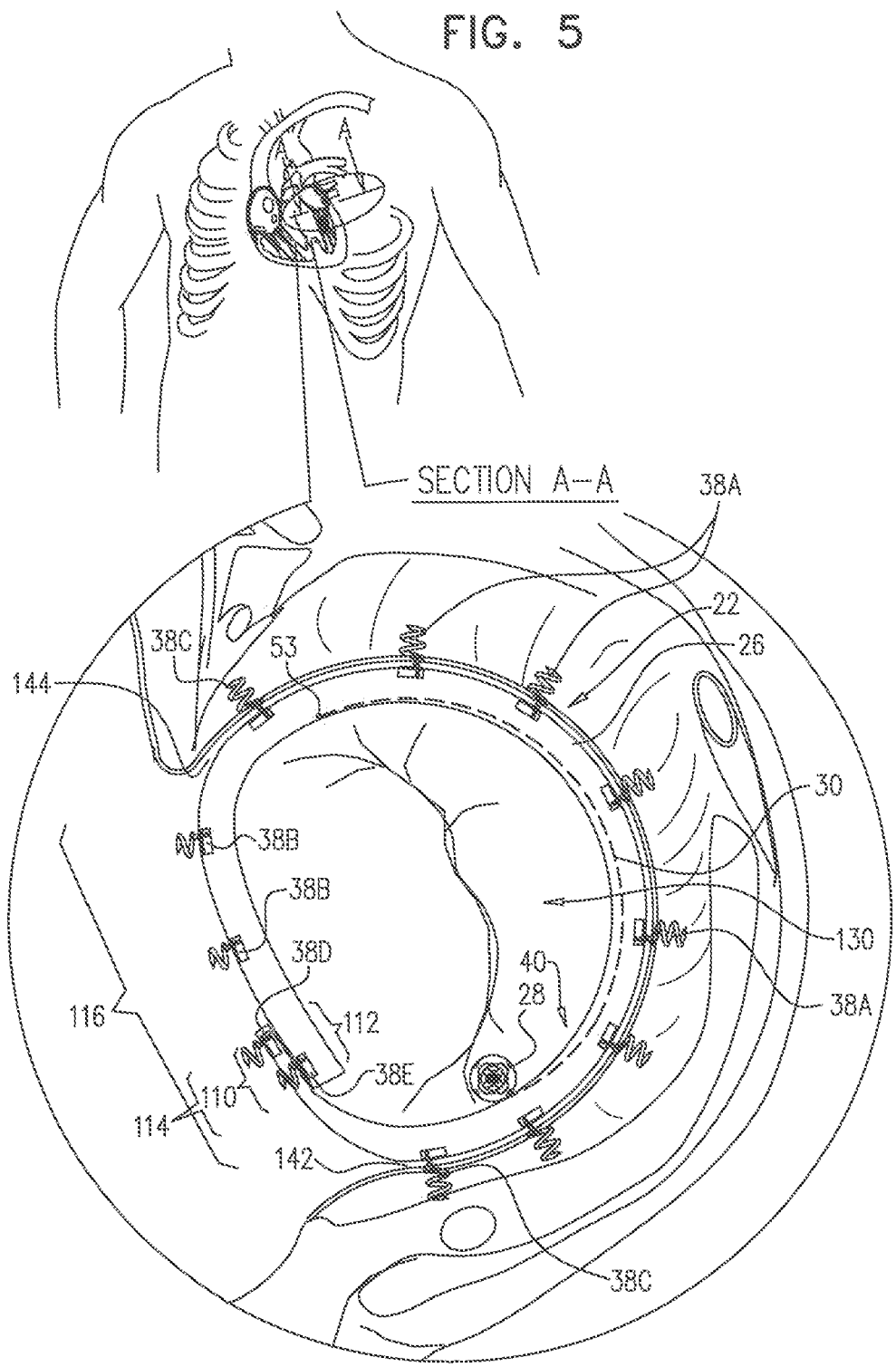
FIG. 5 is a schematic illustration of the implantable structure of FIG. 4 after implantation around the annulus of a mitral valve, in accordance with an application of the present invention.

Reference is now made to FIGS. 4 and 5, which are schematic illustrations of another configuration of implantable structure 22, in accordance with an application of the present invention. FIG. 4 shows implantable structure 22 in a straight, relaxed, non-contracted state, prior to implantation. FIG. 5 shows the implantable structure after implantation around the annulus of mitral valve 130, in accordance with an application of the present invention.

In this configuration, sleeve 26 is implanted in a closed loop. More particularly, a first portion 110 of sleeve 26 longitudinally extends from the first sleeve end (i.e., the end of the sleeve to which contracting mechanism 28, e.g., housing 44 thereof, is closest) toward contracting mechanism 28, e.g., housing 44 thereof (but typically does not extend all of the way to the contracting mechanism), and a second portion 112 of the sleeve longitudinally extends from the second sleeve end (i.e., the end of the sleeve to which second member end 53 is closest) toward second member end 53 (but typically does not extend all of the way to the second member end). As shown in FIG. 5, once implanted, sleeve 26 is arranged in a closed loop, such that first and second portions 110 and 112 of the sleeve together define a longitudinally overlapping portion 114 of the sleeve. The overlapping portion typically has a length of at least 2 mm (e.g., at least 5 mm), no more than 60 mm (e.g., no more than 50 mm), and/or between 2 mm (e.g., 5 mm) and 60 mm (e.g., 50 mm), and/or a length that is at least 1% of a total length of the sleeve, no more than 40% of the total length (e.g., no more than 30%), and/or between 1% and 40% (e.g., 30%) of the total length of the sleeve, measured when the sleeve is in a straight, relaxed, non-contracted state.

For some applications, at least one of tissue anchors 38 (labeled as 38E in FIGS. 4 and 5) penetrates both first and second portions 110 and 112 of the sleeve at overlapping portion 114. Such a mutual anchor helps ensure that the first and second portions remain tightly coupled together and to the tissue, so that the sleeve retains its closed loop shape. For some applications in which tissue anchor 38E comprises a coupling head and a tissue coupling element, such as described hereinbelow with reference to FIG. 19D, 19E, 19F, 19G, 19I, or 19J, the tissue coupling element penetrates both first and second portions 110 and 112 of the sleeve at overlapping portion 114, and the coupling head is positioned within one of first and second portions 110 and 112 of the sleeve at the overlapping portion. For example, in the deployment configuration shown in FIG. 5, the coupling head of anchor 38E is positioned within second portion 112.

This configuration of implantable structure 22 may be implanted using the procedure described hereinabove with reference to FIGS. 2A-I, with the following differences. Unlike in the deployment shown in FIGS. 2G-I, in this configuration sleeve 26 is deployed as a closed band around the entire annulus of the native valve, including an anterior portion 116 of the annulus (on the aortic side of the valve) between fibrous trigones 142 and 144. Typically, both first and second portions 110 and 112 of sleeve 26 (and thus overlapping portion 114) are positioned along anterior portion 116 of the annulus.

For some applications, during the implantation procedure, the first sleeve end (i.e., the end of the sleeve to which contracting mechanism 28, e.g., housing 44 thereof, is closest) is placed along at least a portion of anterior portion 116 and first portion 110 is extended along this portion. At least one anchor 38D is deployed through the wall of first portion 110 of sleeve 26 into cardiac tissue at the anterior portion of the annulus. Additional anchors 38A and/or 38C are deployed through the wall of the sleeve around the non-anterior remainder of the annulus, including the posterior portion thereof, as described hereinabove with reference to FIG. 2H. (Anchors 38C, if provided, are deployed beyond the ends of the contracting portion of contracting member 30, while anchors 38A are deployed along the portion of the sleeve including the contracting portion of the contracting member.)

A portion of the sleeve is placed on at least a portion of anterior portion 116 of the annulus, and, typically, one or more anchors 38B are deployed through the wall of the sleeve into tissue at the anterior portion of the annulus.

The sleeve is further extended around the annulus until second portion 112 overlaps with previously-deployed first portion 110 at overlapping portion 114, forming a complete ring. At least one anchor 38E is deployed from within second portion 112 through the wall of the sleeve and into the cardiac tissue, typically at anterior portion 116 of the annulus, or at a portion of the annulus near anterior portion 116. Typically, anchor 38E is deployed such that it additionally passes through previously-deployed first portion 110 (passing through the wall of first portion 110 twice). (Optionally, anchors 38B and/or 38E are of a different configuration than anchors 38A, 38C, and/or 38D, such as described hereinbelow with reference to FIGS. 19A-J; anchors 38B and 38E may be of the same configuration as one another, or of different configurations.)

Alternatively, the second sleeve end (i.e., the end of the sleeve to which second member end 53 is closest) is first placed at least partially along anterior portion 116, in which case second portion 112 is deployed before first portion 110, and anchor 38E is deployed from within first portion 110.

The sleeve may be deployed in either a clockwise direction or a counterclockwise direction, as viewed from the atrium.

Contracting assembly 40 is actuated, e.g., the rotatable structure of contracting mechanism 28 is rotated, in order to tighten implantable structure 22, as described hereinabove with reference to FIG. 2I. Typically, contracting member 30 does not extend along the portion of sleeve 26 deployed along anterior portion 116 of the annulus, and thus does not extend along first portion 110, second portion 112, or overlapping portion 114 of sleeve 26. The portion of the sleeve deployed along anterior portion 116 of the annulus (between the trigones) is thus non-contractible. For some applications, contracting member 30 is positioned along a non-anterior portion of the annulus, which non-anterior portion does not reach either of the fibrous trigones, e.g., does not reach within 5 mm of either of the trigones. Tightening of implantable structure 22 therefore tightens at least a portion of the posterior portion of the annulus, while preserving the length of anterior portion 116 of the annulus. (The anterior portion of the annulus should generally not be contracted because its tissue is part of the skeleton of the heart.) However, the portion of the sleeve deployed along the anterior portion of the annulus prevents dilation of the anterior annulus, because the sleeve is anchored at both ends of the anterior annulus, and, as mentioned above, the sleeve typically comprises a longitudinally non-extensible material. This deployment configuration may help prevent long-term resizing of the anterior annulus, which sometimes occurs after implantation of partial annuloplasty rings, such as C-bands.

For some applications, the non-contractible portion of sleeve 26, or non-contraction-facilitated portion (the portion without contracting member 30) extends somewhat beyond one or both of trigones 142 or 144 (in the posterior direction, away from anterior portion 116 of the annulus), such as up to 20 mm, such as up to 10 mm. In general, since the non-contractible portions of the sleeve are preset, the surgeon is able to decide during the implantation procedure the lengths of the anterior non-contractible area and the posterior contractible area, by selecting the length of overlapping portion 114. The greater the length of overlapping portion 114, the greater the relative length of the posterior contractible portion, and the lesser the relative length of the non-contractible portion.

For some applications, at least one anchor 38C is coupled to cardiac tissue on the posterior side of right fibrous trigone 144, between the trigone and the end of contracting member 30. Similarly, at least one anchor 38C may be coupled to cardiac tissue on the posterior side of left fibrous trigone 142, between the trigone and the other end of contracting member 30 (which, for some applications, is coupled to contracting mechanism 28, as shown in FIG. 5).

For some applications, at least one (either one or both) of first and second longitudinal distances D1 and D2 (described hereinabove with reference to FIG. 1), taken separately, is greater than 40 mm, such as greater than 60 mm. This sleeve portion(s) beyond the contracting portion of contracting member 30 provide the non-contractible portion of the sleeve positioned along anterior portion 116 of the annulus, and, optionally, the non-contractible portion(s) that extend beyond the anterior portion.

Reference is still made to FIGS. 4 and 5, and is additionally made to FIGS. 19A-J, which are schematic illustrations of different configurations of anchors 38, in accordance with respective applications of the present invention. For some applications, anchors 38 deployed along anterior portion 116 of the annulus (between the trigones) are of a different configuration from anchors 38 deployed along the remainder of the annulus (including the posterior portion of the annulus). Unlike the remainder of the annulus, anterior portion 116 does not comprise muscular or fibrous tissue, but rather thinner aortic tissue (typically the anchors positioned along anterior portion 116 enter the aorta below the aortic leaflets). The anchors that are deployed along the remainder of the annulus are configured for strong coupling to the thicker and stronger fibrous tissue of these portions of the annulus. Such anchors may be inappropriate for coupling to anterior portion 116. Anchors 38 are thus provided that are particularly configured for coupling to anterior portion 116.

For these applications, anchors 38 include a plurality of first tissue anchors of a first configuration, and a plurality of second tissue anchors of a second configuration different from the first configuration. (The first tissue anchors are labeled 38A and 38C in FIG. 5, and for the sake of brevity, are referenced as 38A hereinbelow. The second tissue anchors are labeled 38B, 38D, and 38E in FIG. 5, and for the save of brevity, are referenced as 38B hereinbelow.) For some applications, implantable structure 22 comprises more first tissue anchors 38A than second tissue anchors 38B, e.g., at least twice as many first tissue anchors as second tissue anchors.

For these applications, sleeve 26 is typically arranged as a loop. For example, as described hereinabove with reference to FIG. 5, the sleeve may be shaped so as to define first and second sleeve ends, which are coupled to each other (optionally, with overlapping portion 114) to form the loop. Alternatively, as described hereinbelow with reference to FIG. 20, the sleeve may shaped so as to define an integrally closed loop having no sleeve ends. First tissue anchors 38A are coupled to sleeve 26 at intervals along a first longitudinally-contiguous portion of the loop, and second tissue anchors 38B are coupled to sleeve 26 at intervals along a second longitudinally-contiguous portion of the loop different from the first longitudinally-contiguous portion. The second portion of the loop is deployed along anterior portion 116 of the annulus, and the first portion of the loop is deployed along at least a portion of the remainder of the annulus (including the posterior portion of the annulus).

Figure 6:
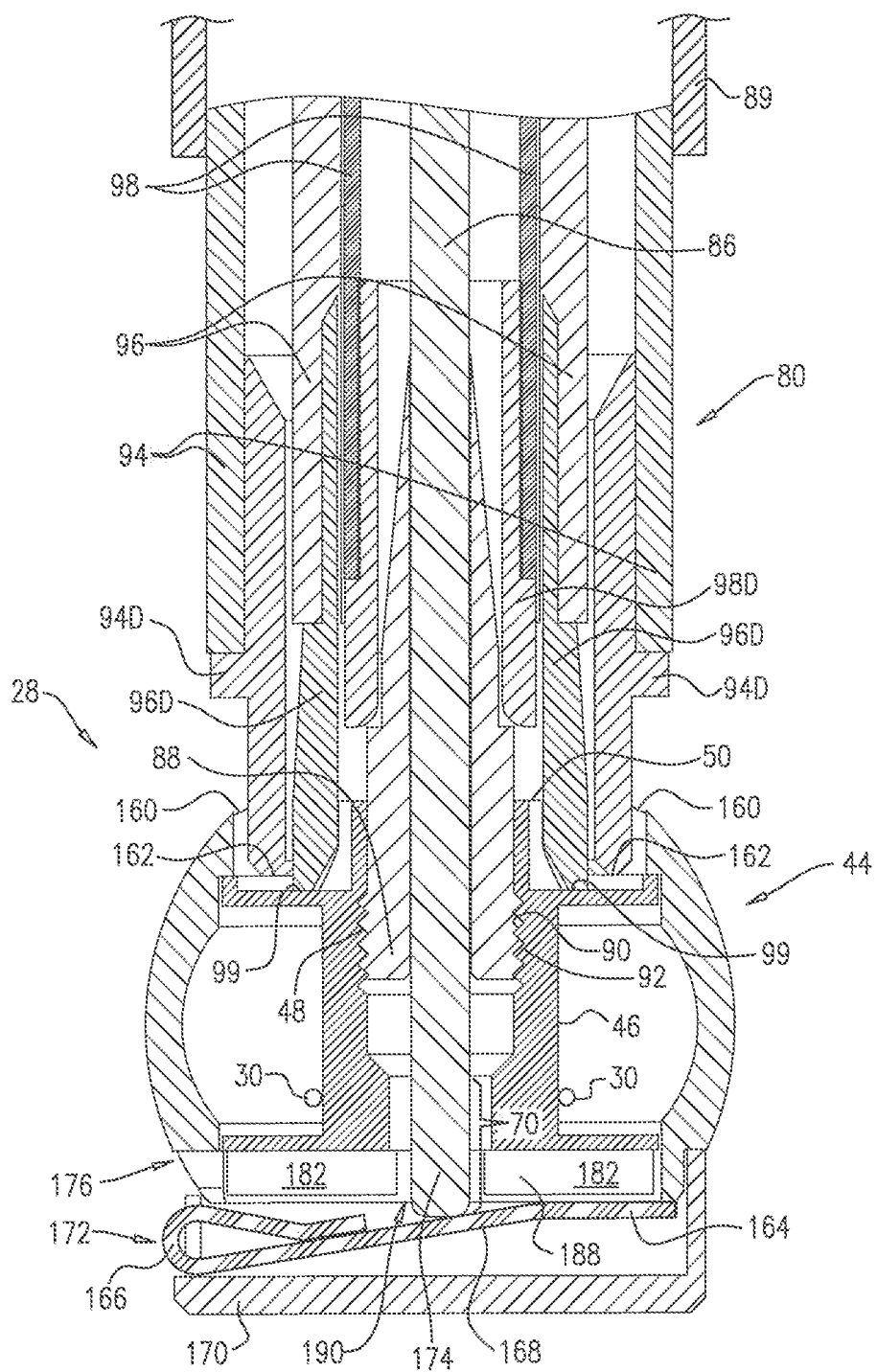
FIG. 6 is schematic cross-sectional illustration of a rotation tool being used to rotate a spool of a contracting mechanism of the implant structures described herein, in accordance with some applications of the present invention.

Reference is now made to FIG. 6, which is a schematic cross-sectional illustration of a configuration of rotation tool 80 being used to rotate the rotatable structure (e.g., a spool 46, as shown) of contracting mechanism 28 of implant structure 22, in accordance with some applications of the present invention. Contracting mechanism 28 is shaped so as to provide a driving interface 48 which facilitates coupling of rotation tool 80 to spool 46 of contracting mechanism 28. Typically, as shown in FIGS. 1 and 4, access to driving interface 48 is provided from outside sleeve 26 via a longitudinal member 86 coupled to contracting mechanism 28. Contracting mechanism 28 comprises longitudinal member 86 that is attached to contracting mechanism 28 and passes out of the body of the patient. In order to readily bring rotation tool 80 to driving interface 48, rotation tool 80 is guided over longitudinal member 86. In this application, rotation tool 80 comprises one or more tubes that pass over the longitudinal member, as described below.

As mentioned above, for some applications, longitudinal member 86 comprises a wire, which may comprise metal. Because the wire is fairly stiff, the wire generally maintains its direction and orientation with respect to contracting mechanism 28. The wire thus readily guides the tubes to the contracting mechanism such that the tubes have a desired orientation and position with respect to the contracting mechanism.

Longitudinal member 86 is removably coupled to contracting mechanism 28, typically to a central portion of an upper surface 50 of spool 46. For some applications, a distal portion 88 of longitudinal member 86 is shaped so as to define a screw thread 90 (i.e., a mechanical structure that is coupled to member 86 at a distal end portion thereof). Distal portion 88 is screwed into a threaded opening 92 of upper surface 50, in order to removably couple longitudinal member 86 to contracting mechanism 28. Typically, the distal portion is initially coupled to the contracting mechanism before implant structure 22 is placed into an atrium of the patient. As described below, the distal portion is decoupled from the contracting mechanism after spool 46 has been rotated to tighten implant structure 22. For some applications, distal portion 88 comprises a discrete element that is fixed to longitudinal member 86, while for other application, distal portion 88 is integral with longitudinal member 86.

For some applications, rotation tool 80 comprises an inner (first) tube 98, an intermediate (second) tube 96, and, optionally, an outer (third) tube 94. Rotation of each of the tubes is independently controlled, such as using techniques described in U.S. patent application Ser. No. 12/689,635 to Zipory et al. (published as US 2010/0280604), entitled, "Over-wire rotation tool," filed Jan. 19, 2010, which is incorporated herein by reference. For some applications, a distal portion of each of tubes 94, 96, and 98 that enters the patient's body comprises braided plastic, and a proximal portion of each of the tubes that does not enter the patient's body comprises a hard material, such as metal (not shown). For example, the distal and proximal portions may have lengths of between 50 and 100 cm and between 50 and 350 cm, respectively. Distal-most portions 94D, 96D, and 98D, respectively, of the distal portions typically comprise a hard material, such as metal, in order to engage other elements, as described immediately below. Typically, the distal-most portions comprise separate elements that are coupled to their respective tubes. For example, the distal-most portions may have lengths of between 1 and 10 mm.

Intermediate tube 96 is configured to rotate spool 46. To this end, intermediate tube 96 (such as distal-most portion 96D thereof) is configured to engage upper surface 50 of spool 46. To enable such engagement, the upper surface typically is shaped so as to define one or more indentations 99 (e.g., grooves), in which corresponding protrusions at the distal end of intermediate tube 96 are positioned, such as by gently rotating tube 96 (or all of the tubes) until such engagement occurs. (Spring may be provided to assist with such engagement.) The radius of intermediate tube 96 is approximately equal to the distance of each of the indentations from a center of upper surface 50, so that the protrusions at the distal end of the tube are aligned with the indentations. Alternatively, the upper surface defines one or more protrusions, which engage indentations on the distal end of tube 96 (configuration not shown). Indentations 99 or the protrusions thus serve as driving interface 48.

Rotation of intermediate tube 96 causes corresponding rotation of spool 46, thereby winding contracting member 30 around the spool, and tightening the contracting member.

An outer tube 94, if provided, is configured to prevent rotation of spool housing 44 during rotation of spool 46. To this end, outer tube 94 (such as distal-most portion 94D thereof) is configured to engage an upper surface 160 of spool housing 44. To enable such engagement, the upper surface typically is shaped so as to define one or more indentations 162 (e.g., grooves), in which corresponding protrusions at the distal end of outer tube 94 are positioned, such as by gently rotating the tube (or all of the tubes) until such engagement occurs. (Springs may be provided to assist with such engagement.) The radius of outer tube 94 is approximately equal to the distance of each of the indentations from a center of spool housing 44, so that the protrusions at the distal end of the tube are aligned with the indentations. Alternatively, the upper surface defines one or more protrusions, which engage indentations on the distal end of tube 94 (configuration not shown).

During rotation of intermediate tube 96 for rotating spool 46, outer tube 94 is held rotationally stationary, thereby stabilizing spool housing 44 and enabling spool 46 to rotate with respect to housing 44 either in a first rotational direction or a second rotational direction that is opposite the first rotational direction. For example, when distal portion 88 is rotated in the first rotational direction, contracting member 30 is wound around spool 46, and when distal portion 88 is rotated in the second rotational direction, contracting member 30 is unwound from around spool 46. As described hereinabove, tool 80 is slid within sheath 89.

Inner tube 98 is configured to decouple longitudinal member 86 from spool 46 after contracting member 30 has been sufficiently wound around the spool, as described above. To this end, a distal portion of the inner tube (such as distal-most portion 98D thereof) is shaped so as to engage a distal portion of longitudinal member 86, which is typically shaped so as to couple with the distal portion of the inner tube.

Rotation of inner tube 98, while intermediate tube 96 is prevented from rotating and thus prevents rotation of spool 46, causes corresponding rotation of longitudinal member 86, and unscrews the longitudinal member from spool 46. Longitudinal member 86 and spool 46 are typically configured such that this unscrewing rotation is in the opposite direction of the rotation of the spool that tightens the contracting member. For example, clockwise rotation of the spool (looking down on the spool) may wind the contracting member around the spool, while counterclockwise rotation of longitudinal member 86 may unscrew the longitudinal member from the spool. To enable the engagement of inner tube 98 with the distal portion of the longitudinal member, the distal portion may include a flat portion.

As shown, spool 46 is shaped to define driving interface 48. For some applications, driving interface 48 is female. For example, the interface may be shaped to define a channel which extends through the cylindrical portion of spool 46 from an opening provided by an upper surface 178 (shown below in FIG. 7A, for example) of spool 46 to an opening provided by a lower surface 180 of spool 46. Alternatively, driving interface 48 is shaped so as to define an indentation (e.g., a groove) that does not extend entirely through the cylindrical portion of the spool. Further alternatively, driving interface 48 is male, and defines a protrusion, e.g., a hexagonal head or a head having another shape.

For some applications, a distal portion of a rotation tool 80, engages spool 46 via driving interface 48 and rotates spool 46 in response to a rotational force applied to the rotation tool. The rotational force applied to the rotation tool rotates spool 46 via the portion of the rotation tool that engages driving interface 48 of spool 46.

Spool 46 typically comprises a locking mechanism that prevents rotation of the spool after contracting member 30 has been tightened. For example, locking techniques may be used that are described with reference to FIG. 4 of above-mentioned U.S. application Ser. No. 12/341,960 to Cabiri (published as US 2010/0161047), and/or with reference to FIGS. 6B, 7, and 8 of U.S. patent application Ser. No. 12/689,635 to Zipory et al. (published as US 2010/0280604), entitled, "Over-wire rotation tool," filed Jan. 19, 2010, which are incorporated herein by reference.

Alternatively, for some applications, contracting mechanism 28 is configured to tighten contracting member 30, crimp the contracting member to hold the contracting member taut, and subsequently cut the excess length of the contracting member.

Distal portion 88 of rotation tool 80 has a head that is male (e.g., comprising a threaded screwdriver head, as shown) having, such as a slot-head, an Allen-head, a Phillips-head, a Robertson-head, or a hex-head. For some applications, distal portion 88 of rotation tool 80 has a head that is female (e.g., comprising a wrench head, having, for example, a square or hex opening), as appropriate for driving interface 48 provided. Typically, the rotation tool comprises a shaft (e.g., tube 94), at least a portion of which is flexible. For some applications, the rotation tool is used that is described in above-referenced U.S. patent application Ser. No. 12/341,960 (published as US 2010/0161047), with reference to FIG. 4 thereof.

FIGS. 7A-B show a relationship among individual components of contracting mechanism 28, in accordance with some applications of the present invention. Contracting mechanism 28 is shown as comprising spool housing 44 which defines an upper surface 160 and a recessed portion 176. Spool 46 is configured to be disposed within housing 44 and defines an upper surface 178, a lower surface 180 and a cylindrical body portion disposed vertically between surfaces 178 and 180. For some applications, a contracting mechanism as shown in FIG. 6B is used, mutatis mutandis. Although some applications of the present invention are described with reference to a contracting mechanism as shown in FIG. 7A, the scope of the present invention includes using the contracting mechanism shown in FIG. 7B in combination with other components of the apparatus described herein.

Reference is now made to FIGS. 6 and 7A. Lower surface 180 of spool 46 is shaped to define one or more (e.g., a plurality, as shown) recesses 182 which define structural barrier portions 188 of lower surface 180. It is to be noted that any suitable number of recesses 182 may be provided, e.g., between 1 and 10 recesses, typically circumferentially (as shown) or otherwise with respect to lower surface 180 of spool 46.

For some applications, as mentioned above, spool 46 comprises a locking mechanism 164 (FIG. 6). For some applications, locking mechanism 164 is coupled, e.g., welded, at least in part to a lower surface of spool housing 44. Typically, locking mechanism 164 defines a mechanical element having a planar surface that defines slits 184. The surface of locking mechanism 164 may also be curved, and not planar. Locking mechanism 164 is shaped to provide a protrusion 166 which projects out of a plane defined by the planar surface of the mechanical element. The slits define a depressible portion 168 of locking mechanism 164 that is disposed in communication with and extends toward protrusion 166. Depressible portion 168 is moveable in response to a force applied thereto by a distal element 70 that extends in a distal direction from distal portion 88 of longitudinal member 86, beyond threaded opening 92 of upper surface 50, as shown in FIG. 6.

It is to be noted that the planar, mechanical element of locking mechanism 164 is shown by way of illustration and not limitation and that any suitable mechanical element having or lacking a planar surface but shaped to define at least one protrusion may be used together with locking mechanism 164.

A cap 170 is provided that is shaped so as to define a planar surface and an annular wall having an upper surface 186 that is coupled to, e.g., welded to, a lower surface of spool housing 44. The annular wall of cap 170 is shaped so as to define a recessed portion 172 of cap 170 that is in alignment with recessed portion 176 of spool housing 44.

For some applications, spool 46 of contracting mechanism 28 is shaped to provide a hole 42 or other coupling mechanism for coupling the first end portion of contracting member 30 to the spool, and thereby to contracting mechanism 28.

Reference is again made to FIG. 6, and is additionally made to FIG. 8, which is another cross-sectional illustration of contracting mechanism 28, in accordance with an application of the present invention. FIG. 6 shows contracting mechanism 28 in an unlocked state, while FIG. 8 shows the contracting mechanism in a locked state.

In the unlocked state shown in FIG. 6, protrusion 166 of locking mechanism 164 is disposed within recessed portion 172 of cap 170. Longitudinal member 86 is shaped so as to define a distal force applicator 174 that extends distally, typically beyond screw thread 90. In the unlocked state, the force applicator extends through spool 46 and pushes against depressible portion 168 of locking mechanism 164. The depressible portion is thus pressed downward, as shown in FIG. 6, freeing protrusion 166 from within a recess 190 defined by structural barrier portions 188 of the lower portion of spool 46. Additionally, protrusion 166 is freed from within recessed portion 176 provided by spool housing 44. As a result, contracting mechanism 28 is unlocked, and spool 46 may be rotated with respect to spool housing 44.

Cap 170 functions to restrict distal pushing of depressible portion 168 beyond a desired distance so as to inhibit deformation of locking mechanism 164. For applications in which contracting mechanism 28 is implanted in heart tissue, cap 170 also provides an interface between contracting mechanism 28 and the heart tissue. This prevents interference of heart tissue on contracting mechanism 28 during the locking and unlocking thereof. Additionally, cap 170 prevents damage to heart tissue by depressible portion 168 as it is pushed downward.

In the locked state shown in FIG. 8, protrusion 166 is positioned within a recess 190 of spool 46. Typically, the locked state is the resting state of locking mechanism 162. Depressible portion 168 is disposed in a horizontal position, in response to removal of distal force applicator 174 from within spool 46. Depressible portion 168 has a tendency to assume the horizontal position, as shown, and in the absence of a downward pushing force applied to depressible portion 168 by force applicator 174, depressible portion 168 returns to its horizontal position from its pushed-down state, as shown in FIG. 8. In this horizontal position, protrusion 166 of locking mechanism 164 is removed from recessed portion 172 of cap 170 and is returned within a recess 190 of spool 46 and thereby restricts movement of spool 46 and locks contracting mechanism 28. Additionally, protrusion 166 of locking mechanism 164 returns in part within recessed portion 176 of spool housing 44. Thus, recessed portion 176 of spool housing 44 provides supplemental locking of locking mechanism 164.

It is to be noted that although contracting mechanism 28 in FIG. 8 is shown without contracting member 30 for clarity of illustration, contracting member 30 is coupled to a portion of contracting mechanism 28.

For some applications, system 20 further comprises a flexible pusher element, such as described and shown in US Patent Application Publication 2010/0286767, which is incorporated herein by reference, with reference to FIG. 8 thereof. The pusher element aids with accurately positioning successive anchors 38 during an implantation procedure, such as described hereinabove with reference to FIGS. 2H and 2I. For some applications, system 20 further comprises a pusher tube that is applied to proximal end 49 of sleeve 26, such as described in the above-mentioned '604 publication, with reference to FIGS. 14 and/or 18A-B thereof. For some applications, system 20 further comprises a steerable tube, such as described in the above-mentioned '604 publication, with referenced to FIG. 15 thereof, or with reference to FIG. 16 thereof. For some applications, system 20 further comprises a pulling wire, such as described in the above-mentioned '604 publication, with referenced to FIG. 17 thereof. For some applications, system 20 further comprises an external control handle, such as described in the above-mentioned '604 publication, with referenced to FIG. 19 thereof. For some applications, contracting assembly 40 and implant structure 22 are configured as described with reference to FIG. 23 of the above-mentioned '604 publication, mutatis mutandis.

For some applications of the present invention, system 20 is used to treat an atrioventricular valve other than the mitral valve, i.e., the tricuspid valve. For these applications, implantable structure 22 and other components of system 20 described hereinabove as being placed in the left atrium are instead placed in the right atrium. Although implantable structure 22 is described hereinabove as being placed in an atrium, for some application the implantable structure is instead placed in either the left or right ventricle.

Reference is now made to FIG. 9, which is a schematic illustration of implant structure 22 comprising a force-distributing element 540 in a vicinity of proximal end 49 of structure 22, in accordance with some applications of the present invention. Implant structure 22 of FIG. 9 is similar to implant structure 22 with the exception that contracting mechanism 28 is coupled to sleeve 26 in a vicinity of distal end 51, and implant structure 22 of FIG. 9 is couplable to force-distributing element 540. Additionally, implant structure 22 of FIG. 9 does not necessarily (but can) define two areas (having respective distances D1 and D2 in FIG. 1) through which member 30 does not pass. That is, implant structure 22 of FIG. 9 defines only one primary area through which member 30 does not pass (i.e., the portion of sleeve 26 between site 36 and proximal end 49 of sleeve 26). A distal-most anchor 512 of anchors 38 is coupled to distal end of sleeve 26 typically but not necessarily distal to contracting mechanism 28.

As described hereinabove, second end 53 of contracting member 30 is coupled to the sleeve at a second site 36 that is a longitudinal distance from end 49 of sleeve 26, which end 49 is longitudinally opposite the end 51 of sleeve 26. A first end portion 530 of contracting member 30 is coupled to contracting mechanism 28 at first site 34 of sleeve 26. Thus, as described hereinabove, rotation of the rotatable structure of contracting mechanism 28, or other actuation of contracting assembly 40, typically applies a longitudinal contracting force only between first and second sites 34 and 36, which longitudinally contracts at least a portion, e.g. all, of the sleeve only between first and second sites 34 and 36.

As described hereinabove, one or more anchors 38 is coupled to the sleeve in the portion of sleeve between site 36 and end 49 of sleeve 26. It is to be noted that even though only one anchor is shown (i.e., anchor 534), more than one anchor may be coupled to the portion of sleeve between site 36 and end 49 of sleeve 26. Additionally, the next-most-proximal anchor 532 may be disposed under site 36. Thus, a proximal-most anchor 534 is coupled to the sleeve in a non-contracting-member portion 510, that is between site 36 and end 49 of sleeve 26 and has excess portions of sleeve 26 which are not anchored to the annulus.

Force-distributing element 540 typically comprises a longitudinally-non-compressible element (e.g., a cylindrical element, as shown), which comprises one or more protrusions 542 for coupling element 540 to sleeve 26. Typically, protrusions 542 puncture sleeve 26, which typically comprises a braided mesh. Typically, force-distributing element is advanceable within sleeve 26 following implantation thereof via anchors 38. Typically, element 540 spans over both anchors 532 and 534 in order to distribute forces between anchors 532 and 534. Protrusions 542 are constrainable within an oversheath (not shown) which is advanced within the lumen of sleeve 26 in order to advance element 540 within the sleeve. Oversheath is then removed to expose protrusions 542 in order to enable protrusions 542 to protrude and engage sleeve 26, as shown. For some applications, protrusions 542 are constrainable because the entire element 540 comprises a stent or tube which is constrainable within the oversheath. Typically, element 540 is rigid along a longitudinal axis of sleeve 26 but is flexible along a plane perpendicular to the axis. For such applications, element 540 may comprise a solid, but flexible cylindrical element, or may comprise a tightly-coiled element which does not compress along the longitudinal axis. For some applications element 540 is entirely rigid. Typically, element 540 comprises a metal (e.g., nitinol, stainless steel, or any other biocompatible material). Typically, element 540 comprises a tube, a coiled element, or a stent shaped so as to define a lumen. Alternatively, element 540 does not comprise a lumen and is solid (e.g., a rod).

For some applications, force-distributing element 540 has a length of at least 3 mm, e.g., at least 8 mm, or at least 16 mm.

Force-distributing element 540 generally distributes force applied by contraction of contracting assembly 40 (i.e., mechanism 28 and member 30) over anchors 532 and 534 (and/or any other additional anchor disposed between site 36 and end 49).

As is described hereinbelow with reference to FIGS. 17A-C, deployment manipulator 24 is coupled to sleeve 26 and comprises an elongate outer tube 66. Tube 66 is positioned within sleeve 26 and functions to facilitate advancement of sleeve 26 onto the annulus during implantation. Typically, the one or more anchors are coupled to an anchor driver (as described hereinbelow) which slides through the lumen of manipulator 24 (i.e., through tube 66). A proximal implant-advancement tube 33 slides along tube 66 of manipulator 24. A distal end of implant-advancement tube 33 comprises one or more coupling elements 29 which are configured to removably couple the distal end of implant-advancement tube 33 to proximal end 49 of sleeve 26, as described hereinbelow. Coupling elements 29 hold sleeve 26 surrounding deployment manipulator 24. As shown in FIG. 9, sleeve 26 comprises a coupling-element coupler 536 which is shaped so as to define one or more openings 538 for coupling elements 29 to sleeve 26.

For some applications, coupling elements 29 are configured to have a natural tendency to flex inwards toward a central longitudinal axis of tube 33, and the tube 66, when positioned within the lumen of sleeve 26, pushes coupling elements 29 outwards away from the longitudinal axis, thereby causing coupling elements 29 to engage sleeve 26. For example, coupling elements 29 may be curved to define outwardly-directed ends that push against or pierce sleeve 26. Such pushing against or piercing engages sleeve 26, which, as mentioned above, may comprise braided or woven fabric. Upon removal of tube 66 from within sleeve 26, coupling elements 29 are allowed to assume their natural inwardly-flexed position, thereby releasing sleeve 26 from coupling elements 29 (i.e., when elements 29 move away from openings 538), and decoupling the sleeve from implant-advancement tube 33.

Reference is now made to FIGS. 10A-B, 11-12 and 13A-B, which are schematic illustrations of implant structure 22 comprising an approximating element 551 in a vicinity of proximal end 49 of structure 22, in accordance with some applications of the present invention. Implant structure 22 of FIGS. 10A-B, 11-12 and 13A-B are similar to implant structure 22 of FIG. 9, as described hereinabove, with the exception that implant structure 22 shown in FIGS. 10A-B, 11-12 and 13A-B comprise approximating element 551. Typically, implant structure 22 comprises force-distributing element 540, as described hereinabove with reference to FIG. 9. For such applications, force-distributing element 540 functions as a structural, reference component to provide a reference force to approximating element 551. For some applications, implant 540 does not comprise force-distributing element 540, but rather any other structural element, e.g., a metal ring, which functions as a structural, reference component to provide a reference force to approximating element 551.

Typically, approximating element 551 changes a spatial orientation of at least a portion of a portion of sleeve 26 that is between the structural, reference-force component (e.g., force-distributing element 540) and end 49, or to non-contracting-member portion 510. For some applications, this portion of the portion includes end 49. For other applications, this portion includes the entire portion of sleeve 26 that is between the structural, reference-force component. For such applications, portion 510 defines, at least in part, excess portions of sleeve 26 which do not need to be anchored to the annulus of the valve. For example, only a portion of sleeve 26 may be anchored along the annulus of the valve, leaving excess portions of sleeve 26. In such an instance, approximating element 551 changes the spatial orientation of the excess portion of sleeve 26 so as to reposition such excess portion, either by compressing the excess portion (as shown in FIGS. 10A-B, 11-12) or by deflecting the excess portion (as shown in FIGS. 13A-B). Thus, for applications in which system 20 comprises approximating element 551 to accommodate for the excess portions of sleeve 26 which do not need to be anchored to the annulus, the physician is able to use any length of sleeve 26 prior to implantation, without necessarily having to size the native annulus prior to implantation or without having to cut the excess portions of the sleeve, following anchoring of the sleeve.

Figure 10B:
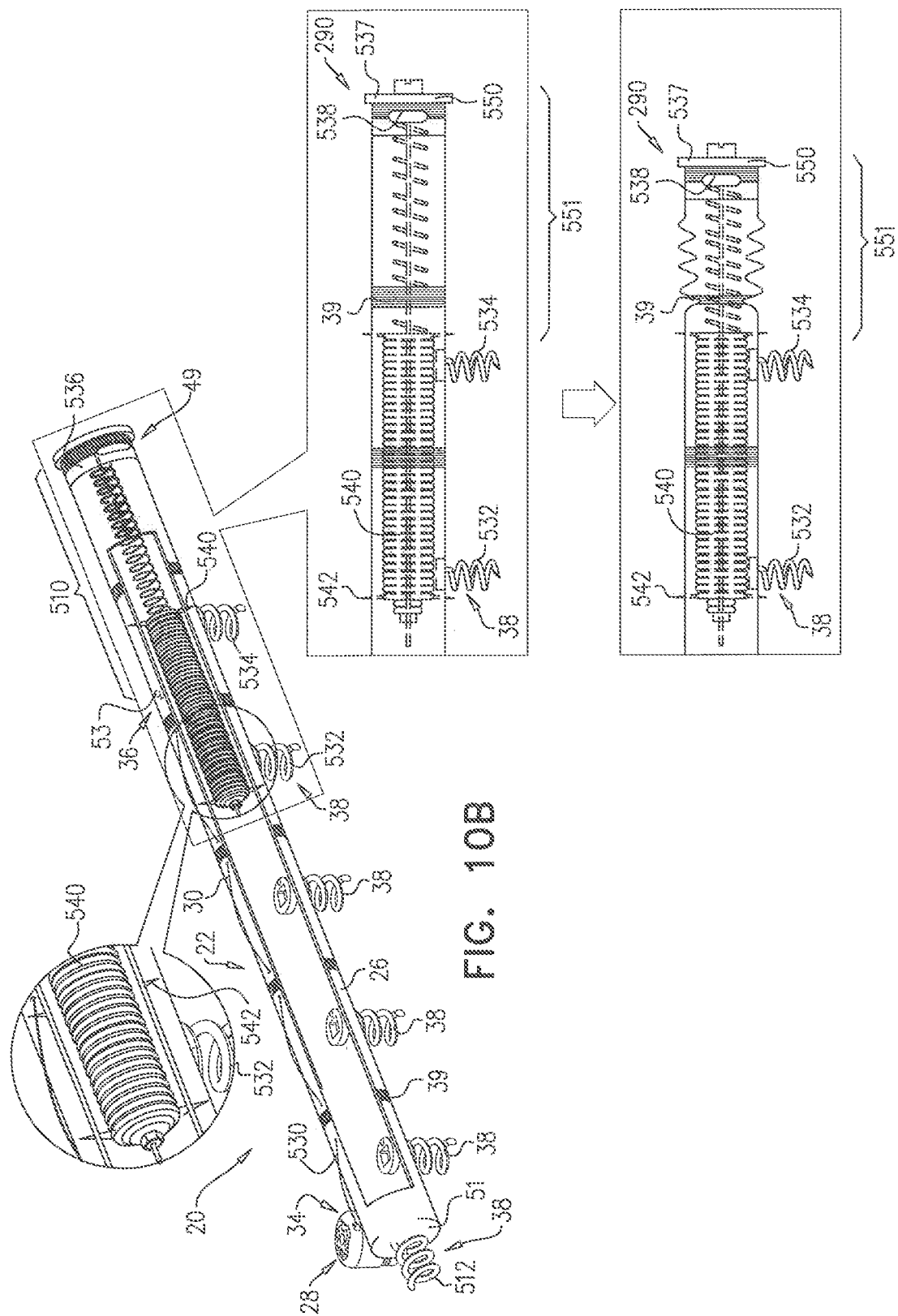

FIGS. 10A-B show implant structure 22 coupled to approximating element 551 comprising a screw shaft 552 and is shaped so as to define a female screw thread 554. As the physician rotates screw shaft 552 into thread 554, at least a portion of portion 510 of sleeve 26 (or the portion of sleeve 26 between the structural, reference-force component (e.g., element 540) and end 49) is shortened and/or compressed, as shown in the bottom enlarged image. As such, approximating element 551, in such an application, defines a second contracting mechanism, or a sleeve-shortening element, in order to contracting mechanism 28.

Typically, the structural, reference component (e.g., force-distributing element 540, in FIGS. 10A-B) is shaped so as to define thread 554, or is coupled to a structural element which is shaped so as to define thread 554. For some applications, system 10 comprises closure element 290, which comprises a plug 550 in such applications which is couplable to end 49 of sleeve 26. For some applications, a proximal end of shaft 552 is coupled to plug 550. Additionally, for such applications in which approximating element 551 comprises shaft 552 and thread 554, plug 550 is shaped so as to provide a screwdriver head 537 for engaging a rotating tool in order to rotate screw shaft 552 with respect to thread 554. For some applications, plug 550 comprises coupling elements which couple to openings 538 of coupling-element coupler 536 (described hereinabove with reference to FIG. 9) in similar manner to coupling elements 29.

Following anchoring of implant structure 22, element 540 is positioned within the lumen of sleeve 26, as described hereinabove, in order to distribute forces between the proximal anchors 532 and 534, and also to function as the structural, reference component for approximating element 551. Then screw shaft 552 is screwed into place with respect to thread 554, either on its own, or coupled to plug 550. Plug 550 functions to close the opening provided by proximal end 49 of sleeve following the removal of deployment manipulator 24 (not shown).

As shown in FIG. 10A, force-distributing element 540 comprises a tubular structure, e.g., a tube, a rod, or a stent, by way of illustration and not limitation.

FIG. 10B shows force-distributing element 540 comprising a coiled element having a plurality of longitudinally-non-compressible coils.

Figure 11:
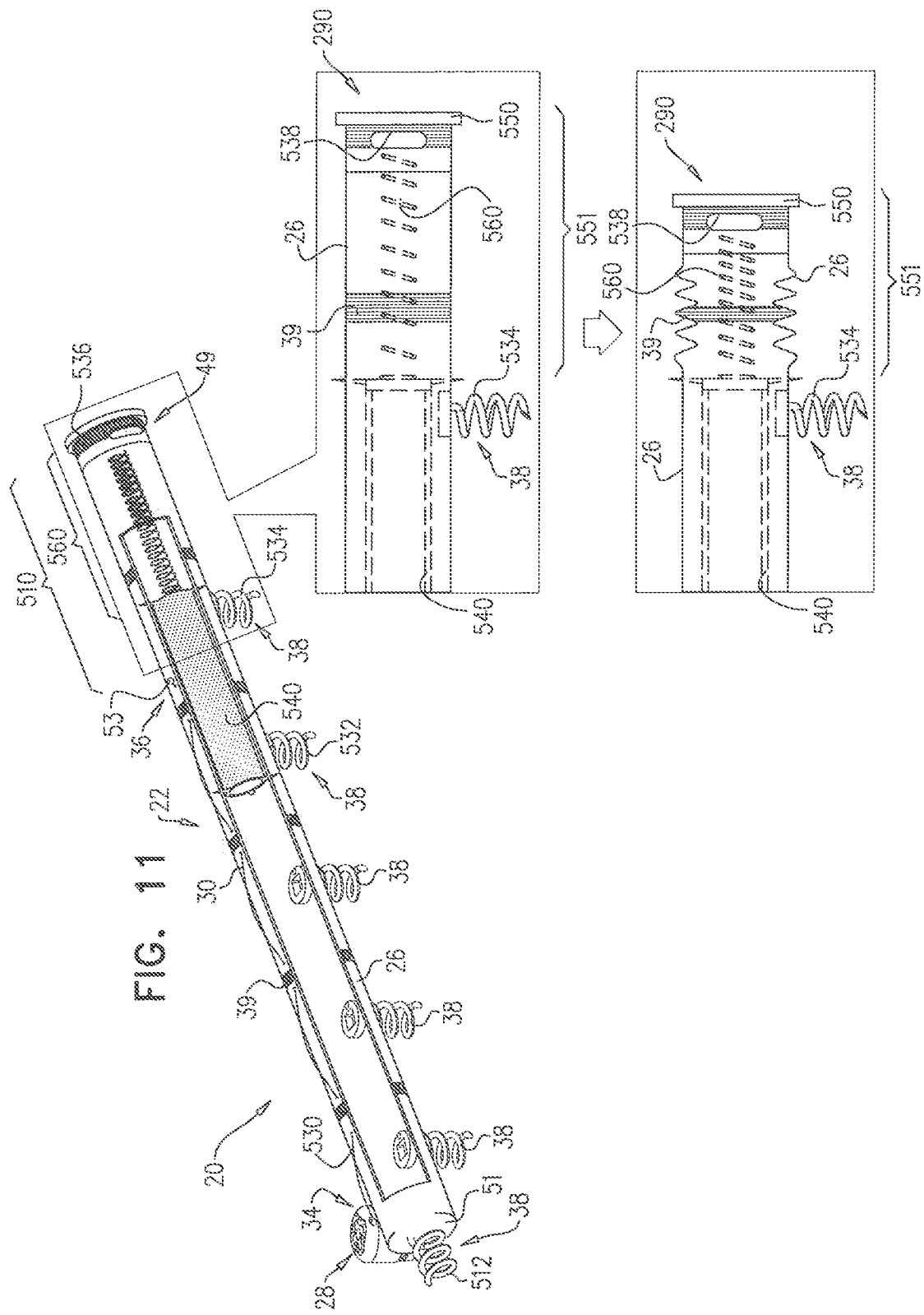

FIG. 11 shows implant structure 22 coupled to approximating element 551 comprising a spring 560. Typically, spring 560 has a tendency to compress, as shown in the bottom enlarged image of FIG. 11. Alternatively, spring 560 is made to compress by pushing plug 550 distally and locking plug 550 to sleeve 26. During compression of spring 560, at least a portion of portion 510 of sleeve (or the portion of sleeve 26 between the structural, reference-force component (e.g., element 540) and end 49) is shortened and/or compressed. As such, approximating element 551, in such an application, defines a second contracting mechanism, or a sleeve-shortening element, in order to contracting mechanism 28.

Typically, a distal end of spring 560 is coupled to the structural, reference component (e.g., force-distributing element 540, in FIGS. 10A-B) while a proximal end of spring 560 is coupled to plug 550.

FIG. 12 shows approximating element 551 comprising both (1) screw shaft 552 and thread 554 (described herein-above with reference to FIGS. 10A-B), and (2) spring 560 (described hereinabove with reference to FIG. 11). As such, approximating element 551, in such an application, defines a second contracting mechanism, or a sleeve-shortening element, in order to contracting mechanism 28.

FIGS. 13A-B show approximating element 551 comprising a deflecting element 570. Deflecting element 570 comprises a shape-memory material (e.g., nitinol), which is configured to deflect portion 510 having the excess sleeve portion toward a wall 580 of the heart adjacent the annulus. For some applications, deflecting element 570 comprises a wire. For some applications, deflecting element 570 comprises a tube. For some applications, deflecting element 570 comprises a spring.

For some applications, deflecting element 570 functions as a stiffening element which prevents twisting of sleeve 26 during the anchoring of sleeve 26 to the annulus.

As shown, implant structure 22 comprises a contracting-member-receiving element 574 which is coupled to sleeve 26 via protrusions 542 and through which a distal portion of contracting member 30 slides. As shown by way of illustration and not limitation, receiving element 574 comprises force distributing element 540 (described hereinabove with reference to FIG. 9). Second end 53 of contracting member 30 is coupled to a stopper 572. As contracting mechanism 28 is actuated, mechanism 28 pulls on member 30 in order to contract structure 22. During actuation, second end 53 of member 30 is pulled toward contracting-member-receiving element 574 until stopper 572 engages with contracting-member-receiving element 574. Upon continued actuation of mechanism 28, and once stopper 572 engages element 574, then contracting member 30 contracts implant structure 22. Contracting-member-receiving element 574 thus ensures that (1) contracting member 30 remains positioned along an upper portion of sleeve 26, and (2) that the lumen of sleeve 26 is mostly free of member 30, such that member 30 will not get in the way of or be entangled during implantation of anchors 38.

It is to be noted that deflection element 570 may be used independently or in combination with any one of approximating elements 551 shown herein, namely, shaft 553 and thread 552 (shown in FIGS. 10A-B and 12) and/or spring 560 (shown in FIGS. 11 and 12) in order to facilitate compressing of at least a portion of portion 510 defining excess portions of sleeve 26 that are not anchored to the annulus.

Figure 14A:
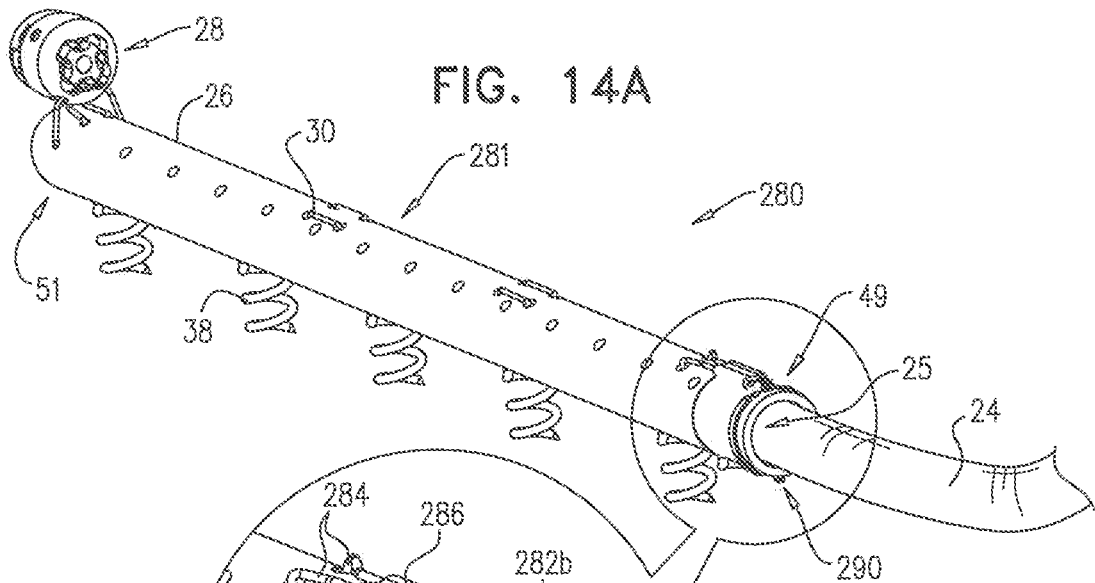
FIGS. 14A-B are schematic illustrations of an implant structure comprising a sleeve having at least one opening and a closure mechanism for the opening, in accordance with some applications of the present invention.
Figure 14B:
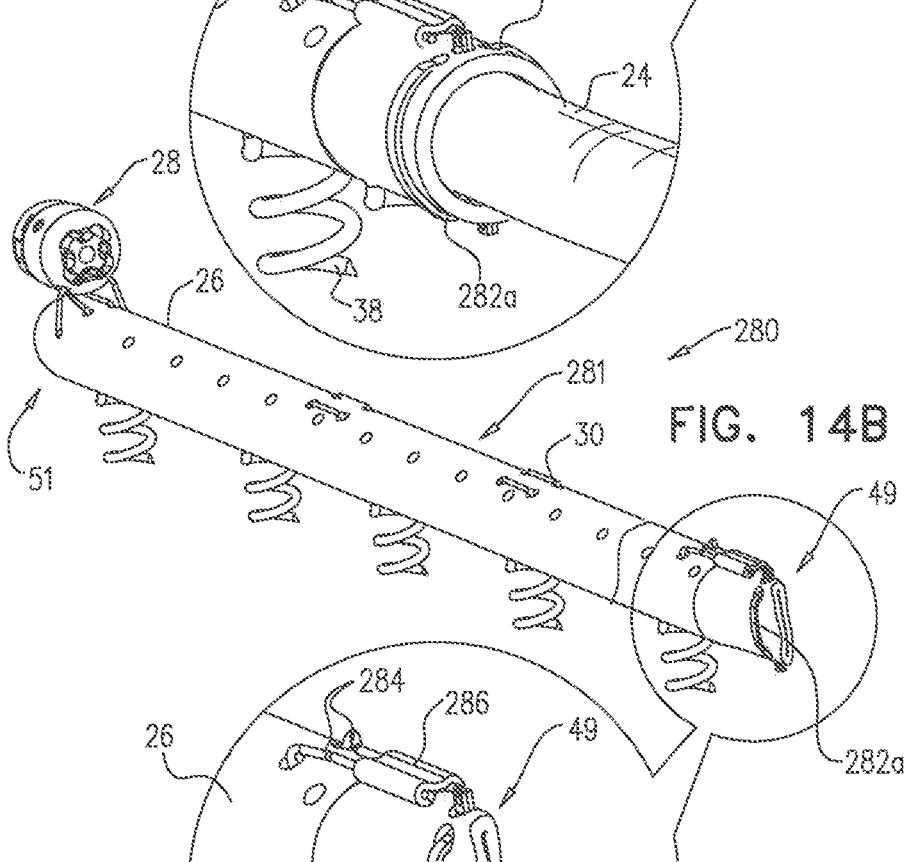

FIGS. 14A-B show a system 280 comprising an implant structure 281 and closure element 290 comprising a closure mechanism comprising self-closing strips 282*a* and 282*b*, in accordance with some applications of the present invention. Implant structure 281 is generally similar to implant structure 22, as described hereinabove with reference to FIGS. 1 and 4, for example, with the exception that implant structure comprises a closure element 290 at proximal end 49 of structure 281. Closure element 290 comprises strips 282*a* and 282*b*.

Strips 282*a* and 282*b* are typically coupled to (e.g., by being threaded through) portions of proximal end 49 (i.e., a first free end) of sleeve 26 of structure 281 in the vicinity of an opening 25. Proximal end 49 of sleeve 26 is shaped so as to define an opening 25 for passage therethrough of manipulator 24 (described hereinabove) into a lumen of sleeve 26. Strips 282*a* and 282*b* define generally arcuate elements which comprise a flexible material (e.g., nitinol). Strips 282*a* and 282*b* have a tendency to close and assume the configuration shown in FIG. 14B. Strips 282*a* and 282*b* are opened from their closed state when a tool (e.g., such as manipulator 24, as shown, and described hereinabove with reference to FIG. 2G-I or 3, or delivery tube 332 described hereinbelow with reference to FIGS. 24A-E and 25A-D) is advanced within the lumen of sleeve 26 (as shown in FIG. 14A). Once the tool is removed from within the lumen, strips 282a and 282b assume their biased state thereby closing opening 25 at proximal end 49 of structure 281. Thus, strips 282 are automatically-activatable when the delivery tool is removed from the lumen of sleeve 26.

Strips 282a and 282b are coupled to respective strings 284 which couple strips 282a and 282b to sleeve 26. Strings 284 are crimped together by a crimp 286.

As shown in FIG. 14A, manipulator 24 is advanceable within the lumen of sleeve 26 so as to facilitate anchoring of structure 281 using anchors 38, in a manner as described herein with reference to FIGS. 2A-I, 3, and 17A-C, with regard to the implantation of implant structure 22 along the annulus of the mitral valve. Following the anchoring, contracting mechanism 28 is actuated in order to adjust a dimension of structure 281. As described hereinabove, contracting mechanism 28 adjusts a tension of contracting member 30 coupled thereto. Contracting mechanism 28 and contracting member 30 are coupled to sleeve 26. Since contracting member 30 is threaded through sleeve 26 one or more times, as shown, the adjusting of the tension of contracting mechanism 30 adjusts the dimension of sleeve 26 and thereby, of implant structure 281. Following the adjusting, manipulator 24 is then removed from the body of the patient, allowing strips 282a and 282b to close around opening 25, and structure 281 remains within the heart. It is to be noted that structure 281 may comprise a stiffening element described hereinbelow with reference to FIG. 15.

Figure 15:
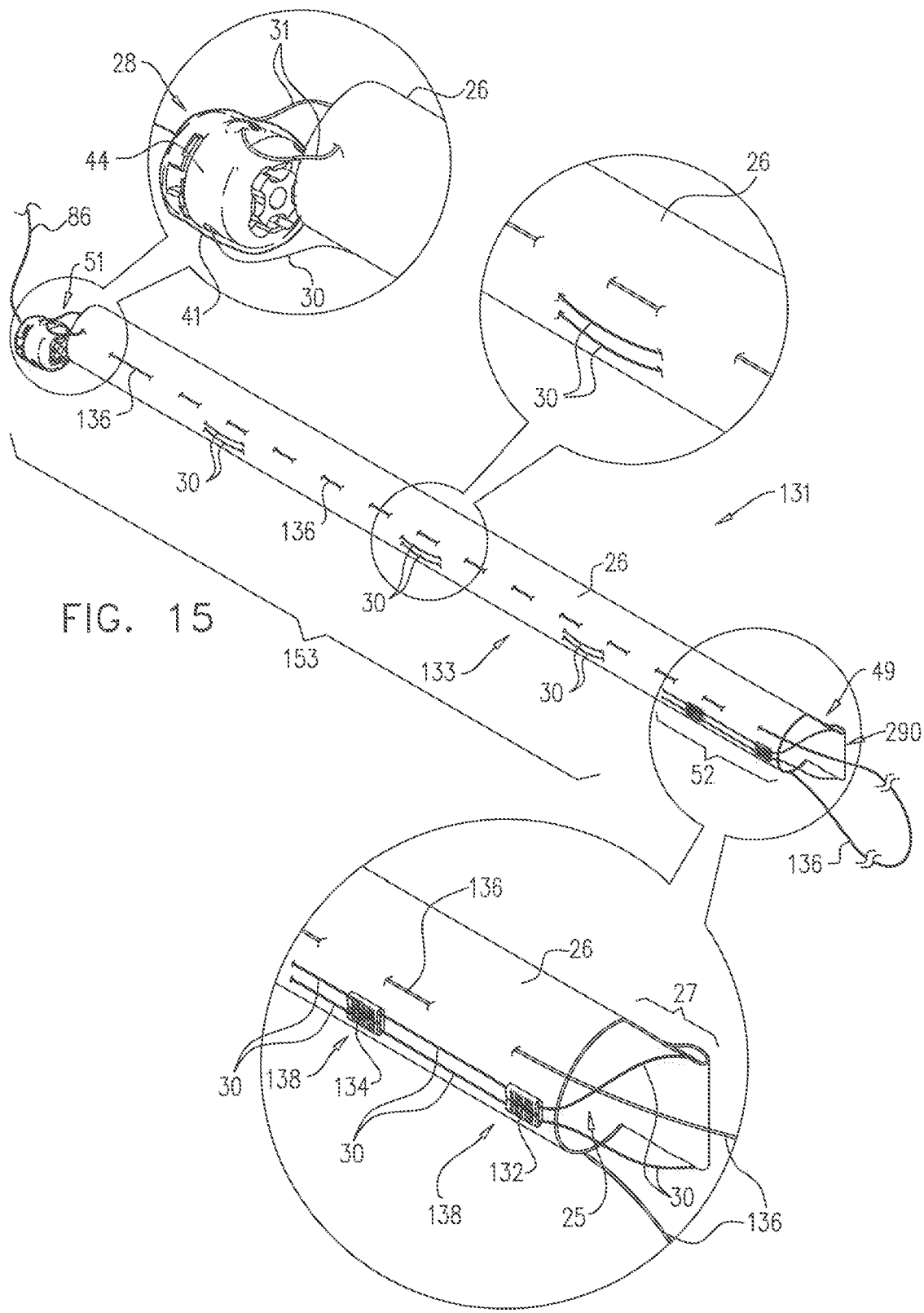
FIG. 15 is a schematic illustration of an implant structure comprising a sleeve having at least one end flap and a contracting mechanism, in accordance with some applications of the present invention.

FIGS. 15 and 16 are schematic illustrations of a system 131 for repairing a dilated atrioventricular valve, such as a mitral valve, in accordance with some applications of the present invention. System 131 comprises an adjustable implant structure 133, shown alone in FIG. 15 in a non-contracted state, and anchor deployment manipulator 24, shown alone in FIG. 16. For some applications, implant structure 133 comprises an annuloplasty ring, e.g., a partial annuloplasty ring. Implant structure 133 comprises a flexible sleeve 26. At least a distal portion of anchor deployment manipulator 24 is advanceable within sleeve 26, as shown hereinbelow, and, from within the sleeve, deploys a plurality of tissue anchors through a wall of the sleeve into cardiac tissue, thereby anchoring or otherwise fastening implant structure 133 around at least a portion of the valve annulus. Typically, sleeve 26 has a length of between 50 mm and 150 mm (e.g., between 70 mm and 120 mm), and a diameter of between 1 mm and 10 mm (e.g., between 2.5 mm and 3.5 mm). Implant structure 133 is generally similar to implant structure 22, as described hereinabove with reference to FIGS. 1 and 4, for example, with the exception that implant structure comprises a closure element 290 at proximal end 49 of structure 133.

Sleeve 26 is typically configured to be placed only partially around the valve annulus (i.e., to assume a C-shape), and, once anchored in place, to be contracted so as to circumferentially tighten the valve annulus. Alternatively, implant structure 133 is configured to be placed entirely around the valve annulus. In order to tighten the annulus, implant structure 133 comprises a contracting mechanism 28 that actuates a flexible elongated contracting member 30 which extends along implant structure 133. As shown, contracting member 30 is threaded one or more times through sleeve 26. For applications in which implant structure 133 comprises a partial annuloplasty ring as shown, sleeve 26 comprises first and second free ends, respectively (i.e., proximal and distal ends 49 and 51, respectively). Proximal end 49 (i.e., a first free end) of sleeve 26 is shaped so as to define an opening 25 for passage therethrough of manipulator 24 into a lumen of sleeve 26. Proximal end 49 is shaped so as to provide a first end flap 27 which is coupled to (e.g., by being looped through) a portion of contracting member 30. When contracting mechanism 28 is actuated, contracting member 30 is pulled or released in order to close or open flap 27 over opening 25. Thus, implant structure 133 comprises a closure element (e.g., closure element 290) for closing opening 25. For such an application, closure element 290 comprises flap 27 and the portion of contracting member 30 coupled thereto. Typically, closure element 290 is remotely-controlled by the operating physician.

Following the closing of flap 27 over opening 25, contracting mechanism 28 facilitates contracting of implant structure 133. Contracting mechanism 28 is described in more detail hereinbelow. In addition, system 131 comprises a plurality of tissue anchors, typically between about 5 and about 20 anchors, such as about 10 or about 16 anchors. The anchors are configured to be deployed through the wall of sleeve 26 by anchor deployment manipulator 24. The insertion of the anchors into the sleeve and deployment of the anchors into cardiac tissue is described in detail hereinbelow.

It is noted that although closure element 290 is shown in FIG. 15 as including closure element 290, the scope of the present invention includes using other closure elements for closing opening 25. For example, a plug (such as a silicone plug) may be used to close the opening. Or, an elastomeric band (such as a silicone band) may be configured to automatically close the opening, upon removal of the manipulator therefrom. Or, flap 27 may be folded over and an anchor (e.g., a tissue anchor 38, as described herein) may be used to anchor the folded-over flap to the patient's tissue.

Typically, the closure elements described herein reduce the likelihood of a thrombosis forming inside sleeve 26, by closing opening 25, relative to if opening 25 were left opened. Alternatively or additionally, the closure elements described herein are used to close opening 25 for a different reason.

Typically, the closure of opening 25 (e.g., using the closure elements described herein) and the deployment of implant structure 133 is performed during a single procedure, e.g., by deploying the implant structure and closing opening 25 via a single catheter. For some applications (not shown), sleeve 26 defines openings 25 at first and second ends thereof, and closure elements are used to close the openings at the first and second ends of the sleeve.

Flexible sleeve 26 may comprise a braided, knitted, or woven mesh or a tubular structure comprising ePTFE or DACRON™. For some applications, the braid comprises metal and fabric fibers. The metal fibers, which may comprise Nitinol for example, may help define the shape of the sleeve, e.g., hold the sleeve open to provide space for passage and manipulation of deployment manipulator 24 within the sleeve. The fabric fibers may promote tissue growth into the braid. Optionally, the sleeve is somewhat elastic, which gives the sleeve a tendency to longitudinally contract, thereby helping tighten the sleeve. For example, the sleeve may be bellows-shaped or accordion-shaped.

Reference is now made to FIGS. 15, 16, and 17A-C, which are schematic illustrations of a procedure for implanting implant structure 133 to repair a mitral valve, in accordance with some applications of the present invention. It is to be noted that structure 133 may be implanted in the same manner as structure 22, described hereinabove with reference to FIGS. 2A-I and 3. Typically, the sleeve is configured to have a tendency to assume a straight shape. This straightness helps the surgeon locate the next site for each subsequent anchor during the implantation procedure, as described hereinabove with reference to FIGS. 2A-I. For example, because sleeve 26 assumes a generally straight shape, the sleeve may help provide an indication of distance between adjacent anchoring sites.

As shown, sleeve 26 is configured to have a controllably variable stiffness. For example, one or more generally stiff stiffening elements 136 (shown in FIG. 1), e.g., a wire or a suture, is threaded one or more times (e.g., a plurality of times) through sleeve 26 to provide the stiffness, and subsequently be removed at the conclusion of the implantation procedure when the stiffness is no longer useful, as is described hereinbelow. Since manipulator 24 and components that are slidable therein are deflectable and steerable, stiffening element 136 helps maintain the relative positioning of manipulator 24 with respect to sleeve 26 in order to prevent manipulator 24 from deploying an anchor through sleeve 26 in a vicinity of contracting member 30. That is, stiffening element 136 helps maintain the shape and integrity of sleeve 26 (i.e., prevents flailing of sleeve 26). For some applications, element 136 is pulled directly by an operating physician. For other applications, element 136 is coupled to a portion of manipulator 24 or a component that is slidable within a lumen of manipulator 24, and is pulled either by the manipulator or any component thereof. Stiffening element 136 helps ensure that the anchors are deployed through sleeve 26 without interfering with contracting member 30.

Elongated contracting member 30 comprises a wire, a ribbon, a rope, or a band, which typically comprises a flexible and/or superelastic material, e.g., nitinol, polyester, stainless steel, or cobalt chrome. For some applications, the wire comprises a radiopaque material. For some applications, contracting member 30 comprises a braided polyester suture (e.g., TICRON™). For some applications, contracting member 30 is coated with polytetrafluoroethylene (PTFE). For some applications, contracting member 30 comprises a plurality of wires that are intertwined to form a rope structure.

By being threaded or sewn through sleeve 26, contracting member 30 is positioned at least partially within a lumen of the sleeve 26 alternatingly inside and outside of the sleeve along the length of the sleeve. Optionally, sleeve 26 defines an internal channel within which member 30 is positioned (configuration not shown). Alternatively, the contracting member is disposed outside the lumen of the sleeve, such as alongside an outer wall of the sleeve. For example, sleeve 26 may define an external channel within which member 30 is positioned, or the sleeve may comprise or be shaped so as to define external coupling elements, such as loops or rings (configuration not shown). For some applications, contracting member 30 is positioned approximately opposite the portion of sleeve 26 through which the anchors are deployed, as described hereinabove.

For some applications of the present invention, contracting mechanism 28 comprises a rotatable structure, such as a spool. The rotatable structure is arranged such that rotation thereof contracts implant structure 133. For some applications, a first end portion of contracting member 30 is coupled to the spool (e.g., by being looped through a portion of the spool). For some applications, contracting mechanism 28 further comprises a housing 44 that houses the rotatable structure, e.g., the spool. A braided fabric mesh 41 surrounds housing 44 so as to facilitate implantation thereof and induce fibrosis around housing 44. The spool is positioned in a vicinity of (e.g., within 1 cm of) end 51 of sleeve 26, as shown. As shown, a second end portion of contracting member 30 is coupled to sleeve 26 in a vicinity of (e.g., within 0.5 cm of) end 49 of the sleeve 26, opposite end 51 to which the contracting mechanism 28 is positioned. Typically, contracting mechanism 28 is sutured to sleeve 26 by coupling threads 31.

In the configuration shown, the second end portion of contracting member 30 is looped through a portion of flap 27 and extends back toward end 51 of sleeve 26. The second end portion of contracting member 30 is coupled to sleeve 26 in a vicinity of proximal end 49 of the sleeve at a distance of between 0.2 cm and 2 cm from end 49. Since contracting member 30 is looped through a portion of contracting mechanism 28, the free ends of contracting member 30 are brought together, and together serve as the second end portion of contracting member 30. Alternatively, contracting member 30 is not looped through a portion of contracting mechanism 28, a first end of contracting member 30 is fixedly coupled to contracting mechanism 28, while a second end of contracting member 30 defines the second end portion that is coupled to the portion of sleeve 26.

The second end portion of member 30 is coupled to sleeve 26 by contraction-restricting elements 138, e.g., crimping elements 132 and 134. Crimping elements 132 and 134 restrict contraction of a contraction-restricted portion 52 (or non-contraction-facilitated portion) of sleeve 26 that has a length of between 5 mm and 30 mm. For some applications, the crimping elements are disposed such that the contraction-restricted portion of the sleeve is between 3 and 45 mm from one end of the sleeve. The remaining portion of sleeve 26, i.e., a contraction-facilitated portion 153 (or contractible portion) is contractible and expandable in response to respective tightening or loosening of contracting member 30 responsively to the actuation of contracting mechanism 28. Thus, while contraction of implant structure 133 is being ongoing (i.e., while contraction-facilitated portion 153 is being contracted), contraction-restricted portion 52 is restricted from being contracted. For some applications, contraction-restriction portions, each having a length of between 5 mm and 30 mm are disposed, are disposed in the vicinity of both ends of sleeve 26.

Rotation of the spool of contracting mechanism 28 in a first rotational direction winds a portion of contracting member 30 around the spool, thereby pulling the far end of implant structure 133 toward the spool and shortening and tightening implant structure 133.

Alternatively, in some configurations, contracting mechanism 28 is positioned at an intermediary position along the sleeve, rather than in a vicinity of one of the ends. For these configurations, contracting member 30 comprises two contracting members, which are respectively connected to the two ends of the sleeve, and both of which are connected to the spool. Rotating the spool contracts both contracting members. These configurations may be implemented using techniques described in U.S. patent application Ser. No. 12/341,960 to Cabiri (published as US 2010/0161047), which is incorporated herein by reference, with reference to FIG. 15 thereof.

For other applications, contracting member 30 comprises at least one wire (e.g., exactly one wire) that passes through a coupling mechanism of the spool of contracting mechanism 28, in order to couple the wire to the spool. As described hereinabove, the free ends of contracting member 30 are brought together, and together serve as the second end portion of contracting member 30, and may be coupled to one of the several locations of sleeve 26 mentioned hereinabove. In this configuration, approximately the longitudinal center of the wire serves as first end of the contracting member.

FIG. 16 shows manipulator 24 comprising elongate outer tube 66 (sometimes referred to herein, including in the claims, as a "deployment manipulator tube") having a tube lumen and a distal end 64 which defines an opening for passage therethrough of the one or more anchors. Typically, the one or more anchors are coupled to an anchor driver (as described hereinbelow) which slides through the lumen of manipulator 24 (i.e., through tube 66). A proximal implant-advancement tube 33 slides along tube 66 of manipulator 24. A distal end of implant-advancement tube 33 is coupled to a coupler 139 which increases friction at a distal end of implant-advancement tube 33 so as to facilitate a sliding of implant-advancement tube 33 along tube 66 of manipulator 24, while temporarily maintaining the distal end of implant-advancement tube 33 in place with respect to tube 66 of manipulator 24. Coupler 139 comprises one or more (e.g., two, as shown) coupling elements 29 which are configured to removably couple the distal end of implant-advancement tube 33 to proximal end 49 of sleeve 26, as described hereinbelow. Coupling elements 29 hold sleeve 26 surrounding deployment manipulator 24.

For some applications, coupling elements 29 are configured to have a natural tendency to flex inwards toward a central longitudinal axis of tube 33, and the tube 66, when positioned within the lumen of sleeve 26, pushes coupling elements 29 outwards away from the longitudinal axis, thereby causing coupling elements 29 to engage sleeve 26. For example, coupling elements 29 may be curved to define outwardly-directed ends that push against or pierce sleeve 26. Such pushing against or piercing engages sleeve 26, which, as mentioned above, may comprise braided or woven fabric. Upon removal of tube 66 from within sleeve 26, coupling elements 29 are allowed to assume their natural inwardly-flexed position, thereby releasing sleeve 26 from the coupling elements, and decoupling the sleeve from implant-advancement tube 33.

FIGS. 17A-C are schematic illustrations of manipulator 24 advanced into a lumen of sleeve 26 of implant structure 133 in order to deploy one or more tissue anchors 38, in accordance with some applications of the present invention. Anchor deployment manipulator 24 is advanced into a lumen of sleeve 26, and, from within the lumen, deploys anchors 38 through a wall of the sleeve and into cardiac tissue, thereby anchoring the sleeve around a portion of the valve annulus. Typically, implant structure 133 and anchor deployment manipulator 24 are introduced into the heart via a sheath 104, as described hereinabove with reference to FIGS. 2A-I and 3.

As shown in FIG. 17B, an anchor driver 68 is slidable within a lumen of tube 66 of manipulator 24. Anchor driver 68 is coupled at a distal end thereof to a driving interface 69 that is either male (e.g., comprising a screwdriver head, having, such as a slot-head, an Allen-head, a Phillips-head, a Robertson-head, or a hex-head) or female (e.g., comprising a wrench head, having, for example, a square or hex opening), as appropriate for the driving interface provided. Anchor driver 68 is steerable and deflectable independently of the steerability and deflectability of tube 66 of manipulator 24.

For some applications, at least one of anchors 38 is deployed from a distal end 60 of deployment manipulator 24 while the distal end is positioned such that a central longitudinal axis 62 through distal end 60 of deployment manipulator 24 forms an angle of between about 45 and 90 degrees with the wall of sleeve 26 at the point at which the anchor penetrates the wall, such as between about 75 and 90 degrees, e.g., about 90 degrees (as shown hereinabove with reference to FIGS. 2A-I and 3). For other applications, as shown in FIG. 17B, at least one of anchors 38 is deployed from driving interface 69 while interface 69 is positioned such that a central longitudinal axis through the distal end of interface 69 forms an angle of between about 45 and 135 degrees with the wall of sleeve 26 at the point at which the anchor penetrates the wall, such as between about 75 and 100 degrees, e.g., about 90 degrees. Thus, manipulator 24 has steerability and anchor driver 68 has steerability that is independent from the steerability of manipulator 24. For some applications of the present invention, the steerability of manipulator 24 is in a different plane than the steerability of anchor driver 68.

This anchor-penetration point is typically at a portion of the sleeve that extends distally beyond distal end 64 of deployment manipulator 24. Typically, all of the anchors are deployed at such angles, with the possible exception of the first anchor deployed near the distal end of the sleeve.

Reference is now made to FIG. 17B. As shown, deployment manipulator 24 comprises outer tube 66 and anchor driver 68 which is at least partially positioned within tube 66. Anchor driver 68 comprises an elongated, flexible shaft 70, having at its distal end a driver head 72. Rotation of anchor driver 68 screws anchors 38 into the cardiac tissue. Each of anchors 38 is shaped so as to define a coupling head 74 and a tissue coupling element 76. The anchors are typically rigid. Tissue coupling elements 76 may, for example, be helical or spiral in shape (e.g., having the shape of a corkscrew), as shown in the figures, may comprise screws, or may have other shapes. Coupling heads 74 may be either male (e.g., a hex or square protrusion) or female (e.g., a straight slot, a hex opening, a Phillips opening, or a Robertson opening). The use of helical anchors, which are screwed into the cardiac tissue, generally minimizes the force that needs to be applied during deployment of the anchors into the cardiac tissue. Alternatively, the anchors may comprise staples, clips, spring-loaded anchors, or other tissue anchors otherwise known in the art.

For some applications, outer tube 66 of deployment manipulator 24 is steerable, as known in the catheter art. To provide steering functionality to deployment manipulator 24, outer tube 66 typically comprises one or more steering wires, the pulling and releasing of which cause deflection of the distal tip of the tube.

For some applications of the present invention, each of tissue coupling elements 76 is shaped so as to define a longitudinal axis 78 (shown in FIG. 3B), and is configured to penetrate the cardiac tissue in a direction parallel to longitudinal axis 78. Deployment manipulator 24 is configured to deploy tissue coupling element 76 from distal end 64 of the deployment manipulator through the wall of sleeve 26 in a direction parallel to longitudinal axis 78 and parallel to a central longitudinal axis through a distal end of deployment manipulator 24 (i.e., axis 65 is shown hereinabove in FIG. 3).

For some applications, the plurality of anchors are applied using the deployment manipulator by loading a first one of the anchors onto the anchor driver, and deploying the anchor into the cardiac tissue. The anchor driver is withdrawn from the patient's body (typically while leaving outer tube 66 of the deployment manipulator in place in the sleeve), and a second one of the anchors is loaded onto the anchor driver.

The anchor driver is reintroduced into the outer tube of the deployment manipulator, and the second anchor is deployed. These steps are repeated until all of the anchors have been deployed. Alternatively, the entire deployment manipulator, including the anchor driver, is removed from the body and subsequently reintroduced after being provided with another anchor. Techniques for use with the refillable deployment manipulator may be practiced in combination with techniques described in U.S. patent application Ser. No. 12/689, 635 to Zipory et al. (published as US 2010/0280604), entitled, "Over-wire rotation tool," filed Jan. 19, 2010, which is incorporated herein by reference, and with techniques described in PCT Patent Application PCT/IL2010/000358 to Zipory et al. (published as WO 10/128503), entitled, "Deployment techniques for annuloplasty ring," filed May 4, 2010, which is incorporated herein by reference. Further alternatively, the deployment manipulator is configured to simultaneously hold a plurality of anchors, and to deploy them one at a time.

Reference is again made to FIGS. 17A-C. FIG. 17A shows the slidable advancement of manipulator 24 through the lumen of sleeve 26 of implant structure 133. Manipulator 24 slides proximally from distal end 51 of sleeve 26 in order to facilitate implantation of anchors 38 within cardiac tissue of the patient. As shown in FIG. 17B, a first tissue anchor 38 is implanted in a vicinity of end 51 (e.g., at end 51 as shown). Anchor 38 is implanted when anchor driver 68 is rotated in order to corkscrew anchor 38 into the tissue. Following the anchoring of anchor 38 in the vicinity of end 51, manipulator 24 is withdrawn proximally so as to anchor a second anchor 38 into cardiac tissue.

Typically, the first anchor 38 is deployed most distally in sleeve 26 (generally at or within a few millimeters of end 51 of sleeve 26), and each subsequent anchor is deployed more proximally, such that sleeve 26 is gradually pulled off (i.e., withdrawn from) deployment manipulator 24 in a distal direction during the anchoring procedure. Typically, as the sleeve is pulled off the deployment manipulator, the deployment manipulator is moved generally laterally along the cardiac tissue, as shown in FIGS. 17B-C.

The pushing of sleeve 26 distally from manipulator 24 is facilitated by implant-advancement tube 33. Implant-advancement tube 33 passes over outer tube 66 of manipulator 24, and pushes gently in a distal direction on proximal end 49 of sleeve 26. The implant-advancement tube is held in place against proximal end 49 of sleeve 26, typically by an external control handle (not shown for clarity of illustration) that is coupled to respective proximal ends of manipulator 24, tube 66, anchor driver 68, and implant-advancement tube 33. In order to release sleeve 26, outer tube 66 is retracted proximally, while implant-advancement tube 33 remains in place to apply a reference force to sleeve 26 with respect to outer tube 66, helping advance and release sleeve 26 from outer tube 66, as tube 66 is withdrawn. If the implant-advancement tube were not provided, the wall of sleeve 26 might snag on outer tube 66 (as mentioned above, the sleeve may comprise braided or woven fabric). In addition, if such snagging occurs, gentle pushing with the implant-advancement tube in the distal direction may help free the snag.

In the configuration shown in FIG. 17A, implant-advancement tube 33 comprises one or more coupling elements 29 (such as exactly one coupling element or exactly two coupling elements) at a distal end of tube 38. Coupling elements 29 are configured to removably couple proximal end 49 of sleeve 26 to the distal end of implant-advancement tube 33, thereby preventing sleeve 26 from moving distally with respect to outer tube 66 of deployment manipulator 24, such as using the external control handle, while manipulator 24 is pulled proximally. Alternatively, both implant-advancement tube 33 and manipulator 24 are pulled proximally (e.g., by pulling proximally the external control handle) and implant-advancement tube 33 thereby applies a passive counter force in order to resist proximal end 49 of sleeve 26 in a manner in which, responsively to the passive force, proximal end 49 of sleeve 26 is advanced distally.

During the anchoring procedure, stiffening element 136 maintains relative dispositions of manipulator and/or anchor driver 68 with respect to sleeve 26. As shown, stiffening element 136 is threaded along sleeve 26. The relative stiffness of stiffening element 136 to the flexibility of sleeve 26 maintains sleeve 26 in a relative spatial configuration in which contracting member 30 remains above tube 66 of manipulator 24 and/or anchor driver 68. In such a manner, stiffening element 136 helps ensure that anchors 38 do not interfere with contracting member 30 and that the portion of sleeve 26 that is opposite contracting member 30 is anchored to the annulus. Stiffening element 136 is loosely coupled (i.e., is not fixed by being knotted or otherwise fastened) to a distal end 35 thereof (shown in FIG. 3A) to a distal portion of sleeve 26 in a vicinity of end 51 of sleeve 26. A proximal end of stiffening element 136 is coupled to a coupler 37 (or a ring) which is coupled to implant-advancement tube 33. As sleeve 26 is slid gradually distally from outer tube 66 of manipulator 24, as described hereinabove, since coupler 37 is fixed to implant-advancement tube 33, the successive distal portions of stiffening element 136 are decoupled, by being unthreaded, from sleeve 26 responsively to the distal sliding of sleeve 26 from tube 66 of manipulator 24.

FIG. 17C shows anchoring of an additional tissue anchor 38 to the annulus of the valve. As described hereinabove, with each successive anchor 38 that is deployed, successive portions of sleeve 26 are slid off tube 66 of manipulator 24. For some applications, portions of stiffening element 136 are unthreaded from sleeve 26.

Following the anchoring of sleeve 26 by anchoring a suitable number of anchors around a desired portion of the annulus of the valve, sleeve 26 is slid off of manipulator 24 and decoupled from coupling elements 29 in order to release sleeve 26 from coupling elements 29. Proximal withdrawal of outer tube 66 from sleeve 26 (into or through implant-advancement tube 33) allows coupling elements 29 to assume their natural inwardly-flexed position, thereby releasing sleeve 26 from the coupling elements, and decoupling the sleeve from the implant-advancement tube. As described hereinabove, sleeve 26 is advanced off deployment manipulator 24, including outer tube 66, in a distal direction during the anchoring procedure. Outer tube 66 of deployment manipulator 24 is proximally withdrawn completely from the sleeve at the conclusion of the anchoring procedure. The flexing of the coupling elements releases the sleeve at the conclusion of the procedure. As implant-advancement tube 33 is decoupled from sleeve 26 and is withdrawn proximally, implant-advancement tube 33 pulls on stiffening element 136 in order to entirely decouple, by unthreading stiffening element 136 from sleeve 26.

Figure 17D:
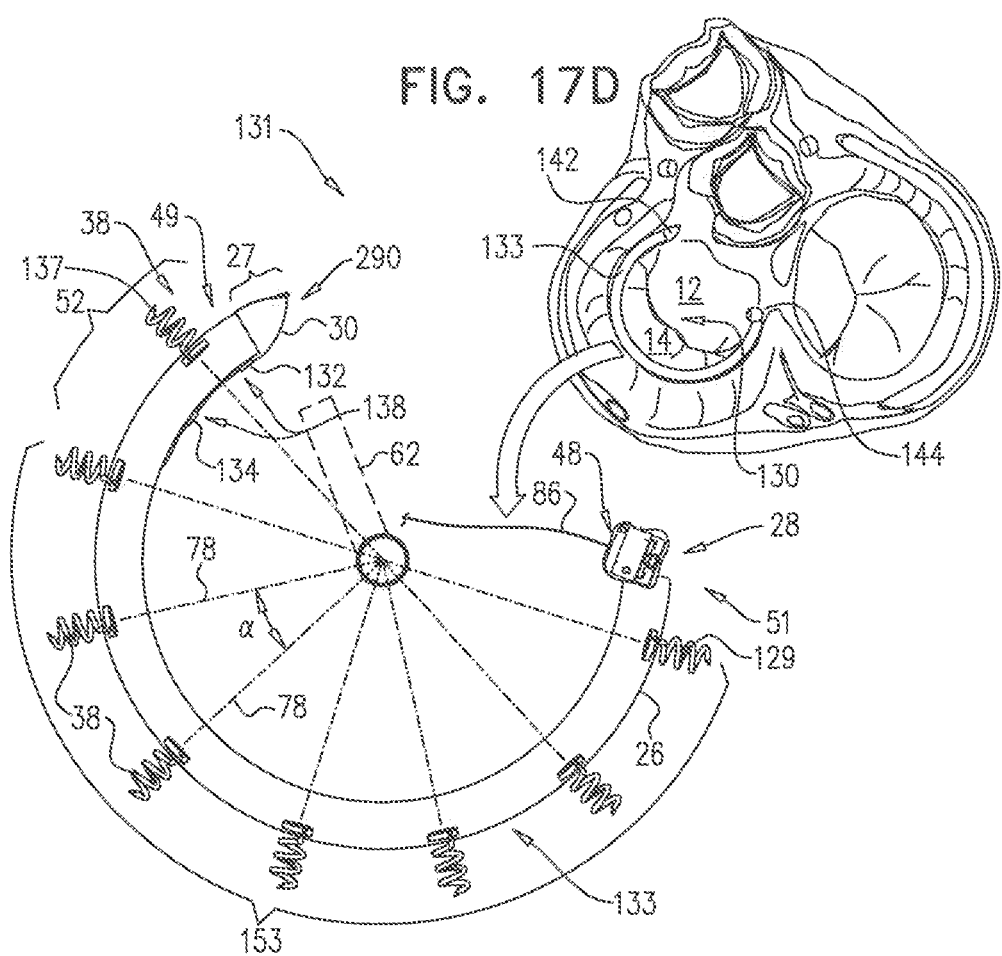
FIGS. 17D-E are schematic illustrations of the closing of the end flap of the implant structure of FIG. 15 following the anchoring of the structure to the annulus, in accordance with some applications of the present invention.

Reference is now made to FIG. 17D, which is a schematic illustration of implant structure 133 anchored to the annulus of a mitral valve 130 of the patient, in accordance with some applications of the present invention. A plurality of tissue anchors (e.g., 8 tissue anchors as shown by way of illustration and not limitation) anchor implant structure 133 to the annulus. As shown, in some applications of the present invention, proximal end 49 of structure 133 is anchored in a vicinity of a first trigone 142 (e.g., at first trigone 142) of valve 130 by a first anchor 137, and distal end 51 of structure 133 is anchored in a vicinity of a second trigone 144 (e.g., at second trigone 144) of valve 130 by a second anchor 129. In such an embodiment in which proximal and distal ends 49 and 51 are anchored to the annulus of the valve, both contraction-restricted portion 52 of sleeve 26 and contraction-facilitated portion 153 of sleeve 26 are disposed along a portion of the annulus that is between trigones 142 and 144 and along a junction of the annulus and a posterior leaflet 14 and portions of anterior leaflet 12. In such an application, since contraction-restricted portion 52 is disposed along the portion of the annulus, only a section of the portion of the annulus (i.e., the section along which contraction-facilitated portion 153 is disposed) is contracted by implant structure 133. For some applications, the sleeve defines two contraction-restricted portions 52, as described hereinabove. For such applications, typically upon implantation of the sleeve at the annulus, the contraction-restriction portions are disposed in the vicinity of trigones 142 and 144.

FIG. 17D shows implant structure 133 following extraction of manipulator 24 from within the lumen of sleeve 26. Immediately following the extraction of manipulator 24, flap 27 of closure element 290 is disposed in an opened state, as shown. Additionally, implant structure 133 is shown in a non-contracted state having an angle α (alpha) between respective longitudinal axes 78 of successive anchors 38, angle α being between 10 degrees and 30 degrees.

As shown in FIGS. 15 and 17A-D, implant structure 133 comprises a contracting mechanism, such as contracting mechanism 28. Contracting mechanism 28 comprises a rotatable structure, arranged such that initial rotation of the rotatable structure in a first rotational direction in order to pull contracting member 30, closes flap 27 over the opening at end 49 of implant structure 133, and further rotation of the rotatable structure in the first rotational direction contracts at least a portion (e.g., the entire contraction-facilitated portion 153) of implant structure 133. It is to be noted that the rotatable structure is capable of being rotated bidirectionally such that following rotation of the rotatable structure in the first rotational direction in order to contract implant structure 133, the rotatable structure may be rotated initially in a second rotational direction that is opposite the first rotational direction, in order slacken contracting member 30 to expand at least a portion (e.g., the entire contraction-facilitated portion 153) of implant structure 133. In response to further rotation of the rotatable structure in the second rotational direction, flap 27 is opened. Implant structure 133 further comprises a longitudinal member 86, such as a wire, which is coupled to contracting mechanism 28 and passes out of the body of the patient.

Figure 17E:
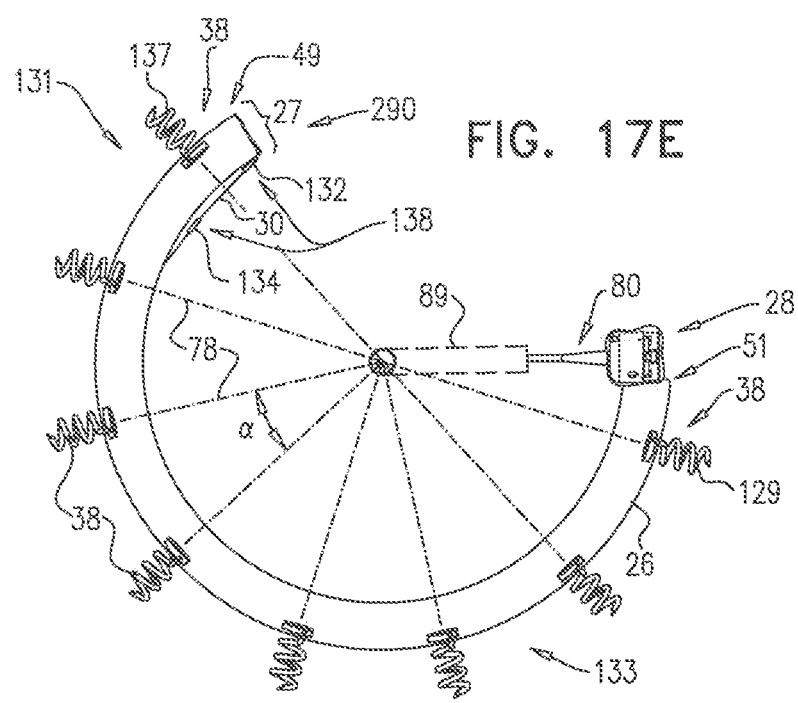
Figure 17F:
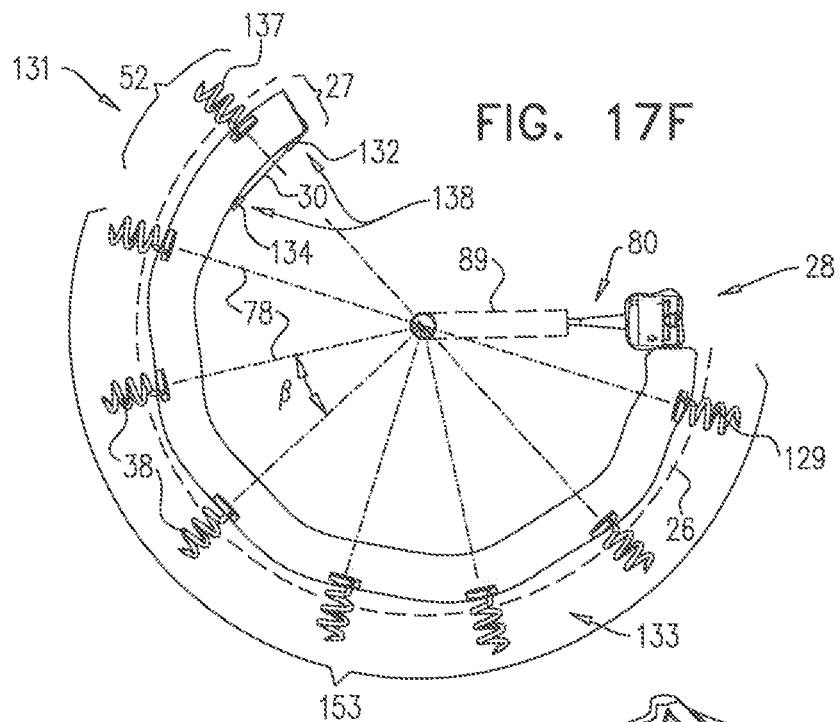
FIG. 17F shows contraction of at least part of the implant structure of FIG. 15, in accordance with some applications of the present invention.

Reference is now made to FIGS. 17E-F, which are schematic illustrations of a rotation tool 80 used to facilitate contraction of implant structure 133 by actuating contracting mechanism 28. A tool, such as rotation tool 80, is provided for rotating the rotatable structure. Tool 80 is configured to be guided over longitudinal member 86, to engage the rotatable structure of contracting mechanism 28, and to rotate the rotatable structure in response to a rotational force applied to the tool.

Reference is now made to FIGS. 17D-E. As shown in FIG. 17D, contracting mechanism 28 is shaped so as to provide a driving interface 48 which facilitates coupling of rotation tool 80 to the rotatable structure of contracting mechanism 28. In order to readily bring the rotation tool to driving interface 48, rotation tool 80 is guided over (as shown in FIG. 3E) the longitudinal member, or alongside the longitudinal member (configuration not shown). Alternatively, longitudinal member 86 comprises a suture or other highly flexible element. For some applications, the longitudinal member comprises a tube, through which rotation tool 80 is passed to bring the tool to the driving interface 48. For some applications, longitudinal member 86 has a diameter of between 0.1 and 1 mm, such as 0.4 mm.

For some applications, longitudinal member 86 is looped through contracting mechanism 28, and both ends of the longitudinal member are brought together and extend outside of the patient's body. The longitudinal member is decoupled from the contracting mechanism by releasing one end of the longitudinal member, and pulling on the other end to draw the longitudinal member away from the contracting mechanism.

For some applications, contracting mechanism 28 is positioned in a vicinity of (e.g., within 1 cm of) distal end 51 of sleeve 26, and access to driving interface 48 is provided from outside sleeve 26, as shown in FIGS. 17E-F (in which the contracting mechanism is positioned in a vicinity of end 51 of the sleeve).

For some applications in which access to driving interface 48 is provided from outside sleeve 26, the rotation tool is initially removably attached to the driving interface, prior to the commencement of the implantation procedure, and is subsequently decoupled from the driving interface after the rotatable structure has been rotated. In these applications, contracting mechanism 28 may be positioned in a vicinity of distal end 51 or proximal end 49 of sleeve 26, or at an intermediate location along the sleeve. Optionally, at least a portion of a shaft of the rotation tool is positioned within a sheath 89 which advances through an access sheath that is disposed within the vasculature of the patient.

FIG. 17E shows implant structure 133 prior to contraction thereof. Contracting mechanism 28 is initially rotated in a first rotational direction so as to close flap 27 over the opening at end 49 of implant structure 133. As shown during the initial pulling of contracting member 30 by initial rotation of the rotatable structure of contracting mechanism 28, the angle between respective longitudinal axes 78 of successive anchors 38 remains angle α (alpha).

In FIG. 17F, contracting mechanism 28 is actuated further by rotation tool 80 in order to contract at least a portion of structure 133 (i.e., at least a portion or all of contraction-facilitated portion 153 of structure 133). As shown, an angle β (beta) between respective longitudinal axes 78 of successive anchors 38 of contraction-facilitated portion 153, angle β being between 5 degrees and 25 degrees, and being smaller than angle α (alpha) shown in FIGS. 17D-E. Additionally, as shown in FIG. 17F, sleeve 26 at contraction-facilitated portion 153 is shown as being in a contracted state (i.e., wavy, as shown), while sleeve 26 at contraction-restricted portion 52 is shown in a non-contracted state (i.e., straight, as shown).

Figure 18:
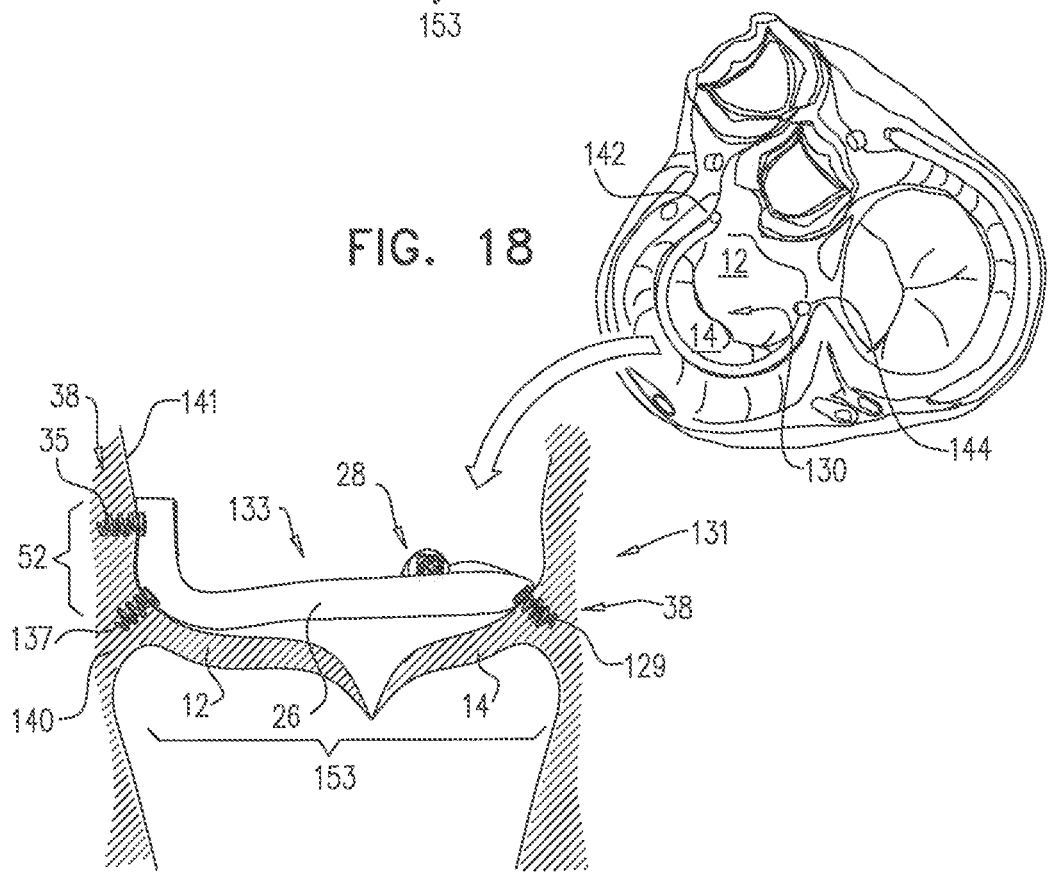
FIG. 18 is a schematic illustration showing a portion of the implant structure of FIG. 15 being coupled to a portion of an atrial wall of a heart of a patient; in accordance with some applications of the present invention.

Reference is now made to FIG. 18, which is a schematic illustration showing a portion of implant structure 133 being coupled to a portion of an atrial wall 141 of the heart of the patient, in accordance with some applications of the present invention. For some applications, a portion (e.g., the entire portion) of contraction-restricted portion 52 of is anchored to the portion of atrial wall 141. For such applications, the entire contraction-facilitated portion 153 may be coupled to the annulus of valve 130 along a portion of the annulus that is between trigones 142 and 144 and along a junction of the annulus and a posterior leaflet 14 and portions of anterior leaflet 12. In such an application, since contraction-restricted portion 52 is not disposed along the portion of the annulus, the entire portion of the annulus (i.e., the section along which contraction-facilitated portion 153 is disposed) is contracted by implant structure 133.

It is to be noted, as shown that first anchor 137 is anchored to the annulus in a vicinity of first trigone 142 (e.g., at first trigone 142), and second anchor 129 is anchored to the annulus in a vicinity of second trigone 144 (e.g., at second trigone 144).

Reference is now made to FIGS. 17D and 18. It is to be noted that implant structure 133, shown in either application in FIG. 17D or 18, has the same length when elongated along a longitudinal axis (i.e., when not formed into a curved structure, as shown). It is to be noted that anchoring structure to the annulus of valve 130 using either application as shown in FIG. 17D or 18 depends on the level of distention of valve 130 of a given patient. That is, for patients having a greater degree of distention, the entire structure 133 is coupled to the annulus along the portion thereof that is between first and second trigones 142 and 144, respectively, and along the junction of the annulus and posterior leaflet 14 and portions of anterior leaflet 12. For patients having a lesser degree of distention, excess portions of structure 133 may be anchored to the portion of atrial wall 141. It is to be noted that the portion of atrial wall 141 to which the portion of structure 133 is anchored may be a portion of a free wall of the atrium, as shown, or a portion of the interatrial septum (not shown). Typically, contraction-restricted portion 52 is anchored to the portion of atrial wall 141.

Reference is made to FIGS. 19A-C, which are schematic illustrations of a configuration of one of anchors 38A, in accordance with an application of the present invention. For some applications, each of first tissue anchors 38A comprises a helical tissue coupling element 200, and a tool-engaging head 202, fixed to one end of the tissue coupling element (the proximal end of the tissue coupling element, opposite the distal end that first penetrates the tissue). Anchor 38A comprises a hard material, such as metal, e.g., steel, Nitinol, or stainless steel SS316LVM. Anchor 38A may be manufactured from a single piece of material, or coupling element 200 and tool-engaging head 202 may be manufactured from separate pieces of material and fixed together.

Typically, helical tissue coupling element 200 has an inner diameter D3 of at least 1.5 mm, no greater than 2.5 mm, and/or between 1.5 and 2.5 mm, e.g., 1.8 mm, along an entire length thereof along a central longitudinal axis 210 of the anchor (although the inner diameter is shown as being constant along the entire length of coupling element 200, the inner diameter optionally varies along the length of the coupling element). An outer diameter D4 of helical tissue coupling element 200 may be, for example, at least 2.4 mm, no greater than 5 mm, and/or between 2.4 and 5 mm, e.g., 2.4 mm.

Tool-engaging head 202 is shaped so as to define an engaging opening 212 that passes entirely through the tool-engaging head along axis 210. The engaging opening is typically at least partially non-circular, such as in order to engage a rotating deployment element of a deployment tool. For example, as shown in FIGS. 5A-C, engaging opening 212 may be shaped so as to define a proximal non-circular internal engaging surface 220, and a distal circular non-engaging surface 222. Proximal engaging surface 220 is shaped to engage a rotating deployment element, such that rotation of the deployment element rotates tool-engaging head 202 and anchor 38A. For example, proximal engaging surface 220 may be rectangular (e.g., square), teethed (e.g., defining a plurality of squares with which the rotating element can engage), star-shaped, polygonal (e.g., octagonal), or any other appropriate non-circular shape.

A portion of the deployment element may pass partially or completely through distal non-engaging surface 222, without engaging this surface. The non-engaging surface may serve as a shoulder, which pushes against the tissue, providing resistance when the anchor has been sufficiently screwed into the tissue. Optionally, the deployment element does not pass entirely through distal non-engaging surface 222, such that the deployment element does not press against or into the tissue. Alternatively, the deployment element may protrude slightly from the distal non-engaging surface 222, when no force is applied to the deployment element by the tissue. Optionally, when the anchor is pressed against the tissue, inner spaces in the tool-engagement head 202 of the anchor allow the deployment element to sink into the anchor, and not press against the tissue. Engaging opening 212 typically has a cross-sectional area (perpendicular to axis 210) of at least 0.8 mm2, such as at least 1.2 mm2.

For some applications, a proximal-most portion 224 of helical tissue coupling element 200, at the end which is fixed to tool-engaging head 202, is generally straight and oriented generally parallel to axis 210, i.e., at angle of between 0 and 15 degrees with the axis, such as 0 degrees. Proximal-most portion 224 typically has a length of between 0.5 and 2 mm, such as about 1 mm.

The outer perimeter of tool-engaging head 202 is typically circular, and an outer diameter D5 of tool-engaging head 202 may be, for example, at least 2 mm, no greater than 7 mm, and/or between 2 and 7 mm, such as between 2.5 and 5 mm, e.g., 2.4 mm, 2.5 mm, or 3 mm.

The outer diameter of anchor 38A may be, for example, at least 2 mm, no greater than 7 mm, and/or between 2 and 7 mm, such as between 2.5 and 5 mm. The entire length of anchor 38A, measured along axis 210, is typically at least 2.5 mm, no greater than 10 mm, and/or between 2.5 and 10 mm, such as between 3 and 4.5 mm. A length L1 of tissue coupling element 200, measured along axis 210, may be at least 2.5 mm, no greater than 10 mm, and/or between 2.5 and 10 mm, such as between 3 and 4.5 mm. Typically, helical tissue coupling element 200 has between 3 and 5 turns.

The proximal end of tissue coupling element 200 is typically fixed to tool-engaging head 202 near the outer perimeter of the tool-engaging head, such that the tissue coupling element does not block engaging opening 212. For example, as labeled in the top-view of the anchor in FIG. 19C, the tissue coupling element may be fixed to the tool-engaging head such that one or more of the following dimension characterize the anchor:

a distance D7 between (a) a center 226 of the proximal end of tissue coupling element 200 and (b) an outer perimeter of tool-engaging head 202 is no greater than 20% of a width D5 of tool-engaging head 202 (the width is a diameter for applications in which the head is circular), such as no greater than 10% of width D3. For example, distance D7 may be between 0.1 and 0.3 mm, e.g., 0.2 mm;

a distance D8 between (a) a most radially-inward portion 228 of the proximal end of tissue coupling element 200 (i.e., the portion of the proximal end that is closest to central longitudinal axis 210 of the anchor) and (b) the outer perimeter of tool-engaging head 202 is no greater than 40% of width D5 of tool-engaging head 202 (the width is a diameter for applications in which the head is circular), such as no greater than 30% of width D5, or no greater than 20% of width D5. For example, distance D8 may be between 0.3 and 0.5 mm, e.g., 0.4 mm; and/or a distance between (a) a most radially-outward portion 230 of the proximal end of tissue coupling element 200 (i.e., the portion of the proximal end that is furthest from central longitudinal axis 210 of the anchor) and (b) the outer perimeter of tool-engaging head 202 is no greater than 10% of width D5 of tool-engaging head 202 (the width is a diameter for applications in which the head is circular), such as no greater than 5% of width D5, e.g., 0. For example, the distance may be between 0 and 0.1 mm, e.g., 0 mm.

Anchor 38A, including both helical tissue coupling element 200 and tool-engaging head 202, is thus shaped so as to provide a channel along the entire length of the anchor, through which a flexible inner shaft can pass, and through which a rotating deployment element can pass when in its radially-compressed state. More generally, as shown in FIG. 5B, the channel is sized and shaped such that a right circular cylinder 232 could be placed within the channel, coaxial with anchor 38A (i.e., the axis of the cylinder coincides with central longitudinal axis 210 of anchor 38A), and along the entire length of the tissue anchor, the cylinder having a diameter D6 of at least 1 mm, such as at least 2 mm. It is to be understood that cylinder 232 is an abstract geometric shape, rather than an element of an embodiment of the invention, and, as such, is perfectly cylindrical, i.e., is not shaped so as to define any grooves or other surface or internal anomalies. No portion of anchor 38A intersects central longitudinal axis 210.

Figure 19D:
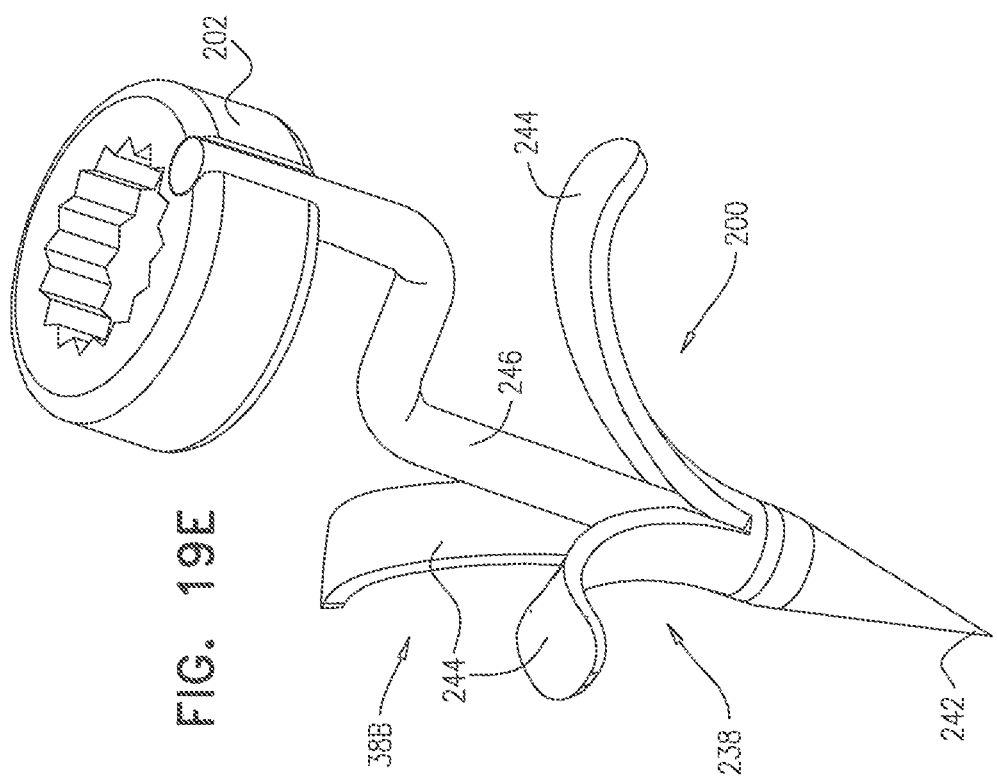

Reference is made to FIG. 19D, which is a schematic illustration of a configuration of one of second tissue anchors 38B, in accordance with an application of the present invention. In this configuration, second tissue anchor 38B may be generally similar to first tissue anchor 38A (e.g., as described hereinabove with reference to FIGS. 19A-C), except that second tissue anchor 38B differs from first tissue anchor 38A in size. For example, second tissue anchor 38B may be smaller than first tissue anchor 38A. Typically, a length L2 of tissue coupling element 200 of second tissue anchor 38B, measured along axis 210, is less than length L1 of tissue coupling element 200 of first tissue anchor 38A. For example, length L2 may be between 25% and 75% of length L1, and/or at least 2 mm, no more than 6 mm, and/or between 2 and 6 mm, such as at least 2 mm, no more than 4 mm, and/or between 2 and 4 mm. Alternatively or additionally, helical tissue coupling element 200 of second tissue anchor 38B has fewer turns than does helical tissue coupling element 200 of first tissue anchor 38A. For some applications, helical tissue coupling element 200 of second tissue anchor 38B has between 25% and 75% of the turns of helical tissue coupling element 200 of first tissue anchor 38B. For example, helical tissue coupling element 200 of second tissue anchor 38B may have at least one turn, no more than three turns, and/or between one and three turns.

For some applications, each of tissue coupling element 200 of first tissue anchor 38A and tissue coupling element 200 of second tissue anchor 38B is shaped so as to define a shape selected from the group consisting of: a helix, a spiral, and a screw shaft, and the lengths of the coupling elements are measured along a longitudinal axis of the shape. Alternatively or additionally, the tissue coupling element of second tissue anchor 38B has fewer turns than does the tissue coupling element of first tissue anchor 38A.

For some applications, such as when second tissue anchors 38B are helical, second tissue anchors 38B alternatively or additionally differ from first tissue anchors 38A in that tissue coupling elements 200 of second tissue anchors 38B are rectangular in cross-section, rather than circular, which may provide a greater tissue surface contact area. Alternatively or additionally, helical second tissue anchors 38B may be shaped so as to define barbs, such as described hereinbelow with reference to FIG. 19I, mutatis mutandis.

Figure 19E:
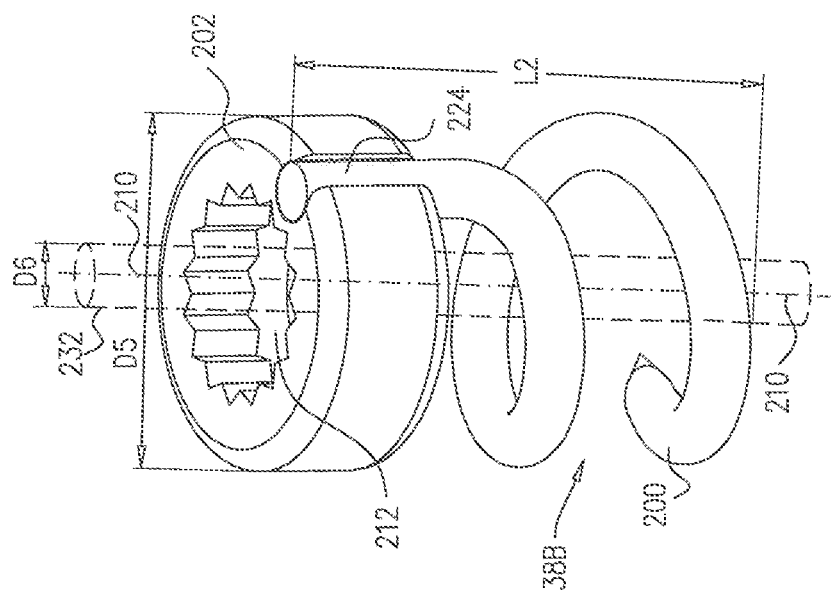

Reference is made to FIG. 19E, which is a schematic illustration of another configuration of one of second tissue anchors 38B, in accordance with an application of the present invention. In this configuration, each of tissue coupling elements 200 of second tissue anchors 38B is shaped similar to a harpoon 238, which is shaped so as to define a sharp tip 242 and plurality of spikes 244 (e.g., three) that extend toward tool-engaging head 202. Spikes 244 are flexible (for example, they may comprise Nitinol or another shape memory alloy). For some applications, spikes 244 are initially crimped straight within a bore of a needle (not shown); after the needle and spikes are inserted into the tissue, the needle is withdrawn, leaving the spikes to expand radially outward in the tissue, so as to assume the configuration shown in FIG. 5F. Typically, tissue coupling element 200 is coupled to tool-engaging head 202 by a shaft 246.

Reference is made to FIG. 19F, which is a schematic illustration of another configuration of one of second tissue anchors 38B, in accordance with an application of the present invention. In this configuration, each of tissue coupling elements 200 is shaped so as to define a plurality (e.g., three) spiked arms 248, which are coupled to tool-engaging head 202 by a shaft 280, and a sharp tip 249. Spiked arms 248 typically are flexible (for example, they may comprise Nitinol or another shape memory alloy). After the sharp tip and spiked arms are inserted into the tissue, the spikes expand radially outward and toward the tool-engaging head in the tissue, so as to assume the configuration shown in FIG. 19F.

Reference is made to FIG. 19G, which is a schematic illustration of another configuration of one of second tissue anchors 38B, in accordance with an application of the present invention. In this configuration, each of tissue coupling elements 200 is shaped so as to define a screw shank 282, which is coupled to tool-engaging head 202. Shank 282 is shaped so as to define a screw thread 284, and is typically tapered.

Reference is made to FIG. 19H, which is a schematic illustration of yet another configuration of one of second tissue anchors 38B, in accordance with an application of the present invention. In this configuration, each of tissue coupling elements 200 is shaped similar to a septal occluder, e.g., the Amplatzer® PFO Occluder (AGA Medical Corporation, Plymouth, MN, USA). For example, tissue coupling element 200 may be similar to the configuration shown in FIGS. 12A-C of US Patent Application Publication 2009/0326648 to Machold et al., or FIGS. 21A-B of US Patent Application Publication 2010/0130992 to Machold et al., both of which publications are incorporated herein by reference. For some applications, tissue coupling element 200 comprises a mesh shaped into first and second discs 286 and 288, and a narrower waist section 289 between the two discs. The mesh may comprise wire, such as Nitinol, or a soft material, such as silicone. The wall of the sleeve and the tissue of the annuls are squeezed between the first and second discs, thereby anchoring the sleeve to the tissue.

Reference is made to FIG. 19I, which is a schematic illustration of another configuration of one of second tissue anchors 38B, in accordance with an application of the present invention. In this configuration, each of tissue coupling elements 200 is shaped as a shaft 294 from which barbs 296 protrude radially outward and away from the tip of the tissue coupling elements.

For some applications, second tissue anchors 38B comprise sutures which are placed using a delivery tool.

Reference is made to FIG. 19J, which is a schematic illustration of a configuration of a third tissue anchor 38C, in accordance with an application of the present invention. In this configuration, third tissue anchor 38C may be generally similar to first tissue anchor 38A (e.g., as described hereinabove with reference to FIGS. 19A-C), except that helical tissue coupling element 200 of third tissue anchor 38C extends from a middle portion of tool-engaging head 202. In such an application, tool-engaging head 202 is not a channel, but rather provides a female groove for engaging a tool to head 202. Head 202 provides a surface in a middle portion thereof to which is coupled proximal-most portion 224 of helical tissue coupling element 200.

For some applications, third tissue anchor 38C comprises a suture which is placed using a delivery tool.

Figure 20:
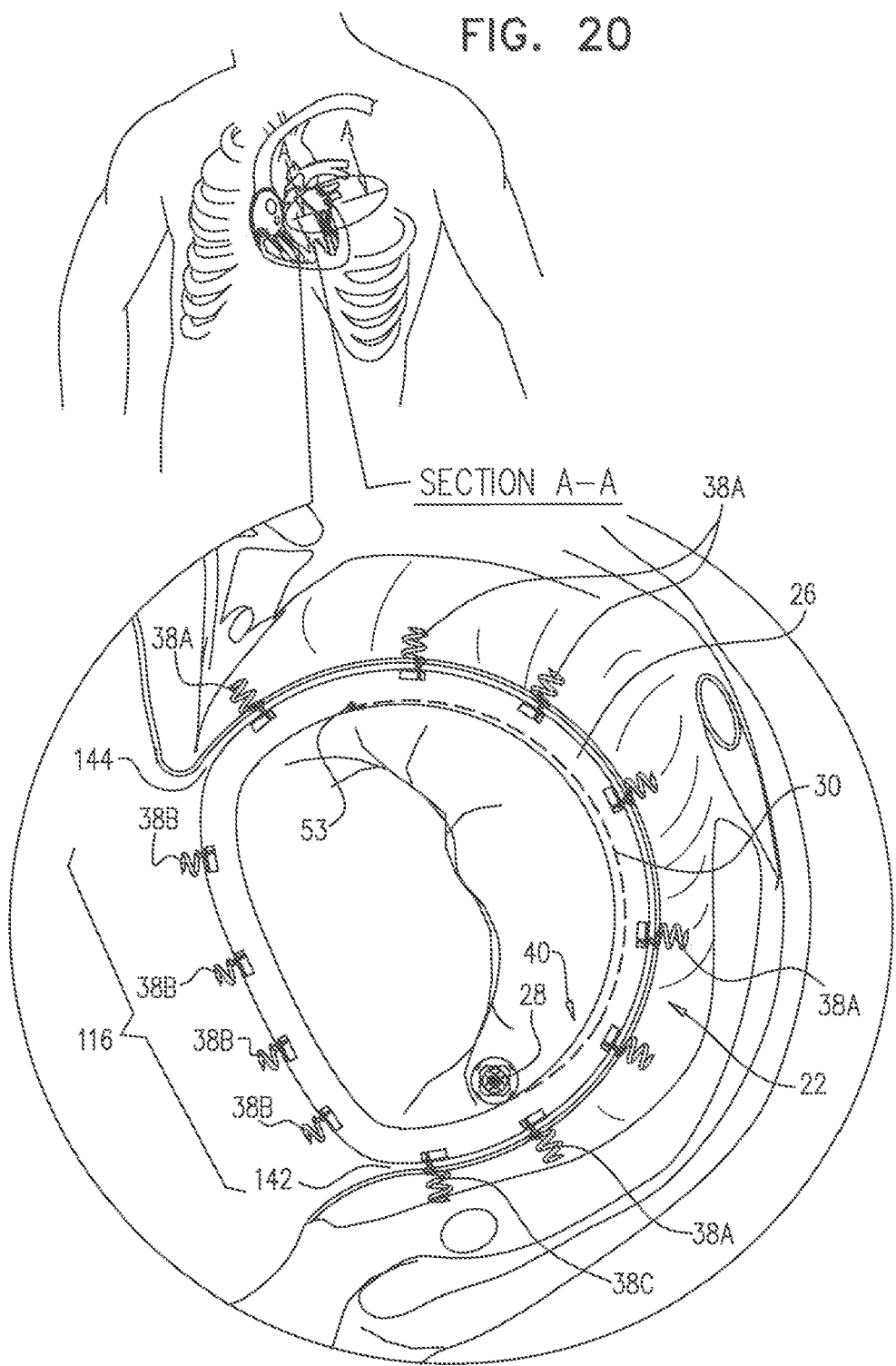
FIG. 20 is a schematic illustration of a closed-loop configuration of the implantable structure of FIG. 1, in accordance with an application of the present invention.

Reference is made to FIG. 20, which is a schematic illustration of an alternative closed-loop configuration of implantable structure 22, in accordance with an application of the present invention. In this configuration, flexible sleeve 26 is shaped so as to define an integrally closed loop having no sleeve ends. For some applications, anchors 38 deployed along anterior portion 116 of the annulus are of a different configuration from anchors 38 deployed along the remainder of the annulus, as described hereinabove with reference to FIGS. 4-5 and 19A-J. The anchors may be configured as any one of the anchors described hereinabove with reference to FIGS. 19A-J.

Typically, contracting member 30 does not extend along the portion of sleeve 26 deployed along anterior portion 116 of the annulus. The portion of the sleeve deployed along anterior portion 116 of the annulus (between the trigones) is thus non-contractible. Tightening of implantable structure 22 therefore tightens at least a portion of the posterior portion of the annulus, while preserving the length of anterior portion 116 of the annulus. (The anterior portion of the annulus should generally not be contracted because its tissue is part of the skeleton of the heart.) However, the portion of the sleeve deployed along the anterior portion of the annulus prevents dilation of the anterior annulus, because the sleeve is anchored at both ends of the anterior annulus, and, as mentioned above, the sleeve typically comprises a longitudinally non-extensible material. This deployment configuration may help prevent long-term resizing of the anterior annulus, which sometimes occurs after implantation of partial annuloplasty rings, such as C-bands.

For some applications, the non-contractible portion of sleeve 26 (the portion without contracting member 30) extends somewhat beyond one or both of trigones 142 or 144 (in the posterior direction, away from anterior portion 116 of the annulus), such as up to 20 mm, such as up to 10 mm.

For some applications, at least one anchor 38 is coupled to cardiac tissue on the posterior side of right fibrous trigone 144, between the trigone and the end of contracting member 30. Similarly, at least one anchor 38 may be coupled to cardiac tissue on the posterior side of left fibrous trigone 142, between the trigone and the other end of contracting member 30 (which, for some applications, is coupled to contracting mechanism 28, as shown in FIG. 20).

Figure 21:
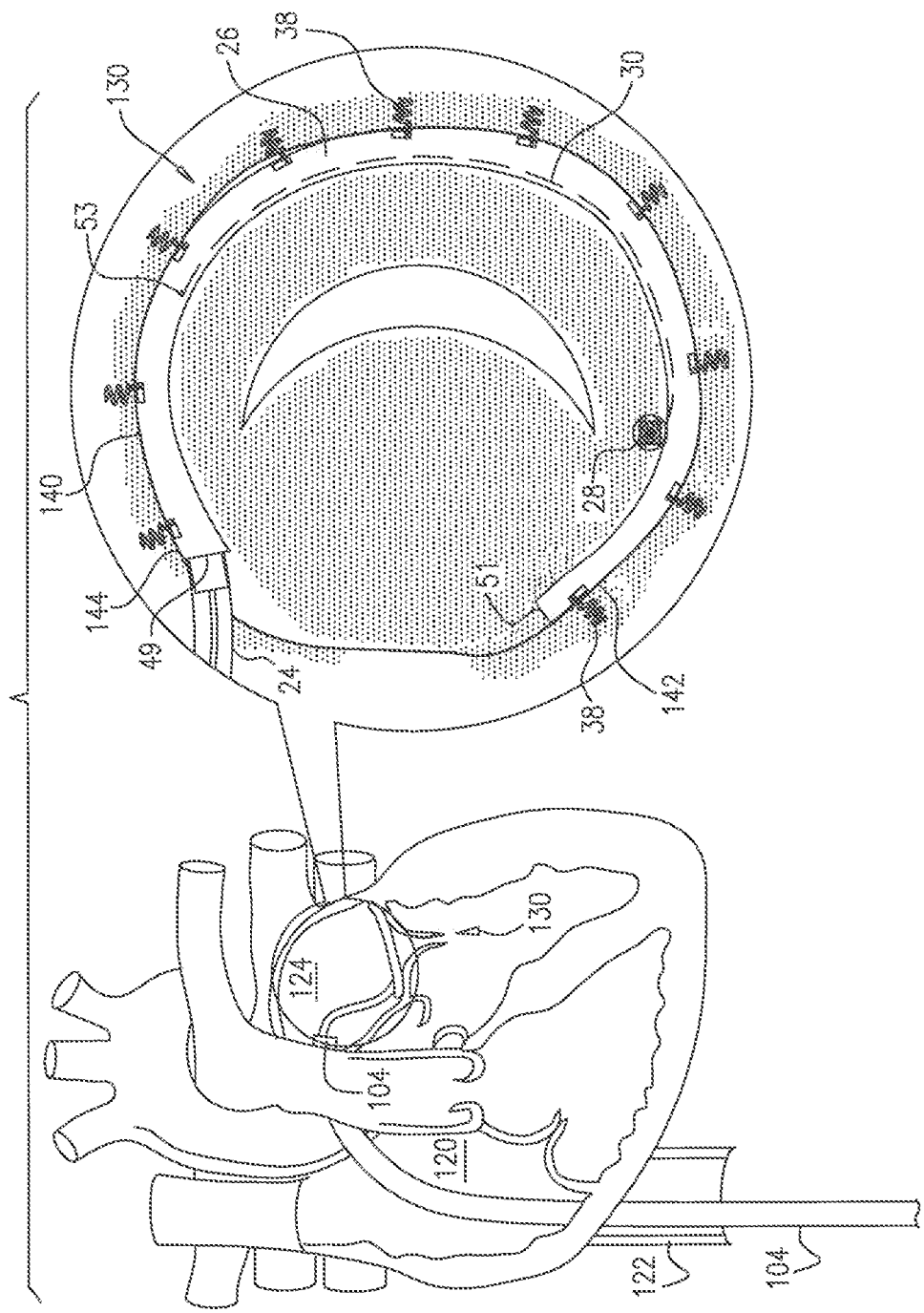
FIG. 21 is a schematic illustration of yet another configuration of the implantable structure of FIG. 1, prior to implantation, in accordance with an application of the present invention.

Reference is now made to FIGS. 21 and 22, which are schematic illustrations of another configuration of implantable structure 22, in accordance with an application of the present invention. FIG. 21 shows implantable structure 22 in a relaxed, non-contracted state, and FIG. 22 shows the implantable structure implanted around mitral valve 130. This configuration of implantable structure 22 is generally similar to the configuration described hereinabove with reference to FIG. 1, except as follows. In this configuration, implantable structure 22 further comprises an elongated linking member 250, which is positioned at least partially along anterior portion 116 of the annulus, so as to join the ends of implantable structure 22 in a complete loop. Over time after implantation, linking member 250 becomes fixed to anterior portion 116 of the annulus, thereby helping prevent long-term dilation of the anterior annulus. Typically, at least a portion (e.g., at least 30%, such as at least 75% or at least 90%) of a length of linking member 250 is disposed within and covered by sleeve 26, into and/or over which fibrous tissue grows over time, helping anchor the linking member to tissue of the anterior annulus. Alternatively or additionally, a separate flexible sleeve or a coating (e.g., a polymeric coating) may be provided that covers at least 20%, e.g., between 20% and 80%, of the linking member. Typically, in the configuration of implantable structure 22 shown in FIGS. 21 and 22, none of anchors 38 is coupled to anterior portion 116 of the annulus.

Linking member 250 has first and second linking member ends 252 and 254. Second linking member end 254 comprises (e.g., is shaped so as to define, or is fixed to) a first coupling element 256. First linking member end 252 is disposed longitudinally between second linking member end 252 and a first sleeve end (either proximal end 49, as shown, or distal end 51, not shown), exclusive. Second linking member 254 either protrudes from the second end of the sleeve, or is recessed within the second end of the sleeve (as shown, the second end of the sleeve is distal end 51). A longitudinal portion of linking member 250 in a vicinity of first linking member end 252 is coupled to the sleeve. For example, the portion may be threaded through the fabric of the sleeve, and/or sewn (e.g., sutured) to the fabric of the sleeve to hold the linking member in place during deployment, and the linking member may be held in place after implantation by one or more of anchors 38. Optionally, the linking member is not initially coupled to the sleeve, but is instead held in place by a delivery tool during the implantation procedure, until being coupled to the sleeve by one or more of the anchors, for example. The coupled longitudinal portion may have a length of between 2 and 10 mm, and optionally includes first linking member end 252 of the linking member.

Implantable structure 22 further comprises a second coupling element 260, which is configured to be coupleable to first coupling element 256. Second coupling element 260 typically is coupled to implantable structure 22 within 1.5 cm of the first end of sleeve 26 (opposite the end mentioned above near which first linking member end 252 is fixed), measured when the sleeve is fully longitudinally extended. As mentioned above, in the configuration shown in FIGS. 21 and 22, this first end is proximal end 49.

For some applications, such as shown in FIGS. 21 and 22, contracting mechanism 28 (e.g., housing 44 thereof) is disposed along sleeve 26 within 1.5 cm of the first sleeve end (i.e., the same end of the sleeve near which the second coupling element is coupled). Second coupling element 260 may be coupled to contracting mechanism 28 (e.g., to housing 44). Alternatively, second coupling element 260 may be otherwise coupled to sleeve 26 (such as directly coupled), in which case contracting mechanism 28, e.g., housing 44 thereof, may be coupled to sleeve 26 at a greater longitudinal distance from the end of the sleeve, and one or more of anchors 38 may be coupled to the sleeve longitudinally between the contracting mechanism and the sleeve end, such as described hereinabove with reference to FIGS. 1, 2A-I, 4, and 5.

Typically, linking member 250 is substantially longitudinally non-extensible, i.e., its length is fixed. Typically, linking member 250 comprises metal, such as Nitinol or stainless steel. For some applications, the linking member has a length of at least 2 cm, no more than 6 cm, and/or between 2 and 6 cm.

For some applications, the linking member is configured as a spring, which is typically curved, so as to be elastic in a radial direction, i.e., to be compressible like a bow or deflected beam. In these applications, the linking member is oriented such that it is pressed by elasticity against the anterior portion of the mitral annulus, i.e., the outer wall of the aorta, thereby holding the sleeve covering the linking member against the aortic wall.

For some applications, at least two of tissue anchors 38 are coupled to sleeve 26 at respective, different longitudinal sites alongside linking member 250, within 6 cm of first linking member end 252, such as within 2 to 6 cm of the first end. These tissue anchors may help set the proper direction of curvature of the linking member, for applications in which the linking member is curved.

Reference is made to FIGS. 23A-B, which are schematic illustrations of coupling elements 256 and 260, in accordance with respective applications of the present invention. For some applications, at least one of first and second coupling elements 256 and 260 comprises a hook 270. Alternatively or additionally, for some applications, at least one of the first and second coupling elements comprises a loop 272. In the configuration shown in FIG. 23A (and FIGS. 21 and 22), first coupling element 256 comprises hook 270, and second coupling element 260 comprises a loop 272. In the configuration shown in FIG. 23B, both first and second coupling elements 256 and 260 comprises respective loops 272, and the coupling elements are coupled together such as by placing one of anchors 38 through both loops and into cardiac tissue.

Reference is now made to FIGS. 24A-E, which are schematic illustrations of a configuration of system 20 comprising a coiled element 240, in accordance with some applications of the present invention. Implantable structure 22 is generally similar to the configuration of implantable structure 22 described hereinabove with reference to FIGS. 1, 4 and 5, or with reference to FIG. 20 or 21-23B, mutatis mutandis, with the exception that coiled element 240 is advanced within the lumen of sleeve 26 during the implantation procedure, as described hereinbelow, or is prepositioned in the sleeve prior to commencement of the implantation procedure. In this configuration, implantable structure 22 is typically configured to not contract the posterior portion of the annulus along the middle scallop (P2) of the posterior leaflet, and to contract portions of the annulus along (a) a lateral scallop (P1) of the posterior leaflet and extending to left fibrous trigone 142, and (b) the medial scallop (P3) of the posterior leaflet and extending to right fibrous trigone 144.

Implantable structure 22 is implanted along the annulus of the native mitral valve, such as described hereinabove with reference to FIGS. 2A-I, mutatis mutandis. During the implantation procedure, typically after deploying anchors 38, a contraction-restricting-element advancement tube 330 is advanced toward implantable structure 22 through a lumen of a delivery tube 332. It is to be noted that deployment manipulator 24 (shown in FIGS. 2G-I) may be advanced within delivery tube 332 during the anchoring of implantable structure 22 to the annulus. For some applications, advancement tube 330 may be slidable within sheath 104 (shown in FIGS. 2B-G).

As shown in FIG. 24A, advancement tube 330 is advanced within the lumen of sleeve 26 until approximately one of the fibrous trigones (e.g., right fibrous trigone 144, in the direction of implantation shown in FIG. 24A), generally in the vicinity of contracting mechanism 28, e.g., housing 44 thereof. Alternatively, advancement tube 330 is advanced to near the end of the sleeve, before the overlapping portion through which anchor 38E passes.

For some applications, delivery tube 332 is also advanceable within the lumen of sleeve 26 (not shown for clarity of illustration).

Figure 24B:
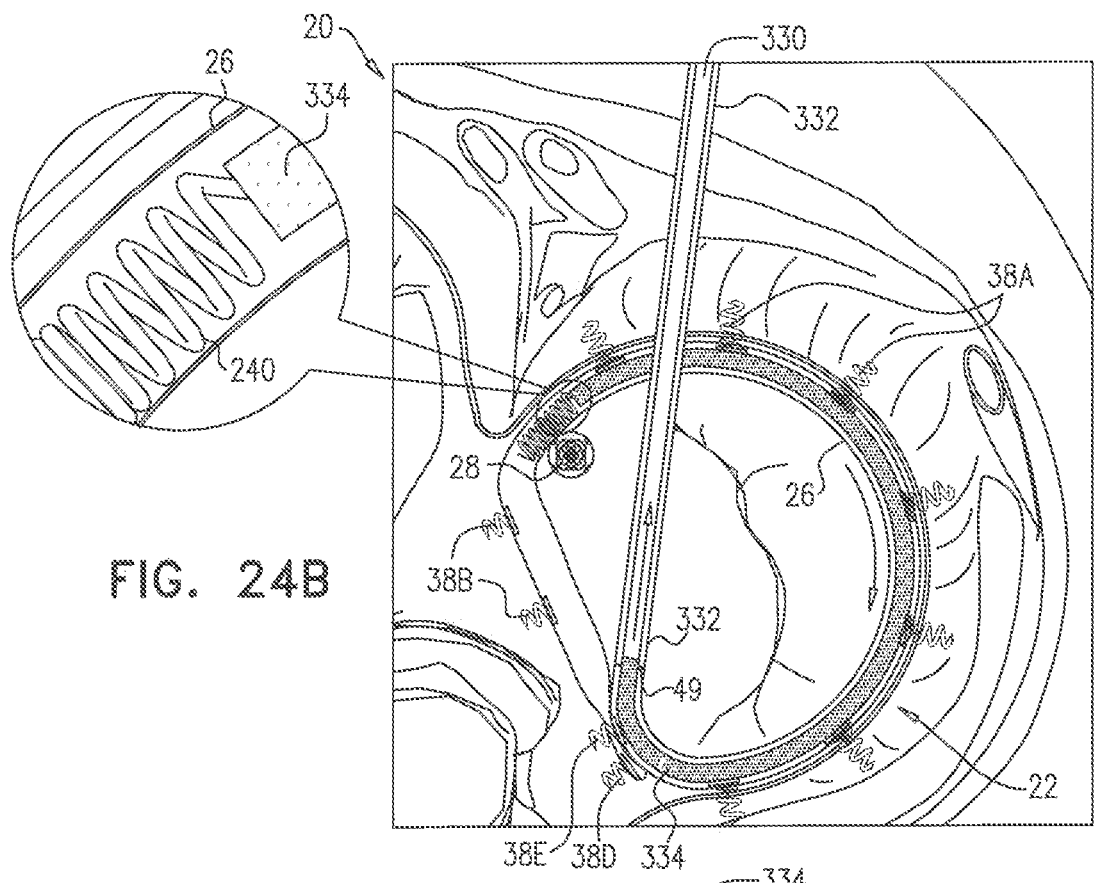

As shown in FIG. 24B, advancement tube 330 houses an overtube 334 which, in turn, houses coiled element 240. Coiled element 240 comprises a flexible material, e.g., Nitinol, which is biased to assume the coiled shape shown in FIG. 10C. For some applications in which the coiled element comprises such a flexible material, coiled element 240 is disposed within overtube 334 in a state in which coiled element 240 is generally straightened from its coiled state, i.e., at least partially uncoiled. In order to deploy element 240 within the lumen of sleeve 26, overtube 334 is retracted in the direction indicated by the arrow in FIG. 24B. For some applications, a pusher (not shown) disposed within overtube 334 proximally to element 240 pushes on element 240 as overtube 334 is retracted. During the deployment of coiled element 240, successive portions of element 240 are exposed from within overtube 334 and assume the predetermined coiled configuration, as shown.

Figure 24C:
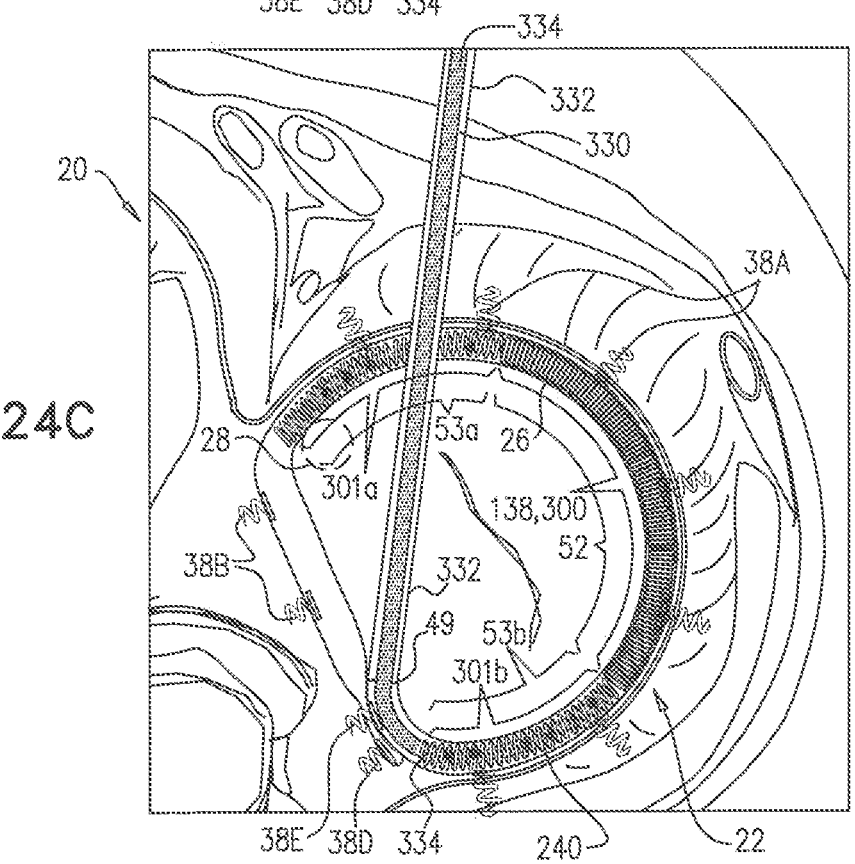

As shown in FIG. 24C, coiled element 240 is advanced within the lumen of sleeve 26 and comprises a contraction-restricting portion 300 (which defines a contraction-restricting element 138) and contractible portions 301a and 301b. In its deployed configuration, i.e., its coiled configuration, element 240 is typically shaped so as to define a diameter of between 2 and 6 mm, e.g., 3 mm.

Figure 24D:
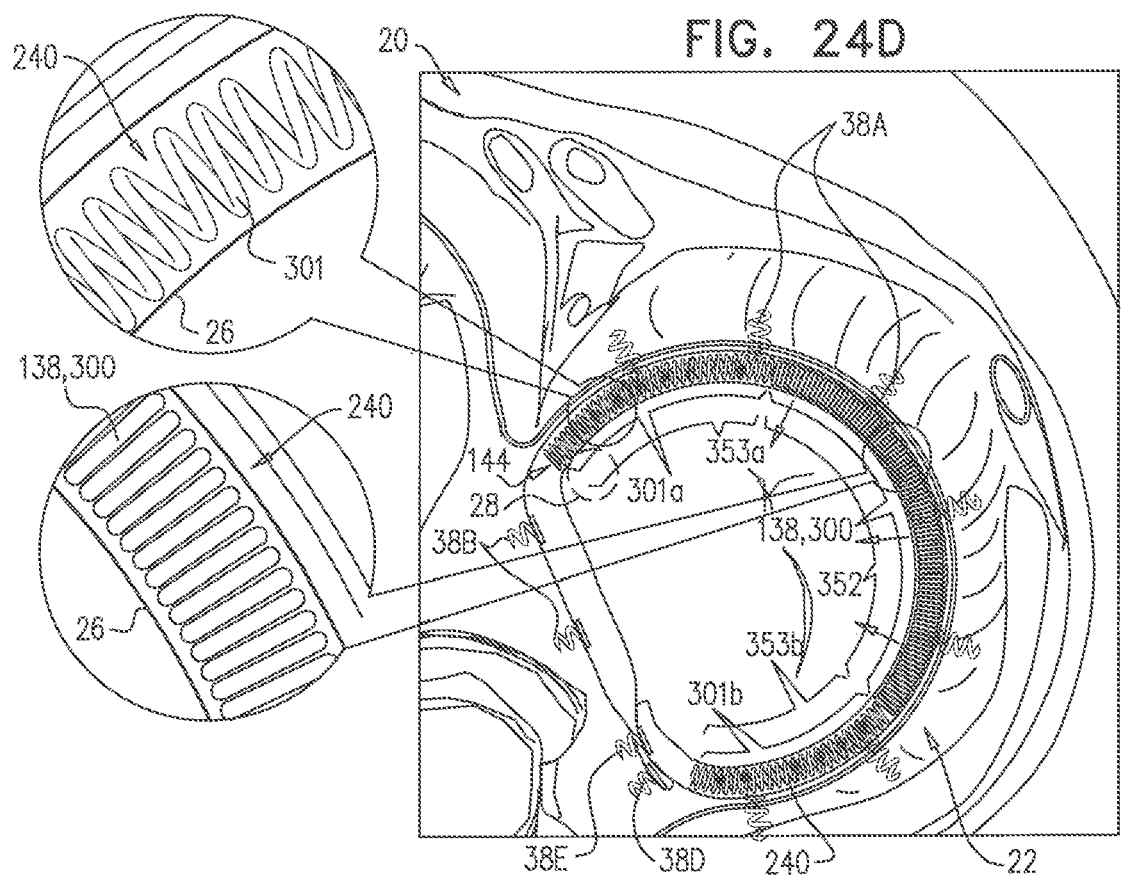

As shown in FIG. 24D, following the advancement of coiled element 240 within the lumen of sleeve 26, overtube 334, advancement tube 330, and delivery tube 332 are removed from within the body of the patient, and the opening at proximal end 49 of implantable structure 22 is typically closed, such as by closure element 290, described hereinabove with reference to FIGS. 10A-B, 11-12, 13A-B, 14A-B, 15-16, 17A-F, and 18.

As shown in FIGS. 24C-D, contraction-restricting portion 300 is a coiled portion of element 240 that is non-compressible, and contractible portions 301a and 301b (that are coupled to, or flank, contraction-restricting portion 300) are respective portions of element 240 that are compressible. Contraction-restricting portion 300 defines a pitch that is smaller than that of portions 301a and 301b (as shown in the blow-ups in FIG. 24D). Thus, if coiled element 240 were to be positioned along a longitudinal axis, contraction-restricting portion 300 would restrict contraction of element 240 (and thereby implantable structure 22) along the longitudinal axis, while contractible portions 301a and 301b would allow contraction of element 240 (and thereby implantable structure 22) along the longitudinal axis. When coiled element 240 is positioned within the lumen of sleeve 26, as shown in FIGS. 24C-D, (1) contraction-restricting portion 300 defines a contraction-restricted portion 352 (or non-contraction-facilitated portion) of structure 22 that is disposed along the portion of the annulus at the posterior leaflet, and (2) contractible portions 301a and 301b define respective contractible portions 353*a* and 353*b* (or contraction-facilitated portions) of structure 22 that are contractible and expandable in response to respective tightening or loosening of contracting member 30 (not shown for clarity of illustration) responsively to the actuation of contracting assembly 40. For some applications, contraction-restricting portion 300 has a length of more than 3 mm and/or less than 120 mm (e.g., a length of 3 mm-120 mm), and defines contraction-restricted portion 352, portion 352 having a length of more than 3 mm and/or less than 120 mm (e.g., a length of 3 mm-120 mm). During the ongoing contraction of structure 22 responsively to the actuation of contracting assembly 40, contractible portions 301*a* and 301*b* facilitate longitudinal contraction of portions 353*a* and 353*b*, respectively, while contraction-restricting portion 300 restricts longitudinal contraction of portion 352, but facilitates radial movement of portion 352 toward the center of the valve (i.e., in the direction as indicated by the arrows). This radial movement of portion 352 brings the posterior leaflet toward the anterior leaflet.

Figure 24E:
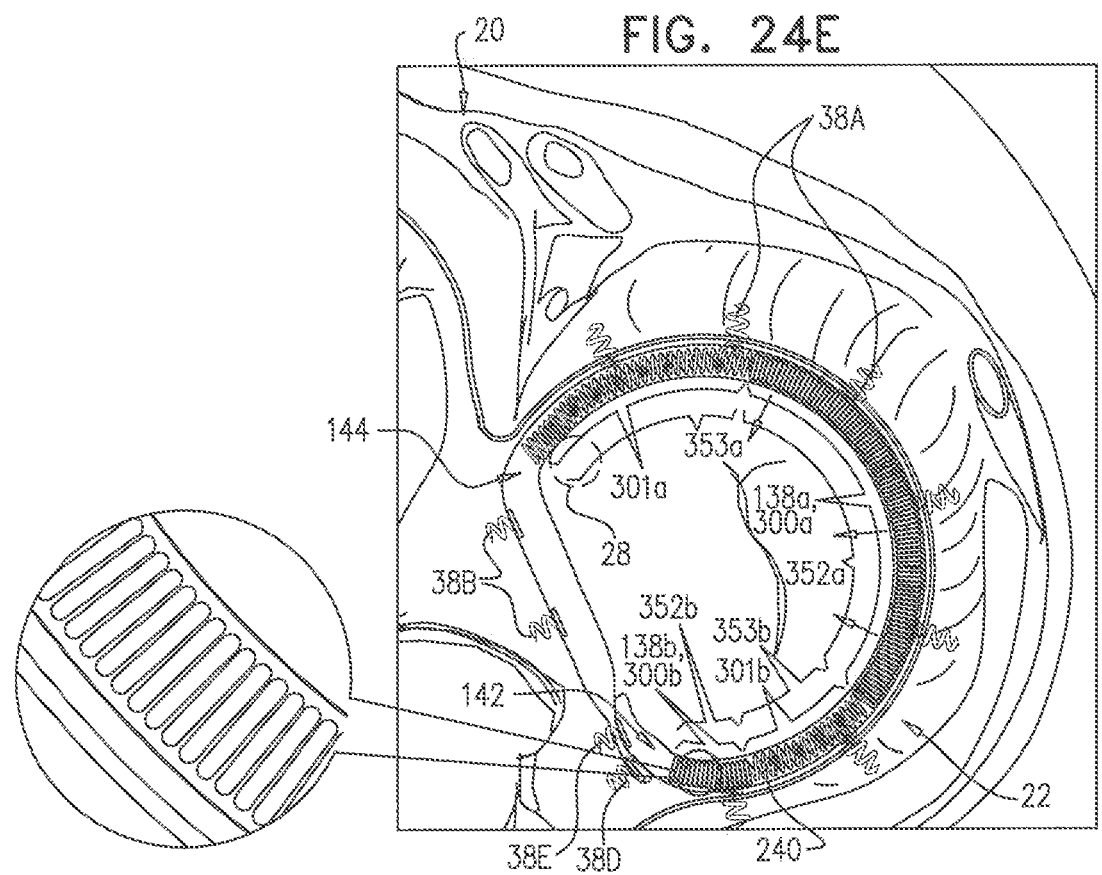

It is to be noted that one contraction-restricting portion 300 and two contractible portions 301*a* and 301*b* are shown in FIGS. 24A-D by way of illustration and not limitation, and that coiled element 240 may comprise any suitable number of portions 300 or 301. For example, in FIG. 24E coiled element 240 is shown defining two contraction-restricting portions 300*a* and 300*b*, and two contractible portions 301*a* and 301*b*. When coiled element 240 is positioned within the lumen of sleeve 26, as shown in FIG. 24E, (1) contraction-restricting portion 300*a* defines contraction-restricted portion 352*a* of structure 22 that is disposed along the portion of the annulus at the posterior leaflet, (2) contraction-restricting portion 300*b* defines contraction-restricted portion 352*b* of structure 22 that is disposed in a vicinity of trigone 142, and (3) contractible portions 301*a* and 301*b* define respective contractible portions 353*a* and 353*b* of structure 22 that are contractible and expandable in response to respective tightening or loosening of contracting member 30 (not shown for clarity of illustration) responsively to the actuation of contracting assembly 40. Typically, contraction-restricted portion 352*a* comprises more than 10% (e.g., more than 20%), and/or less than 60% (e.g., less than 30%) of the resting length of coiled element 240. For some applications, each of contractible portions 353*a* and 353*b* comprises less than 50% (e.g., less than 20%, or less than 10%) of the resting length of coiled element 240. For some applications, the total length of the contractible portions of coiled element 240 comprises less than 50%, e.g., less than 30%, of the resting length of the coiled element.

In the configuration shown in FIG. 24E, coiled element 240 defines two contraction-restricting portions 300*a* and 300*b*, one of which is disposed along the portion of the annulus at the posterior leaflet, and one of which is disposed in a vicinity of one of the trigones. However, the scope of the present invention includes configuration in which coiled element 240 defines three contraction-restricting portions 300, one of which is disposed along the portion of the annulus at the posterior leaflet, and two of which are disposed in vicinities of respective trigones of the subject. For some applications, coiled element 240 defines two contraction-restricting portions 300, which are disposed in vicinities of respective trigones of the subject, e.g., as described with reference to FIG. 28.

For some applications, the implantable structures described herein are configured such that the contraction-restricted portions and the contractible portions of the implantable structures are disposed adjacent to respective portions of the mitral annulus, so as to facilitate reshaping of the mitral annulus in a desired manner. The lengths of the contraction-restricted portions and the contractible portions typically correspond to the corresponding portions of the mitral annulus. Typically, upon placement of the implantable structures described herein at the mitral annulus, contraction-restricted portions 352 and contractible portions 353 are asymmetrically disposed with respect to the mitral annulus. Further typically, lengths of the contraction-restricted portions and the contractible portions are not equal to one another. Alternatively, lengths of the contraction-restricted portions and the contractible portions are equal to one another.

Reference is again made to FIGS. 24A-E. It is to be noted that although system 20 is advanced and implanted within the heart of the patient using a minimally-invasive procedure, any suitable procedure may be used to advance and implant system 20, e.g., a transcatheter procedure or a surgical procedure, such as an open-heart surgical procedure.

Figure 25B:
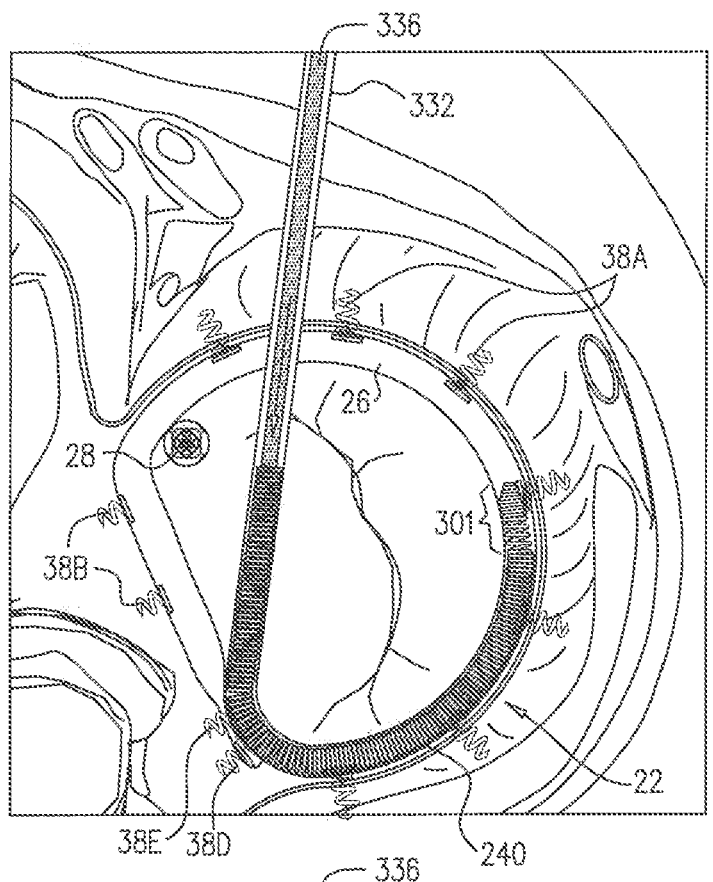
Figure 25C:
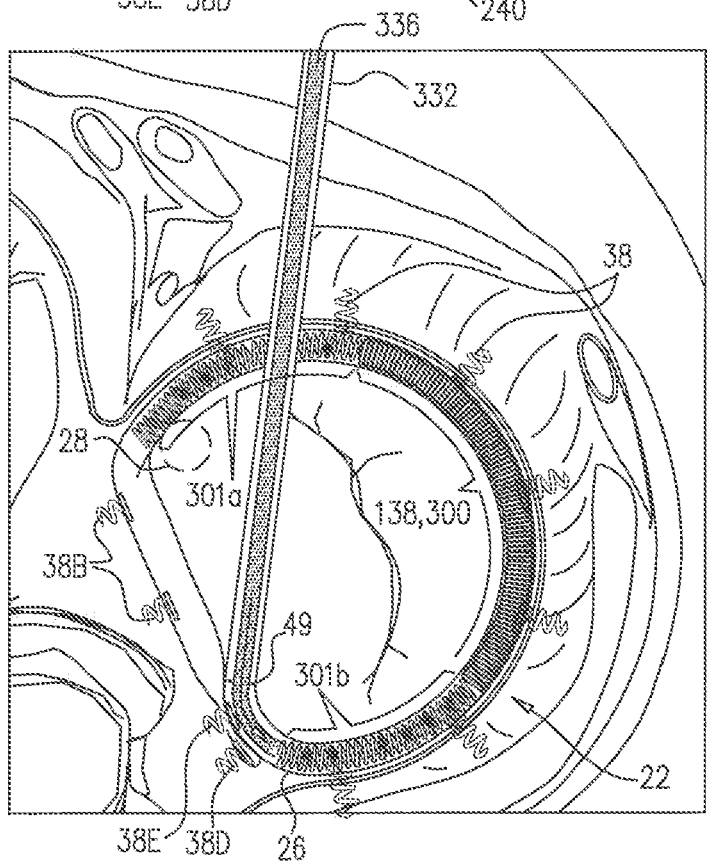
Figure 25D:
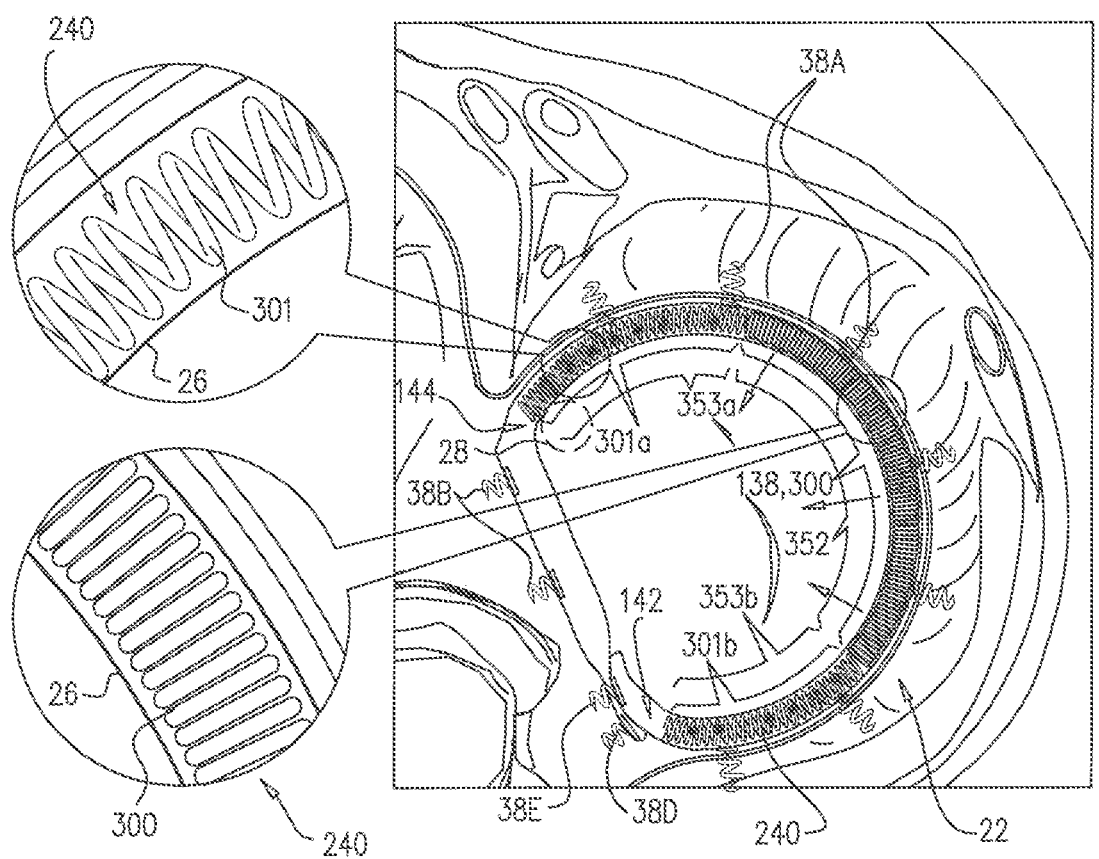

Reference is now made to FIGS. 25A-D, which are schematic illustrations of another configuration of system 20, in accordance with an application of the present invention. This configuration is similar to the configuration described hereinabove with reference to FIGS. 24A-E, with the exception that coiled element 240 is not advanced within overtube 334. Coiled element 240 is instead advanced directly within the lumen of delivery tube 332 and into the lumen of sleeve 26 in its coiled state, as shown in FIGS. 25A-C. Typically, a pushing tube 336 slides within delivery tube 332 proximally to coiled element 240 in order to push coiled element 240 from within the lumen of delivery tube 332. Typically, delivery tube 332 is advanced within the lumen of sleeve 26 until approximately one of the fibrous trigones (e.g., right fibrous trigone 144, in the direction of implantation shown in FIG. 25A), generally in the vicinity of contracting mechanism 28, e.g., housing 44 thereof. Alternatively, advancement tube 330 is advanced to near the end of the sleeve, before the overlapping portion through which anchor 38E passes, and coiled element 240 is positioned within the lumen of sleeve 26 when tube 332 is retracted and pushing tube 336 pushes on coiled element 240.

Figure 25E:
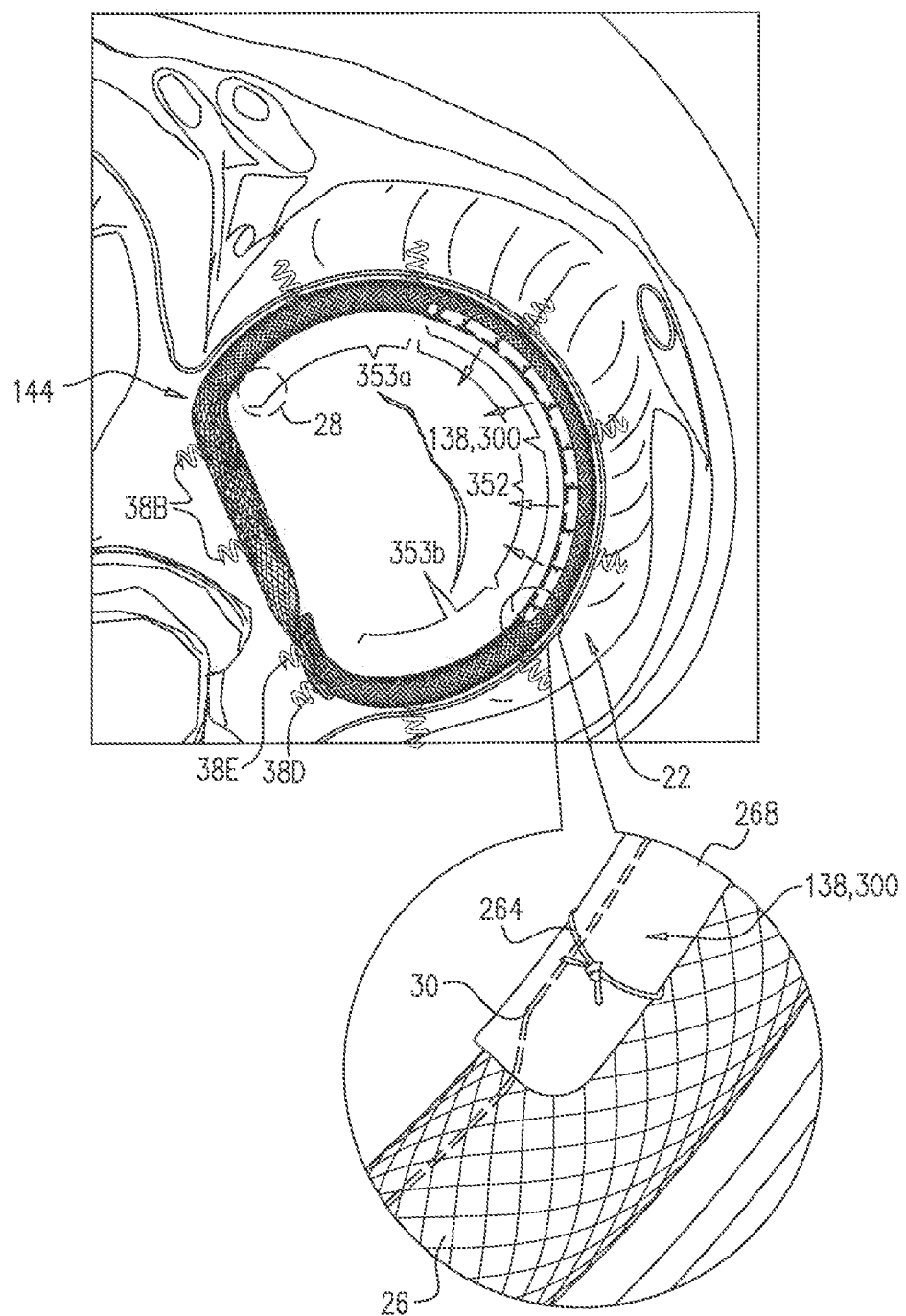

FIG. 25E is a schematic illustration of another configuration of system 20, in accordance with an application of the present invention. In this configuration, contraction-restricting portion 300 comprises a contraction-restricting segment 268 that is coupled to an outer surface of sleeve 26. For some applications, segment 268 comprises a coiled element, as described hereinabove. For other applications, segment 268 comprises a tubular element comprising a material, e.g., a semi-rigid material (such as Nitinol, polyethylene, and/or silicone, e.g., high-rigidity silicone), which restricts compression along a longitudinal axis of segment 268.

Typically, segment 268 is coupled to sleeve 26 by being sutured thereto via sutures 264, by way of illustration and not limitation, typically before implant structure 22 is advanced within the body of the patient. Segment 268 may be coupled to sleeve 26 using any suitable coupling technique. Segment 268 is typically coupled to sleeve 26 prior to advancing implant structure 22 within the body of the patient.

Segment 268 is typically coupled to portion of sleeve 26 designated for implantation along the annulus of the valve at the posterior leaflet. Alternatively or additionally, segment 268 is coupled to a portion of the sleeve designated for implantation in a vicinity of one or both trigones 144 and 142. The coupling of segment 268 to the portion of sleeve 26 defines contraction-restricted portion 352 of structure 22, while the remaining portions of sleeve 26 not coupled to segment 268 define contractible portions 353a and 353b of structure 22. In general, the techniques described hereinabove with respect to contraction-restricting portion 300, with reference to FIGS. 24A-E and 25A-E, may be applied to segment 268, mutatis mutandis.

Following the implantation of structure 22 along the annulus, portions of implantable structure 22 are contracted using contracting assembly 40, as described hereinabove. During the ongoing contraction of structure 22 responsively to the actuation of contracting assembly 40, contractible portions 353a and 353b are contracted, while contraction-restricting portion 300 restricts longitudinal contraction of contraction-restricted portion 352, but facilitates radial movement of portion 352 toward the center of the valve (i.e., in the direction as indicated by the arrows). This radial movement of portion 352 brings the posterior leaflet toward the anterior leaflet.

Following the contracting of structure 22 by mechanism 28, the opening at proximal end 49 of implantable structure 22 may be closed, such as by closure element 290, described hereinabove with reference to FIGS. 10A-B, 11-12, 13A-B, 14A-B, 15-16, 17A-F, and 18.

It is to be noted that although contraction-restricting segment 268 is shown in FIG. 25E as comprising a tubular element, for some applications, a different element, e.g., a suture, is used to define contraction-restricted portion 352 of implantable structure 22. For example, coiled element 240 may be placed inside sleeve 26. One or more contraction-restricting elements (e.g., a suture, a staple, a ratchet mechanism, and/or a bracket) are placed around portions of the coiled element, in order to decrease the pitch of the coiled element at the portions, thereby reducing the contractibility of the portions.

For some applications, a healthcare professional places the contraction-restricting element around given portions of the coiled element intra-procedurally, the portions of the coiled element corresponding to respective portions of a subject's mitral annulus. For example, subsequent to determining the size of the subject's mitral valve, and before placing the implantable structure inside the patient's body, the healthcare professional may place contraction-restricting element around given portions of the coiled element, in order to reduce the contractibility of the portions. For some applications, the healthcare professional applies sutures to the coiled element while the element is disposed inside the sizer. For some applications, the sizer is used to guide the suturing and to prevent the healthcare professional from placing a suture through contracting member 30.

Figure 26:
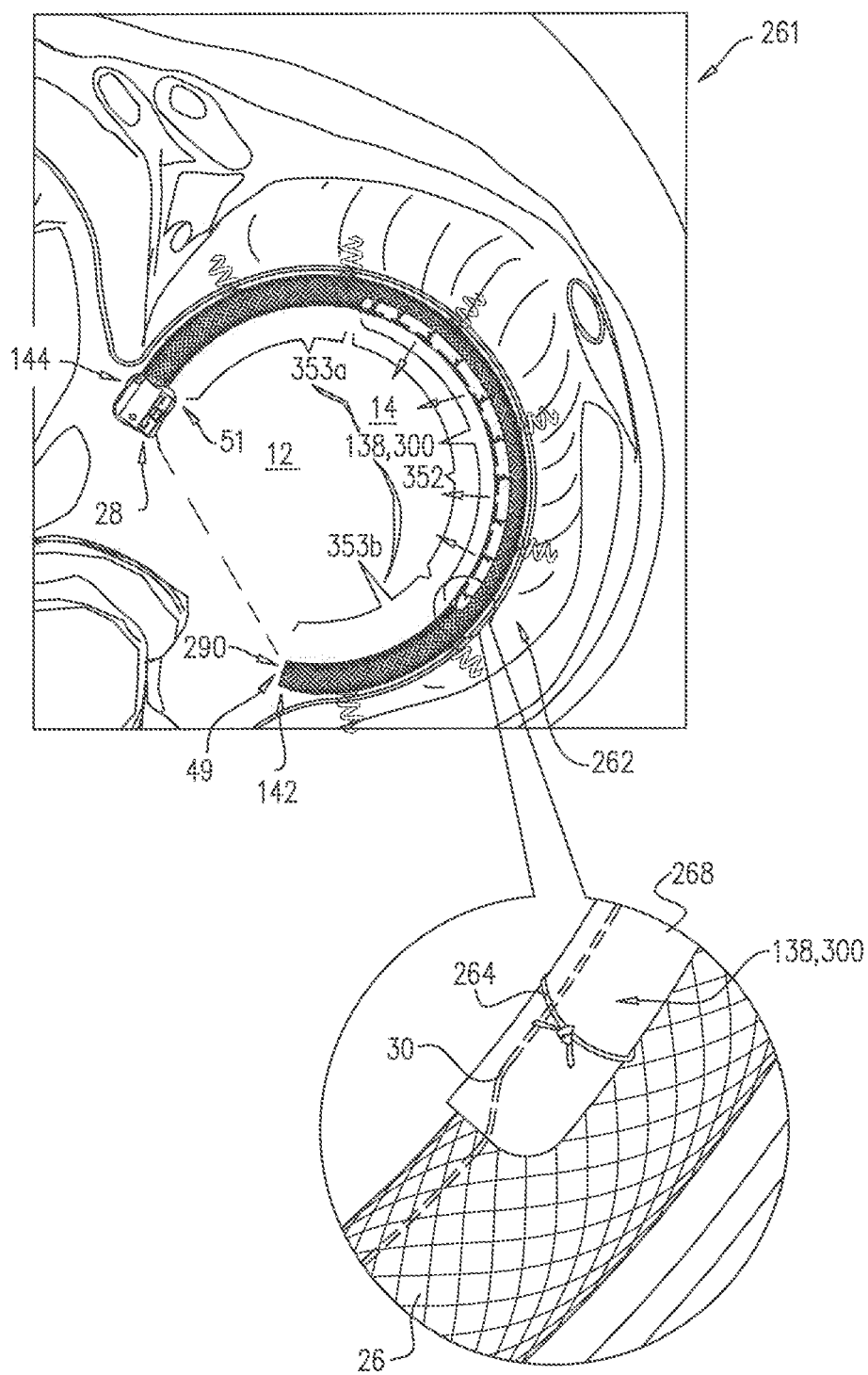
FIG. 26 is a schematic illustration of an implant structure, in accordance with some applications of the present invention.

FIG. 26 is a schematic illustration of a system 261 comprising an implant structure 262 and contraction-restricting element 300 comprising contraction-restricting segment 268 that is coupled to an outer surface of sleeve 26, in accordance with some applications of the present invention. Implant structure 262 is generally similar to implant structure 22, as described hereinabove with reference to FIG. 25E, with the exception that implant structure 262 defines a partial annuloplasty ring structure.

Implant structure 262 is generally similar to implant structure 22, as described hereinabove with reference to FIGS. 1, 4, 15, 17A-F, and 18-21, with the exception that contraction-restricting element 138 is coupled to the outer surface of sleeve 26, and implant structure 262 typically does not comprise crimping element(s) 132 or 134. Structure 262 is typically implanted along the annulus in a manner as described hereinabove with reference to FIGS. 2A-I, 3, and 17A-C, with regard to the implantation of implant structures 22 and 133 along the annulus of the mitral valve.

Reference is now made to FIGS. 24A-E, 25A-E, and 26. It is to be noted that although structure 22 is shown in FIGS. 24A-E and 25A-E, as being placed along the annulus in a manner as to define an overlapping region, the scope of the present invention includes structure 22 shown in FIGS. 24A-E and 25A-E placed along the annulus as a partial ring structure, as shown in FIG. 26.

Figure 27:
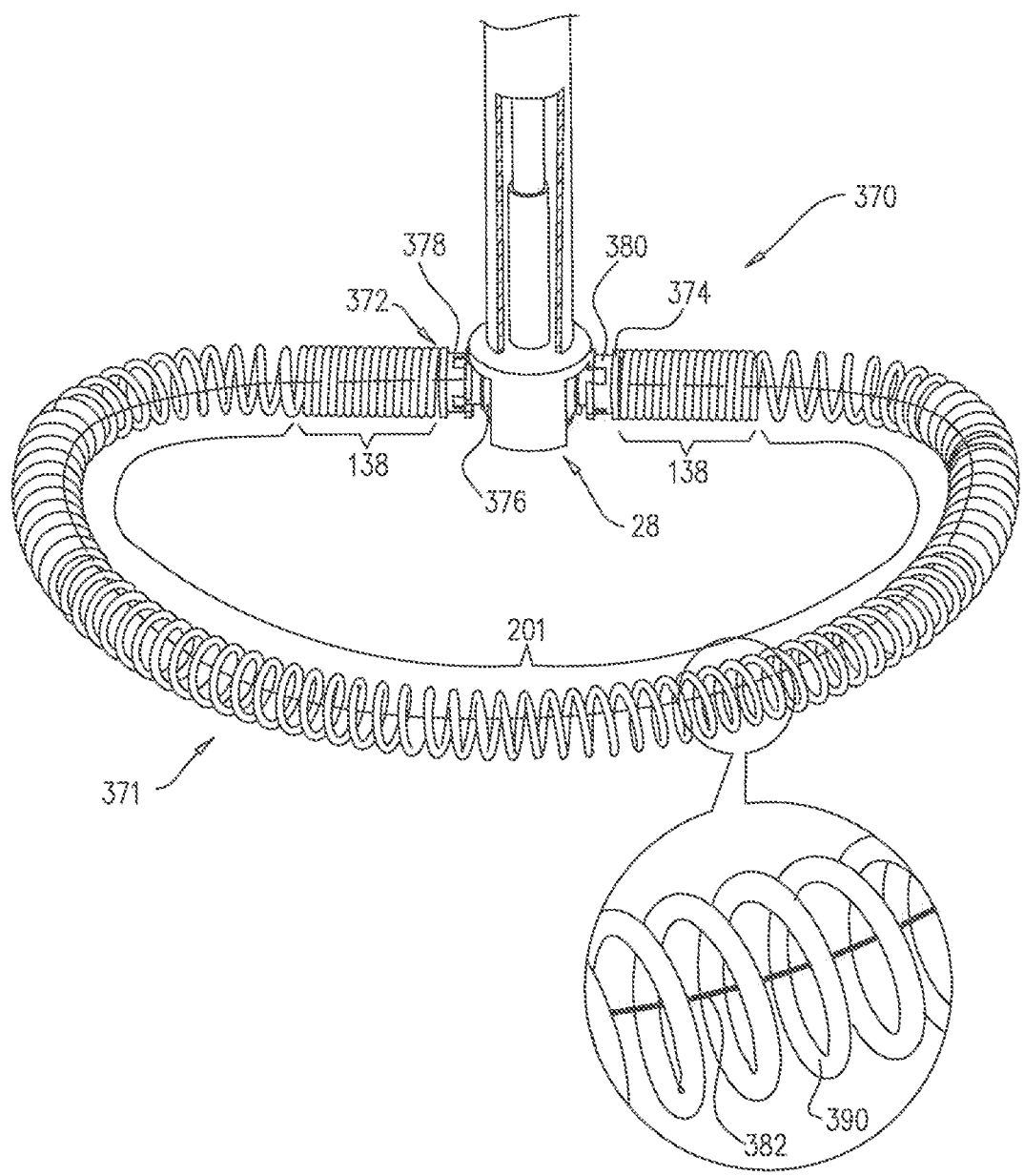
FIG. 27 is a schematic illustration of an implant structure configured to treat the mitral valve having a contraction-restricting element, in accordance with some applications of the present invention.

Reference is now made to FIG. 27, which is a schematic illustration of coiled element 390, in accordance with some applications of the present invention. For some applications, techniques described herein are practiced in combination with techniques described in U.S. patent application Ser. No. 12/341,960 to Cabiri (published as US 2010/0161047), which is incorporated herein by reference. FIG. 27 is generally similar to FIG. 5 of the aforementioned Cabiri application. FIG. 27 shows a system 370 for repairing a dilated annulus of a subject comprising an annuloplasty structure 371 that defines an annuloplasty ring, in accordance with some applications of the present invention. Annuloplasty structure 371 comprises first and second ends 372 and 374, respectively, which are coupled to (e.g., welded to) a housing 376 that houses contracting mechanism 28 (which is generally as described hereinabove). Housing 376 is shaped to provide first and second coupling members 378 and 380 which are coupled to first and second ends 302 and 304, of structure 371, respectively.

For some applications, structure 371 comprises a linear, elongate structure in a resting configuration thereof. Prior to implantation, first and second ends 372 and 374 of structure 371 are welded or otherwise attached to coupling members 378 and 380, respectively, thereby facilitating the formation of structure 371 into a substantially ring-shaped structure. As described in U.S. patent application Ser. No. 12/341,960 to Cabiri (published as US 2010/0161047), structure 371 typically comprises a body portion (e.g., coiled element 390) defining a lumen for housing flexible member 382. A first end of flexible member 382 is coupled to contracting mechanism 28, while a second end of flexible member 382 is coupled to second end 304 of structure 371.

As shown, structure 371 defines a substantially ring-shaped configuration, e.g., a "D"-shaped configuration, as shown, which conforms to the shape of the annulus of a mitral valve of the subject. Prior to contracting of structure 371, the coiled element 390 is relaxed and structure 371 defines a first perimeter thereof. Coiled element provides contraction-restricting elements 138 which comprise a material in a configuration in which portions 49 are flexible and less longitudinally compressible, e.g., not longitudinally compressible, with respect to a contractible portion 201 of coiled element 390, for example, as described hereinabove. Contraction-restricting elements 138 are configured to be disposed in the vicinity of the trigones of the mitral valve of the heart, e.g., along the fibrous portion of the annulus that is between the trigones when structure 371 is anchored, sutured, fastened or otherwise coupled to the annulus of the mitral valve. Contraction-restricting elements 138 impart rigidity to structure 371 in the portion thereof that is disposed between the fibrous trigones such that structure 371 better mimics the conformation and functionality of the mitral valve.

Typically, both contraction-restricting elements 138 have a combined length of 10-50 mm.

Structure 371 defines contractible portion 201 and contraction-restricting elements 138. Typically, a radius of curvature at a center of the contractible portion of coiled element 390 is smaller than a radius of curvature at a center of contraction-restricting elements 138, when no external force is applied to the annuloplasty structure.

It is to be noted that contractible portion 201 and contraction-restricting elements 138 of structure 371 comprise a coiled element by way of illustration and not limitation. For example, contractible portion 201 and contraction-restricting elements 138 may comprise stent-like struts, or a braided mesh. In either configuration, contraction-restricting elements 138 are chronically longitudinally compressed in a resting state of structure 371.

For some applications coiled element 390 is used in combination with implant structure 22 (described with reference to FIGS. 10A-11E), the coiled element defining two contraction-restricting elements 138, which are disposed in vicinities of respective trigones of the subject.

Reference is now made to FIG. 28, which is a schematic illustration of another configuration of implantable structure 22, in accordance with an application of the present invention. This configuration of implantable structure 22 is generally similar to the configuration described hereinabove with reference to FIG. 1, except as follows. Contracting assembly 40 comprises first and second longitudinal contracting members 30A and 30B, having respective first member ends and respective second member ends 53A and 53B. Contracting members 30A and 30B have respective first and second member ends, and respective first member end portions, which extend from the respective first member ends toward the respective second member ends along only respective longitudinal portions of the contracting members. The first member end portions, e.g., the first member ends, are coupled to contracting mechanism 28, e.g., a rotatable structure, such as spool 46. Second member end 53A of first contracting member 30A is coupled to sleeve 26 at a first site 39A at a first longitudinal distance from the first sleeve end. Second member end 53B of second contracting member 30B is coupled to sleeve 26 at a second site 39B at a second longitudinal distance from the second sleeve end.

Contracting mechanism 28, e.g., the rotatable structure, such as spool 46, is positioned at an intermediary third site along the sleeve, longitudinally between first and second sites 39A and 39B, exclusive. For example, the contracting mechanism may be positioned a longitudinal distance from one of the ends of the sleeve, which longitudinal distance equals between 30% and 70% of the length of the sleeve. Contracting mechanism 28 and longitudinal members 30A and 30B are arranged to longitudinal contract the sleeve, for example, are arranged such that rotation of the rotatable structure longitudinally contracts the sleeve, such as by winding contracting members 30A and 30B around the spool, thereby contracting both of the longitudinal contracting members.

For some applications, at least one (either one or both) of the first and second longitudinal distances, taken separately, when measured when the sleeve is in a straight, relaxed, non-contracted state, is at least 3 mm, e.g., at least 5 mm, such as at least 9 mm, e.g., at least 14 mm. For some applications, each of the first and second longitudinal distances is at least 3 mm, e.g., at least 5 mm, such as at least 9 mm, e.g., at least 14 mm. For some application, one of the first and second longitudinal distances is at least 3 mm, such as at least 5 mm (e.g., at least 9 mm, or at least 14 mm), and the other of the first and second longitudinal distances is less than 5 mm, such as less than 3 mm, e.g., is equal to 0 mm.

For some applications, the techniques of this configuration are implemented using techniques described in US Patent Application Publication 2010/0161047, which is incorporated herein by reference, with reference to FIG. 15 thereof, mutatis mutandis.

Figure 29A:
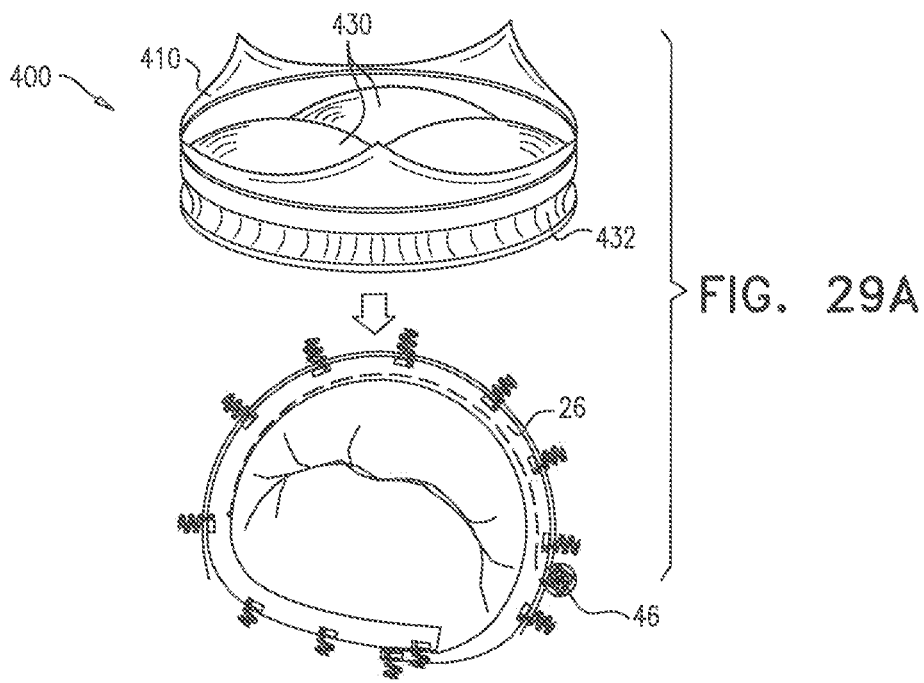
FIGS. 29A-B and 30 are schematic illustrations of a valve prosthesis assembly, in accordance with respective applications of the present invention.
Figure 29B:
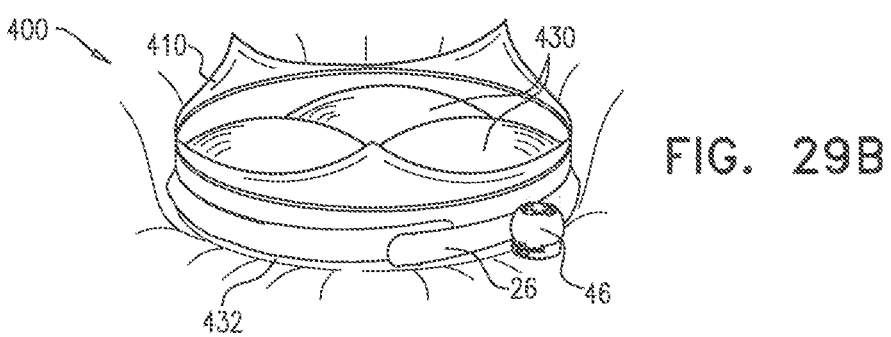
Figure 30:
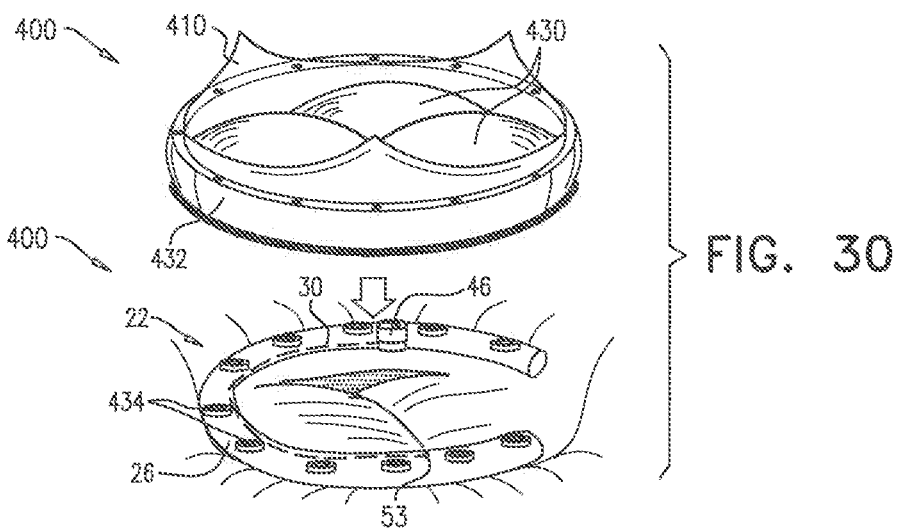

Reference is made to FIGS. 29A-B and 30, which are schematic illustrations of a valve prosthesis assembly 400, in accordance with respective applications of the present invention. Valve prosthesis assembly 400 comprises a prosthetic heart valve 410 that is couplable to a base ring 422. Prosthetic heart valve 410 is used to replace a native diseased heart valve. Valve 410 comprises a plurality of artificial leaflets 430, which comprise a pliant material. Valve 410 may implement techniques known in the artificial valve art, such as described, for example, in US Patent Application Publication 2007/0255400 to Parravicini et al., US Patent Application Publication 2004/0122514 to Fogarty et al., US Patent Application Publication 2007/0162111 to Fukamachi et al., and/or US Patent Application Publication 2008/0004697 to Lichtenstein et al., all of which are incorporated herein by reference.

Valve 410 further comprises an annular base 432, to which artificial leaflets 430 are coupled. Annular base 432 is configured to be couplable to base ring 422 during an implantation procedure. For example, as show in FIG. 30, base ring 422 may comprise one or more coupling elements 434, such as clips or magnets, which are configured to be coupled to corresponding coupling elements on a lower surface of annular base 432 (not visible in the figures). Alternatively or additionally, annular base 432 may be configured to be placed within the opening defined by base ring 422, as shown in FIG. 29A. To hold the annular base coupled to the base ring, the base ring is tightened around the annular base, as shown in FIG. 29B, typically using one or more of the techniques described hereinabove for contracting implant structures. Typically, valve prosthesis assembly 400, such as annular base 432 thereof, is configured to push and hold open the intact diseased native leaflets.

Base ring 422 implements one or more of the techniques of implantable structure 22 described hereinabove. In particular, base ring 422 may be coupled to the annulus of the native diseased valve using the anchoring techniques described hereinabove. In addition, base ring 422 typically comprises sleeve 26 and contracting mechanism 28, which may, for some applications, comprise a rotatable structure 46, such as a spool, which is typically implemented using techniques described herein. The contracting mechanism is arranged to contract base ring 422, e.g., the rotatable structure is arranged such that rotation thereof contracts base ring 422, typically using techniques described herein. Such tightening may serve to couple base ring 422 to annular base 432, as shown in FIG. 29B. Alternatively or additionally, such tightening sets the desired dimensions of the base ring, in order to align the coupling elements of the base ring with those of valve 410, thereby enabling tight coupling, such as for the applications described with reference to FIG. 30.

For some applications, as shown in FIG. 30, base ring 422 comprises a partial ring, such as described hereinabove with reference to FIGS. 2A-I. For other applications, as shown in FIGS. 29A-B, the base ring is arranged as a full ring, such as described hereinabove with reference to FIGS. 5, 20, and 22.

Valve prosthesis assembly 400 is typically implanted in a minimally invasive transcatheter or percutaneous procedure. The procedure begins with the introduction and implantation of base ring 422 into the heart, such as using techniques for implanting implantable structure 22, described hereinabove with reference to FIGS. 2A-I. Prosthetic heart valve 410 is subsequently introduced into the heart and coupled to base ring 422, as described above. Valve prosthesis assembly 400 is typically used for replacement of a diseased native mitral valve, aortic valve, tricuspid valve, or pulmonary valve.

Reference is now made to FIGS. 1-30. Implant structures 22, 133, 262, 281, and 371 may be advanced toward annulus 140 in any suitable procedure, e.g., a transcatheter procedure, a percutaneous procedure, a minimally invasive procedure, or an open heart procedure (in which case one or more elements of systems 20, 131, 261, 280, and 370 are typically rigid). Regardless of the approach, the procedure typically includes the techniques described hereinabove with reference to FIGS. 2A-I and 3.

It is to be noted that the positioning of contraction-restricting element(s) 138 may be placed along implant structures 22, 133, 262, 281, and 371 is anywhere along implant structures 22, 133, 222, 262, 281, and 371.

For some applications, following initial contraction of implant structures 22, 133, 222, 262, 281, and 371 during the implantation procedure, implant structures 22, 133, 222, 262, 281, and 371 may be further contracted or relaxed at a later time after the initial implantation, such as between several weeks and several months after the initial implantation. Using real-time monitoring, tactile feedback and optionally in combination with fluoroscopic imaging, a rotation tool or anchor driver 68 of deployment manipulator 24 is reintroduced into the heart and used to contract or relax implant structures 22, 133, 222, 262, 281, and 371.

Although implant structures 22, 133, 222, 262, 281, and 371 has been described hereinabove as comprising a partial annuloplasty ring, for some applications of the present invention, implant structure 22 instead comprises a full annuloplasty ring. Implant structures 22, 133, 222, 262, 281, and 371 may comprise an annular portion of a structure, a ring, or a partial ring, which facilitate coupling thereto of a prosthetic valve which replaces the native atrioventricular valve. Typically, implant structures 22, 133, 222, 262, 281, and 371 function to treat (e.g., facilitate repair or replacement of) the native atrioventricular valve of the patient.

For some applications of the present invention, systems 20, 131, 261, 220, 260, and 280, and 370 are used to treat an atrioventricular valve other than the mitral valve, i.e., the tricuspid valve. For these applications, implant structures 22, 133, 222, 262, 281, and 371 and other components of systems 20, 131, 261, 220, 260, and 280, and 370 described hereinabove as being placed in the left atrium are instead placed in the right atrium. Although implant structures 22, 133, 222, 262, 281, and 371 are described hereinabove as being placed in an atrium, for some application implant structures 22, 133, 222, 262, 281, and 371 are instead placed in either the left or right ventricle.

Features of implant structures 22, 133, 222, 262, 281, and 371 described with reference to respective figures are not limited to the prostheses shown in those figures. Rather, features of the implant structures shown in any of the figures could be used in combination with any of the other features described herein, mutatis mutandis. Examples of the features that may be combined with each other include, but are not limited to:

crimping elements 132 and 134,
flap 27,
stiffening elements 136
coiled element 240,
linking member 250,
contraction-restricting segment 268,
self-closing strips 282*a* and 282*b*,
plug 550,
approximating element 551,
screw 552 and thread 554,
spring 560,
deflecting element 570, and
force-distributing element 540.

Reference is now made to FIGS. 1-30. It is to be noted that any of the closure elements 290 described herein (for example, in FIGS. 10A-B, 11-12, 13A-B, 14A-B, 15-16, 17A-F, and 18) or, other closure elements known in the art may be used independently or in combination for closing the opening at the end of sleeve 26 of any of the implants described herein. For example, a plug (such as a silicone plug), and/or a band (such as a silicone band) may be used to close the opening. Alternatively, flap 27 may be folded over and an anchor (e.g., a tissue anchor 38, as described herein) may be used to anchor the folded-over flap to the patient's tissue.

Typically, the closure elements described herein reduce the likelihood of a thrombosis forming inside sleeve 26, by closing the opening of the sleeve end, relative to if the opening were left opened. Alternatively or additionally, the closure elements described herein are used to close the opening for a different reason.

Typically, the closure of the opening (e.g., using the closure elements described herein) and the deployment of implant structure 22 is performed during a single procedure, e.g., by deploying the implant structure and closing the opening via a single catheter. For some applications (not shown), sleeve 26 defines openings at both thereof, and closure elements are used to close the openings at both of the ends of the sleeve.

Reference is now made to FIGS. 1-30. It is to be noted that any of the implants described herein include a plurality of radiopaque markers 39, as described hereinabove with reference to FIG. 1.

Reference is now made to FIGS. 1-30. It is to be noted that the scope of the present invention includes use of any of the implants described herein to treat any cardiac valve, e.g., a tricuspid valve, a mitral valve, a pulmonary valve, and an aortic valve. Additionally, the scope of the present invention includes methods for implanting any of the implants described herein, including open-hear/surgical, transluminal/transcatheter, and/or minimally invasive such as by intercostals or percutaneous access.

For some applications, the scope of the present invention includes embodiments described in the following applications, which are incorporated herein by reference. In an embodiment, techniques and apparatus described in one or more of the following applications are combined with techniques and apparatus described herein:

PCT Publication WO 08/068756 to Gross et al., entitled, "Segmented ring placement," filed Dec. 5, 2007;

PCT Publication WO 10/004546 to Gross et al., entitled, "Annuloplasty devices and methods of delivery therefor," filed on Jun. 15, 2009;

PCT Publication WO 10/073246 to Cabiri et al., entitled, "Adjustable annuloplasty devices and mechanisms therefor," filed Dec. 22, 2009;

PCT Publication WO/2010/128502 to Maisano et al., entitled, "Implantation of repair chords in the heart," filed May 4, 2010;

U.S. patent application Ser. No. 12/608,316 to Miller et al., entitled, "Tissue anchor for annuloplasty ring," filed on Oct. 29, 2009, which published as US Patent Application Publication 2011/0106247

U.S. patent application Ser. No. 12/689,693 to Hammer et al., entitled, "Deployment techniques for annuloplasty ring," filed on Jan. 19, 2010, which published as US Patent Application Publication 2010/0280605; and/or PCT Publication WO/2010/128503 to Zipory et al., entitled, "Deployment techniques for annuloplasty ring and over-wire rotation tool," filed May 4, 2010.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for treating a native valve of a heart of a patient, the method comprising:
    anchoring multiple anchors of an implant into tissue around an annulus of the native valve, such that the implant forms a closed loop around the annulus, the implant including an elongate contracting member;
    at the annulus, incorporating a force-distribution element into the implant such that the force-distribution element extends along a longitudinal portion of the elongate contracting member; and
    circumferentially tightening the annulus by drawing the anchors closer together by actuating a contracting mechanism that is coupled to the elongate contracting member, such that:
        the contracting mechanism applies a longitudinal tensioning force to the elongate contracting member, and
        the force-distribution element distributes the longitudinal tensioning force over at least two of the anchors.

2. The method according to claim 1, wherein the force-distribution element is cylindrical, and wherein the step of incorporating the force-distribution element into the implant comprises incorporating the cylindrical force-distribution element into the implant.

3. The method according to claim 1, wherein the contracting mechanism includes a rotatable structure, and wherein the step of actuating the contracting mechanism comprises rotating the rotatable structure.

4. The method according to claim 3, wherein the step of rotating the rotatable structure comprises rotating the rotatable structure such that the contracting member is pulled proximally into the contracting mechanism.

5. The method according to claim 1, wherein the method further comprises locking the longitudinal tensioning force in the contracting member using a locking bead.

6. The method according to claim 1, wherein the step of anchoring the multiple anchors comprises anchoring the multiple anchors such that a first portion of the implant and a second portion of the implant together define a longitudinally-overlapping portion of the implant.

7. The method according to claim 6, further comprising attaching the first portion of the implant to the second portion of the implant.

8. The method according to claim 7, wherein the step of attaching the first portion of the implant to the second portion of the implant comprises attaching the first portion of the implant to the second portion of the implant using at least one of the anchors.

9. The method according to claim 1, wherein the force-distribution element includes a tightly-coiled element, and wherein the step of incorporating the force-distribution element into the implant comprises incorporating the tightly-coiled element into the implant.

10. The method according to claim 9, wherein the force-distribution element does not compress along a longitudinal axis thereof, and wherein the step of incorporating the force-distribution element into the implant comprises incorporating the force-distribution element that does not compress along the longitudinal axis into the implant.

11. The method according to claim 10, wherein the force-distribution element is flexible, and wherein the step of incorporating the force-distribution element into the implant comprises incorporating the force-distribution element that is flexible into the implant.

12. The method according to claim 1, wherein the force-distribution element defines a lumen therethrough, and wherein the step of incorporating the force-distribution element into the implant comprises incorporating the force-distribution element that defines the lumen into the implant.

13. The method according to claim 1, wherein the step of actuating the actuating mechanism comprises actuating the contracting mechanism while the contracting mechanism is disposed within the heart.

14. A method for use at an annulus of a valve of a heart of a subject, the method comprising:
    anchoring multiple anchors of an implant to tissue of the annulus;
    at the annulus, incorporating a force-distribution element into the implant such that the force-distribution element extends along a longitudinal portion of the implant;
    arranging the implant into a closed loop around the annulus; and
    longitudinally contracting the implant by applying a longitudinal tensioning force to a contracting member of the implant such that the force-distribution element distributes the longitudinal tensioning force over at least two of the anchors.

15. The method according to claim 14, wherein the step of arranging the implant into the closed loop around the annulus comprises overlapping a first portion and a second portion of the implant to define a longitudinally-overlapping portion of the implant.

16. The method according to claim 15, wherein the step of anchoring the multiple anchors of the implant to the tissue comprises driving at least one of the anchors through the first portion and the second portion and into the tissue.

17. The method according to claim 14, wherein the force-distribution element includes a tightly-coiled element, and wherein the step of incorporating the force-distribution element into the implant comprises incorporating the tightly-coiled element into the implant.

18. The method according to claim 14, wherein the step of applying the longitudinal tensioning force to the contracting member comprises applying the longitudinal tensioning force to the contracting member by rotating a rotatable structure of a contracting mechanism.

19. The method according to claim 18, wherein the step of rotating the rotatable structure comprises rotating the rotatable structure such that the contracting member is pulled proximally into the contracting mechanism.

20. The method according to claim 14, wherein the method further comprises locking the longitudinal tensioning force in the contracting member using a locking bead.

21. A method for treating a native valve of a heart of a patient, the method comprising:
    anchoring multiple anchors of an implant into tissue around an annulus of the native valve, such that the implant forms a closed loop around the annulus, the implant including an elongate contracting member;

at the annulus, incorporating a force-distribution element into the implant such that the force-distribution element extends along a longitudinal portion of the elongate contracting member; and circumferentially tightening the annulus by drawing the anchors closer together by applying a longitudinal tensioning force to the elongate contracting member, such that the force-distribution element distributes the longitudinal tensioning force over at least two of the anchors.

22. The method according to claim 21, wherein the method further comprises locking the longitudinal tensioning force in the elongate contracting member using a locking bead.

23. The method according to claim 21, wherein the step of applying the longitudinal tensioning force to the elongate contracting member comprises applying the longitudinal tensioning force to the elongate contracting member by rotating a rotatable structure of a contracting mechanism.

24. The method according to claim 21, wherein the force-distribution element defines a lumen therethrough, and wherein the step of incorporating the force-distribution element into the implant comprises incorporating the force-distribution element that defines the lumen into the implant.

25. The method according to claim 21, wherein the force-distribution element does not compress along a longitudinal axis thereof, and wherein the step of incorporating the force-distribution element into the implant comprises incorporating the force-distribution element that does not compress along the longitudinal axis into the implant.

26. The method according to claim 21, wherein the force-distribution element is cylindrical, and wherein the step of incorporating the force-distribution element into the implant comprises incorporating the cylindrical force-distribution element into the implant.

* * * * *